United States Patent
Röhrig et al.

(10) Patent No.: US 10,167,280 B2
(45) Date of Patent: Jan. 1, 2019

(54) SUBSTITUTED OXOPYRIDINE DERIVATIVES

(71) Applicant: BAYER PHARMA AKTIENGESELLSCHAFT, Berlin (DE)

(72) Inventors: Susanne Röhrig, Hilden (DE); Eloisa Jimenez Nunez, Wuppertal (DE); Karl-Heinz Schlemmer, Wuppertal (DE); Adrian Tersteegen, Wuppertal (DE); Henrik Teller, Schwaan (DE); Alexander Hillisch, Solingen (DE); Stefan Heitmeier, Wülfrath (DE); Martina Victoria Schmidt, Köln (DE); Jens Ackerstaff, Düsseldorf (DE); Jan Stampfuß, Düsseldorf (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/513,977

(22) PCT Filed: Sep. 22, 2015

(86) PCT No.: PCT/EP2015/071660
§ 371 (c)(1),
(2) Date: Mar. 23, 2017

(87) PCT Pub. No.: WO2016/046166
PCT Pub. Date: Mar. 31, 2016

(65) Prior Publication Data
US 2017/0291892 A1    Oct. 12, 2017

(30) Foreign Application Priority Data
Sep. 24, 2014   (EP) .................................... 14186084

(51) Int. Cl.
| | | |
|---|---|---|
| *C07D 213/79* | (2006.01) | |
| *C07D 213/81* | (2006.01) | |
| *A61K 31/44* | (2006.01) | |
| *C07D 413/14* | (2006.01) | |
| *C07D 401/12* | (2006.01) | |
| *C07D 405/12* | (2006.01) | |
| *C07D 413/12* | (2006.01) | |
| *C07D 401/14* | (2006.01) | |
| *C07D 405/14* | (2006.01) | |

(52) U.S. Cl.
CPC ......... *C07D 413/14* (2013.01); *C07D 213/79* (2013.01); *C07D 213/81* (2013.01); *C07D 401/12* (2013.01); *C07D 401/14* (2013.01); *C07D 405/12* (2013.01); *C07D 405/14* (2013.01); *C07D 413/12* (2013.01)

(58) Field of Classification Search
None
See application file for complete search history.

(56) References Cited

U.S. PATENT DOCUMENTS

| | | |
|---|---|---|
| 9,434,690 B2 | 9/2016 | Röhrig et al. |
| 9,475,809 B2 | 10/2016 | Röhrig et al. |
| 2016/0052884 A1 | 2/2016 | Röhrig et al. |
| 2016/0152613 A1 | 6/2016 | Röhrig et al. |
| 2016/0272637 A1 | 9/2016 | Röhrig et al. |
| 2016/0368903 A1 | 12/2016 | Röhrig et al. |
| 2017/0035739 A1 | 2/2017 | Röhrig et al. |

FOREIGN PATENT DOCUMENTS

| | | |
|---|---|---|
| EP | 1 526 131 | 4/2005 |
| WO | 2006/030032 | 3/2006 |
| WO | 2008/079787 | 7/2008 |
| WO | WO 2008079787 A2 * | 7/2008 |
| WO | 2013/056034 | 4/2013 |
| WO | 2014/154794 | 10/2014 |
| WO | 2014/160592 | 10/2014 |
| WO | 2015/011087 | 1/2015 |
| WO | 2015/063093 | 5/2015 |
| WO | 2015/120777 | 8/2015 |

OTHER PUBLICATIONS

Patani et al, Chem. Rev., vol. 96, pp. 3147-3176 (Year: 1996).*
International Search Report for PCT/EP2015/071660, five pages, dated Dec. 11, 2015.
Written Opinion of the ISA for PCT/EP2015/071660, five pages, dated Dec. 11, 2015.

* cited by examiner

*Primary Examiner* — Zinna Northington Davis
(74) *Attorney, Agent, or Firm* — Nixon & Vanderhye P.C.

(57) ABSTRACT

The invention relates to substituted oxopyridine derivatives and to processes for preparation thereof, and also to the use thereof for production of medicaments for treatment and/or prophylaxis of diseases, especially of cardiovascular disorders, preferably thrombotic or thromboembolic disorders, and oedemas, and also ophthalmic disorders.

16 Claims, No Drawings

SUBSTITUTED OXOPYRIDINE DERIVATIVES

This application is the U.S. national phase of International Application No. PCT/EP2015/071660, filed 22 Sep. 2015, which designated the U.S. and claims priority to Patent Application No. EP 14186084.1, filed 24 Sep. 2014; the entire contents of each of which are hereby incorporated by reference.

The invention relates to substituted oxopyridine derivatives and to processes for preparation thereof, and also to the use thereof for production of medicaments for treatment and/or prophylaxis of diseases, especially of cardiovascular disorders, preferably thrombotic or thromboembolic disorders, and oedemas, and also ophthalmic disorders.

Blood coagulation is a protective mechanism of the organism which helps to "seal" defects in the wall of the blood vessels quickly and reliably. Thus, loss of blood can be avoided or kept to a minimum. Haemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a final joint reaction path, are distinguished. Here, factors Xa and IIa (thrombin) play key roles: Factor Xa bundles the signals of the two coagulation paths since it is formed both via factor VIIa/tissue factor (extrinsic path) and via the tenase complex (intrinsic path) by conversion of factor X. The activated serine protease Xa cleaves prothrombin to thrombin which, via a series of reactions, transduces the impulses from the cascade to the coagulation state of the blood.

In the more recent past, the traditional theory of two separate regions of the coagulation cascade (extrinsic and intrinsic path) has been modified owing to new findings: In these models, coagulation is initiated by binding of activated factor VIIa to tissue factor (TF). The resulting complex activates factor X, which in turn leads to generation of thrombin with subsequent production of fibrin and platelet activation (via PAR-1) as injury-sealing end products of haemostasis. Compared to the subsequent amplification/propagation phase, the thrombin production rate in this first phase is low and as a result of the occurrence of TFPI as inhibitor of the TF-FVIIa-FX complex is limited in time.

A central component of the transition from initiation to amplification and propagation of coagulation is factor XIa: in positive feedback loops, thrombin activates, in addition to factor V and factor VIII, also factor XI to factor XIa, whereby factor IX is converted into factor IXa, and, via the factor IXa/factor VIIIa complex generated in this manner, the factor X is activated and thrombin formation is in turn therefore highly stimulated leading to strong thrombus growth and stabilizing the thrombus.

In addition, it becomes the focus that, in addition to the stimulation via tissue factor, the coagulation system can be activated particularly on negatively charged surfaces, which include not only surface structures of foreign cells (e.g. bacteria) but also artificial surfaces such as vascular prostheses, stents and extracoporeal circulation. On the surface, initially factor XII (FXII) is activated to factor XIIa which subsequently activates factor XI, attached to cell surfaces, to factor XIa. This leads to further activation of the coagulation cascade as described above. In addition, factor XIIa also activates bound plasma prokallikrein to plasma kallikrein (PK) which, in a potentiation loop, firstly leads to further factor XII activation, overall resulting in amplification of the initiation of the coagulation cascade. In addition, PK is an important bradykinin-releasing protease which, inter alia, thus leads to increased endothelial permeability. Further substrates that have been described are prorenin and prourokinase, whose activation may influence the regulatory processes of the renin-angiotensin system and fibrinolysis. The activation of PK is therefore an important link between coagulative and inflammatory processes.

Uncontrolled activation of the coagulation system or defective inhibition of the activation processes may lead to the formation of local thromboses or embolisms in vessels (arteries, veins, lymph vessels) or cardiac cavities. In addition, systemic hypercoagulability may lead to system-wide formation of thrombi and finally to consumption coagulopathy in the context of a disseminated intravasal coagulation. Thromboembolic complications may also occur in extracorporeal circulatory systems such as during haemodialysis and also in vascular prostheses or prosthetic heart valves and stents.

In the course of many cardiovascular and metabolic disorders, there is an increased tendency for coagulation and platelet activation owing to systemic factors such as hyperlipidaemia, diabetes or smoking, owing to changes in blood flow with stasis, for example in atrial fibrillation, or owing to pathological changes in vessel walls, for example endothelial dysfunctions or atherosclerosis. This unwanted and excessive activation of coagulation may, by formation of fibrin- and platelet-rich thrombi, lead to thromboembolic disorders and thrombotic complications with life-threatening conditions. Inflammable processes may also be involved here. Accordingly, thromboembolic disorders are still one of the most frequent causes of morbidity and mortality in most industrialized countries.

The anticoagulants known from the prior art, that is to say substances for inhibiting or preventing blood coagulation, have various disadvantages. Accordingly, in practice, efficient treatment methods or the prophylaxis of thrombotic/thromboembolic disorders is found to be very difficult and unsatisfactory.

In the therapy and prophylaxis of thromboembolic disorders, use is made, firstly, of heparin which is administered parenterally or subcutaneously. Because of more favourable pharmacokinetic properties, preference is these days increasingly given to low-molecular-weight heparin; however, the known disadvantages described hereinbelow encountered in heparin therapy cannot be avoided either in this manner. Thus, heparin is orally ineffective and has only a comparatively short half-life. In addition, there is a high risk of bleeding, there may in particular be cerebral haemorrhages and bleeding in the gastrointestinal tract, and there may be thrombopaenia, alopecia medicomentosa or osteoporosis. Low-molecular-weight heparins do have a lower probability of leading to the development of heparin-induced thrombocytopaenia; however, they can also only be administered subcutaneously. This also applies to fondaparinux, a synthetically produced selective factor Xa inhibitor having a long half-life.

A second class of anticoagulants are the vitamin K antagonists. These include, for example, 1,3-indanediones and in particular compounds such as warfarin, phenprocoumon, dicumarol and other coumarin derivatives which nonselectively inhibit the synthesis of various products of certain vitamin K-dependent coagulation factors in the liver.

Owing to the mechanism of action, the onset of action is only very slow (latency to the onset of action 36 to 48 hours). The compounds can be administered orally; however, owing to the high risk of bleeding and the narrow therapeutic index complicated individual adjustment and monitoring of the patient are required. In addition, other side-effects such as gastrointestinal problems, hair loss and skin necroses have been described.

More recent approaches for oral anticoagulants are in various phases of clinical evaluation or in clinical use, and have demonstrated their effectiveness in various studies. However, taking these medicaments can also lead to bleeding complications, particularly in predisposed patients. Thus, for antithrombotic medicaments, the therapeutic window is of central importance: The interval between the therapeutically active dose for coagulation inhibition and the dose where bleeding may occur should be as large as possible so that maximum therapeutic activity is achieved at a minimum risk profile.

In various in vitro and in vivo models with, for example, antibodies as factor XIa inhibitors, but also in factor XIa knock-out models, the antithrombotic effect with small/no prolongation of bleeding time or extension of blood volume was confirmed. In clinical studies, elevated factor XIa concentrations were associated with an increased event rate. In contrast, factor XI deficiency (haemophilia C) did not lead to spontaneous bleeding and was apparent only in the course of surgical operations and traumata, but did show protection with respect to certain thromboembolic events.

In addition, plasma kallikrein (PK) is associated with other disorders, which are associated with increased vascular permeability or chronic inflammatory disorders such as is the case in diabetic retinopathy, macular oedema and hereditary angiooedema or chronic inflammatory intestinal disorders. Diabetic retinopathy is primarily caused by microvascular deficiency, which leads to basal membrane thickening of the vessels and loss of vascularized pericytes followed by vascular occlusion and retinal ischaemia which, owing to the retinal hypoxia thus caused, may lead to enhanced vessel permeability with subsequent formation of a macular oedema and, due to all of the processes present, to the patient going blind. In hereditary angiooedema (HAE), reduced formation of the physiological kallikrein inhibitor C1-esterase inhibitor causes uncontrolled plasma kallikrein activation and hence inflammations with fulminant oedema formation and severe pain. From experimental animal models, there are indications that inhibition of plasma kallikrein inhibits increased vascular permeability and may therefore prevent formation of a macular oedema and/or diabetic retinopathy or may improve the acute symptoms of HAE. Oral plasma kallikrein inhibitors could also be used for prophylaxis of HAE.

The kinins generated by means of plasma kallikrein especially have a causative role in the progression of chronic inflammatory intestinal disorders (CID). Their pro-inflammatory effect via activation of bradykinin receptors induces and potentiates the disease progression. Studies on Crohn's disease patients show a correlation between the kallikrein concentration in the intestinal epithelium and the degree of intestinal inflammation. Activation of the kallikrein-kinin system was likewise observed in experimental animal studies. Inhibition of bradykinin synthesis by kallikrein inhibitors could accordingly be used also for prophylaxis and/or therapy of chronic inflammatory intestinal disorders.

Furthermore, for many disorders the combination of antithrombotic and antiinflammatory principles may also be particularly attractive to prevent the mutual enhancement of coagulation and inflammation.

It is therefore an object of the present invention to provide novel compounds for the treatment of cardiovascular disorders, in particular of thrombotic or thromboembolic disorders, and/or oedematous disorders, and/or ophthalmic disorders, in particular diabetic retinopathy and/or macular oedema, in humans and animals, which compounds have a wide therapeutic bandwidth.

WO 2006/030032 describes inter alia substituted pyridinones as allosteric modulators of the mGluR2 receptor, and WO 2008/079787 describes substituted pyridin-2-ones and their use as glucokinase activators. WO 2014/154794, WO 2014/160592, WO 2015/011087 and WO 2015/063093 describe substituted pyridin-2-one and their use as factor XIa inhibitors.

The invention provides compounds of the formula

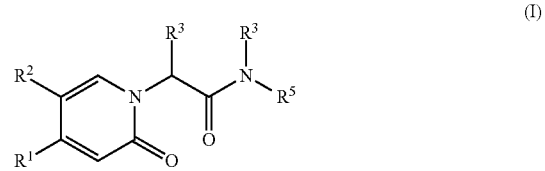

in which
R$^1$ is a group of the formula

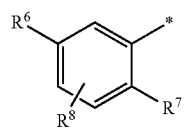

where * is the attachment point to the oxopyridine ring,
R$^6$ is bromine, chlorine, fluorine, methyl, difluoromethyl, trifluoromethyl, methoxy, difluoromethoxy, trifluoromethoxy or methylamino,
R$^7$ is bromine, chlorine, fluorine, cyano, nitro, hydroxyl, methyl, difluoromethyl, trifluoromethyl, methoxy, ethoxy, difluoromethoxy, trifluoromethoxy, ethynyl, 3,3,3-trifluoroprop-1-yn-1-yl or cyclopropyl,
R$^8$ is hydrogen, chlorine or fluorine,
R$^2$ is hydrogen, bromine, chlorine, fluorine, cyano, C$_1$-C$_3$-alkyl, difluoromethyl, trifluoromethyl, 1,1-difluoroethyl, 2,2-difluoroethyl, 2,2,2-trifluoroethyl, C$_1$-C$_3$-alkoxy, difluoromethoxy, trifluoromethoxy, 1,1-difluoroethoxy, 2,2-difluoroethoxy, 2,2,2-trifluoroethoxy, methylcarbonyl or cyclopropyl,
R$^3$ is hydrogen, C$_1$-C$_5$-alkyl, C$_1$-C$_4$-alkoxy, difluoromethyl, trifluoromethyl, 1,1-difluoroethyl, 1,1,2,2,2-pentadeuteroethyl, 3,3,3-trifluoro-2-hydroxyprop-1-yl, 3,3,3-trifluoro-2-methoxyprop-1-yl, 3,3,3-trifluoro-2-ethoxyprop-1-yl, prop-2-yn-1-yl, cyclopropyloxy or cyclobutyloxy,
where alkyl may be substituted by a substituent selected from the group consisting of fluorine, cyano, hydroxyl, difluoromethyl, trifluoromethyl, methoxy, ethoxy, difluoromethoxy, trifluoromethoxy, C$_3$-C$_6$-cycloalkyl, 4- to 6-membered oxoheterocyclyl, 1,4-dioxanyl, oxazolyl, pyrazolyl, oxadiazolyl, dihydrooxazolyl, phenyl and pyridyl,
in which cycloalkyl may be substituted by 1 to 2 substituents selected independently from the group consisting of fluorine, hydroxyl, methyl, ethyl, methoxy, ethoxy, difluoromethyl, trifluoromethyl, difluoromethoxy and trifluoromethoxy,
and
in which oxoheterocyclyl may be substituted by 1 to 2 substituents selected independently from the group consisting of oxo, fluorine, methyl, ethyl, difluoromethyl and trifluoromethyl,
and
in which oxazolyl, pyrazolyl and oxadiazolyl may be substituted by 1 to 2 substituents selected independently from the group consisting of methyl and ethyl,
$R^4$ is hydrogen,
$R^5$ is a group of the formula

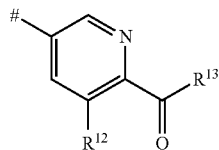

where # is the attachment point to the nitrogen atom,
$R^{12}$ is hydrogen or fluorine,
$R^{13}$ is hydroxyl or —$NHR^{14}$,
in which
$R^{14}$ is hydrogen or $C_1$-$C_4$-alkyl,
and the salts thereof, the solvates thereof and the solvates of the salts thereof.

Compounds according to the invention are the compounds of the formula (I) and the salts, solvates and solvates of the salts thereof, and also the compounds encompassed by formula (I) and specified hereinafter as working example(s), and the salts, solvates and solvates of the salts thereof, to the extent that the compounds encompassed by formula (I) and specified hereinafter are not already salts, solvates and solvates of the salts.

The compounds according to the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, especially HPLC chromatography on an achiral or chiral phase.

If the compounds according to the invention can occur in tautomeric forms, the present invention encompasses all the tautomeric forms.

The present invention also encompasses all suitable isotopic variants of the compounds according to the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulphur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labeled with $^3H$ or $^{14}C$ isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by the processes known to those skilled in the art, for example by the methods described further down and the procedures described in the working examples, by using corresponding isotopic modifications of the respective reagents and/or starting compounds.

Preferred salts in the context of the present invention are physiologically acceptable salts of the compounds according to the invention. However, the invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Solvates in the context of the invention are described as those forms of the compounds according to the invention which form a complex in the solid or liquid state by coordination with solvent molecules. Hydrates are a specific form of the solvates in which the coordination is with water.

The present invention additionally also encompasses prodrugs of the compounds according to the invention. The term "prodrugs" encompasses compounds which for their part may be biologically active or inactive but are converted during their residence time in the body to compounds according to the invention (for example by metabolism or hydrolysis).

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

In the context of the present invention, unless specified otherwise, the substituents are defined as follows:

Alkyl is a straight-chain or branched alkyl radical having 1 to 5 carbon atoms, preferably 1 to 4 carbon atoms, particularly preferably 1 to 3 carbon atoms, by way of example and with preference methyl, ethyl, n-propyl, isopropyl, 2-methylprop-1-yl, n-butyl, tert-butyl and 2,2-dimethylprop-1-yl.

Alkoxy is a straight-chain or branched alkoxy radical having 1 to 4 carbon atoms, preferably 1 to 3 carbon atoms, by way of example and with preference methoxy, ethoxy, n-propoxy, isopropoxy, 2-methylprop-1-oxy, n-butoxy and tert-butoxy.

Cycloalkyl is a monocyclic cycloalkyl group having 3 to 6 carbon atoms; illustrative and preferred examples of cycloalkyl include cyclopropyl, cyclobutyl, cyclopentyl and cyclohexyl.

4- to 6-membered oxoheterocyclyl in the definition of the $R^3$ radical is a saturated monocyclic radical having 4 to 6 ring atoms in which one ring atom is an oxygen atom, by way of example and with preference oxetanyl, tetrahydrofuranyl and tetrahydro-2H-pyranyl.

4- to 6-membered thioheterocyclyl in the definition of the $R^3$ radical is a saturated monocyclic radical having 4 to 6 ring atoms in which one ring atom is a sulphur atom, by way of example and with preference thientanyl, tetrahydrothienyl and tetrahydro-2H-thiopyranyl.

In the formulae of the group which may represent $R^1$, the end point of the line marked by * in each case does not represent a carbon atom or a $CH_2$ group, but is part of the bond to the atom to which $R^1$ is attached.

In the formulae of the group which may represent $R^5$, the end point of the line marked by # in each case does not represent a carbon atom or a $CH_2$ group, but is part of the bond to the atom to which $R^5$ is attached.

Preference is given to compounds of the formula (I) in which
$R^1$ is a group of the formula

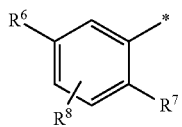

where * is the attachment point to the oxopyridine ring,
$R^6$ is bromine, chlorine, fluorine, methyl, difluoromethyl, trifluoromethyl, methoxy, difluoromethoxy or trifluoromethoxy,
$R^7$ is bromine, chlorine, fluorine, cyano, nitro, hydroxyl, methyl, difluoromethyl, trifluoromethyl, methoxy, ethoxy, difluoromethoxy, trifluoromethoxy, ethynyl, 3,3,3-trifluoroprop-1-yn-1-yl or cyclopropyl,
$R^8$ is hydrogen, chlorine or fluorine,
$R^2$ is hydrogen, bromine, chlorine, fluorine, cyano, $C_1$-$C_3$-alkyl, difluoromethyl, trifluoromethyl, 1,1-difluoroethyl, 2,2-difluoroethyl, 2,2,2-trifluoroethyl, $C_1$-$C_3$-alkoxy, difluoromethoxy, trifluoromethoxy, 1,1-difluoroethoxy, 2,2-difluoroethoxy, 2,2,2-trifluoroethoxy, methylcarbonyl or cyclopropyl,
$R^3$ is hydrogen, $C_1$-$C_5$-alkyl, $C_1$-$C_4$-alkoxy, difluoromethyl, trifluoromethyl, 1,1-difluoroethyl, 1,1,2,2,2-pentadeuteroethyl, 3,3,3-trifluoro-2-hydroxyprop-1-yl, 3,3,3-trifluoro-2-methoxyprop-1-yl, 3,3,3-trifluoro-2-ethoxyprop-1-yl, prop-2-yn-1-yl, cyclopropyloxy or cyclobutyloxy,
where alkyl may be substituted by a substituent selected from the group consisting of fluorine, cyano, hydroxyl, difluoromethyl, trifluoromethyl, methoxy, ethoxy, difluoromethoxy, trifluoromethoxy, $C_3$-$C_6$-cycloalkyl, 4- to 6-membered oxoheterocyclyl, 1,4-dioxanyl, oxazolyl, phenyl and pyridyl,
in which cycloalkyl may be substituted by 1 to 2 substituents selected independently from the group consisting of fluorine, hydroxyl, methyl, ethyl, methoxy, ethoxy, difluoromethyl, trifluoromethyl, difluoromethoxy and trifluoromethoxy,
and
in which oxoheterocyclyl may be substituted by 1 to 2 substituents selected independently from the group consisting of oxo, fluorine, methyl, ethyl, difluoromethyl and trifluoromethyl,
and
in which oxazolyl may be substituted by 1 or 2 substituents selected independently from the group consisting of methyl and ethyl,
$R^4$ is hydrogen,
$R^5$ is a group of the formula

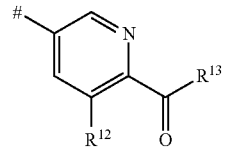

where # is the attachment point to the nitrogen atom,
$R^{12}$ is hydrogen or fluorine,
$R^{13}$ is hydroxyl or —$NHR^{14}$,
in which
$R^{14}$ is hydrogen or $C_1$-$C_4$-alkyl,
and the salts thereof, the solvates thereof and the solvates of the salts thereof.

Preferred compounds of the formula (I) are also those in which
$R^1$ is a group of the formula

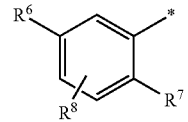

where * is the attachment point to the oxopyridine ring,
$R^6$ is chlorine,
$R^7$ is fluorine, cyano, difluoromethyl or difluoromethoxy,
$R^8$ is hydrogen,
$R^2$ is chlorine, cyano, methoxy or difluoromethoxy,
$R^3$ is methyl, ethyl, n-propyl or n-butyl,
where methyl may be substituted by a substituent selected from the group consisting of cyclopropyl, cyclobutyl, cyclohexyl, tetrahydro-2H-pyranyl, oxazolyl and pyridyl, in which cyclobutyl and cyclohexyl may be substituted by 1 to 2 substituents selected independently from the group consisting of hydroxyl and methoxy,
and
in which oxazolyl may be substituted by a methyl substituent,
and
where ethyl, n-propyl and n-butyl may be substituted by a substituent selected from the group consisting of methoxy and trifluoromethoxy,
$R^4$ is hydrogen,
$R^5$ is a group of the formula

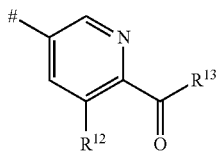

where # is the attachment point to the nitrogen atom,
$R^{12}$ is hydrogen or fluorine,
$R^{13}$ is hydroxyl or —NHR$^{14}$,
in which
$R^{14}$ is hydrogen, methyl or ethyl,
and the salts thereof, the solvates thereof and the solvates of the salts thereof.

Preferred compounds of the formula (I) are also those in which
$R^1$ is a group of the formula

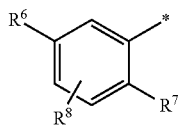

steht,
where * is the attachment point to the oxopyridine ring,
$R^6$ is chlorine,
$R^7$ is fluorine or cyano,
$R^8$ is hydrogen,
$R^2$ is chlorine, methoxy or difluoromethoxy,
$R^3$ is methyl or ethyl,
where methyl may be substituted by a substituent selected from the group consisting of tetrahydro-2H-pyranyl, oxazolyl and pyridyl,
in which oxazolyl may be substituted by a methyl substituent,
and
where ethyl may be substituted by a methoxy substituent,
$R^4$ is hydrogen,
$R^5$ is a group of the formula

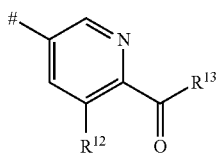

where # is the attachment point to the nitrogen atom,
$R^{12}$ is hydrogen,
$R^{13}$ is hydroxyl or —NHR$^{14}$,
in which
$R^{14}$ is hydrogen or methyl,
and the salts thereof, the solvates thereof and the solvates of the salts thereof.

Preferred compounds of the formula (I) are also those in which
$R^1$ is a group of the formula

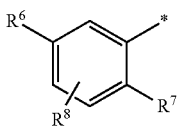

where * is the attachment point to the oxopyridine ring,
$R^6$ is chlorine,
$R^7$ is cyano,
$R^8$ is hydrogen,
$R^2$ is chlorine or methoxy,
$R^3$ is methyl or ethyl,
where methyl is substituted by a substituent selected from the group consisting of tetrahydro-2H-pyranyl, oxazolyl and pyridyl,
in which oxazolyl may be substituted by a methyl substituent,
and
where ethyl may be substituted by a methoxy substituent,
$R^4$ is hydrogen,
$R^5$ is a group of the formula

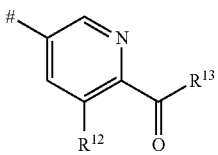

where # is the attachment point to the nitrogen atom,
$R^{12}$ is hydrogen,
$R^{13}$ is hydroxyl or —NHR$^{14}$,
in which
$R^{14}$ is hydrogen or methyl,
and the salts thereof, the solvates thereof and the solvates of the salts thereof.

Preferred compounds of the formula (I) are also those in which
$R^1$ is a group of the formula

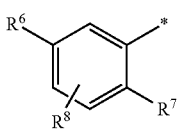

steht,
where * is the attachment point to the oxopyridine ring,
$R^6$ is chlorine,
$R^7$ is cyano,
$R^8$ is hydrogen.

Preference is also given to compounds of the formula (I) in which $R^2$ is chlorine or methoxy.

Preferred compounds of the formula (I) are also those in which
$R^3$ is methyl or ethyl,
where methyl is substituted by a substituent selected from the group consisting of tetrahydro-2H-pyranyl, oxazolyl and pyridyl,
in which oxazolyl may be substituted by a methyl substituent,
and
where ethyl may be substituted by a methoxy substituent.

Preferred compounds of the formula (I) are also those in which
$R^5$ is a group of the formula

steht,
where # is the attachment point to the nitrogen atom,
$R^{12}$ is hydrogen,
$R^{13}$ is hydroxyl or —NHR$^{14}$,
in which
$R^{14}$ is hydrogen or methyl.

Preference is also given to compounds of the formula (Ia)

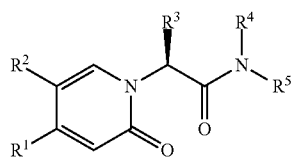

(Ia)

in which $R^1$, $R^2$, $R^3$, $R^4$ and $R^5$ are as defined above.

The invention further provides a process for preparing the compounds of the formula (I), or the salts thereof, solvates thereof or the solvates of the salts thereof, wherein

[A] The Compounds of the Formula

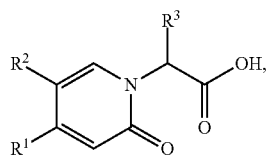

(II)

in which
$R^1$, $R^2$ and $R^3$ have the definition given above
are reacted in the first stage with compounds of the formula (III)

$$\text{HN}\begin{matrix}R^4\\|\\\phantom{N}\end{matrix}R^5$$

in which
$R^4$ and $R^5$ have the definition given above,
in the presence of a dehydrating reagent, and
optionally converted in a second stage by acidic or basic ester hydrolysis to compounds of the formula (I),
or

[B] The Compounds of the Formula

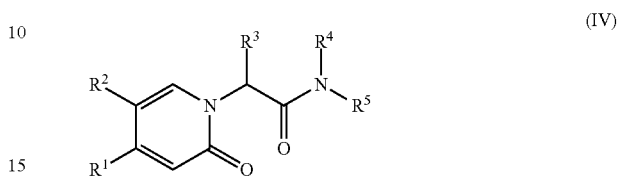

(IV)

in which
$R^2$, $R^3$, $R^4$ and $R^5$ have the definition given above and
$X^1$ is chlorine, bromine or iodine
are reacted with compounds of the formula $R^1$-Q  (V)

in which
$R^1$ is as defined above, and
Q is —B(OH)$_2$, a boronic ester, preferably boronic acid pinacol ester, or —BF$_3^-$K$^+$,
under Suzuki coupling conditions to give compounds of the formula (I).

The reaction of the first stage according to process [A] is generally effected in inert solvents, optionally in the presence of a base, preferably within a temperature range from 0° C. to room temperature at standard pressure.

Examples of suitable dehydrating reagents here include carbodiimides, for example N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide), or carbonyl compounds such as carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino) phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), (benzotriazol-1-yloxy)bis-dimethylaminomethylium fluoroborate (TBTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or ethyl hydroxyiminocyanoacetate (Oxyma), or (1-cyano-2-ethoxy-2-oxoethylideneaminooxy)dimethylaminomorpholinocarbenium hexafluorophosphate (COMU), or N-[(dimethylamino)(3H-[1,2,3]triazolo[4,5-b]pyridin-3-yloxy)methylidene]-N-methylmethanaminium hexafluorophosphate, or 2,4,6-tripropyl-1,3,5,2,4,6-trioxatriphosphinane 2,4,6-trioxide (T3P), or mixtures of these, with bases. The condensation is preferably conducted with HATU or with T3P.

Bases are, for example, alkali metal carbonates such as sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or diisopropylethylamine, or pyridine. The condensation is preferably conducted with diisopropylethylamine or pyridine.

Inert solvents are, for example, halogenated hydrocarbons such as dichloromethane or trichloromethane, hydrocarbons such as benzene, or other solvents such as nitromethane, dioxane, dimethylformamide, dimethyl sulphoxide or acetonitrile. It is also possible to use mixtures of the solvents. Particular preference is given to dimethylformamide.

The compounds of the formula (III) are known, can be synthesized from the corresponding starting compounds by known processes or can be prepared analogously to the processes described in the Examples section.

In an acidic ester hydrolysis, the reaction of the second step according to process [A] is generally carried out in inert solvents, preferably in a temperature range from room temperature to 60° C. at atmospheric pressure.

Inert solvents are, for example, halogenated hydrocarbons such as dichloromethane, trichloromethane, carbon tetrachloride or 1,2-dichloroethane, or ethers such as tetrahydrofuran or dioxane, preference being given to dichloromethane.

Acids are, for example, trifluoroacetic acid or hydrogen chloride in dioxane, preference being given to trifluoroacetic acid.

In a basic ester hydrolysis, the reaction of the second step according to process [A] is generally carried out in inert solvents, preferably within a temperature range from room temperature up to the reflux of the solvents at standard pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water, preference being given to a mixture of tetrahydrofuran and water.

Bases are, for example, alkali metal hydroxides such as sodium hydroxide, lithium hydroxide or potassium hydroxide, or alkali metal carbonates such as caesium carbonate, sodium carbonate or potassium carbonate, or alkoxides such as potassium tert-butoxide or sodium tert-butoxide, preference being given to lithium hydroxide.

The reaction in process [B] is generally effected in inert solvents, in the presence of a catalyst, optionally in the presence of an additional reagent, optionally in a microwave, preferably within a temperature range from room temperature to 150° C. at standard pressure to 3 bar.

Catalysts are, for example, palladium catalysts customary for Suzuki reaction conditions, preference being given to catalysts such as dichlorobis(triphenylphosphine)palladium, tetrakistriphenylphosphinepalladium(0), palladium(II) acetate/triscyclohexylphosphine, tris(dibenzylideneacetone) dipalladium, bis(diphenylphosphaneferrocenyl)palladium (II) chloride, 1,3-bis(2,6-diisopropylphenyl)imidazol-2-ylidene(1,4-naphthoquinone)palladium dimer, allyl(chloro)(1,3-dimesityl-1,3-dihydro-2H-imidazol-2-ylidene) palladium, palladium(II) acetate/dicyclohexyl(2',4',6'-triisopropylbiphenyl-2-yl)phosphine, [1,1-bis(diphenylphosphino)ferrocene]palladium(II) chloride monodichloromethane adduct or XPhos precatalyst [(2'-aminobiphenyl-2-yl)(chloro)palladium dicyclohexyl(2',4',6'-triisopropylbiphenyl-2-yl)phosphane (1:1)], preference being given to tetrakistriphenylphosphinepalladium(0), [1,1-bis-(diphenylphosphino)ferrocene]palladium(II) chloride monodichloromethane adduct or XPhos precatalyst [(2'-aminobiphenyl-2-yl)(chloro)palladium dicyclohexyl(2',4',6'-triisopropylbiphenyl-2-yl)phosphine (1:1)].

Additional reagents are, for example, potassium acetate, caesium carbonate, potassium carbonate or sodium carbonate, potassium tert-butoxide, caesium fluoride or potassium phosphate, where these may be present in aqueous solution; preferred are additional reagents such as potassium carbonate or aqueous potassium phosphate solution.

Inert solvents are, for example, ethers such as dioxane, tetrahydrofuran or 1,2-dimethoxyethane, hydrocarbons such as benzene, xylene or toluene, or carboxamides such as dimethylformamide or dimethylacetamide, alkyl sulphoxides such as dimethyl sulphoxide, or N-methylpyrrolidone or acetonitrile, or mixtures of the solvents with alcohols such as methanol or ethanol and/or water; preference is given to tetrahydrofuran, dioxane or acetonitrile.

The compounds of the formula (V) are known or can be synthesized by known processes from the appropriate starting materials.

The compounds of the formula (II) are known or can be prepared by

[C] Reacting Compounds of the Formula

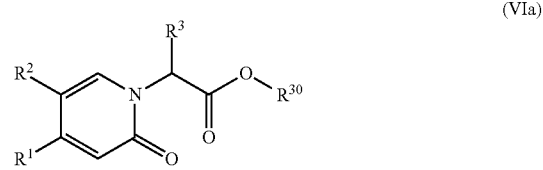

(VIa)

in which
$R^1$, $R^2$ and $R^3$ have the definition given above, and
$R^{30}$ is tert-butyl,
with an acid,
or

[D] Reacting Compounds of the Formula

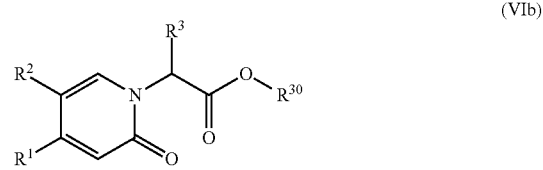

(VIb)

in which
$R^1$, $R^2$ and $R^3$ have the definition given above, and
$R^{30}$ is methyl or ethyl,
with a base.

The compounds of the formulae (VIa) and (VIb) together form the group of the compounds of the formula (VI).

The reaction according to process [C] is generally carried out in inert solvents, preferably in a temperature range from room temperature to 60° C. at atmospheric pressure.

Inert solvents are, for example, halogenated hydrocarbons such as dichloromethane, trichloromethane, carbon tetrachloride or 1,2-dichloroethane, or ethers such as tetrahydrofuran or dioxane, preference being given to dichloromethane.

Acids are, for example, trifluoroacetic acid or hydrogen chloride in dioxane, preference being given to trifluoroacetic acid.

The reaction in process [D] is generally carried out in inert solvents, preferably within a temperature range from room temperature up to the reflux of the solvents at standard pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water, preference being given to a mixture of tetrahydrofuran and water.

Bases are, for example, alkali metal hydroxides such as sodium hydroxide, lithium hydroxide or potassium hydroxide, or alkali metal carbonates such as caesium carbonate, sodium carbonate or potassium carbonate, or alkoxides such as potassium tert-butoxide or sodium tert-butoxide, preference being given to lithium hydroxide.

The compounds of the formula (VI) are known or can be prepared by

[E] Reacting Compounds of the Formula

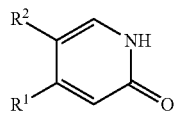
(VII)

in which
$R^1$ and $R^2$ have the definition given above,
with compounds of the formula

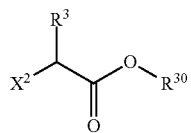
(VIII)

in which
$R^3$ has the definition given above,
$R^{30}$ is methyl, ethyl or tert-butyl, and
$X^2$ is chlorine, bromine, iodine, methanesulphonyloxy or trifluoromethanesulphonyloxy,
or

[F] Reacting Compounds of the Formula

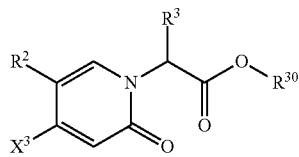
(IX)

in which
$R^2$ and $R^3$ have the definition given above,
$R^{30}$ is methyl, ethyl or tert-butyl, and
$X^3$ is chlorine, bromine or iodine
with compounds of the formula (V) under Suzuki coupling conditions.

The reaction according to process [E] is generally carried out in inert solvents, optionally in the presence of a base, preferably in a temperature range from room temperature to reflux of the solvents at atmospheric pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvents with water; preference is given to dimethylformamide.

Bases are, for example, alkali metal hydroxides such as sodium hydroxide, lithium hydroxide or potassium hydroxide, or alkali metal carbonates such as caesium carbonate, sodium carbonate or potassium carbonate, or potassium tert-butoxide or sodium tert-butoxide, sodium hydride or a mixture of these bases or a mixture of sodium hydride and lithium bromide; preference is given to potassium carbonate or sodium hydride.

The compounds of the formula (VIII) are known or can be synthesized by known processes from the appropriate starting materials.

The reaction in process [F] is carried out as described for process [B].

The compounds of the formula (VII) are known or can be prepared by reacting compounds of the formula

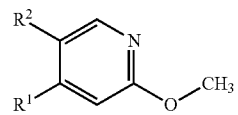
(X)

in which
$R^1$ and $R^2$ have the definition given above,
with pyridinium hydrochloride or pyridinium hydrobromide.

The reaction is generally effected in inert solvents, preferably in a temperature range of from 80° C. to 120° C. at atmospheric pressure.

Inert solvents are, for example, hydrocarbons such as benzene, or other solvents such as nitromethane, dioxane, dimethylformamide, dimethyl sulphoxide or acetonitrile. It is also possible to use mixtures of the solvents. Particular preference is given to dimethylformamide.

The compounds of the formula (X) are known or can be prepared by reacting compounds of the formula

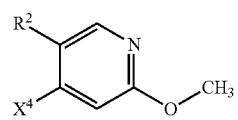
(XI)

in which
$R^2$ is as defined above, and
$X^4$ is chlorine, bromine or iodine
with compounds of the formula (V) under Suzuki coupling conditions.

The reaction is effected as described for process [B].

The compounds of the formula (XI) are known or can be synthesized by known processes from the appropriate starting materials.

The compounds of the formula (IX) are known or can be prepared by reacting compounds of the formula

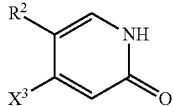 (XII)

in which
R² is as defined above, and
X³ is chlorine, bromine or iodine
with compounds of the formula (VIII).

The reaction is effected as described for process [E].

The compounds of the formula (XII) are known or can be synthesized by known processes from the appropriate starting materials.

The compounds of the formula (IV) are known or can be prepared by reacting compounds of the formula

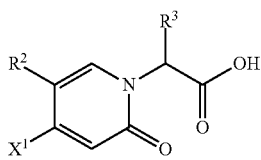 (XIII)

in which
R² and R³ have the definition given above, and
X¹ is chlorine, bromine or iodine
with compounds of the formula (III) in the presence of a dehydrating reagent.

The reaction is effected as described for process [A].

The compounds of the formula (XIII) are known or can be prepared by

[G] Reacting Compounds of the Formula

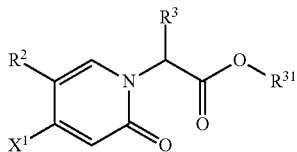 (XIVa)

in which
R² and R³ have the definition given above,
R³¹ is tert-butyl, and
X¹ is chlorine, bromine or iodine
with an acid,
or

[H] Reacting Compounds of the Formula

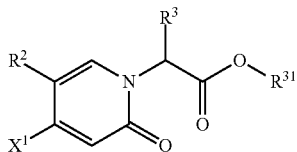 (XIVb)

in which
R² and R³ have the definition given above,
R³¹ is methyl or ethyl, and
X¹ is chlorine, bromine or iodine
with a base.

The compounds of the formulae (XIVa) and (XIVb) together form the group of the compounds of the formula (XIV).

The reaction according to process [G] is carried out as described for process [C].

The reaction according to process [H] is carried out as described for process [D].

The compounds of the formula (XIV) are known or can be prepared by reacting compounds of the formula

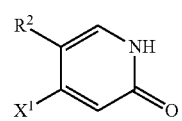 (XV)

in which
R² has the definition given above, and
X¹ is chlorine, bromine or iodine
with compounds of the formula

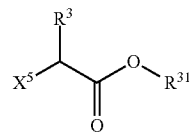 (XVI)

in which
R³ has the definition given above,
R³¹ is methyl, ethyl or tert-butyl, and
X⁵ is chlorine, bromine, iodine, methanesulphonyloxy or trifluoromethanesulphonyloxy.

The reaction is effected as described for process [E].

The compounds of the formulae (XV) and (XVI) are known or can be synthesized by known processes from the appropriate starting compounds.

In an alternative process, the compounds of the formula (VI) can be prepared by reacting compounds of the formula

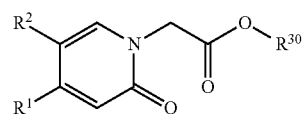 (XVII)

in which
R¹ and R² have the definition given above, and
R³⁰ is methyl, ethyl or tert-butyl,
with compounds of the formula

R³—X⁶ (XVIII)

in which
R³ is as defined above, and
X⁶ is chlorine, bromine, iodine, methanesulphonyloxy, trifluoromethanesulphonyloxy or para-toluenesulphonyloxy.

The reaction is generally effected in inert solvents, if appropriate in the presence of a base, preferably in a temperature range from −78° C. to room temperature at atmospheric pressure.

Inert solvents are, for example, halogenated hydrocarbons, such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water; preference is given to tetrahydrofuran.

Bases are, for example, potassium tert-butoxide or sodium tert-butoxide, sodium hydride, N-butyllithium or lithium bis(trimethylsilyl)amide, preference is given to lithium bis(trimethylsilyl)amide.

The compounds of the formula (XVII) are known or can be synthesized by the processes described above, for example process [E], from the appropriate starting materials.

The compounds of the formula (XVIII) are known or can be synthesized by known processes from the appropriate starting materials.

In an alternative process, the compounds of the formula (II) can be prepared by reacting compounds of the formula

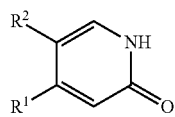
(VII)

in which
$R^1$ and $R^2$ have the definition given above,
with compounds of the formula

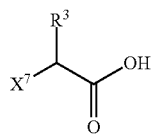
(XIX)

in which
$R^3$ is as defined above, and
$X^7$ is chlorine, bromine or iodine.

The reaction is generally effected in inert solvents, if appropriate in the presence of a base, preferably in a temperature range from −10° C. to 90° C. at atmospheric pressure.

Inert solvents are, for example, halogenated hydrocarbons, such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water; preference is given to tetrahydrofuran.

Bases are, for example, potassium tert-butoxide or sodium tert-butoxide, sodium hydride or lithium bis(trimethylsilyl)amide or a mixture of magnesium di-tert-butoxide and potassium tert-butoxide, preference is given to a mixture of magnesium di-tert-butoxide and potassium tert-butoxide.

The compounds of the formula (XIX) are known or can be synthesized by known processes from the appropriate starting materials.

In an alternative process, the compounds of the formula (XIII) can be prepared by reacting compounds of the formula

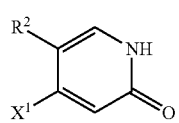
(XV)

in which
$R^2$ has the definition given above, and
$X^1$ is chlorine, bromine or iodine
with compounds of the formula

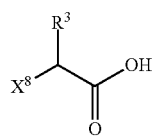
(XX)

in which
$R^3$ is as defined above, and
$X^8$ is chlorine, bromine or iodine.

The reaction is effected as described for the reaction of compounds of the formula (VII) with compounds of the formula (XIX).

The compounds of the formula (XX) are known or can be synthesized by known processes from the appropriate starting materials.

The preparation of the starting compounds and of the compounds of the formula (I) can be illustrated by the synthesis scheme below.

Scheme 1:

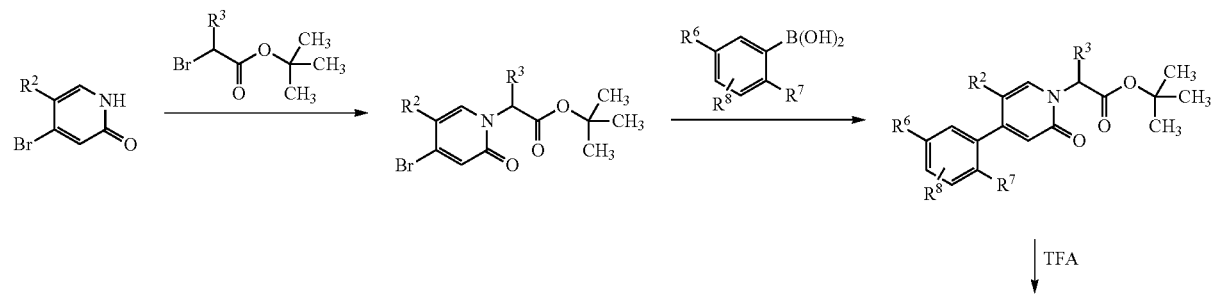

-continued

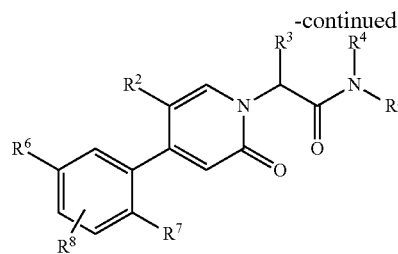 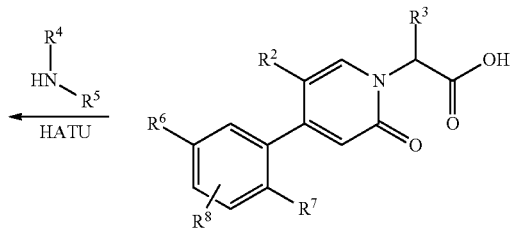

The compounds according to the invention have an unforeseeable useful pharmacological activity spectrum and good pharmacokinetic characteristics. They are compounds that influence the proteolytic activity of the serine protease factor XIa (FXIa) and/or the serine protease plasma kallikrein (PK). The compounds according to the invention inhibit the enzymatic cleavage of substrates, catalysed by FXIa and/or PK, which have essential roles in the activation of blood coagulation, in the aggregation of blood platelets via reduction of the thrombin necessary for the PAR-1 activation of the platelets, and in inflammatory processes, which particularly involve an increase in vascular permeability.

They are therefore suitable for use as medicaments for the treatment and/or prophylaxis of diseases in humans and animals.

The present invention further provides for the use of the compounds according to the invention for the treatment and/or prophylaxis of disorders, in particular cardiovascular disorders, preferably thrombotic or thromboembolic disorders and/or thrombotic or thromboembolic complications, and/or ophthalmic disorders, in particular of diabetic retinopathy or macular oedema, and/or inflammatory disorders, in particular those associated with excess plasma kallikrein activity, such as hereditary angiooedema (HAE) or chronic inflammatory disorders, particularly of the intestine such as Crohn's disease.

Factor XIa (FXIa) is an important enzyme in the context of coagulation, which can be activated both by thrombin and factor XIIa (FXIIa), and is therefore involved in two essential processes of coagulation: It is a central component of the transition from initiation to amplification and propagation of coagulation: in positive feedback loops, thrombin activates, in addition to factor V and factor VIII, also factor XI to factor XIa, whereby factor IX is converted into factor IXa, and, via the factor IXa/factor VIIIa complex generated in this manner, the factor X is activated and thrombin formation is in turn therefore highly stimulated, leading to strong thrombus growth and stabilizing the thrombus.

Moreover, factor XIa is an important component for the intrinsic initiation of coagulation: In addition to the stimulation via tissue factor (TF), the coagulation system can be activated also particularly on negatively charged surfaces, which include not only surface structures of foreign cells (e.g. bacteria) but also artificial surfaces such as vascular prostheses, stents and extracorporeal circulation. On the surface, initially factor XII (FXII) is activated to factor XIIa (FXIIA) which subsequently activates FXI, attached to cell surfaces, to FXIa. This leads to further activation of the coagulation cascade as described above.

In contrast, thrombin generation in the initiation phase remains uninfluenced via TF/factor VIIa and factor X activation and finally thrombin formation, the physiological reaction on vascular injuries. This could explain why no prolongations of bleeding times were found in FXIa knockout mice, as in rabbits and other species, with administration of FXIa inhibitor. This low bleeding tendency caused by the substance is of great advantage for use in humans, particularly in patients with increased risk of bleeding.

In addition, factor XIIa also activates plasma prokallikrein to plasma kallikrein (PK) in the context of the intrinsic activation which, inter alia, in a potentiation loop, leads to further factor XII activation, overall resulting in amplification of the initiation of the coagulation cascade on surfaces. A PK-inhibiting activity of a compound according to the invention thus reduces coagulation via surface activation and thus has an anticoagulatory effect. An advantage could be in the combination of factor XIa inhibitory activity and PK inhibitory activity allowing a balanced antithrombotic effect.

Accordingly, the compounds according to the invention are suitable for the treatment and/or prophylaxis of disorders or complications which may arise from the formation of clots.

For the purpose of the present invention, the "thrombotic or thromboembolic disorders" include disorders which occur both in the arterial and in the venous vasculature and which can be treated with the compounds according to the invention, in particular disorders in the coronary arteries of the heart, such as acute coronary syndrome (ACS), myocardial infarction with ST segment elevation (STEMI) and without ST segment elevation (non-STEMI), stable angina pectoris, unstable angina pectoris, reocclusions and restenoses after coronary interventions such as angioplasty, stent implantation or aortocoronary bypass, but also thrombotic or thromboembolic disorders in further vessels leading to peripheral arterial occlusive disorders, pulmonary embolisms, venous thromboembolisms, venous thromboses, in particular in deep leg veins and kidney veins, transitory ischaemic attacks and also thrombotic stroke and thromboembolic stroke.

Stimulation of the coagulation system may occur by various causes or associated disorders. In the context of surgical interventions, immobility, confinement to bed, infections, inflammation or cancer or cancer therapy, inter alia, the coagulation system can be highly activated, and there may be thrombotic complications, in particular venous thromboses. The compounds according to the invention are therefore suitable for the prophylaxis of thromboses in the context of surgical interventions in patients suffering from cancer. The compounds according to the invention are therefore also suitable for the prophylaxis of thromboses in patients having an activated coagulation system, for example in the stimulation situations described.

The inventive compounds are therefore also suitable for the prevention and treatment of cardiogenic thromboembolisms, for example brain ischaemias, stroke and systemic thromboembolisms and ischaemias, in patients with acute, intermittent or persistent cardiac arrhythmias, for example atrial fibrillation, and in patients undergoing cardioversion, and also in patients with heart valve disorders or with artificial heart valves.

In addition, the inventive compounds are suitable for the treatment and prevention of disseminated intravascular coagulation (DIC) which may occur in connection with sepsis inter alia, but also owing to surgical interventions, neoplastic disorders, burns or other injuries and may lead to severe organ damage through microthromboses.

Thromboembolic complications furthermore occur in microangiopathic haemolytical anaemias and by the blood coming into contact with foreign surfaces in the context of extracorporeal circulation, for example haemodialysis, ECMO ("extracorporeal membrane oxygenation"), LVAD ("left ventricular assist device") and similar methods, AV fistulas, vascular and heart valve prostheses.

Moreover, the compounds according to the invention are suitable for the treatment and/or prophylaxis of disorders involving microclot formation or fibrin deposits in cerebral blood vessels which may lead to dementia disorders such as vascular dementia or Alzheimer's disease. Here, the clot may contribute to the disorder both via occlusions and by binding further disease-relevant factors.

Moreover, the compounds according to the invention are suitable in particular for the treatment and/or prophylaxis of disorders where, in addition to the pro-coagulant component, the pro-inflammatory component also plays an essential role. Mutual enhancement of coagulation and inflammation in particular can be prevented by the compounds according to the invention, thus decisively lowering the probability of thrombotic complications. In this case, both the factor XIa-inhibitory component (via inhibition of thrombin production) and the PK-inhibitory component can contribute to the anticoagulant and antiinflammatory effect (e.g. via bradykinin). Therefore, the treatment and/or prophylaxis in the context of atherosclerotic vascular disorders, inflammations in the context of rheumatic disorders of the locomotor system, inflammatory disorders of the lung, such as pulmonary fibroses, inflammatory disorders of the kidney, such as glomerulonephritides, inflammatory disorders of the intestine, such as Crohn's disease or ulcerative colitis, or disorders which may be present in the context of a diabetic underlying disease, such as diabetic retinopathy or nephropathy, may be considered, inter alia.

Kinins generated by means of plasma kallikrein, inter alia, have a causative role in the progression of chronic inflammatory intestinal disorders (CID). Their pro-inflammatory effect via activation of bradykinin receptors induces and potentiates the disease progression. Studies on Crohn's disease patients show a correlation between the kallikrein concentration in the intestinal epithelium and the degree of intestinal inflammation. Activation of the kallikrein-kinin system was likewise observed in experimental animal studies. Inhibition of bradykinin synthesis by kallikrein inhibitors could accordingly be used also for prophylaxis and/or therapy of chronic inflammatory intestinal disorders.

Moreover, the compounds according to the invention can be used for inhibiting tumour growth and the formation of metastases, and also for the prophylaxis and/or treatment of thromboembolic complications, for example venous thromboembolisms, for tumour patients, in particular those undergoing major surgical interventions or chemo- or radiotherapy.

In addition, the inventive compounds are also suitable for the prophylaxis and/or treatment of pulmonary hypertension.

In the context of the present invention, the term "pulmonary hypertension" includes pulmonary arterial hypertension, pulmonary hypertension associated with disorders of the left heart, pulmonary hypertension associated with pulmonary disorders and/or hypoxia and pulmonary hypertension owing to chronic thromboembolisms (CTEPH).

"Pulmonary arterial hypertension" includes idiopathic pulmonary arterial hypertension (IPAH, formerly also referred to as primary pulmonary hypertension), familial pulmonary arterial hypertension (FPAH) and associated pulmonary arterial hypertension (APAH), which is associated with collagenoses, congenital systemic-pulmonary shunt vitia, portal hypertension, HIV infections, the ingestion of certain drugs and medicaments, with other disorders (thyroid disorders, glycogen storage disorders, Morbus Gaucher, hereditary teleangiectasia, haemoglobinopathies, myeloproliferative disorders, splenectomy), with disorders having a significant venous/capillary contribution, such as pulmonary-venoocclusive disorder and pulmonary-capillary haemangiomatosis, and also persisting pulmonary hypertension of neonatants.

Pulmonary hypertension associated with disorders of the left heart includes a diseased left atrium or ventricle and mitral or aorta valve defects.

Pulmonary hypertension associated with pulmonary disorders and/or hypoxia includes chronic obstructive pulmonary disorders, interstitial pulmonary disorder, sleep apnoea syndrome, alveolar hypoventilation, chronic high-altitude sickness and inherent defects.

Pulmonary hypertension owing to chronic thromboembolisms (CTEPH) comprises the thromboembolic occlusion of proximal pulmonary arteries, the thromboembolic occlusion of distal pulmonary arteries and non-thrombotic pulmonary embolisms (tumour, parasites, foreign bodies).

The present invention further provides for the use of the inventive compounds for production of medicaments for the treatment and/or prophylaxis of pulmonary hypertension associated with sarcoidosis, histiocytosis X and lymphangiomatosis.

In addition, the substances according to the invention are also useful for the treatment of pulmonary and hepatic fibroses.

In addition, the compounds according to the invention are also suitable for the treatment and/or prophylaxis of disseminated intravascular coagulation in the context of an infectious disease, and/or of systemic inflammatory syndrome (SIRS), septic organ dysfunction, septic organ failure and multiorgan failure, acute respiratory distress syndrome (ARDS), acute lung injury (ALI), septic shock and/or septic organ failure.

In the course of an infection, there may be a generalized activation of the coagulation system (disseminated intravascular coagulation or consumption coagulopathy, hereinbelow referred to as "DIC") with microthrombosis in various organs and secondary haemorrhagic complications. Moreover, there may be endothelial damage with increased permeability of the vessels and diffusion of fluid and proteins into the extravasal space. As the infection progresses, there may be failure of an organ (for example kidney failure, liver failure, respiratory failure, central-nervous deficits and cardiovascular failure) or multiorgan failure.

In the case of DIC, there is a massive activation of the coagulation system at the surface of damaged endothelial cells, the surfaces of foreign bodies or crosslinked extravascular tissue. As a consequence, there is coagulation in small vessels of various organs with hypoxia and subsequent organ dysfunction. A secondary effect is the consumption of coagulation factors (for example factor X, prothrombin and fibrinogen) and platelets, which reduces the coagulability of the blood and may result in heavy bleeding.

Compounds according to the invention which inhibit plasma kallikrein alone or in combination with factor XIa, are also useful for the treatment and/or prophylaxis of disorders in the course of which plasma kallikrein is involved. In addition to the anticoagulant activity, plasma kallikrein is an important bradikinin-releasing protease which, inter alia, thus leads to increased endothelial permeability. The compounds can therefore be used for the treatment and/or prophylaxis of disorders involving oedema formations such as ophthalmic disorders, in particular, diabetic retinopathy or macular oedema or hereditary angiooedema.

"Ophthalmic disorders" in the context of the present invention include in particular disorders such as diabetic retinopathy, diabetic macular oedema (DME), macular oedema, macular oedema associated with retinal vein occlusion, age-related macular degeneration (AMD), choroidal neovascularization (CNV), choroidal neovascular membranes (CNVM), cystoid macular oedema (CME), epiretinal membranes (ERM) and macular perforations, myopia-associated choroidal neovascularization, angioid streaks, vascular streaks, retina detachment, atrophic changes of the retinal pigment epithelium, hypertrophic changes of the retinal pigment epithelium, retinal vein occlusion, choroidal retinal vein occlusion, retinitis pigmentosa, Stargardt's disease, retinopathy of prematurity, glaucoma, inflammatory eye disorders such as uveitis, scleritis or endophthalmitis, cataract, refraction anomalies such as myopia, hyperopia or astigmatism and keratoconus, disorders of the anterior eye such as corneal angiogenesis as sequela of, for example, keratitis, cornea transplantation or keratoplasty, corneal angiogenesis as sequela of hypoxia (for example by excessive use of contact lenses), pterygium conjunctivae, subcorneal oedema and intracorneal oedema.

The compounds according to the invention are also suitable for the primary prophylaxis of thrombotic or thromboembolic disorders and/or inflammatory disorders and/or disorders with increased vascular permeability in patients in which gene mutations lead to enhanced activity of the enzymes, or increased levels of the zymogens and these are established by relevant tests/measurements of the enzyme activity or zymogen concentrations.

The present invention further provides for the use of the compounds according to the invention for the treatment and/or prophylaxis of disorders, especially the disorders mentioned above.

The present invention further provides for the use of the compounds according to the invention for production of a medicament for the treatment and/or prophylaxis of disorders, especially the disorders mentioned above.

The present invention further provides a method for the treatment and/or prophylaxis of disorders, especially the disorders mentioned above, using a therapeutically effective amount of a compound according to the invention.

The present invention further provides the compounds according to the invention for use in a method for the treatment and/or prophylaxis of disorders, especially the disorders mentioned above, using a therapeutically effective amount of a compound according to the invention.

The present invention further provides medicaments comprising a compound according to the invention and one or more further active ingredients.

In addition, the compounds according to the invention can also be used for preventing coagulation ex vivo, for example for the protection of organs to be transplanted against organ damage caused by formation of clots and for protecting the organ recipient against thromboemboli from the transplanted organ, for preserving blood and plasma products, for cleaning/pretreating catheters and other medical auxiliaries and instruments, for coating synthetic surfaces of medical auxiliaries and instruments used in vivo or ex vivo or for biological samples which may comprise factor XIa or plasma kallikrein.

The present invention furthermore provides a method for preventing the coagulation of blood in vitro, in particular in banked blood or biological samples which may comprise factor XIa or plasma kallikrein or both enzymes, which method is characterized in that an anticoagulatory effective amount of the compound according to the invention is added.

The present invention further provides medicaments comprising a compound according to the invention and one or more further active ingredients, in particular for the treatment and/or prophylaxis of the disorders mentioned above. Preferred examples of active ingredients suitable for combinations include:

lipid-lowering substances, especially HMG-CoA (3-hydroxy-3-methylglutaryl-coenzyme A) reductase inhibitors, for example lovastatin (Mevacor), simvastatin (Zocor), pravastatin (Pravachol), fluvastatin (Lescol) and atorvastatin (Lipitor);

coronary therapeutics/vasodilatators, especially ACE (angiotensin converting enzyme) inhibitors, for example captopril, lisinopril, enalapril, ramipril, cilazapril, benazepril, fosinopril, quinapril and perindopril, or AII (angiotensin II) receptor antagonists, for example embusartan, losartan, valsartan, irbesartan, candesartan, eprosartan and temisartan, or β-adrenoceptor antagonists, for example carvedilol, alprenolol, bisoprolol, acebutolol, atenolol, betaxolol, carteolol, metoprolol, nadolol, penbutolol, pindolol, propanolol and timolol, or alpha-1-adrenoceptor antagonists, for example prazosine, bunazosine, doxazosine and terazosine, or diuretics, for example hydrochlorothiazide, furosemide, bumetanide, piretanide, torasemide, amiloride and dihydralazine, or calcium channel blockers, for example verapamil and diltiazem, or dihydropyridine derivatives, for example nifedipin (Adalat) and nitrendipine (Bayotensin), or nitro preparations, for example isosorbide 5-mononitrate, isosorbide dinitrate and glycerol trinitrate, or substances causing an increase in cyclic guanosine monophosphate (cGMP), for example stimulators of soluble guanylate cyclase, for example riociguat;

plasminogen activators (thrombolytics/fibrinolytics) and compounds which promote thrombolysis/fibrinolysis such as inhibitors of the plasminogen activator inhibitor (PAI inhibitors) or inhibitors of the thrombin-activated fibrinolysis inhibitor (TAFI inhibitors), for example tissue plasminogen activator (t-PA, for example Actilyse®), streptokinase, reteplase and urokinase or plasminogen-modulating substances causing increased formation of plasmin;

anticoagulatory substances (anticoagulants), for example heparin (UFH), low-molecular-weight heparins (LMW), for example tinzaparin, certoparin, parnaparin, nadroparin, ardeparin, enoxaparin, reviparin, dalteparin, danaparoid, semuloparin (AVE 5026), adomiparin (M118) and EP-42675/ORG42675;

direct thrombin inhibitors (DTI), for example Pradaxa (dabigatran), atecegatran (AZD-0837), DP-4088, SSR- 182289A, argatroban, bivalirudin and tanogitran (BIBT-986 and prodrug BIBT-1011), hirudin;

direct factor Xa inhibitors, for example rivaroxaban, apixaban, edoxaban (DU-176b), betrixaban (PRT-54021), R-1663, darexaban (YM-150), otamixaban (FXV-673/RPR-130673), letaxaban (TAK-442), razaxaban (DPC-906), DX-9065a, LY-517717, tanogitran (BIBT-986, prodrug: BIBT-1011), idraparinux and fondaparinux, substances which inhibit the aggregation of platelets (platelet aggregation inhibitors, thrombocyte aggregation inhibitors), for example acetylsalicylic acid (for example aspirin), P2Y12 antagonists, for example ticlopidine (Ticlid), clopidogrel (Plavix), prasugrel, ticagrelor, cangrelor, elinogrel, PAR-1 antagonists, for example vorapaxar, PAR-4 antagonists, EP3 antagonists, for example DG041;

platelet adhesion inhibitors such as GPVI and/or GPIb antagonists, for example Revacept or caplacizumab;

fibrinogen receptor antagonists (glycoprotein-IIb/IIIa antagonists), for example abciximab, eptifibatide, tirofiban, lamifiban, lefradafiban and fradafiban;

recombinant human activated protein C, for example Xigris or recombinant thrombomodulin;

and also antiarrhythmics;

inhibitors of VEGF and/or PDGF signal paths, for example aflibercept, ranibizumab, bevacizumab, KH-902, pegaptanib, ramucirumab, squalamin or bevasiranib, apatinib, axitinib, brivanib, cediranib, dovitinib, lenvatinib, linifanib, motesanib, pazopanib, regorafenib, sorafenib, sunitinib, tivozanib, vandetanib, vatalanib, Vargatef and E-10030;

inhibitors of angiopoietin-Tie signal paths, for example AMG386;

inhibitors of Tie2 receptor tyrosine kinase;

inhibitors of the integrin signal paths, for example volociximab, cilengitide and ALG1001;

inhibitors of the PI3K-Akt-mTor signal paths, for example XL-147, perifosine, MK2206, sirolimus, temsirolimus and everolimus;

corticosteroids, for example anecortave, betamethasone, dexamethasone, triamcinolone, fluocinolone and fluocinolone acetonide;

inhibitors of the ALK1-Smad1/5 signal path, for example ACE041;

cyclooxygenase inhibitors, for example bromfenac and nepafenac;

inhibitors of the kallikrein-kinin system, for example safotibant and ecallantide;

inhibitors of the sphingosine 1-phosphate signal paths, for example sonepcizumab;

inhibitors of the complement-C5a receptor, for example eculizumab;

inhibitors of the 5HT1a receptor, for example tandospirone;

inhibitors of the Ras-Raf-Mek-Erk signal path; inhibitors of the MAPK signal paths; inhibitors of the FGF signal paths; inhibitors of endothelial cell proliferation; apoptosis-inducing active ingredients;

photodynamic therapy consisting of an active ingredient and the action of light, the active ingredient being, for example, verteporfin.

"Combinations" for the purpose of the invention mean not only dosage forms which contain all the components (so-called fixed combinations) and combination packs which contain the components separate from one another, but also components which are administered simultaneously or sequentially, provided that they are used for the prophylaxis and/or treatment of the same disease. It is likewise possible to combine two or more active ingredients with one another, meaning that they are thus each in two-component or multicomponent combinations.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay, which control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

Suitable administration forms for extraocular (topic) administration are those which operate in accordance with the prior art, which release the active ingredient rapidly and/or in a modified or controlled manner and which contain the active ingredient in crystalline and/or amorphized and/or dissolved form, for example eye drops, sprays and lotions (e.g. solutions, suspensions, vesicular/colloidal systems, emulsions, aerosols), powders for eye drops, sprays and lotions (e.g. ground active ingredient, mixtures, lyophilisates, precipitated active ingredient), semisolid eye preparations (e.g. hydrogels, in-situ hydrogels, creams and ointments), eye inserts (solid and semisolid preparations, e.g. bioadhesives, films/wafers, tablets, contact lenses).

Intraocular administration includes, for example, intravitreal, subretinal, subscleral, intrachoroidal, subconjunctival, retrobulbar and subtenon administration. Suitable administration forms for intraocular administration are those which operate in accordance with the prior art, which release the active ingredient rapidly and/or in a modified or controlled manner and which contain the active ingredient in crystalline and/or amorphized and/or dissolved form, for example preparations for injection and concentrates for preparations for injection (e.g. solutions, suspensions, vesicular/colloidal systems, emulsions), powders for preparations for injection (e.g. ground active ingredient, mixtures, lyophilisates, precipitated active ingredient), gels for preparations for injection (semisolid preparations, e.g. hydrogels, in-situ hydrogels) and implants (solid preparations, e.g. biodegradable and nonbiodegradable implants, implantable pumps).

Preference is given to oral administration or, in the case of ophthalmologic disorders, extraocular and intraocular administration.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The compounds according to the invention can be converted to the administration forms mentioned. This can be accomplished in a manner known per se by mixing with inert, non-toxic, pharmaceutically suitable excipients. These auxiliaries include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctants.

The present invention further provides medicaments comprising at least one inventive compound, preferably together with one or more inert non-toxic pharmaceutically suitable auxiliaries, and the use thereof for the purposes mentioned above.

In the case of parenteral administration, it has generally been found to be advantageous to administer amounts of about 5 to 250 mg every 24 hours to achieve effective results. In the case of oral administration, the amount is about 5 to 500 mg every 24 hours.

In spite of this, it may be necessary, as the case may be, to deviate from the amounts specified, specifically depending on body weight, administration route, individual behaviour towards the active ingredient, type of formulation, and time or interval of administration.

Unless stated otherwise, the percentages in the tests and examples which follow are percentages by weight; parts are parts by weight. Solvent ratios, dilution ratios and concentration data for liquid/liquid solutions are based in each case on volume. "w/v" means "weight/volume". For example, "10% w/v" means: 100 ml of solution or suspension contain 10 g of substance.

A) EXAMPLES

Abbreviations:
Boc tert-butyloxycarbonyl
Ex. Example
d day(s), doublet (in NMR)
TLC thin-layer chromatography
DCM dichloromethane
DCI direct chemical ionization (in MS)
dd doublet of doublets (in NMR)
DIC N,N'-diisopropylcarbodiimide
DIEA N,N-diisopropylethylamine
DMAP 4-dimethylaminopyridine
DMF N,N-dimethylformamide
DMSO dimethyl sulphoxide
eq. equivalent(s)
ESI electrospray ionization (in MS)
h hour(s)
HATU O-(7-azabenzotriazol-1-yl)-N,N,N',N'-tetramethyluronium hexafluorophosphate
HPLC high-pressure, high-performance liquid chromatography
HV high vacuum
LC-MS liquid chromatography-coupled mass spectroscopy
LDA lithium diisopropylamide
m multiplet (in NMR)
min minute(s)
MS mass spectroscopy
NMR nuclear magnetic resonance spectroscopy
Oxima ethyl hydroxyiminocyanoacetate
q quartet or quadruplet (in NMR)
quant. quantitative
quin quintet (in NMR)
RP reversed phase (in HPLC)
RT room temperature
$R_t$ retention time (in HPLC)
s singlet (in NMR)
sxt sextet (in NMR)
SFC supercritical fluid chromatography (with supercritical carbon dioxide as mobile phase)
t triplet (in NMR)
THF tetrahydrofuran
TFA trifluoroacetic acid
T3P 2,4,6-tripropyl-1,3,5,2,4,6-trioxatriphosphinane 2,4,6-trioxide
Xantphos 4,5-bis(diphenylphosphino)-9,9-dimethylxanthene
XPhos precatalyst [(2'-aminobiphenyl-2-yl)(chloro)palladium dicyclohexyl(2',4',6'-triisopropylbiphenyl-2-yl)phosphane (1:1)], J. Am. Chem. Soc. 2010, 132, 14073-14075

HPLC, LC-MS and GC Methods:

Method 1: Instrument: Waters ACQUITY SQD UPLC System; column: Waters Acquity UPLC HSS T3 1.8µ 50 mm×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 208-400 nm.

Method 2: Instrument: Waters ACQUITY SQD UPLC System; column: Waters Acquity UPLC HSS T3 1.8µ 50 mm×1 mm; eluent A: 1 l water+0.25 ml 99% formic acid, eluent B: 1 l acetonitrile+0.25 ml 99% formic acid; gradient: 0.0 min 95% A→6.0 min 5% A→7.5 min 5% A; oven: 50° C.; flow rate: 0.35 ml/min; UV detection: 210-400 nm.

Method 3: Instrument: Micromass Quattro Premier with Waters UPLC Acquity; column: Thermo Hypersil GOLD 1.9µ 50 mm×1 mm; eluent A: 1 l water+0.5 ml 50% formic acid, eluent B: 1 l acetonitrile+0.5 ml 50% formic acid; gradient: 0.0 min 97% A→0.5 min 97% A→3.2 min 5% A→4.0 min 5% A; oven: 50° C.; flow rate: 0.3 ml/min; UV detection: 210 nm.

Method 4: MS instrument: Waters (Micromass) Quattro Micro; HPLC instrument: Agilent 1100 Series; column: YMC-Triart C18 3µ 50 mm×3 mm; eluent A: 1 l water+0.01 mol ammonium carbonate, eluent B: 1 l acetonitrile; gradient: 0.0 min 100% A→2.75 min 5% A→4.5 min 5% A; oven: 40° C.; flow rate: 1.25 ml/min; UV detection: 210 nm.

Method 5: MS instrument: Waters (Micromass) QM; HPLC instrument: Agilent 1100 series; column: Agilent ZORBAX Extend-C18 3.0 mm×50 mm 3.5 micron; eluent A: 1 l water+0.01 mol ammonium carbonate, eluent B: 1 l acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 6: MS instrument: Waters (Micromass) ZQ; HPLC instrument: Agilent 1100 series; column: Agilent ZORBAX Extend-C18 3.0 mm×50 mm 3.5 micron; eluent A: 1 l water+0.01 mol ammonium carbonate, eluent B: 1 l acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 7: Instrument: Thermo DFS, Trace GC Ultra; column: Restek RTX-35, 15 m×200 μm×0.33 μm; constant flow rate of helium: 1.20 ml/min; oven: 60° C.; inlet: 220° C.; gradient: 60° C., 30° C./min→300° C. (hold for 3.33 min).

Method 8: Instrument: Agilent MS Quad 6150; HPLC: Agilent 1290; column: Waters Acquity UPLC HSS T3 1.8μ 50 mm×2.1 mm; eluent A: 1 l water+0.25 ml 99% formic acid, eluent B: 1 l acetonitrile+0.25 ml 99% formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 9: Instrument: Thermo Scientific DSQII, Thermo Scientific Trace GC Ultra; column: Restek RTX-35MS, 15 m×200 μm×0.33 μm; constant flow rate of helium: 1.20 ml/min; oven: 60° C.; inlet: 220° C.; gradient: 60° C., 30° C./min→300° C. (hold for 3.33 min).

Method 10: MS instrument type Thermo Scientific FT-MS; UHPLC+ instrument type Thermo Scientific UltiMate 3000; column Waters, HSST3, 2.1 mm×75 mm, C18 1.8 μm; eluent A 1 l of water+0.01% formic acid; eluent B 1 l of acetonitrile+0.01% formic acid; gradient 0.0 min 10% B→2.5 min 95% B→3.5 min 95% B; oven 50° C.; flow rate 0.90 ml/min; UV detection 210 nm/optimum integration path 210-300 nm.

Method 11: MS instrument: Waters (Micromass) Quattro Micro; instrument: Waters UPLC Acquity; column: Waters BEH C18 1.7μ, 50 mm×2.1 mm; eluent A: 1 l water+0.01 mol ammonium formate, eluent B: 1 l acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm.

Microwave: The microwave reactor used was a "single-mode" instrument of the Emrys™ Optimizer type.

When compounds according to the invention are purified by preparative HPLC by the above-described methods in which the eluents contain additives, for example trifluoroacetic acid, formic acid or ammonia, the compounds according to the invention may be obtained in salt form, for example as trifluoroacetate, formate or ammonium salt, if the compounds according to the invention contain a sufficiently basic or acidic functionality. Such a salt can be converted to the corresponding free base or acid by various methods known to the person skilled in the art.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x CF$_3$COOH", "x Na$^+$" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Starting Compounds

General Method 1A: Preparation of a Boronic Acid

To a solution of the appropriate pyridine derivative in tetrahydrofuran (about 3 ml/mmol) at −78° C. was added lithium diisopropylamide (2 M in tetrahydrofuran/heptane/ethylbenzene), the mixture was stirred for 2 to 4 h and then triisopropyl borate was then added quickly. The reaction mixture was maintained at −78° C. for a further 2 to 3 h and then slowly thawed to RT overnight. After addition of water, the tetrahydrofuran was removed under reduced pressure and the aqueous phase was extracted twice with ethyl acetate. The aqueous phase was acidified with aqueous hydrochloric acid (2M), generally resulting in formation of a precipitate which was filtered off, washed with water and dried. The aqueous phase was extracted three times with ethyl acetate. The combined organic phases were dried (sodium sulphate or magnesium sulphate), filtered and concentrated under reduced pressure.

General Method 2A: Suzuki Coupling

A flask which had been dried by heating and flushed with argon was initially charged with 1.0 eq. of the appropriate boronic acids, 1.0 eq. of the aryl bromide or aryl iodide, 3.0 eq. of potassium carbonate and 0.1 eq. of [1,1-bis(diphenylphosphino)ferrocene]palladium(II) chloride/monodichloromethane adduct or tetrakis(triphenylphosphine)palladium (0). The flask was then evacuated three times and in each case vented with argon. Dioxane (about 6 ml/mmol) was added, and the reaction mixture was stirred at 110° C. for a number of hours until substantially complete conversion had been achieved. The reaction mixture was then filtered through Celite and the filtrate was concentrated under reduced pressure. Water was added to the residue. After addition of ethyl acetate and phase separation, the organic phase was washed once with water and once with saturated aqueous sodium chloride solution, dried (sodium sulphate or magnesium sulphate), filtered and concentrated under reduced pressure. The crude product was then purified either by means of normal phase chromatography (eluent: cyclohexane/ethyl acetate mixtures or dichloromethane/methanol mixtures) or preparative RP-HPLC (water/acetonitrile gradient or water/methanol gradient).

General Method 3A: Methoxypyridine Cleavage 20 eq. of pyridinium hydrochloride or pyridinium hydrobromide were added to a solution of the appropriate methoxypyridine in dimethylformamide (10-12.5 ml/mmol) and the mixture was stirred at 100° C. for a number of hours to days, with further pyridinium hydrochloride or pyridinium hydrobromide possibly being added, until substantially complete conversion had been achieved. Subsequently, the reaction solution was concentrated under reduced pressure and the residue was stirred with water. The precipitate formed was filtered off, washed with water and dried under reduced pressure.

General Method 4A: N-Alkylation of 2-Pyridinone Derivatives with the Appropriate 2-Bromo- or 2-Chloropropanoic Ester Derivatives in the Presence of Potassium Carbonate To a solution of 1.0 eq. of the appropriate 2-pyridinone derivative in dimethylformamide (5-10 ml/mmol) under argon and at RT were added 1.2 eq. of the appropriate 2-bromo- or 2-chloropropanoic ester derivative and 1.5 eq. of potassium carbonate, and the mixture was stirred at 100° C. After removal of the dimethylformamide and addition of water/ethyl acetate and phase separation, the organic phase was washed with water and with saturated aqueous sodium chloride solution, dried (sodium sulphate or magnesium sulphate), filtered and concentrated under reduced pressure. The crude product was then purified either by means of normal phase chromatography (eluent: cyclohexane/ethyl acetate mixtures or dichloromethane/methanol mixtures) or preparative RP-HPLC (water/acetonitrile gradient or water/methanol gradient).

General Method 5A: Amide Coupling with HATU/DIEA

To a solution of the appropriate carboxylic acid (1.0 eq.) in dimethylformamide (7-15 ml/mmol) under argon and at RT were added the amine (1.1 eq.), N,N-diisopropylethylamine (2.2 eq.) and a solution of HATU (1.2 eq.) in a little dimethylformamide. The reaction mixture was stirred at RT. After addition of water/ethyl acetate and phase separation, the organic phase was washed with water and with saturated aqueous sodium chloride solution, dried (sodium sulphate or magnesium sulphate), filtered and concentrated under reduced pressure. The crude product was then purified either by means of normal phase chromatography (eluent: cyclohexane/ethyl acetate mixtures or dichloromethane/methanol mixtures) or preparative RP-HPLC (water/acetonitrile gradient or water/methanol gradient).

General Method 5B: Amide Coupling using T3P/Pyridine

A solution of the appropriate carboxylic acid or carboxylic acid hydrochloride (1 eq.) and the appropriate amine or amine hydrochloride (1.1-1.9 eq.) in pyridine (about 0.1 M) was heated to 60° C., and T3P (50% in ethyl acetate, 1.5-15 eq.) was added dropwise. Alternatively, T3P was added at RT and the mixture was then stirred at RT or heated to 50 to 90° C. After 1 to 20 h, the reaction mixture was cooled to RT and either purified directly by means of preparative RP-HPLC (water-acetonitrile gradient or water-methanol gradient) or admixed with water and ethyl acetate. The aqueous phase was extracted with ethyl acetate. The combined organic phases were washed with aqueous buffer solution (pH=5), with saturated aqueous sodium hydrogencarbonate solution and with saturated aqueous sodium chloride solution, dried over sodium sulphate and concentrated under reduced pressure. The crude product was then optionally purified either by means of normal phase chromatography (eluent: cyclohexane/ethyl acetate mixtures or dichloromethane/methanol mixtures) or preparative RP-HPLC (water/acetonitrile gradient or water/methanol gradient).

General Method 6A: Hydrolysis of a Tert-Butyl Ester or a Boc-Protected Amine using TFA To a solution of 1.0 eq. of the appropriate tert-butyl ester derivative in dichloromethane (about 5-10 ml/mmol) at RT were added 20 eq. of TFA, and the mixture was stirred at RT for 1 to 8 h. The reaction mixture was then concentrated under reduced pressure and the residue was co-evaporated repeatedly with dichloromethane and toluene and dried under reduced pressure. The crude product was then optionally purified either by means of normal phase chromatography (eluent: cyclohexane/ethyl acetate mixtures or dichloromethane/methanol mixtures) or preparative RP-HPLC (water/acetonitrile gradient or water/methanol gradient).

General Method 6B: Hydrolysis of a Tert-Butyl Ester using Hydrogen Chloride in Dioxane A solution of 1.0 eq. of the appropriate tert-butyl ester derivative in 4M hydrogen chloride in dioxane (concentration of the tert-butyl ester derivative about 0.1M) was either stirred at RT for 2 to 48 h or treated in an ultrasound bath for 2 to 5 h. The reaction mixture was then concentrated under reduced pressure and the residue was co-evaporated repeatedly with tetrahydrofuran and dried under reduced pressure. The crude product was converted without further purification.

General Method 6C: Hydrolysis of a Tert-Butyl Ester using Lithium Hydroxide

To a solution of 1.0 eq. of the appropriate tert-butyl ester in tetrahydrofuran/ethanol (1:2, 15-50 ml/mmol) at RT was added lithium hydroxide (2-5 eq.). The reaction mixture was stirred at RT to 60° C., saturated aqueous ammonium chloride solution was then added and the mixture was adjusted to pH 1 using aqueous hydrochloric acid (1N). After addition of water/ethyl acetate and phase separation, the aqueous phase was extracted three times with ethyl acetate. The combined organic phases were dried (sodium sulphate or magnesium sulphate), filtered and concentrated under reduced pressure. The crude product was then purified either by means of normal phase chromatography (cyclohexane/ethyl acetate mixtures or dichloromethane/methanol mixtures) or preparative RP-HPLC (water/acetonitrile gradient or water/methanol gradient).

General Method 7A: Preparation of Triflates

A solution of the appropriate alcohol (1 eq.) was initially charged in dichloromethane (0.1M), and at −20° C. lutidine (1.1-1.5 eq.) or triethylamine (1.1-1.5 eq.) and trifluoromethanesulphonic anhydride (1.05-1.5 eq.) were added in succession. The reaction mixture was stirred at −20° C. for another 1 h and then diluted with three times the amount (based on the reaction volume) of methyl tert-butyl ether. The organic phase was washed three times with a 3:1 mixture of saturated aqueous sodium chloride solution/1N hydrochloric acid and finally with saturated aqueous sodium hydrogencarbonate solution, dried (sodium sulphate or magnesium sulphate) and filtered, and the solvent was removed under reduced pressure. The crude product was used in the next stage without further purification.

General Method 8A: Alkylation of Acetic Esters with Triflates

To a solution of the appropriate acetic ester (1 eq.) in tetrahydrofuran (0.1-0.2M) under argon and at −78° C. was added dropwise lithium bis(trimethylsilyl)amide (1.0M in THF, 1.1-1.3 eq.), and the mixture was stirred for 15 min. The appropriate alkyl triflate (1.5-2.0 eq.) was then added neat or as a solution in THF. The resulting reaction mixture was stirred at −78° C. for another 15 min and at RT for another 1 h. Saturated aqueous ammonium chloride solution was added to the reaction mixture. After phase separation, the aqueous phase was extracted with ethyl acetate. The combined organic phases were dried (sodium sulphate or magnesium sulphate), filtered and concentrated under reduced pressure. The crude product was then purified either by means of normal phase chromatography (eluent: cyclohexane/ethyl acetate mixtures or dichloromethane/methanol mixtures) or preparative RP-HPLC (water/acetonitrile gradient or water/methanol gradient).

General Method 8B: Alkylation of Acetic Esters with Halides

To a solution of the appropriate acetic ester in THF (about 10 ml/mmol) under argon and at −78° C. were added 1.1 eq. of lithium bis(trimethylsilyl)amide (1.0M in THF), and the mixture was stirred at −78° C. for 10 min. A solution of the appropriate iodide/bromide/chloride in THF was then added, and the reaction mixture was stirred at −78° C. for 10 min and further in an ice bath and then quenched with water. After addition of ethyl acetate and phase separation, the aqueous phase was extracted twice with ethyl acetate. The combined organic phases were dried (sodium sulphate), filtered and concentrated under reduced pressure. The crude product was then purified either by flash chromatography (silica gel 60, eluent: cyclohexane/ethyl acetate mixtures or dichloromethane/methanol mixtures) or preparative HPLC (Reprosil C18, water/acetonitrile gradient or water/methanol gradient).

General Method 9A: Nitro Reduction with Iron

The appropriate nitro compound was dissolved in an ethanol/water mixture (5:1) (about 2-3M), and concentrated hydrochloric acid (0.5-1 eq.) and iron powder (3-8 eq.) were added. The reaction mixture was heated at 80 to 100° C. until the reaction had gone to completion (about 1 to 6 h). The hot reaction mixture was filtered through kieselguhr. The filtercake was washed with methanol and the filtrate was concentrated under reduced pressure. The crude product was then purified either by means of normal phase chromatography (eluent: cyclohexane/ethyl acetate mixtures or dichloromethane/methanol mixtures) or preparative RP-HPLC (water/acetonitrile gradient or water/methanol gradient).

General Method 10A: Preparation of Tert-Butyl Esters

A solution of the appropriate carboxylic acid (1 eq.) in toluene (0.15-0.05 M) was heated to 60 to 100° C., and N,N-dimethylformamide di-tert-butyl acetal (4 eq.) was added dropwise. The reaction mixture was stirred at 60 to 100° C. for 1 to 5 h and cooled to RT, and ethyl acetate was added. The organic phase was washed with saturated aqueous sodium hydrogencarbonate solution and with saturated aqueous sodium chloride solution, dried (sodium sulphate), filtered and concentrated under reduced pressure. The crude product was used in the next stage without purification.

Example 1.1A

5-Nitropyridine-2-carboxamide

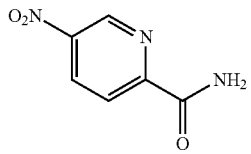 [SMILES: NC(=O)c1ccc([N+](=O)[O-])cn1]

According to General Method 5B, 4.00 g (23.8 mmol) of 5-nitropyridine-2-carboxylic acid and 1.91 g (35.7 mmol, 1.5 eq.) of ammonium chloride were reacted. After workup, the crude product was used for the next stage without further purification.

LC/MS [Method 1]: $R_t$=0.39 min; MS (ESIpos): m/z=168 (M+H)$^+$,

Example 1.1B

5-Aminopyridine-2-carboxamide

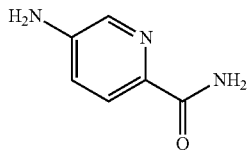

According to General Method 9A, the crude product (about 23.8 mmol) 5-nitropyridine-2-carboxamide was reacted. The product obtained was purified by means of normal phase chromatography (eluent: dichloromethane/methanol (9:1) with 1.5% concentrated ammonia). Yield: 1.40 g (42% of theory)

LC/MS [Method 5]: $R_t$=0.50 min; MS (ESIpos): m/z=138 (M+H)$^+$, $^1$H-NMR (400 MHz, DMSO-d$_6$): δ [ppm]=7.89 (d, 1H), 7.70 (d, 1H), 7.64 (bs, 1H), 7.11 (bs, 1H), 6.95 (dd, 1H), 5.90 (s, 2H).

Example 1.2A

N-Methyl-5-nitropyridine-2-carboxamide

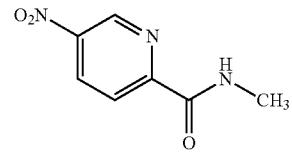

According to General Method 5B, 500 mg (2.97 mmol) of 5-nitropyridine-2-carboxylic acid and 301 mg (4.46 mmol, 1.5 eq.) of methylamine hydrochloride were reacted. Yield: 459 mg (83% of theory)

LC/MS [Method 3]: $R_t$=1.26 min; MS (ESIpos): m/z=181 (M+H)$^+$, $^1$H-NMR (400 MHz, DMSO-d$_6$): δ [ppm]=9.36 (d, 1H), 9.11-8.92 (m, 1H), 8.75 (dd, 1H), 8.26 (d, 1H), 2.85 (d, 3H).

Example 1.2B

5-Amino-N-methylpyridine-2-carboxamide

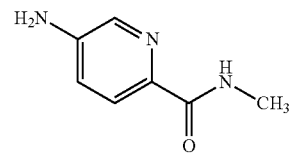

According to General Method 9A, 487 mg (2.55 mmol, 1 eq.) of N-methyl-5-nitropyridine-2-carboxamide were reacted. The crude product was purified by means of normal phase chromatography (eluent: dichloromethane/methanol 5-10%). Yield: 225 mg (86% purity, 50% of theory)

$^1$H-NMR (400 MHz, DMSO-d$_6$): δ [ppm]=8.32-8.19 (m, 1H), 7.89 (d, 1H), 7.68 (d, 1H), 6.96 (dd, 1H), 5.88 (s, 2H), 2.75 (d, 3H).

Example 1.3A tert-Butyl 5-nitropyridine-2-carboxylate

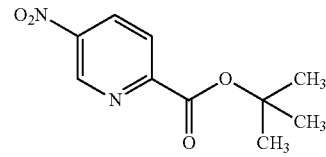 [SMILES: CC(C)(C)OC(=O)c1ccc([N+](=O)[O-])cn1]

According to General Method 10A, 1000 mg (5.95 mmol) of 5-nitropyridine-2-carboxylic acid were reacted. The crude product was used in the next stage without purification. Yield: 600 mg (45% of theory)

HPLC [Method 1]: $R_t$=0.89 min, $^1$H-NMR (400 MHz, DMSO-$d_6$): δ [ppm]=9.44 (d, 1H), 8.73 (dd, 1H), 8.22 (d, 1H), 1.58 (s, 9H).

Example 1.3B tert-Butyl 5-aminopyridine-2-carboxylate

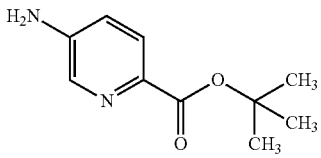

A solution of 600 mg (2.68 mmol) of tert-butyl 5-nitropyridine-2-carboxylate in 12 ml of ethyl acetate was hydrogenated in the presence of 60 mg of palladium (10% on activated carbon) at RT and standard pressure. The reaction mixture was filtered through Celite and the filtrate was concentrated under reduced pressure and dried. The crude product was hydrogenated again in the presence of 60 mg of palladium (10% on activated carbon) at RT and standard pressure. The reaction mixture was then filtered through Celite and the filtrate was concentrated under reduced pressure and dried. The crude product was used without further purification in the next stage. Yield: 498 mg (89% of theory)

HPLC [Method 8]: $R_t$=0.79 min, $^1$H-NMR (400 MHz, DMSO-$d_6$): δ [ppm]=7.95 (d, 1H), 7.68 (d, 1H), 6.89 (dd, 1H), 6.07 (s, 2H), 1.50 (s, 9H).

Example 1.4A

Methyl 5-[(tert-butoxycarbonyl)amino]-3-fluoropyridine-2-carboxylate

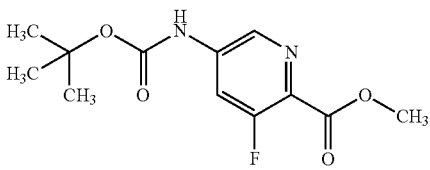 [SMILES: COC(=O)c1ncc(NC(=O)OC(C)(C)C)cc1F]

A microwave vial was initially charged with 700 mg (2.99 mmol) of methyl 5-bromo-3-fluoropyridine-2-carboxylate, 1402 mg (11.96 mmol, 4 eq.) of tert-butyl carbamate, 34 mg (0.15 mmol, 0.05 eq.) of palladium(II) acetate, 173 mg (0.299 mmol, 0.10 eq.) of 4,5-bis(diphenylphosphino)-9,9-dimethylxanthene and 4873 mg (14.96 mmol, 5 eq.) of caesium carbonate and purged with argon, and then 28 ml of dioxane were added. The reaction mixture was stirred in the microwave at 140° C. for 30 min. The cooled suspension was partitioned between ethyl acetate and water, and the aqueous phase was extracted once more with ethyl acetate. The combined organic phases were washed once each with water and with saturated aqueous sodium chloride solution, dried and concentrated. The crude product was purified by means of normal phase flash chromatography (eluent: cyclohexane/ethyl acetate, 0% to 50%). Yield: 405 mg (90% purity, 45% of theory).

$^1$H-NMR (400 MHz, DMSO-$d_6$): δ [ppm]=10.26 (s, 1H), 8.52-8.48 (m, 1H), 7.92 (dd, 1H), 3.84 (s, 3H), 1.50 (s, 9H).

Example 1.4B

5-[(tert-Butoxycarbonyl)amino]-3-fluoropyridine-2-carboxylic acid

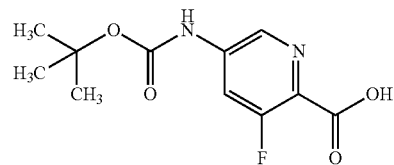 [SMILES: CC(C)(C)OC(=O)Nc1cnc(C(=O)O)c(F)c1]

450 mg (1.52 mmol, 91% purity) of methyl 5-[(tert-butoxycarbonyl)amino]-3-fluoropyridine-2-carboxylate were dissolved in 16 ml of methanol, 987 mg (3.03 mmol, 2 eq.) of caesium carbonate and 3.9 ml of water were added and the mixture was stirred at 60° C. for 4 h. Methanol was removed from the reaction mixture on a rotary evaporator and the aqueous residue was adjusted to pH 4 with 700-800 μl of 6 N hydrochloric acid. The reaction mixture was extracted twice with 30 ml each time of ethyl acetate. The combined organic phases were dried (sodium sulphate) and concentrated. The residue and the aqueous phase were each purified by means of preparative HPLC (RP18 column, eluent: acetonitrile/water gradient with addition of 0.15% formic acid) and then combined. Yield: 325 mg (84% of theory).

LC/MS [Method 1]: $R_t$=0.72 min; MS (ESIpos): m/z=257 (M+H)$^+$, $^1$H-NMR (400 MHz, DMSO-$d_6$): δ [ppm]=13.13 (bs, 1H), 10.20 (s, 1H), 8.51-8.47 (m, 1H), 7.89 (dd, 1H), 1.50 (s, 9H)

Example 1.4C tert-Butyl (6-carbamoyl-5-fluoropyridin-3-yl)carbamate

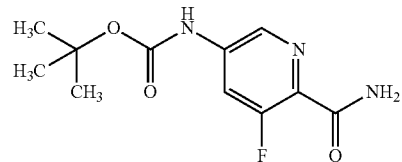 [SMILES: CC(C)(C)OC(=O)Nc1cnc(C(N)=O)c(F)c1]

According to General Method 5B, 275 mg (1.07 mmol) of 5-[(tert-butoxycarbonyl)amino]-3-fluoropyridine-2-carboxylic acid and 86 mg (1.61 mmol) of ammonium chloride in 2.0 ml of pyridine were reacted. Yield: 190 mg (69% of theory).

LC/MS [Method 1]: $R_t$=0.70 min; MS (ESIpos): m/z=256 (M+H)$^+$, $^1$H-NMR (400 MHz, DMSO-$d_6$): δ [ppm]=10.11 (s, 1H), 8.46-8.40 (m, 1H), 7.91-7.80 (m, 2H), 7.46 (bs, 1H), 1.50 (s, 9H)

Example 1.4D

5-Amino-3-fluoropyridine-2-carboxamide hydrochloride

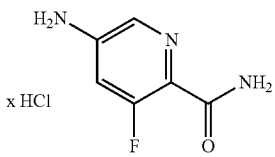

According to General Method 6B, 220 mg (0.86 mmol) of tert-butyl (6-carbamoyl-5-fluoropyridin-3-yl)carbamate in 10.0 ml of hydrogen chloride in dioxane (4 M) were reacted. Yield: 155 mg (94% of theory)

LC/MS [Method 11]: $R_t$=0.40 min; MS (ESIpos): m/z=156 (M+H)$^+$.

Example 2.1A 2,5-Dimethoxypyridin-4-ylboronic acid

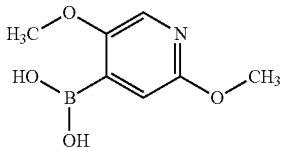

According to General Method 1A, 11.53 g (82.9 mmol) of 2,5-dimethoxypyridine were reacted. The desired product precipitated out after acidification of the aqueous phase. Yield: 9.53 g (61% of theory)

LC/MS [Method 1]: $R_t$=0.47 min; MS (ESIpos): m/z=184 (M+H)$^+$

Example 2.1B

4-Chloro-2-(2,5-dimethoxypyridin-4-yl)benzonitrile

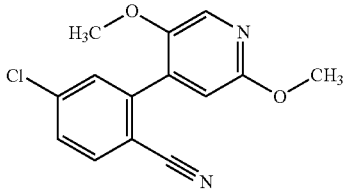 [SMILES: COc1cc(-c2cc(Cl)ccc2C#N)c(OC)cn1]

According to General Method 2A, 7.87 g (95% purity, 40.86 mmol) of 2,5-dimethoxypyridin-4-ylboronic acid were reacted with 8.85 g (40.86 mmol) of 2-bromo-4-chlorobenzonitrile in the presence of [1,1-bis(diphenylphosphino)ferrocene]palladium(II) chloride/dichloromethane monoadduct. Yield: 6.23 g (92% purity, 51% of theory).

LC/MS [Method 1]: $R_t$=1.08 min; MS (ESIpos): m/z=275 (M+H)$^+$

Example 2.1C

4-Chloro-2-(5-methoxy-2-oxo-1,2-dihydropyridin-4-yl)benzonitrile

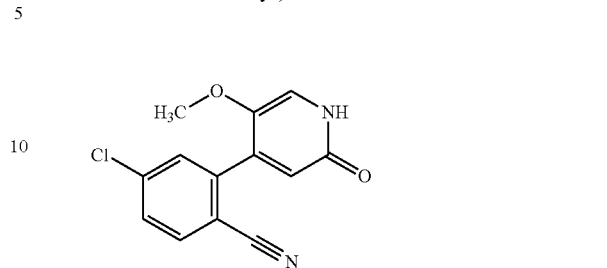

According to General Method 3A, 7.23 g (92% purity, 24.21 mmol) of 4-chloro-2-(2,5-dimethoxypyridin-4-yl)benzonitrile were reacted with pyridinium hydrochloride. Yield: 6.66 g (91% purity, 96% of theory).

LC/MS [Method 1]: $R_t$=0.76 min; MS (ESIpos): m/z=261 (M+H)$^+$ $^1$H-NMR (400 MHz, DMSO-d$_6$): δ [ppm]=11.45 (br. s, 1H), 7.98 (d, 1H), 7.75-7.67 (m, 2H), 7.29 (br. s, 1H), 6.43 (s, 1H), 3.64 (s, 3H).

Example 2.1D tert-Butyl 2-[4-(5-chloro-2-cyanophenyl)-5-methoxy-2-oxopyridin-1(2H)-yl]butanoate (racemate)

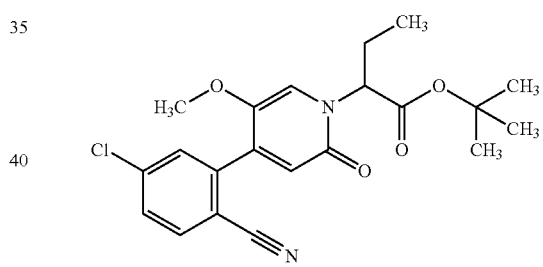

To a solution of 5.0 g (13.3 mmol) of tert-butyl [4-(5-chloro-2-cyanophenyl)-5-methoxy-2-oxopyridin-1(2H)-yl]acetate under argon and at −78° C. were added dropwise 14.0 ml (1.0M in THF, 14.0 mmol, 1.05 eq.) of lithium bis(trimethylsilyl)amide in 100 ml of tetrahydrofuran, and the mixture was stirred at −78° C. for 15 min. 2.6 g (14.7 mmol, 1.1 eq.) of neat ethyl trifluoromethanesulphonate were then added dropwise. The cooling bath was removed and the reaction mixture was stirred at RT for another 1 h. The reaction mixture was cooled to 0° C., and saturated aqueous ammonium chloride solution was added. After phase separation, the aqueous phase was extracted twice with methyl-tert-butyl ether. The combined organic phases were dried (sodium sulphate), filtered and concentrated under reduced pressure. The crude product was then purified by means of flash chromatography (340 g of silica gel, eluent: cyclohexane-ethyl acetate mixtures 8:1, 4:1). The product-containing fractions were combined and concentrated under reduced pressure. The residue was dissolved in hot methyl tert-butyl ether and the solution was left to stand on the open bench, and after 10 min the mixture had crystallized almost completely. The crystals were filtered off and washed twice with methyl tert-butyl ether. The combined filtrates were concentrated under reduced pressure and the residue was re-crystallized as described. The two crystal batches were combined and dried under reduced pressure. Yield: 4.2 g (78% of theory)

LC/MS [Method 1]: $R_t$=1.05 min; MS (ESIpos): m/z=403 (M+H)$^+$, $^1$H-NMR (400 MHz, DMSO-d$_6$): δ [ppm]=7.99 (d, 1H), 7.77-7.70 (m, 2H), 7.36 (s, 1H), 6.50 (s, 1H), 5.03 (dd, 1H), 3.64 (s, 3H), 2.19-2.06 (m, 2H), 1.40 (s, 9H), 0.85 (t, 3H).

Example 2.1E

2-[4-(5-Chloro-2-cyanophenyl)-5-methoxy-2-oxopyridin-1(2H)-yl]butanoic acid (racemate)

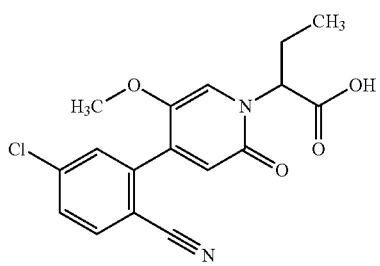 [SMILES: CCC(C(=O)O)n1cc(OC)c(-c2cc(Cl)ccc2C#N)cc1=O]

To a solution of 4.1 g (10.2 mmol) of tert-butyl 2-[4-(5-chloro-2-cyanophenyl)-5-methoxy-2-oxopyridin-1(2H)-yl] butanoate (racemate) in 40 ml of dichloromethane under argon and at RT were added 7.8 ml (101.8 mmol, 10 eq.) of trifluoroacetic acid, the mixture was stirred at RT for 1 h, a further 7.8 ml (101.8 mmol, 10 eq.) of trifluoroacetic acid were added, the mixture was stirred at RT for 1 h, a further 7.8 ml (101.8 mmol, 10 eq.) of trifluoroacetic acid were added and the mixture was stirred at RT for 1 h. On completion of conversion, the reaction mixture was concentrated under reduced pressure and the residue was co-evaporated three times with dichloromethane and once with toluene and dried under reduced pressure. The residue was taken up in 100 ml of ethyl acetate and washed repeatedly with a highly dilute aqueous sodium hydrogencarbonate solution (where the pH of the wash water should not exceed pH 3-4 since the product otherwise has good solubility in water). The organic phase was subsequently dried (sodium sulphate), filtered and concentrated under reduced pressure. The residue was stirred in methyl tert-butyl ether, filtered, washed twice with methyl tert-butyl ether and dried under reduced pressure. Yield: 2.9 g (83% of theory)

LC/MS [Method 1]: $R_t$=0.81 min; MS (ESIpos): m/z=347 (M+H)$^+$, $^1$H-NMR (400 MHz, DMSO-d$_6$): δ [ppm]=12.97 (s, 1H), 7.99 (d, 1H), 7.77-7.70 (m, 2H), 7.41 (s, 1H), 6.49 (s, 1H), 5.09 (dd, 1H), 3.64 (s, 3H), 2.21-2.09 (m, 2H), 0.84 (t, 3H).

Example 3.1A

2-Methoxyethyl trifluoromethanesulphonate

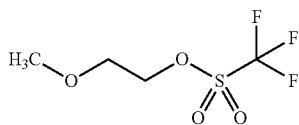

At −78° C., 16.3 g (57.8 mmol) of trifluoromethanesulphonic anhydride were initially charged in 20 ml of dichloromethane, and a solution of 4.00 g (52.6 mmol) of 2-methoxyethanol and 5.85 g (57.8 mmol) of triethylamine in 20 ml of dichloromethane was slowly added dropwise such that the internal temperature did not exceed −50° C. The mixture was left to stir at −78° C. for 15 min and then warmed to RT. The mixture was diluted with 100 ml of methyl tert-butyl ether and washed three times with in each case 50 ml of a 3:1 mixture of saturated aqueous sodium chloride solution and 1N hydrochloric acid. The organic phase was dried over sodium sulphate and concentrated under reduced pressure at RT. This gave 13 g of the crude product which was directly reacted further.

Example 3.1B tert-Butyl 2-[4-(5-chloro-2-cyanophenyl)-5-methoxy-2-oxopyridin-1(2H)-yl]-4-methoxybutanoate (racemate)

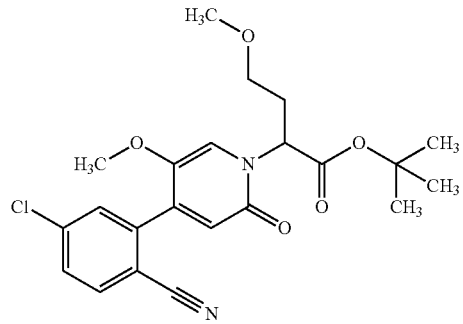 [SMILES: COCCC(C(=O)OC(C)(C)C)n1cc(OC)c(-c2cc(Cl)ccc2C#N)cc1=O]

8.09 g (21.6 mmol) of tert-butyl [4-(5-chloro-2-cyanophenyl)-5-methoxy-2-oxopyridin-1(2H)-yl]acetate were initially charged in 180 ml of THF, and the mixture was cooled to −78° C. 23.7 ml of lithium bis(trimethylsilyl)amide (1M in THF) were added dropwise, and the mixture was left to stir for a further 15 min. 8.99 g (43.2 mmol) of 2-methoxyethyl trifluoromethanesulphonate were then added dropwise, and the mixture was left to stir at −78° C. for 15 min and at RT for a further 45 min. Saturated aqueous ammonium chloride solution was then added, and the mixture was extracted repeatedly with ethyl acetate. The combined organic phases were dried over sodium sulphate and concentrated under reduced pressure. The residue was purified by means of flash chromatography (silica gel 50, cyclohexane-ethyl acetate gradient). Yield: 7.87 g (95% purity, 80% of theory).

LC/MS [Method 1]: $R_t$=1.02 min; MS (ESIpos): m/z=433 (M+H)$^+$,

1H-NMR (400 MHz, DMSO-d$_6$): δ [ppm]=8.01-7.96 (m, 1H), 7.76-7.69 (m, 2H), 7.37 (s, 1H), 6.48 (s, 1H), 5.11 (dd, 1H), 3.64 (s, 3H), 3.43-3.35 (m, 1H), 3.20 (s, 3H), 3.19-3.13 (m, 1H), 2.39-2.28 (m, 2H), 1.40 (s, 9H).

Example 3.1C

2-[4-(5-Chloro-2-cyanophenyl)-5-methoxy-2-oxopyridin-1(2H)-yl]-4-methoxybutanoic acid (racemate)

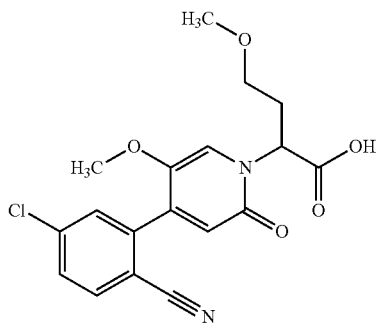 [SMILES: COCCC(C(=O)O)n1cc(OC)c(-c2cc(Cl)ccc2C#N)cc1=O]

7.87 g (95% purity, 17.3 mmol) of tert-butyl 2-[4-(5-chloro-2-cyanophenyl)-5-methoxy-2-oxopyridin-1(2H)-yl]-4-methoxybutanoate-(racemate) were initially charged in 175 ml of dichloromethane. 42 ml (545 mmol) of trifluoroacetic acid were added, and the mixture was left to stir at RT for 3 h. The reaction mixture was concentrated under reduced pressure and repeatedly the residue was taken up in dichloromethane and concentrated again. Then, twice, toluene was added and the mixture was concentrated again. The residue was stirred with acetonitrile and filtered off with suction. Yield 5.81 g (95% purity, 84% of theory)

LC/MS [Method 1]: $R_t$=0.78 min; MS (ESIpos): m/z=377 (M+H)$^+$, $^1$H-NMR (500 MHz, DMSO-d$_6$): δ [ppm]=13.40-12.67 (m, 1H), 7.99 (d, 1H), 7.75 (d, 1H), 7.73 (dd, 1H), 7.43 (s, 1H), 6.48 (s, 1H), 5.14 (t, 1H), 3.64 (s, 3H), 3.41-3.36 (m, 1H), 3.19 (s, 3H), 3.13 (dt, 1H), 2.40-2.31 (m, 2H).

Example 4.1A tert-Butyl [4-(5-chloro-2-cyanophenyl)-5-methoxy-2-oxopyridin-1(2H)-yl]acetate

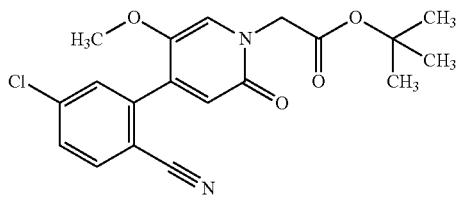 [SMILES: COc1cn(CC(=O)OC(C)(C)C)c(=O)cc1-c1cc(Cl)ccc1C#N]

According to General Method 4A, 516 mg (91% purity, 1.8 mmol) of 4-chloro-2-(5-methoxy-2-oxo-1,2-dihydropyridin-4-yl)benzonitrile were reacted with 1.2 eq. of tert-butyl bromoacetate at 100° C. Yield: 464 mg (68% of theory)

LC/MS [Method 1]: $R_t$=1.00 min; MS (ESIpos): m/z=375 (M+H)$^+$

Example 5.1A 5-(Bromomethyl)-1,3-oxazole

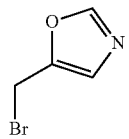

To a solution of 1.83 ml (13.12 mmol, 1.3 eq.) of triethylamine and 1.0 g (10.09 mmol, 1 eq.) of 1,3-oxazol-5-ylmethanol in 14 ml of N,N-dimethylformamide under argon and at 0° C. were added dropwise 1.02 ml (13.12 mmol, 1.3 eq.) of methanesulphonyl chloride, and the mixture was stirred at 0° C. for 1 h. 2.45 g (28.26 mmol, 2.8 eq.) of lithium bromide were then added, and this reaction mixture was stirred at 0° C. for 1 h. After addition of water, the mixture was extracted with ethyl acetate. The combined organic phases were washed with saturated aqueous sodium chloride solution, dried over sodium sulphate and concentrated under reduced pressure. The crude product was then purified by means of normal phase chromatography (eluent: dichloromethane). Yield 1.23 g (80% purity, 60% of theory)

$^1$H-NMR (400 MHz, DMSO-d$_6$): δ [ppm]=8.42 (s, 1H), 7.26 (s, 1H), 4.93 (s, 2H).

Example 5.1B tert-Butyl 2-[4-(5-chloro-2-cyanophenyl)-5-methoxy-2-oxopyridin-1(2H)-yl]-3-(1,3-oxazol-5-yl)propanoate (racemate)

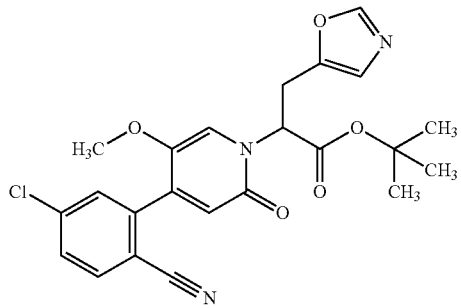 [SMILES: COc1cn(C(Cc2cnco2)C(=O)OC(C)(C)C)c(=O)cc1-c1cc(Cl)ccc1C#N]

According to General Method 8B, 1.5 g (4.00 mmol) of tert-butyl [4-(5-chloro-2-cyanophenyl)-5-methoxy-2-oxopyridin-1(2H)-yl]acetate were reacted with 1.78 g (51% purity, 5.60 mmol, 1.4 eq.) of 5-(bromomethyl)-1,3-oxazole. Yield: 1.89 g (60% purity, 62% of theory).

LC/MS [Method 1]: $R_t$=0.98 min; MS (ESIpos): m/z=456 (M+H)$^+$.

Example 5.1C

2-[4-(5-Chloro-2-cyanophenyl)-5-methoxy-2-oxopyridin-1(2H)-yl]-3-(1,3-oxazol-5-yl)propanoic acid (racemate)

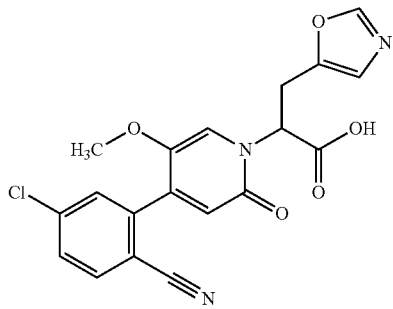 [SMILES: COc1cn(C(Cc2cnco2)C(=O)O)c(=O)cc1-c1cc(Cl)ccc1C#N]

According to General Method 6A, 1.89 g (60% purity, 2.48 mmol) of tert-butyl 2-[4-(5-chloro-2-cyanophenyl)-5-methoxy-2-oxopyridin-1(2H)-yl]-3-(1,3-oxazol-5-yl)propanoate (racemate) in 28 ml of dichloromethane were reacted with 14 ml (435 mmol) of TFA. Yield: 597 mg (80% purity, 48% of theory)

LC/MS [Method 1]: $R_t$=0.70 min; MS (ESIpos): m/z=400 (M+H)$^+$, $^1$H-NMR (400 MHz, DMSO-d$_6$): δ [ppm]=13.24 (br. s, 1H), 8.17 (s, 1H), 8.02-7.93 (m, 1H), 7.77-7.66 (m, 2H), 7.35 (s, 1H), 6.85 (s, 1H), 6.47 (s, 1H), 5.32 (dd, 1H), 3.63-3.72 (m, 1H), 3.58-3.47 (m, 4H).

Example 6.1A 4-(Bromomethyl)-1,3-oxazole

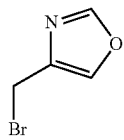

To a solution of 1.91 ml (13.72 mmol, 1.3 eq.) of triethylamine and 1.05 g (10.56 mmol) of 1,3-oxazol-4-ylmethanol in 15 ml of N,N-dimethylformamide under argon and at 0° C. were added dropwise 1.06 ml (13.72 mmol, 1.3 eq.) of methanesulphonyl chloride, and the mixture was stirred at 0° C. for 1 h. 2.57 g (29.56 mmol, 2.8 eq.) of lithium bromide were then added, and the reaction mixture was stirred at 0° C. for 1 h. After addition of water, the mixture was extracted with ethyl acetate. The combined organic phases were washed with saturated aqueous sodium chloride solution, dried over sodium sulphate and concentrated under reduced pressure. The crude product was converted without further workup. Yield 1.97 g (50% purity, 58% of theory)

$^1$H-NMR (400 MHz, DMSO-d$_6$): δ [ppm]=8.40 (s, 1H), 8.18 (s, 1H), 4.59 (s, 2H).

Example 6.1B tert-Butyl 2-[4-(5-chloro-2-cyanophenyl)-5-methoxy-2-oxopyridin-1(2H)-yl]-3-(1,3-oxazol-4-yl)propanoate (racemate)

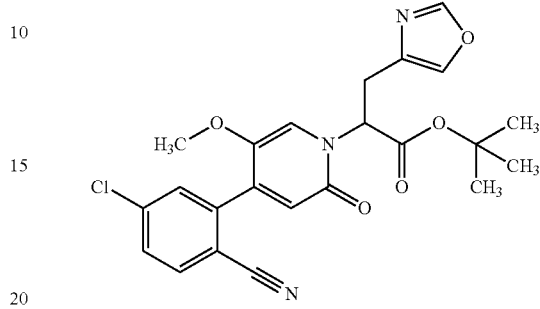

According to General Method 8B, 813 mg (2.17 mmol) of tert-butyl [4-(5-chloro-2-cyanophenyl)-5-methoxy-2-oxopyridin-1(2H)-yl]acetate were reacted with 983.8 mg (50% purity, 3.04 mmol, 1.4 eq.) of 4-(bromomethyl)-1,3-oxazole. Yield: 655 mg (65% of theory)

LC/MS [Method 1]: $R_t$=0.98 min; MS (ESIpos): m/z=456 (M+H)$^+$, $^1$H-NMR (400 MHz, DMSO-d$_6$): δ [ppm]=8.28 (s, 1H), 7.97 (d, 1H), 7.78 (s, 1H), 7.75-7.61 (m, 2H), 7.31 (s, 1H), 6.45 (s, 1H), 5.34 (dd, 1H), 3.56 (s, 3H), 3.50-3.39 (m, 1H), 3.36-3.26 (m, 1H), 1.41 (s, 9H).

Example 6.1C

2-[4-(5-Chloro-2-cyanophenyl)-5-methoxy-2-oxopyridin-1(2H)-yl]-3-(1,3-oxazol-4-yl)propanoic acid (racemate)

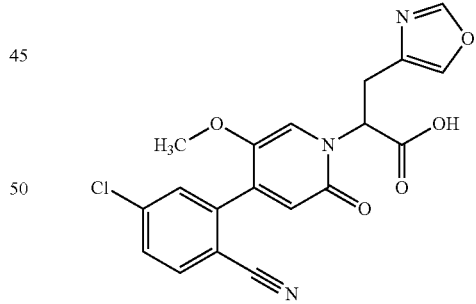

According to General Method 6A, 655 mg (1.41 mmol) of tert-butyl 2-[4-(5-chloro-2-cyanophenyl)-5-methoxy-2-oxopyridin-1(2H)-yl]-3-(1,3-oxazol-4-yl)propanoate (racemate) in 14 ml of dichloromethane were reacted with 7 ml (90.86 mmol) of TFA. Yield: 403 mg (70% of theory)

LC/MS [Method 1]: $R_t$=0.73 min; MS (ESIpos): m/z=400 (M+H)$^+$, $^1$H-NMR (400 MHz, DMSO-d$_6$): δ [ppm]=13.14 (br. s, 1H), 8.26 (s, 1H), 7.97 (d, 1H), 7.78-7.65 (m, 3H), 7.33 (s, 1H), 6.43 (s, 1H), 5.36 (dd, 1H), 3.55 (s, 3H), 3.53-3.43 (m, 1H), 3.38-3.25 (m, 1H).

Example 7.1A

Pyridin-2-ylmethyl methanesulphonate

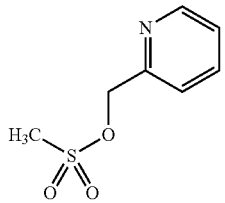

To a solution of 4.00 g (36.65 mmol) of pyridin-2-ylmethanol and 11.24 ml (80.64 mmol, 2.2 eq.) of triethylamine in 122 ml of tetrahydrofuran under argon and at 0° C. was added a solution of 2.84 ml (36.65 mmol, 1 eq.) of methanesulphonyl chloride in 24 ml of tetrahydrofuran, and the mixture was stirred for 3 h. Tetrahydrofuran was removed under reduced pressure. The crude product was then dissolved in dichloromethane, and the resulting mixture was washed with saturated aqueous sodium chloride solution. The organic phase was dried (sodium sulphate), filtered and concentrated under reduced pressure. The crude product was then purified by means of normal phase chromatography (eluent: cyclohexane/ethyl acetate (20-50%) mixtures). Yield: 4.72 g (68% of theory)

LC/MS [Method 3]: $R_t$=0.98 min; MS (ESIpos): m/z=188 (M+H)$^+$, $^1$H-NMR (400 MHz, DMSO-d$_6$): δ [ppm]=8.67-8.48 (m, 1H), 7.89 (td, 1H), 7.54 (d, 1H), 7.42 (ddd, 1H), 5.30 (s, 2H), 3.28 (s, 3H).

Example 7.1B tert-Butyl 2-[4-(5-chloro-2-cyanophenyl)-5-methoxy-2-oxopyridin-1(2H)-yl]-3-(pyridin-2-yl)propanoate (racemate)

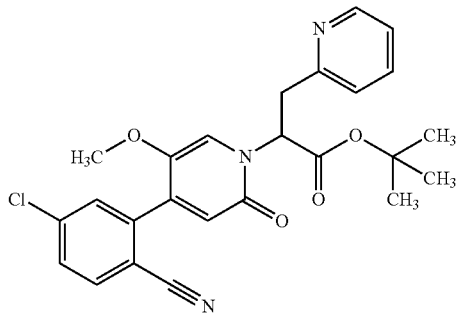 [SMILES: COc1cn(C(Cc2ccccn2)C(=O)OC(C)(C)C)c(=O)cc1-c1cc(Cl)ccc1C#N]

To a solution of 1.50 g (4.00 mmol) of tert-butyl [4-(5-chloro-2-cyanophenyl)-5-methoxy-2-oxopyridin-1(2H)-yl]acetate in 30 ml of tetrahydrofuran under argon and at −78° C. were added dropwise 4.60 ml (1.0M in THF, 1.15 eq.) of lithium bis(trimethylsilyl)amide, and the mixture was stirred for 15 min. 1.06 g (5.6 mmol, 1.4 eq.) of neat pyridin-2-ylmethyl methanesulphonate were then added. The resulting reaction mixture was stirred at −78° C. for another 30 min and at RT for another 1.5 h. Saturated aqueous ammonium chloride solution was added to the reaction mixture. After phase separation, the aqueous phase was extracted with ethyl acetate. The combined organic phases were washed with saturated aqueous sodium chloride solution. The organic phase was dried (sodium sulphate), filtered and concentrated under reduced pressure. The crude product was then purified by means of normal phase chromatography (eluent: dichloromethane/methanol (2-5%) mixtures). Yield 1.99 g (93% purity, 99% of theory)

LC/MS [Method 1]: $R_t$=0.97 min; MS (ESIpos): m/z=466 (M+H)$^+$.

Example 7.1C

2-[4-(5-Chloro-2-cyanophenyl)-5-methoxy-2-oxopyridin-1(2H)-yl]-3-(pyridin-2-yl)propanoic acid (racemate)

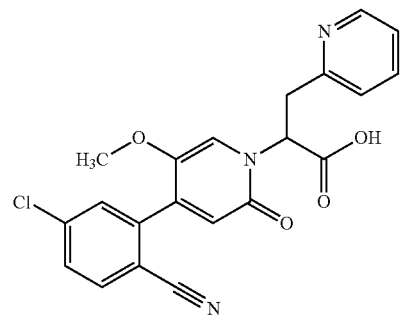 [SMILES: COc1cn(C(Cc2ccccn2)C(=O)O)c(=O)cc1-c1cc(Cl)ccc1C#N]

According to General Method 6A, 1.99 g (93% purity, 3.98 mmol) of tert-butyl 2-[4-(5-chloro-2-cyanophenyl)-5-methoxy-2-oxopyridin-1(2H)-yl]-3-(pyridin-2-yl)propanoate (racemate) in 40 ml of dichloromethane were reacted with 20 ml (259.6 mmol) of TFA. Yield: 220 mg (93% purity, 13% of theory)

LC/MS [Method 1]: $R_t$=0.64 min; MS (ESIpos): m/z=410 (M+H)$^+$, $^1$H-NMR (400 MHz, DMSO-d$_6$): δ [ppm]=13.08 (br. s, 1H), 8.48 (d, 1H), 7.95 (d, 1H), 7.73-7.60 (m, 3H), 7.27 (s, 1H), 7.24-7.11 (m, 2H), 6.40 (s, 1H), 5.55 (t, 1H), 3.66-3.57 (m, 2H), 3.49 (s, 3H).

Example 8.1A tert-Butyl 2-[4-(5-chloro-2-cyanophenyl)-5-methoxy-2-oxopyridin-1(2H)-yl]-3-(pyridin-3-yl)propanoate (racemate)

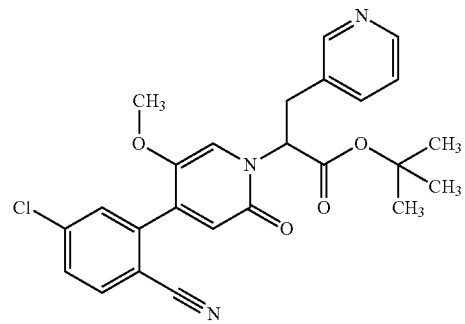 [SMILES: COc1cn(C(Cc2cccnc2)C(=O)OC(C)(C)C)c(=O)cc1-c1cc(Cl)ccc1C#N]

To a solution of 2.40 g (6.40 mmol) of tert-butyl [4-(5-chloro-2-cyanophenyl)-5-methoxy-2-oxopyridin-1(2H)-yl]acetate in 48 ml of tetrahydrofuran under argon and at −78° C. were added dropwise 16.01 ml (1.0M in THF, 2.5 eq.) of lithium bis(trimethylsilyl)amide, and the mixture was stirred for 20 min. Subsequently, 2.27 g (8.96 mmol, 1.4 eq.) of 3-(bromomethyl)pyridine hydrobromide were added. The resulting reaction mixture was stirred at −78° C. for another 30 min and at RT for another 1.5 h. Saturated aqueous ammonium chloride solution was added to the reaction mixture. After phase separation, the aqueous phase was extracted with ethyl acetate. The combined organic phases were washed with saturated aqueous sodium chloride solution. The organic phase was dried (sodium sulphate), filtered and concentrated under reduced pressure. The crude product was then purified by means of normal phase chromatography (eluent: cyclohexane/ethyl acetate (0-100%) mixtures). Yield 2.0 g (90% purity, 62% of theory)

LC/MS [Method 1]: $R_t$=0.84 min; MS (ESIpos): m/z=466 (M+H)$^+$, $^1$H-NMR (400 MHz, DMSO-d$_6$): δ [ppm]=ppm 8.43 (d, 1H), 8.39 (dd, 1H), 7.96 (d, 1H), 7.71 (dd, 1H), 7.65 (d, 1H), 7.55-7.48 (m, 1H), 7.25 (dd, 1H), 7.21 (s, 1H), 6.46 (s, 1H), 5.32 (dd, 1H), 3.54-3.38 (m, 5H), 1.40 (s, 9H).

Example 8.1B

2-[4-(5-Chloro-2-cyanophenyl)-5-methoxy-2-oxopyridin-1(2H)-yl]-3-(pyridin-3-yl)propanoic acid hydrochloride (racemate)

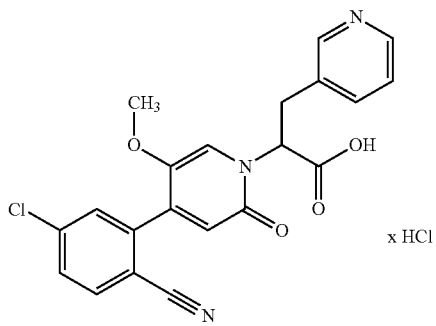 [SMILES: COc1cn(C(Cc2cccnc2)C(=O)O)c(=O)cc1-c1cc(Cl)ccc1C#N]

According to General Method 6B, 2.0 g (3.86 mmol) of tert-butyl 2-[4-(5-chloro-2-cyanophenyl)-5-methoxy-2-oxopyridin-1(2H)-yl]-3-(pyridin-3-yl)propanoate (racemate) and 39 ml of a hydrogen chloride in dioxane (4 M) solution were reacted. Yield: 1.8 g (88% purity, 92% of theory).

LC/MS [Method 1]: $R_t$=0.57 min; MS (ESIpos): m/z=410 (M+H)$^+$, $^1$H-NMR (400 MHz, DMSO-d$_6$): δ [ppm]=8.89 (s, 1H), 8.77 (d, 1H), 8.29 (d, 1H), 7.97 (d, 1H), 7.91 (dd, 1H), 7.77-7.63 (m, 2H), 7.40 (s, 1H), 6.44 (s, 1H), 5.50 (dd, 1H), 3.76 (dd, 1H), 3.65 (dd, 1H), 3.52 (s, 3H).

Example 9.1A tert-Butyl 2-[4-(5-chloro-2-cyanophenyl)-5-methoxy-2-oxopyridin-1(2H)-yl]-3-(pyridin-4-yl)propanoate (racemate)

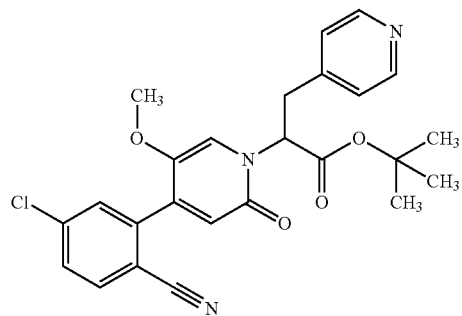 [SMILES: COc1cn(C(Cc2ccncc2)C(=O)OC(C)(C)C)c(=O)cc1-c1cc(Cl)ccc1C#N]

To a solution of 2.25 g (6.00 mmol) of tert-butyl [4-(5-chloro-2-cyanophenyl)-5-methoxy-2-oxopyridin-1(2H)-yl]acetate in 48 ml of tetrahydrofuran under argon and at −78° C. were added dropwise 15.01 ml (1.0M in THF, 2.5 eq.) of lithium bis(trimethylsilyl)amide, and the mixture was stirred for 20 min. Subsequently, 2.13 g (8.40 mmol, 1.4 eq.) of 4-(bromomethyl)pyridine hydrobromide were added. The resulting reaction mixture was stirred at −78° C. for another 30 min and at RT for another 1.5 h. Saturated aqueous ammonium chloride solution was added to the reaction mixture. After phase separation, the aqueous phase was extracted with ethyl acetate. The combined organic phases were washed with saturated aqueous sodium chloride solution. The organic phase was dried (sodium sulphate), filtered and concentrated under reduced pressure. The crude product was then purified by means of normal phase chromatography (eluent: cyclohexane/ethyl acetate (0-100%) mixtures). Yield 2.0 g (87% purity, 62% of theory)

LC/MS [Method 1]: $R_t$=0.76 min; MS (ESIpos): m/z=466 (M+H)$^+$, $^1$H-NMR (400 MHz, DMSO-d$_6$): δ [ppm]=8.46-8.37 (m, 2H), 7.97 (d, 1H), 7.71 (dd, 1H), 7.66 (d, 1H), 7.26-7.13 (m, 3H), 6.45 (s, 1H), 5.36 (t, 1H), 3.53-3.40 (m, 5H), 1.40 (s, 9H).

Example 9.1B

2-[4-(5-Chloro-2-cyanophenyl)-5-methoxy-2-oxopyridin-1(2H)-yl]-3-(pyridin-4-yl)propanoic acid hydrochloride (racemate)

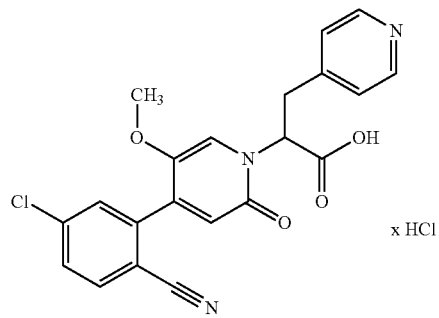 [SMILES: COc1cn(C(Cc2ccncc2)C(=O)O)c(=O)cc1-c1cc(Cl)ccc1C#N]

According to General Method 6B, 2.1 g (3.97 mmol) of tert-butyl 2-[4-(5-chloro-2-cyanophenyl)-5-methoxy-2-oxopyridin-1(2H)-yl]-3-(pyridin-4-yl)propanoate (racemate) and 40 ml of a hydrogen chloride in dioxane (4 M) solution were reacted. Yield: 1.9 g (93% purity, 100% of theory).

LC/MS [Method 1]: $R_t$=0.58 min; MS (ESIpos): m/z=410 (M+H)$^+$, $^1$H-NMR (400 MHz, DMSO-d$_6$): δ [ppm]=8.78 (d, 2H), 7.97 (d, 1H), 7.92 (d, 2H), 7.75-7.66 (m, 2H), 7.42 (s, 1H), 6.44 (s, 1H), 5.63 (dd, 1H), 3.87-3.73 (m, 2H), 3.54 (s, 3H).

Example 10.1A

6-Methoxypyridin-3-ol

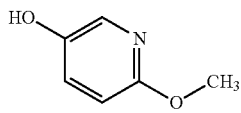

To a solution of 46.0 g (392 mmol) of N-methylmorpholine N-oxide in 500 ml of dichloromethane at RT were added 50 g (327 mmol) of 6-methoxypyridin-3-ylboronic acid, and the mixture was stirred at 50° C. for 14 h. Additional N-methylmorpholine N-oxide was added until conversion was complete. The reaction mixture was concentrated under reduced pressure and the crude product was purified by means of flash chromatography (silica gel 60, cyclohexane/ethyl acetate mixtures). Yield: 32.9 g (80% of theory)

LC/MS [Method 1]: $R_t$=0.37 min; MS (ESIpos): m/z=126 (M+H)$^+$, $^1$H-NMR (400 MHz, DMSO-d$_6$): δ [ppm]=9.27 (s, 1H), 7.67 (d, 1H), 7.16 (dd, 1H), 6.66 (d, 1H), 3.74 (s, 3H).

Example 10.1B

2-Methoxy-5-(tetrahydro-2H-pyran-2-yloxy)pyridine

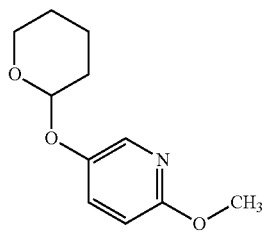

10.1 g (119.9 mmol, 1.5 eq.) of 3,4-dihydro-2H-pyran and 1.4 g (8.0 mmol, 0.1 eq.) of 4-toluenesulphonic acid were added to a solution of 10.0 g (79.9 mmol) of 6-methoxypyridin-3-ol in 150 ml of dichloromethane, and the mixture was stirred at RT for 5 days. After addition of water/dichloromethane and phase separation, the aqueous phase was extracted with dichloromethane. The combined organic phases were dried (sodium sulphate), filtered and concentrated under reduced pressure. Yield: 17.3 g (100% of theory)

LC/MS [Method 1]: $R_t$=0.95 min; MS (ESIpos): m/z=210 (M+H)$^+$.

Example 10.1C

4-Iodo-2-methoxy-5-(tetrahydro-2H-pyran-2-yloxy)pyridine

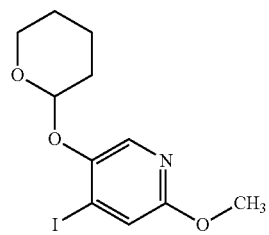 [SMILES: COc1cc(I)c(OC2CCCCO2)cn1]

To a solution of 16.2 g (75.1 mmol) of 2-methoxy-5-(tetrahydro-2H-pyran-2-yloxy)pyridine in 250 ml of THF at −78° C. were added 13.6 ml (90.1 mmol, 1.2 eq.) of 1,2-bis(dimethylamino)ethane and 54.0 ml (86.4 mmol, 1.15 eq.) of n-butyllithium, and the mixture was stirred at −78° C. for 1 h. 24.8 g (97.6 mmol, 1.3 eq.) of iodine were then added, and the reaction mixture was stirred at −78° C. for 1 h and then allowed to come to RT overnight. The reaction mixture was quenched with water and extracted three times with ethyl acetate. The combined organic phases were washed with saturated sodium thiosulphate solution, dried (sodium sulphate), filtered and concentrated under reduced pressure. Yield: 25.1 g (82% purity, 82% of theory).

LC/MS [Method 1]: $R_t$=1.18 min; MS (ESIpos): m/z=336 (M+H)$^+$.

Example 10.1D

4-Iodo-6-methoxypyridin-3-ol

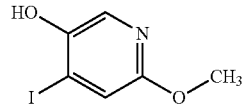

To a solution of 25.1 g (82% purity, 61.3 mmol) of 4-iodo-2-methoxy-5-(tetrahydro-2H-pyran-2-yloxy)pyridine in 50 ml of dioxane and 50 ml of water were added 50 ml (3 molar, 150 mmol) of hydrochloric acid, and the mixture was stirred at RT for 2 h. The reaction mixture was then filtered and the precipitate was rinsed with water and dried under high vacuum. Yield: 13.5 g (93% purity, 81% of theory).

LC/MS [Method 1]: $R_t$=0.76 min; MS (ESIpos): m/z=252 (M+H)$^+$, $^1$H-NMR (400 MHz, DMSO-d$_6$): δ [ppm]=7.70 (s, 1H), 7.22 (s, 1H), 3.74 (s, 3H).

Example 10.1E 5-(Difluoromethoxy)-4-iodo-2-methoxypyridine

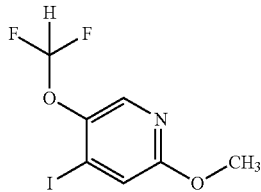

To a solution of 600 mg (93% purity, 2.22 mmol) of 4-iodo-6-methoxypyridin-3-ol in 4.8 ml of acetonitrile were added 4.8 ml of aqueous potassium hydroxide solution (6 M), the mixture was cooled in an ice bath, and 863 μl (75% purity, 3.56 mmol, 1.6 eq.) of difluoromethyl trifluormethanesulphonate [*Angew. Chem. Int. Ed.* 2013, 52, 1-5; *Journal of Fluorine Chemistry* 2009, 130, 667-670] were added with vigorous stirring. The reaction mixture was stirred for 2 min and diluted with 33 ml of water. The aqueous phase was extracted twice with 40 ml each time of diethyl ether. The combined organic phases were dried (sodium sulphate), filtered, concentrated under reduced pressure and dried. The crude product was purified by flash chromatography (silica gel, petroleum ether/ethyl acetate (12-20%) mixtures). Yield: 407 mg (90% purity, 55% of theory)

$^1$H-NMR (400 MHz, DMSO-d$_6$): δ [ppm]=8.1 (s, 1H), 7.45 (s, 1H), 7.16 (t, 1H), 3.84 (s, 3H).

Example 10.1F

4-Chloro-2-[5-(difluoromethoxy)-2-methoxypyridin-4-yl]benzonitrile

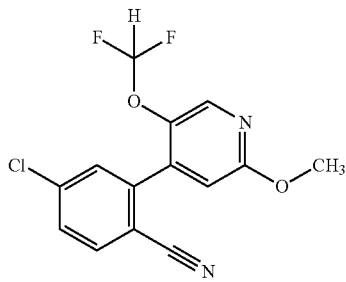 [SMILES: COc1cc(-c2cc(Cl)ccc2C#N)c(OC(F)F)cn1]

According to General Method 2A, 460 mg (90% purity, 1.38 mmol) of 5-(difluoromethoxy)-4-iodo-2-methoxypyridine were reacted with 299 mg (1.65 mmol, 1.2 eq.) of 5-chloro-2-cyanophenylboronic acid in the presence of [1,1-bis(diphenylphosphino)ferrocene]palladium(II) chloride/dichloromethane monoadduct. The crude product was purified by flash chromatography (silica gel, petroleum ether/ethyl acetate (10-15%) mixtures). Yield: 230 mg (80% purity, 43% of theory)

LC/MS [Method 1]: $R_t$=1.12 min; MS (ESIpos): m/z=311 (M+H)$^+$, $^1$H-NMR (400 MHz, DMSO-d$_6$): δ [ppm]=8.26 (s, 1H), 8.06 (d, 1H), 7.82-7.74 (m, 2H), 7.09 (s, 1H), 7.06 (t, 1H), 3.91 (s, 3H).

Example 10.1G

4-Chloro-2-[5-(difluoromethoxy)-2-oxo-1,2-dihydropyridin-4-yl]benzonitrile

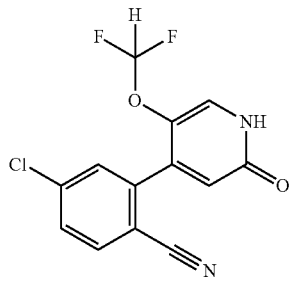 [SMILES: N#Cc1ccc(Cl)cc1-c1cc(=O)[nH]cc1OC(F)F]

According to General Method 3A, 230 mg (80% purity, 0.59 mmol) of 4-chloro-2-[5-(difluoromethoxy)-2-methoxypyridin-4-yl]benzonitrile were reacted with pyridinium hydrobromide. The crude product was purified by flash chromatography (silica gel, dichloromethane/methanol (3-25%) mixtures). Yield: 167 mg (95% of theory)

LC/MS [Method 1]: $R_t$=0.79 min; MS (ESIpos): m/z=297 (M+H)$^+$, $^1$H-NMR (400 MHz, DMSO-d$_6$): δ [ppm]=11.88 (br. s, 1H), 8.03 (d, 1H), 7.80-7.65 (m, 3H), 6.87 (t, 1H), 6.56 (s, 1H).

Example 11.1A tert-Butyl [4-(5-chloro-2-cyanophenyl)-5-(difluoromethoxy)-2-oxopyridin-1(2H)-yl]acetate

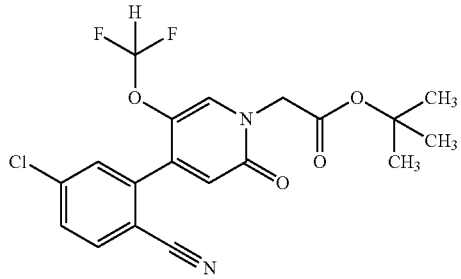 [SMILES: CC(C)(C)OC(=O)Cn1cc(OC(F)F)c(-c2cc(Cl)ccc2C#N)cc1=O]

According to General Method 4B, 1.19 g (92% purity, 3.69 mmol) of 4-chloro-2-[5-(difluoromethoxy)-2-oxo-1,2-dihydropyridin-4-yl]benzonitrile were reacted with 1.2 eq. of tert-butyl bromoacetate at 100° C. Yield: 1.30 g (95% purity, 81% of theory).

LC/MS [Method 1]: $R_t$=0.97 min; MS (ESIpos): m/z=411 (M+H)$^+$, $^1$H-NMR (400 MHz, DMSO-d$_6$): δ [ppm]=8.09-7.97 (m, 2H), 7.81-7.70 (m, 2H), 6.81 (t, 1H), 6.63 (s, 1H), 4.66 (s, 2H), 1.44 (s, 9H).

Example 11.1B tert-Butyl 2-[4-(5-chloro-2-cyanophenyl)-5-(difluoromethoxy)-2-oxopyridin-1(2H)-yl]-3-(pyridin-2-yl)propanoate (racemate)

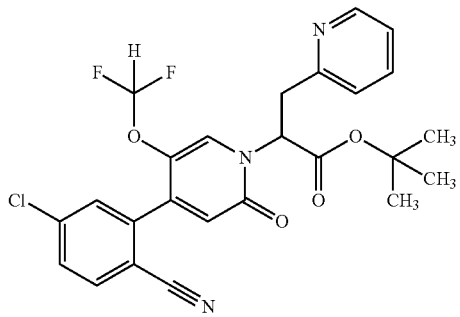 [SMILES: CC(C)(C)OC(=O)C(Cc1ccccn1)n1cc(OC(F)F)c(-c2cc(Cl)ccc2C#N)cc1=O]

To a solution of 800 mg (1.85 mmol) of tert-butyl [4-(5-chloro-2-cyanophenyl)-5-(difluoromethoxy)-2-oxopyridin-1(2H)-yl]acetate in 18 ml of tetrahydrofuran under argon at −78° C. were added dropwise 2.13 ml (1.0 M in THF, 1.15 eq.) of lithium bis(trimethylsilyl)amide, and the mixture was stirred for 15 min. 533 mg (91% purity, 2.59 mmol, 1.4 eq.) of neat pyridin-2-ylmethyl methanesulphonate were then added. The resulting reaction mixture was stirred at −78° C. for another 30 min and at RT for another 1.5 h. Saturated aqueous ammonium chloride solution was added to the reaction mixture. After phase separation, the aqueous phase was extracted with ethyl acetate. The combined organic phases were washed with saturated aqueous sodium chloride solution. The organic phase was dried (sodium sulphate), filtered and concentrated under reduced pressure. The crude product was then purified by means of normal phase chromatography (eluent: cyclohexane/ethyl acetate (0-75%) mixtures). Yield 250 mg (95% purity, 26% of theory)

LC/MS [Method 1]: $R_t$=1.00 min; MS (ESIpos): m/z=502 (M+H)$^+$.

$^1$H-NMR (400 MHz, DMSO-d$_6$): δ [ppm]=8.48 (d, 1H), 8.01 (d, 1H), 7.85 (s, 1H), 7.75 (dd, 1H), 7.72-7.63 (m, 2H), 7.26-7.17 (m, 2H), 6.68 (t, 1H), 6.55 (s, 1H), 5.63 (t, 1H), 3.65-3.55 (m, 2H), 1.37 (s, 9H).

Example 11.1C

2-[4-(5-Chloro-2-cyanophenyl)-5-(difluoromethoxy)-2-oxopyridin-1(2H)-yl]-3-(pyridin-2-yl)propanoic acid-trifluoroacetic acid (racemate)

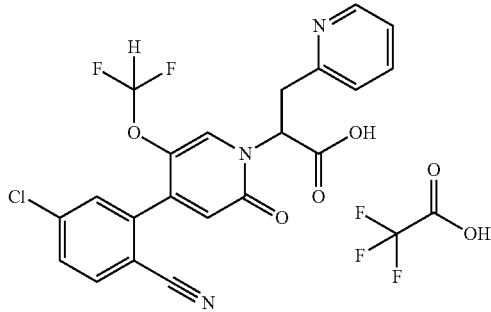

According to General Method 6A, 250 mg (0.47 mmol) of tert-butyl 2-[4-(5-chloro-2-cyanophenyl)-5-(difluoromethoxy)-2-oxopyridin-1(2H)-yl]-3-(pyridin-2-yl)propanoate (racemate) in 8 ml of dichloromethane were reacted with 4 ml of TFA. Yield: 300 mg (86% purity, 97% of theory)

LC/MS [Method 1]: $R_t$=0.66 min; MS (ESIpos): m/z=446 (M+H)$^+$.

$^1$H-NMR (400 MHz, DMSO-d$_6$): δ [ppm]=8.65 (d, 1H), 8.12-7.98 (m, 2H), 7.87 (s, 1H), 7.82-7.67 (m, 2H), 7.58-7.46 (m, 2H), 6.70 (t, 1H), 6.57 (s, 1H), 5.57 (dd, 1H), 3.80 (dd, 1H), 3.68 (dd, 1H).

Example 12.1A 4-(5-Chloro-2-fluorophenyl)-2,5-dimethoxypyridine

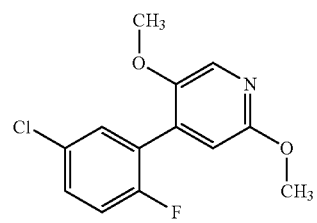 [SMILES: COc1cc(-c2cc(Cl)ccc2F)c(OC)cn1]

According to General Method 2A, 200 mg (1.09 mmol, 1.2 eq.) of (2,5-dimethoxypyridin-4-yl)boric acid were reacted with 274 mg (1.31 mmol) of 2-bromo-4-chloro-1-fluorobenzene in the presence of [1,1-bis(diphenylphosphino)ferrocene]palladium(II) chloride/dichloromethane monoadduct. After workup, the crude product was then purified by means of flash chromatography (silica gel 60, cyclohexane/dichloromethane 0-20% mixtures). Yield: 150 mg (50% of theory)

LC/MS [Method 1]: $R_t$=1.11 min; MS (ESIpos): m/z=268 (M+H)$^+$.

$^1$H-NMR (400 MHz, DMSO-d$_6$): δ [ppm]=8.00 (s, 1H), 7.53 (dd, 1H), 7.49 (dd, 1H), 7.40-7.32 (m, 1H), 6.80 (s, 1H), 3.84 (s, 3H), 3.78 (s, 3H)

Example 12.1B 4-(5-Chloro-2-fluorophenyl)-5-methoxypyridin-2(1H)-one

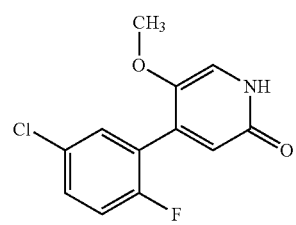 [SMILES: COc1c[nH]c(=O)cc1-c1cc(Cl)ccc1F]

According to General Method 3A, 4.45 g (16.46 mmol) of 4-(5-chloro-2-fluorophenyl)-2,5-dimethoxypyridine were reacted with pyridinium hydrochloride. Yield: 4.00 g (80% purity, 77% of theory).

LC/MS [Method 1]: $R_t$=0.75 min; MS (ESIpos): m/z=254 (M+H)$^+$.

¹H-NMR (400 MHz, DMSO-d₆): δ [ppm]=11.32 (bs, 1H), 7.53 (ddd, 1H), 7.49-7.42 (m, 1H), 7.34 (t, 1H), 7.21 (s, 1H), 6.36 (s, 1H), 3.61 (s, 3H).

Example 12.1C tert-Butyl [4-(5-chloro-2-fluorophenyl)-5-methoxy-2-oxopyridin-1(2H)-yl]acetate

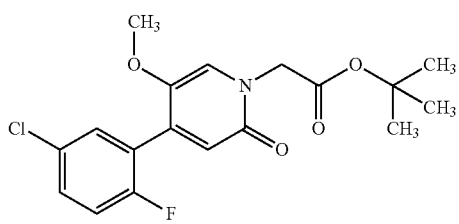 [SMILES: COc1cn(CC(=O)OC(C)(C)C)c(=O)cc1-c1cc(Cl)ccc1F]

According to General Method 4A, 4.0 g (80% purity, 12.62 mmol) of 4-(5-chloro-2-fluorophenyl)-5-methoxypyridin-2(1H)-one were reacted with 1.2 eq. of tert-butyl bromoacetate at 100° C. Yield: 3.85 g (83% of theory)

LC/MS [Method 1]: $R_t$=0.96 min, MS (ESIpos): m/z=368 (M+H)⁺,

¹H-NMR (400 MHz, DMSO-d₆): δ [ppm]=87.58-7.51 (m, 1H), 7.51-7.42 (m, 2H), 7.36 (dd, 1H), 6.42 (s, 1H), 4.58 (s, 2H), 3.59 (s, 3H), 1.44 (s, 9 H).

Example 12.1D tert-Butyl 2-[4-(5-chloro-2-fluorophenyl)-5-methoxy-2-oxopyridin-1(2H)-yl]-3-(pyridin-2-yl)propanoate (racemate)

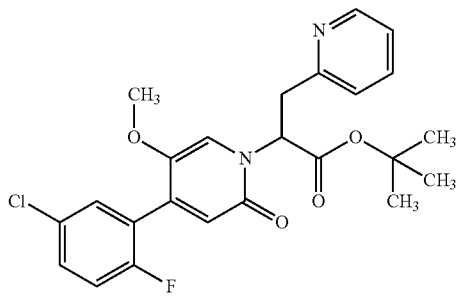 [SMILES: COc1cn(C(Cc2ccccn2)C(=O)OC(C)(C)C)c(=O)cc1-c1cc(Cl)ccc1F]

To a solution of 1.00 g (2.72 mmol) of tert-butyl [4-(5-chloro-2-fluorophenyl)-5-methoxy-2-oxopyridin-1(2H)-yl]acetate in 20 ml of tetrahydrofuran under argon at −78° C. were added dropwise 6.80 ml (1.0 M in THF, 2.5 eq.) of lithium bis(trimethylsilyl)amide, and the mixture was stirred for 15 min. Subsequently, 963 mg (3.81 mmol, 1.4 eq.) of 2-(bromomethyl)pyridine hydrobromide were added. The resulting reaction mixture was stirred at −78° C. for another 30 min and at RT for another 1.5 h. Saturated aqueous ammonium chloride solution was added to the reaction mixture. After phase separation, the aqueous phase was extracted with ethyl acetate. The combined organic phases were washed with saturated aqueous sodium chloride solution. The organic phase was dried (sodium sulphate), filtered and concentrated under reduced pressure. The crude product was then purified by means of normal phase chromatography (eluent: cyclohexane/ethyl acetate (0-70%) mixtures). Yield: 1.04 g (82% of theory)

LC/MS [Method 1]: $R_t$=0.97 min; MS (ESIpos): m/z=459 (M+H)⁺.

¹H-NMR (400 MHz, DMSO-d₆): δ [ppm]=8.49 (dd, 1H), 7.78-7.62 (m, 1H), 7.53 (ddd, 1H), 7.44 (dd, 1H), 7.33 (t, 1H), 7.29-7.12 (m, 3H), 6.37 (s, 1H), 5.60 (dd, 1H), 3.67-3.51 (m, 2H), 3.50 (s, 3H), 1.36 (s, 9H).

Example 12.1E

2-[4-(5-Chloro-2-fluorophenyl)-5-methoxy-2-oxopyridin-1(2H)-yl]-3-(pyridin-2-yl)propanoic acid hydrochloride (racemate)

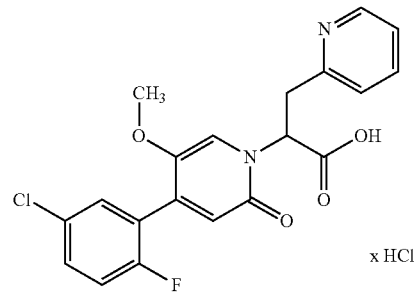 [SMILES: COc1cn(C(Cc2ccccn2)C(=O)O)c(=O)cc1-c1cc(Cl)ccc1F]

According to General Method 6B, 1.04 g (2.22 mmol) of tert-butyl 2-[4-(5-chloro-2-cyanophenyl)-5-methoxy-2-oxopyridin-1(2H)-yl]-3-(pyridin-4-yl)propanoate (racemate) and 22.4 ml of a hydrogen chloride in dioxane (4 M) solution were reacted. Yield: 1.15 g (75% purity, 88% of theory).

LC/MS [Method 1]: $R_t$=0.70 min; MS (ESIpos): m/z=403 (M+H)⁺.

¹H-NMR (400 MHz, DMSO-d₆): δ [ppm]=8.78 (d, 1H), 8.41-8.32 (m, 1H), 7.92-7.74 (m, 2H), 7.54 (ddd, 1H), 7.50-7.41 (m, 2H), 7.38-7.31 (m, 1H), 6.40 (s, 1H), 5.65-5.57 (m, 1H), 3.98 (dd, 1H), 3.74 (dd, 1H), 3.55 (s, 3H).

Example 13.1A (5-Chloro-2-methoxypyridin-4-yl)boronic acid

According to General Method 1A, 10.0 g (69.65 mmol) of 5-chloro-2-methoxypyridine were reacted. The desired product precipitated on acidification with hydrochloric acid (2N). Yield: 10.44 g (91% purity, 73% of theory).

LC/MS [Method 1]: $R_t$=0.50 min; MS (ESIpos): m/z=188 (M+H)⁺

¹H-NMR (400 MHz, DMSO-d₆): δ [ppm]=8.64 (bs, 2H), 8.12 (s, 1H), 6.81 (s, 1H), 3.82 (s, 3H).

Example 13.1B

4-Chloro-2-(5-chloro-2-methoxypyridin-4-yl)benzonitrile

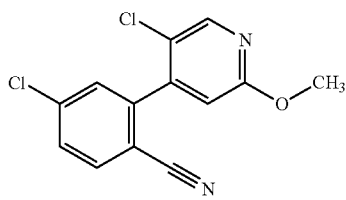 [SMILES: COc1cc(-c2cc(Cl)ccc2C#N)c(Cl)cn1]

According to General Method 2A, 5.36 g (91% purity, 26.03 mmol) of 5-chloro-2-methoxypyridin-4-ylboronic acid were reacted with 5.12 g (23.66 mmol) of 2-bromo-4-chlorobenzonitrile in the presence of [1,1-bis(diphenylphosphino)ferrocene]palladium(II) chloride/dichloromethane monoadduct. After workup, the crude product was then purified by flash chromatography (silica gel 60, cyclohexane/dichloromethane mixtures). Yield: 4.11 g (91% purity, 52% of theory).

LC/MS [Method 1]: $R_t$=1.17 min; MS (ESIpos): m/z=279 (M+H)$^+$.

Example 13.1C

4-Chloro-2-(5-chloro-2-oxo-1,2-dihydropyridin-4-yl)benzonitrile

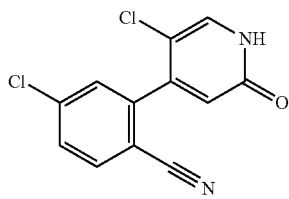 [SMILES: N#Cc1ccc(Cl)cc1-c1cc(=O)[nH]cc1Cl]

According to General Method 3A, 6.34 g (93% purity, 21.12 mmol) of 4-chloro-2-(5-chloro-2-methoxypyridin-4-yl)benzonitrile were reacted with pyridinium hydrochloride. Yield: 4.23 g (76% of theory)

LC/MS [Method 1]: $R_t$=0.82 min; MS (ESIpos): m/z=265 (M+H)$^+$.

Example 13.1D tert-Butyl [5-chloro-4-(5-chloro-2-cyanophenyl)-2-oxopyridin-1(2H)-yl]acetate

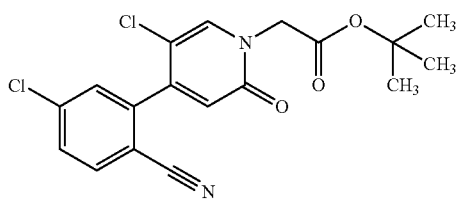 [SMILES: CC(C)(C)OC(=O)Cn1cc(Cl)c(-c2cc(Cl)ccc2C#N)cc1=O]

According to General Method 4A, 3.1 g (11.46 mmol) of 4-chloro-2-(5-chloro-2-oxo-1,2-dihydropyridin-4-yl)benzonitrile were reacted with 1.2 eq. of tert-butyl bromoacetate at 100° C. Yield: 3.65 g (84% of theory)

LC/MS [Method 8]: $R_t$=1.34 min, MS (ESIneg): m/z=377 (M–H)$^-$, $^1$H-NMR (400 MHz, DMSO-d$_6$): δ [ppm]=8.20 (s, 1H), 8.09-8.20 (m, 1H), 7.85-7.72 (m, 2H), 6.67 (s, 1H), 4.65 (s, 2H), 1.44 (s, 9H).

Example 13.1E tert-Butyl 2-[5-chloro-4-(5-chloro-2-cyanophenyl)-2-oxopyridin-1(2H)-yl]-3-(pyridin-2-yl)propanoate (racemate)

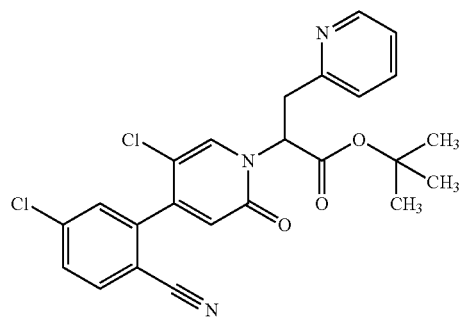 [SMILES: CC(C)(C)OC(=O)C(Cc1ccccn1)n1cc(Cl)c(-c2cc(Cl)ccc2C#N)cc1=O]

To a solution of 1.00 g (2.34 mmol) of tert-butyl [5-chloro-4-(5-chloro-2-cyanophenyl)-2-oxopyridin-1(2H)-yl]acetate in 20 ml of tetrahydrofuran under argon at −78° C. were added dropwise 3.56 ml (1.0 M in THF, 1.35 eq.) of lithium bis(trimethylsilyl)amide, and the mixture was stirred for 15 min. 568 mg (3.03 mmol, 1.15 eq.) of neat pyridin-2-ylmethyl methanesulphonate were then added. The resulting reaction mixture was stirred at −78° C. for another 15 min and at RT for another 45 min. Saturated aqueous ammonium chloride solution was added to the reaction mixture. After phase separation, the aqueous phase was extracted with ethyl acetate. The combined organic phases were washed with saturated aqueous sodium chloride solution. The organic phase was dried (sodium sulphate), filtered and concentrated under reduced pressure. The crude product was then purified by means of normal phase chromatography (eluent: cyclohexane/ethyl acetate (20-50%) mixtures). Yield: 698 mg (56% of theory)

LC/MS [Method 1]: $R_t$=1.09 min; MS (ESIpos): m/z=470 (M+H)$^+$.

$^1$H-NMR (400 MHz, DMSO-d$_6$): δ [ppm]=8.49 (dd, 1H), 8.03 (d, 2H), 7.77 (dd, 1H), 7.73 (d, 1H), 7.69 (td, 1H), 7.26-7.17 (m, 2H), 6.60 (s, 1H), 5.69-5.55 (m, 1H), 3.65-3.55 (m, 2H), 1.40 (s, 9H)

Example 13.1F

2-[5-Chloro-4-(5-chloro-2-cyanophenyl)-2-oxopyridin-1(2H)-yl]-3-(pyridin-2-yl)propanoic acid (racemate)

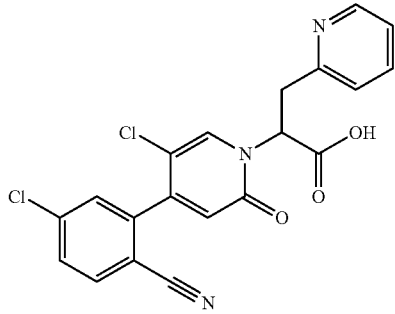 [SMILES: N#Cc1ccc(Cl)cc1-c1cc(=O)n(C(Cc2ccccn2)C(=O)O)cc1Cl]

According to General Method 6A, 698 mg (1.48 mmol) of tert-butyl 2-[5-chloro-4-(5-chloro-2-cyanophenyl)-2-oxopyridin-1(2H)-yl]-3-(pyridin-2-yl)propanoate (racemate) in 24 ml of dichloromethane were reacted with 6 ml (78 mmol) of TFA. The crude product was then purified by means of preparative HPLC (water/acetonitrile/0.1% formic acid gradient). Yield: 298 mg (49% of theory).

LC/MS [Method 1]: $R_t$=0.71 min; MS (ESIpos): m/z=414 (M+H)$^+$, $^1$H-NMR (400 MHz, DMSO-d$_6$): δ [ppm]=13.30 (bs, 1H), 8.52-8.41 (m, 1H), 8.15-7.93 (m, 2H), 7.79-7.71 (m, 2H), 7.67 (td, 1H), 7.28-7.11 (m, 2H), 6.56 (s, 1H), 5.79-5.50 (m, 1H), 3.63 (d, 2H).

Example 14.1A

2-[(Benzyloxy)methyl]tetrahydro-2H-pyran (racemate)

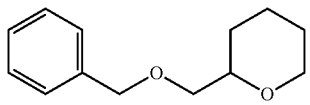 [SMILES: c1ccc(COCC2CCCCO2)cc1]

At 0° C., a solution of 25.0 g (215 mmol) of tetrahydro-2H-pyran-2-ylmethanol (racemate) in 500 ml of THF was slowly added dropwise to a suspension of 9.47 g (237 mmol, 60% in mineral oil) of sodium hydride in 500 ml of THF, and after the addition had ended, the mixture was stirred at 0° C. for another 30 min. 25.7 ml (215 mmol) of benzyl bromide were then added, and the mixture was stirred at 0° C. for another 30 min and at room temperature for another 1 h. The reaction was terminated by addition of 200 ml of saturated aqueous ammonium chloride solution, and the phases were separated. The aqueous phase was extracted twice with 200 ml of methyl tert-butyl ether. The combined organic phases were dried over magnesium sulphate and filtered, and the solvent was removed under reduced pressure. The crude product was purified by column chromatography (ethyl acetate/cyclohexane gradient, 340 g silica cartridge, flow rate: 100 ml/min), giving the title compound. Yield: 41.9 g (94% of theory)

LC/MS [Method 3]: $R_t$=2.18 min; MS (ESIpos): m/z=207 (M+H)$^+$, $^1$H-NMR (400 MHz, DMSO-d$_6$): δ [ppm]=7.37-7.25 (m, 5H), 4.47 (s, 2H), 3.87-3.81 (m, 1H), 3.47-3.28 (m, 4H), 1.80-1.72 (m, 1H), 1.58-1.37 (m, 4H), 1.25-1.13 (m, 1H).

Example 14.1B (R)-2-[(Benzyloxy)methyl]tetrahydro-2H-pyran

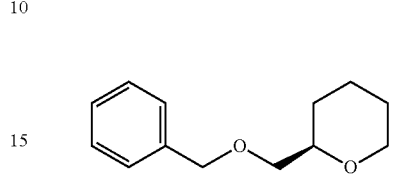

Enantiomer separation of 41.9 g of the racemate from Example 3.12A gave 16.7 g of the title compound Example 3.12B (enantiomer 1): chiral HPLC: $R_t$=5.28 min; 99% ee, purity 93%.

Optical rotation: $[α]_{589}^{20.0}$=+14.9° (c 0.43 g/100 cm$^3$, chloroform)

Separation method: column: OD-H 5 μm 250 mm×20 mm; eluent: 95% isohexane, 5% 2-propanol; temperature: 25° C.; flow rate: 25 ml/min; UV detection: 210 nm.

Analysis: column: OD-H 5 μm 250 mm×4.6 mm; eluent: 95% isohexane, 5% 2-propanol; flow rate: 1 ml/min; UV detection: 220 nm.

Example 14.1C (S)-2-[(Benzyloxy)methyl]tetrahydro-2H-pyran

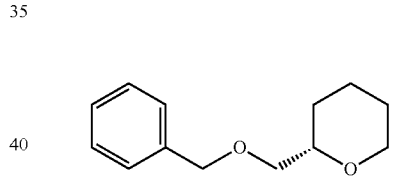

Enantiomer separation of 41.9 g of the racemate from Example 3.12A gave 17.0 g of the title compound Example 3.12C (enantiomer 2): chiral HPLC: $R_t$=7.36 min; 96% ee, 96% purity.

Optical rotation: $[α]_{589}^{20.0}$=−13.9° (c 0.61 g/100 cm$^3$, chloroform)

Separation method: column: OD-H 5 μm 250 mm×20 mm; eluent: 95% isohexane, 5% 2-propanol; temperature: 25° C.; flow rate: 25 ml/min; UV detection: 210 nm.

Analysis: column: OD-H 5 μm 250 mm×4.6 mm; eluent: 95% isohexane, 5% 2-propanol; flow rate: 1 ml/min; UV detection: 220 nm.

Example 14.1D (2S)-Tetrahydro-2H-pyran-2-ylmethanol

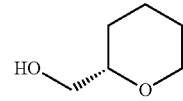

To a solution of 17.0 g (82.4 mmol) of (S)-2-[(benzyloxy)methyl]tetrahydro-2H-pyran (96% ee, 96% purity) in 120 ml of ethanol were added 3.51 g (3.30 mmol) of palladium on carbon (10%), and hydrogenation was effected at room temperature and under standard pressure overnight. Another 1.75 g (1.65 mmol) of palladium on carbon (10%) were then added, and hydrogenation was effected at room temperature for a further 72 h. Subsequently, the reaction mixture was filtered through Celite and the filtrate was concentrated. The residue was purified by chromatography (silica, dichloromethane/methanol gradient) and the product fractions were freed of the solvent at <25° C. and >50 mbar. Yield: 8.23 g (86% of theory)

Optical rotation: $[\alpha]_{589}^{20.0}$=+9.1° (c 0.36 g/100 cm$^3$, chloroform), cf. A. Aponick, B. Biannic, Org. Lett. 2011, 13, 1330-1333.

GC/MS [Method 7]: $R_t$=1.82 min; MS: m/z=116 (M)$^+$,
$^1$H-NMR (400 MHz, DMSO-d$_6$): δ [ppm]=4.51 (t, 1H), 3.87-3.81 (m, 1H), 3.37-3.18 (m, 4H), 1.80-1.71 (m, 1H), 1.59-1.50 (m, 1H), 1.49-1.36 (m, 3H), 1.19-1.05 (m, 1H).

Example 14.1E (2S)-Tetrahydro-2H-pyran-2-ylmethyl trifluoromethanesulphonate

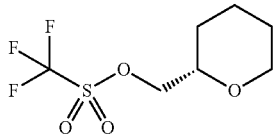 [SMILES: O=S(=O)(OC[C@@H]1CCCCO1)C(F)(F)F]

According to General Method 7A, 330 mg (2.84 mmol) of (2S)-tetrahydro-2H-pyran-2-ylmethanol were reacted with 0.57 ml (3.41 mmol, 1.2 eq.) of trifluoromethanesulphonic anhydride in the presence of 0.48 ml (3.41 mmol, 1.2 eq.) of triethylamine. The crude product was reacted in the next stage without further purification.

$^1$H-NMR (400 MHz, DMSO-d$_6$): δ [ppm]=4.32 (dd, 1H), 4.18 (dd, 1H), 4.00-3.92 (m, 1H), 3.60-3.52 (m, 1H), 3.48-3.39 (m, 1H), 1.85-1.74 (m, 1H), 1.56-1.41 (m, 4H), 1.28-1.14 (m, 1H).

Example 14.1F tert-Butyl 2-[5-chloro-4-(5-chloro-2-cyanophenyl)-2-oxopyridin-1(2H)-yl]-3-[(2S)-tetrahydro-2H-pyran-2-yl]propanoate (diastereomer mixture)

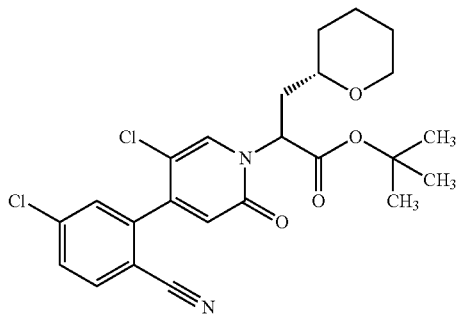 [SMILES: CC(C)(C)OC(=O)C(C[C@@H]1CCCCO1)n1cc(Cl)c(-c2cc(Cl)ccc2C#N)cc1=O]

According to General Method 8A, 2.13 g (5.60 mmol) of tert-butyl 2-[5-chloro-4-(5-chloro-2-cyanophenyl)-2-oxopyridin-1(2H)-yl]-3-[(2S)-tetrahydro-2H-pyran-2-yl]propanoate, 1.70 g (90% purity, 6.16 mmol) of (2S)-tetrahydro-2H-pyran-2-ylmethyl trifluoromethanesulphonate and 5.56 ml (5.56 mmol) of lithium bis(trimethylsilyl)amide (1 M in THF) in 90 ml of THF were reacted. After aqueous workup, the crude product was then purified by means of normal phase chromatography (eluent: cyclohexane/ethyl acetate (15-40%) mixtures). Yield 1.61 g (95% purity, 57% of theory).

LC/MS [Method 1]: $R_t$=1.26 min; MS (ESIpos): m/z=477 (M-15)$^+$.

Example 14.1G

2-[5-Chloro-4-(5-chloro-2-cyanophenyl)-2-oxopyridin-1(2H)-yl]-3-[(2S)-tetrahydro-2H-pyran-2-yl]propanoic acid (diastereomer mixture)

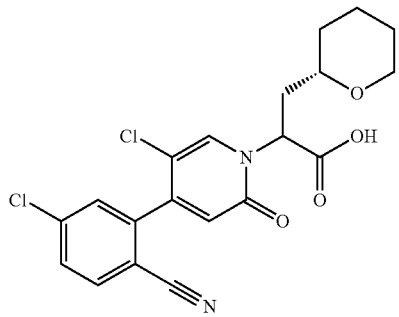 [SMILES: N#Cc1ccc(Cl)cc1-c1cc(=O)n(C(C[C@@H]2CCCCO2)C(=O)O)cc1Cl]

According to General Method 6A, 1.61 g (95% purity, 3.20 mmol) of tert-butyl 2-[5-chloro-4-(5-chloro-2-cyanophenyl)-2-oxopyridin-1(2H)-yl]-3-[(2S)-tetrahydro-2H-pyran-2-yl]propanoate (diastereomer mixture) in 64 ml of dichloromethane were reacted with 12.8 ml of TFA. The crude product was then purified by means of preparative HPLC (water/acetonitrile/0.1% formic acid gradient). Yield: 1.05 g (78% of theory)

LC/MS [Method 1]: $R_t$=0.97 min; MS (ESIpos): m/z=421 (M+H)$^+$,
$^1$H-NMR (400 MHz, DMSO-d$_6$): δ [ppm]=13.09 (bs, 1H), 8.14-8.01 (m, 2H), 7.86-7.74 (m, 2H), 6.67-6.56 (m, 1H), 5.39-5.13 (m, 1H), 3.90-3.75 (m, 1H), 3.27-2.74 (m, 2H), 2.44-2.22 (m, 1H), 2.16-2.00 (m, 1H), 1.79-1.67 (m, 1H), 1.64-1.09 (m, 5H).

Example 15.1A tert-Butyl 2-[5-chloro-4-(5-chloro-2-cyanophenyl)-2-oxopyridin-1(2H)-yl]-3-(1,3-oxazol-4-yl)propanoate (racemate)

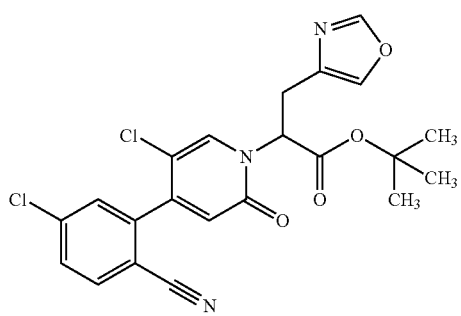 [SMILES: CC(C)(C)OC(=O)C(Cc1cocn1)n1cc(Cl)c(-c2cc(Cl)ccc2C#N)cc1=O]

According to General Method 8B, 600 mg (1.58 mmol) of tert-butyl [5-chloro-4-(5-chloro-2-cyanophenyl)-2-oxopyridin-1(2H)-yl]acetate were reacted with 717.6 mg (50% purity, 2.22 mmol, 1.4 eq.) of 4-(bromomethyl)-1,3-oxazole. Yield: 530 mg (73% of theory)

LC/MS [Method 1]: $R_t$=1.07 min; MS (ESIpos): m/z=460 (M+H)$^+$, $^1$H-NMR (400 MHz, DMSO-d$_6$): δ [ppm]=8.29 (s, 1H), 8.11-7.97 (m, 2H), 7.87-7.69 (m, 3H), 6.62 (s, 1H), 5.45-5.25 (m, 1H), 3.55-3.38 (m, 1H), 3.38-3.25 (m, 1H), 1.41 (s, 9H).

According to General Method 8B, 600 mg (1.39 mmol) of tert-butyl [4-(5-chloro-2-cyanophenyl)-5-(difluoromethoxy)-2-oxopyridin-1(2H)-yl]acetate were reacted with 421 mg (80% purity, 2.08 mmol, 1.5 eq.) of 5-(bromomethyl)-1,3-oxazole. Yield: 320 mg (47% of theory)

LC/MS [Method 1]: $R_t$=0.97 min; MS (ESIpos): m/z=492 (M+H)$^+$, $^1$H-NMR (400 MHz, DMSO-d$_6$): δ [ppm]=8.18 (s, 1H), 8.03 (d, 1H), 7.86 (s, 1H), 7.82-7.71 (m, 2H), 6.90 (s, 1H), 6.72 (t, 1H), 6.62 (s, 1H), 5.35 (dd, 1H), 3.68-3.48 (m, 2H), 1.40 (s, 9H).

Example 15.1B

2-[5-Chloro-4-(5-chloro-2-cyanophenyl)-2-oxopyridin-1(2H)-yl]-3-(1,3-oxazol-4-yl)propanoic acid (racemate)

Example 16.1B

2-[4-(5-Chloro-2-cyanophenyl)-5-(difluoromethoxy)-2-oxopyridin-1(2H)-yl]-3-(1,3-oxazol-5-yl)propanoic acid (racemate)

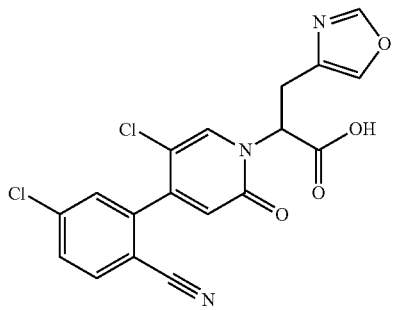 [SMILES: N#Cc1ccc(Cl)cc1-c1cc(=O)n(C(Cc2cocn2)C(=O)O)cc1Cl]

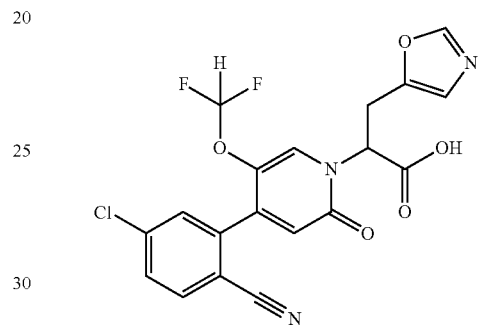

According to General Method 6A, 530 mg (1.15 mmol) of tert-butyl 2-[5-chloro-4-(5-chloro-2-cyanophenyl)-2-oxopyridin-1(2H)-yl]-3-(1,3-oxazol-4-yl)propanoate (racemate) in 12 ml of dichloromethane were reacted with 6 ml (77.9 mmol) of TFA were reacted. Yield: 359 mg (77% of theory)

LC/MS [Method 1]: $R_t$=0.78 min; MS (ESIpos): m/z=404 (M+H)$^+$, $^1$H-NMR (400 MHz, DMSO-d$_6$): δ [ppm]=13.36 (br. s, 1H), 8.26 (s, 1H), 8.11-7.98 (m, 2H), 7.87-7.67 (m, 3H), 6.59 (s, 1H), 5.42 (dd, 1H), 3.59-3.41 (m, 1H), 3.38-3.28 (m, 1 H).

According to General Method 6A, 320 mg (0.65 mmol) of tert-butyl 2-[4-(5-chloro-2-cyanophenyl)-5-(difluoromethoxy)-2-oxopyridin-1(2H)-yl]-3-(1,3-oxazol-5-yl) propanoate (racemate) in 10 ml of dichloromethane were reacted with 5 ml (64.9 mmol) of TFA. Yield: 290 mg (quant.)

LC/MS [Method 1]: $R_t$=0.74 min; MS (ESIpos): m/z=436 (M+H)$^+$, $^1$H-NMR (400 MHz, DMSO-d$_6$): δ [ppm]=13.42 (br. s, 1H), 8.15 (s, 1H), 8.03 (d, 1H), 7.87 (s, 1H), 7.81-7.69 (m, 2H), 6.86 (s, 1H), 6.72 (t, 1H), 6.60 (s, 1H), 5.37 (dd, 1H), 3.64 (dd, 2H), 3.53 (dd, 1H).

Example 16.1A tert-Butyl 2-[4-(5-chloro-2-cyanophenyl)-5-(difluoromethoxy)-2-oxopyridin-1(2H)-yl]-3-(1,3-oxazol-5-yl)propanoate (racemate)

Example 17.1A tert-Butyl 2-[5-chloro-4-(5-chloro-2-cyanophenyl)-2-oxopyridin-1(2H)-yl]-3-(1,3-oxazol-5-yl)propanoate (racemate)

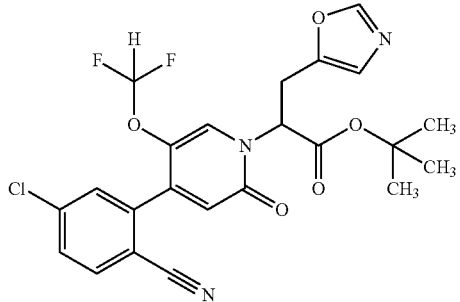 [SMILES: CC(C)(C)OC(=O)C(Cc1cnco1)n1cc(OC(F)F)c(-c2cc(Cl)ccc2C#N)cc1=O]

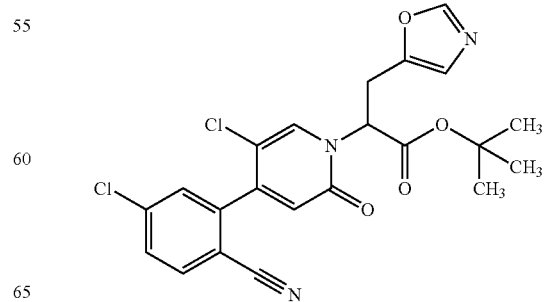

According to General Method 8B, 610 mg (1.61 mmol) of tert-butyl [5-chloro-4-(5-chloro-2-cyanophenyl)-2-oxopyridin-1(2H)-yl]acetate were reacted with 1.57 g (23% purity, 2.25 mmol, 1.4 eq.) of 5-(bromomethyl)-1,3-oxazole. Yield: 468 mg (83% purity, 52% of theory)

LC/MS [Method 1]: $R_t$=1.05 min; MS (ESIpos): m/z=460 (M+H)$^+$.

Example 17.1B

2-[5-Chloro-4-(5-chloro-2-cyanophenyl)-2-oxopyridin-1(2H)-yl]-3-(1,3-oxazol-5-yl)propanoic acid (racemate)

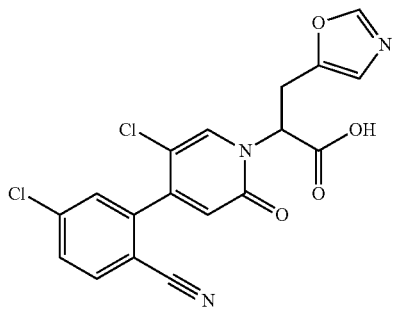 [SMILES: N#Cc1ccc(Cl)cc1-c1cc(=O)n(C(Cc2cnco2)C(=O)O)cc1Cl]

According to General Method 6A, 468 mg (83% purity, 0.84 mmol) of tert-butyl 2-[5-chloro-4-(5-chloro-2-cyanophenyl)-2-oxopyridin-1(2H)-yl]-3-(1,3-oxazol-5-yl)propanoate (racemate) in 9 ml of dichloromethane were reacted with 4.5 ml (58.4 mmol) of TFA. Yield: 290 mg (85% purity, 72% of theory)

LC/MS [Method 1]: $R_t$=0.76 min; MS (ESIpos): m/z=404 (M+H)$^+$, $^1$H-NMR (400 MHz, DMSO-d$_6$): δ [ppm]=13.48 (br. s, 1H), 8.17 (s, 1H), 8.10 (s, 1H), 8.08-8.01 (m, 1H), 7.81-7.75 (m, 2H), 6.87 (s, 1H), 6.64 (s, 1H), 5.39 (br. s, 1H), 3.65 (dd, 1H), 3.56 (dd, 1H).

Example 18.1A

2-Methoxyethyl trifluoromethanesulphonate

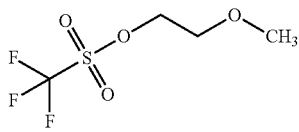

To a solution of 4.0 g (52.56 mmol, 1 eq.) of 2-methoxyethanol and 8.79 ml (63.1 mmol, 1.2 eq.) of triethylamine in 40 ml of diethyl ether under argon at −78° C. were added dropwise 9.29 ml (55.19 mmol, 1.05 eq.) of trifluoromethanesulphonic anhydride and the mixture was stirred for 45 min. The resulting suspension was filtered at −78° C. through a cannula. The filtrate was washed with a mixture of saturated aqueous ammonium chloride solution and 1 M hydrochloric acid (3:1). After phase separation, the aqueous phase was extracted with diethyl ether. The combined organic phases were dried (sodium sulphate), filtered and concentrated under reduced pressure. The crude product was used without further purification. Yield: 9.50 g (95% purity, 82% of theory).

$^1$H-NMR (400 MHz, DMSO-d$_6$): δ [ppm]=4.46-4.37 (m, 2H), 3.66-3.54 (m, 2H), 3.33 (s, 3H)

Example 18.1B tert-Butyl 2-[5-chloro-4-(5-chloro-2-cyanophenyl)-2-oxopyridin-1(2H)-yl]-4-methoxybutanoate (racemate)

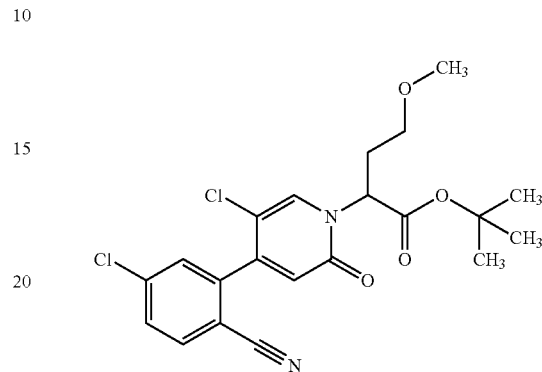

According to General Method 8B, 2.0 g (5.27 mmol) of tert-butyl [5-chloro-4-(5-chloro-2-cyanophenyl)-2-oxopyridin-1(2H)-yl]acetate in the presence of 7.12 ml (7.12 mmol, 1.35 eq.) of lithium bis(trimethylsilyl)amide (1M in THF) were reacted with 1.33 g (95% purity, 6.06 mmol, 1.15 eq.) of 2-methoxyethyl trifluoromethanesulphonate. Yield: 2.10 g (94% purity, 86% of theory).

LC/MS [Method 1]: $R_t$=1.14 min; MS (ESIpos): m/z=437 (M+H)$^+$, $^1$H-NMR (400 MHz, DMSO-d$_6$): δ [ppm]=8.16-8.10 (m, 1H), 8.09-8.02 (m, 1H), 7.73-7.84 (m, 2H), 6.64 (s, 1H), 5.25-5.07 (m, 1H), 3.44-3.36 (m, 1H), 3.22-3.12 (m, 4H), 2.41-2.27 (m, 2H).

Example 18.1C

2-[5-Chloro-4-(5-chloro-2-cyanophenyl)-2-oxopyridin-1(2H)-yl]-4-methoxybutanoate (racemate)

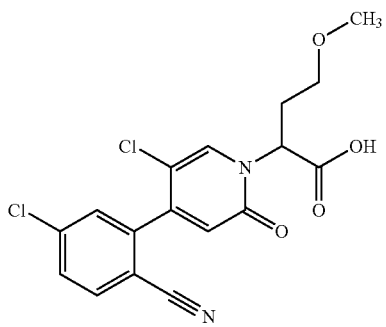 [SMILES: COCCC(C(=O)O)n1cc(Cl)c(-c2cc(Cl)ccc2C#N)cc1=O]

According to General Method 6A, 2.1 g (94% purity, 4.51 mmol) of tert-butyl 2-[5-chloro-4-(5-chloro-2-cyanophenyl)-2-oxopyridin-1(2H)-yl]-4-methoxybutanoate (racemate) were reacted. Yield: 1.89 g (quant.)

LC/MS [Method 1]: $R_t$=0.85 min; MS (ESIpos): m/z=381 (M+H)$^+$, $^1$H-NMR (400 MHz, DMSO-d$_6$): δ [ppm]=13.19 (br. s, 1H), 8.15 (s, 1H), 8.05 (d, 1H), 7.82 (d, 1H), 7.81-7.76 (m, 1H), 6.63 (s, 1H), 5.31-5.13 (m, 1H), 3.46-3.35 (m, 1H), 3.22-3.08 (m, 4H), 2.43-2.27 (m, 2H).

Example 19.1A tert-Butyl 2-[4-(5-chloro-2-fluorophenyl)-5-methoxy-2-oxopyridin-1(2H)-yl]-3-(3-methyl-1,2-oxazol-5-yl)propanoate (racemate)

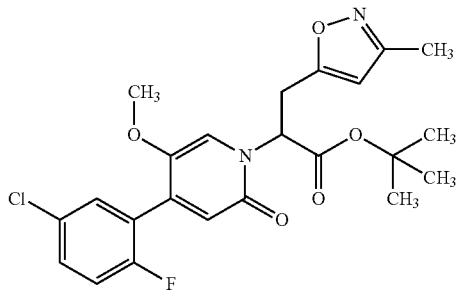 [SMILES: COc1cn(C(Cc2cc(C)no2)C(=O)OC(C)(C)C)c(=O)cc1-c1cc(Cl)ccc1F]

To a solution of 900 mg (2.45 mmol) of tert-butyl [4-(5-chloro-2-fluorophenyl)-5-methoxy-2-oxopyridin-1 (2H)-yl]acetate in 18 ml of tetrahydrofuran under argon at −78° C. were added dropwise 3.06 ml (1.0 M in THF, 1.25 eq.) of lithium bis(trimethylsilyl)amide, and the mixture was stirred for 30 min. Subsequently, 635 mg (3.43 mmol, 1.4 eq.) of 5-(bromomethyl)-3-methyl-1,2-oxazole were added. The resulting reaction mixture was stirred at −78° C. for another 30 min and at RT for another 90 min. Saturated aqueous ammonium chloride solution was added to the reaction mixture. After phase separation, the aqueous phase was extracted with ethyl acetate. The combined organic phases were washed with saturated aqueous sodium chloride solution. The organic phase was dried (sodium sulphate), filtered and concentrated under reduced pressure. The crude product was then purified by means of normal phase chromatography (eluent: cyclohexane/ethyl acetate (0-38%) mixtures). Yield: 1.00 g (88% of theory)

LC/MS [Method 1]: $R_t$=1.10 min; MS (ESIpos): m/z=463 (M+H)$^+$, $^1$H-NMR (400 MHz, DMSO-d$_6$): δ [ppm]=7.54 (ddd, 1H), 7.48 (dd, 1H), 7.35 (t, 1H), 7.31 (s, 1H), 6.43 (s, 1H), 6.13 (s, 1H), 5.35 (dd, 1H), 3.68-3.56 (m, 2H), 3.55 (s, 3H), 2.16 (s, 3H), 1.40 (m, 9H).

Example 19.1B

2-[4-(5-Chloro-2-fluorophenyl)-5-methoxy-2-oxopyridin-1(2H)-yl]-3-(3-methyl-1,2-oxazol-5-yl)propanoic acid (racemate)

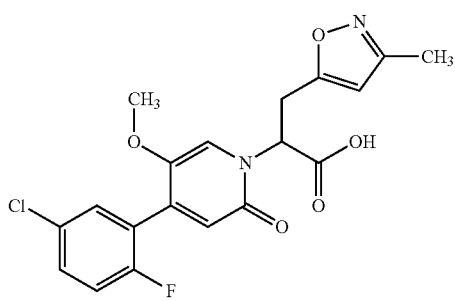 [SMILES: COc1cn(C(Cc2cc(C)no2)C(=O)O)c(=O)cc1-c1cc(Cl)ccc1F]

According to General Method 6B, 1.06 g (3.20 mmol) of tert-butyl 2-[4-(5-chloro-2-fluorophenyl)-5-methoxy-2-oxopyridin-1(2H)-yl]-3-(3-methyl-1,2-oxazol-5-yl)propanoate (racemate) and 23 ml of a hydrogen chloride in dioxane (4 M) solution were reacted. Yield: 0.98 g (90% purity, 95% of theory).

LC/MS [Method 1]: $R_t$=0.78 min; MS (ESIpos): m/z=407 (M+H)$^+$, $^1$H-NMR (400 MHz, DMSO-d$_6$): δ [ppm]=13.26 (bs, 1H), 7.61-7.41 (m, 2H), 7.41-7.24 (m, 2H), 6.41 (s, 1H), 6.11 (s, 1H), 5.39 (dd, 1H), 3.72-3.63 (m, 1H), 3.63-3.56 (m, 1H), 3.54 (s, 3H), 2.15 (s, 3H).

Example 20.1A tert-Butyl 5-({2-[4-(5-chloro-2-cyanophenyl)-5-methoxy-2-oxopyridin-1(2H)-yl]butanoyl}amino) pyridine-2-carboxylate (racemate)

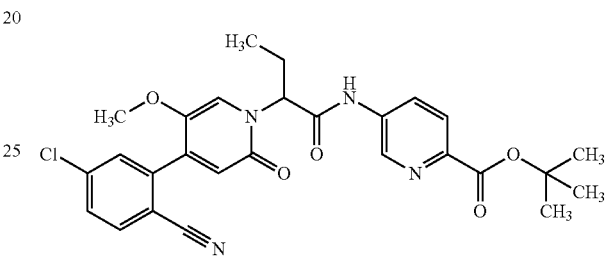

According to General Method 5B, 150 mg (0.43 mmol) of 2-[4-(5-chloro-2-cyanophenyl)-5-methoxy-2-oxopyridin-1 (2H)-yl]butanoic acid (racemate) and 136 mg (0.65 mmol, 1.5 eq.) of tert-butyl 5-aminopyridine-2-carboxylate were reacted. The crude product was purified by means of normal phase chromatography (eluent: 1-4% dichloromethane/methanol mixtures). Yield: 200 mg (88% of theory)

LC/MS [Method 1]: $R_t$=1.10 min; MS (ESIpos): m/z=523 (M+H)$^+$, $^1$H-NMR (400 MHz, DMSO-d$_6$): δ [ppm]=11.01 (s, 1H), 8.86 (d, 1H), 8.25 (dd, 1H), 8.02-7.97 (m, 2H), 7.76-7.71 (m, 2H), 7.49 (s, 1H), 6.55 (s, 1H), 5.63 (dd, 1H), 3.69 (s, 3H), 2.27-2.14 (m, 2H), 1.55 (s, 9H), 0.91 (t, 3H).

Example 21.1A tert-Butyl 2-[4-(5-chloro-2-cyanophenyl)-5-methoxy-2-oxopyridin-1(2H)-yl]-3-(1-methyl-1H-pyrazol-3-yl)propanoate (racemate)

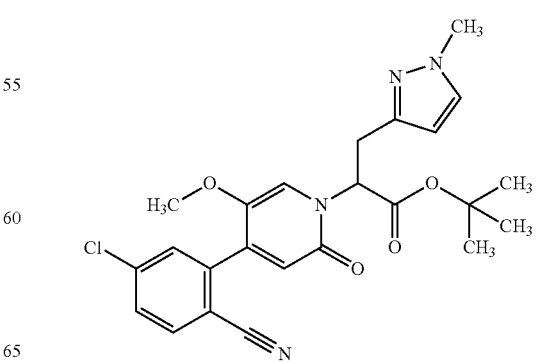

To a solution of 750 mg (2.00 mmol) of tert-butyl [4-(5-chloro-2-cyanophenyl)-5-methoxy-2-oxopyridin-1(2H)-yl]acetate in 15 ml of THF under argon at −70° C. were added 2.50 ml (2.50 mmol, 1.25 eq.) of 1 N lithium bis(trimethylsilyl)amide in THF, and the mixture was stirred for 30 min. Subsequently, 725 mg (1.91 mmol, 46% purity, 0.95 eq.) of 3-(bromomethyl)-1-methyl-1H-pyrazole were added, the mixture was stirred at −70° C. for 30 min and then stirred while coming to RT for 2 h. To the reaction mixture were added 10 ml of saturated aqueous ammonium chloride solution, 10 ml of water and 80 ml of ethyl acetate. The aqueous phase was extracted once with ethyl acetate, and the combined organic phases were washed once with saturated aqueous sodium chloride solution, then dried and concentrated. The crude product was purified by means of normal phase flash chromatography (eluent: dichloromethane/methanol, 0-10%). Yield: 1.01 g (85% purity, 92% of theory).

LC/MS [Method 1]: $R_t$=0.99 min; MS (ESIpos): m/z=469 (M+H)$^+$, $^1$H-NMR (400 MHz, DMSO-d$_6$): δ [ppm]=7.97 (d, 1H), 7.75-7.66 (m, 2H), 7.50 (d, 1H), 7.30 (s, 1H), 6.44 (s, 1H), 5.96 (d, 1H), 5.29 (dd, 1H), 3.73 (s, 3H), 3.55 (s, 3H), 3.49-3.37 (m, 1H), 3.36-3.27 (m, 1H), 1.41 (s, 9H)

Example 21.1B

2-[4-(5-Chloro-2-cyanophenyl)-5-methoxy-2-oxopyridin-1(2H)-yl]-3-(1-methyl-1H-pyrazol-3-yl)propanoic acid (racemate)

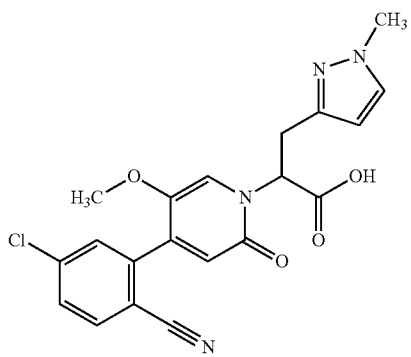 [SMILES: COc1cn(C(Cc2ccn(C)n2)C(=O)O)c(=O)cc1-c1cc(Cl)ccc1C#N]

To 1.02 g (1.85 mmol, 85% purity) of tert-butyl 2-[4-(5-chloro-2-cyanophenyl)-5-methoxy-2-oxopyridin-1(2H)-yl]-3-(1-methyl-1H-pyrazol-3-yl)propanoate (racemate) were added 18 ml of 4 N hydrogen chloride in dioxane and the mixture was stirred at RT overnight. The reaction mixture was concentrated and lyophilized. The residue was purified by means of preparative HPLC (RP18 column, eluent: acetonitrile/water gradient with addition of 0.1% formic acid). Yield: 620 mg (81% of theory).

LC/MS [Method 1]: $R_t$=0.77 min; MS (ESIpos): m/z=413 (M+H)$^+$, $^1$H-NMR (400 MHz, DMSO-d$_6$): δ [ppm]=13.05 (bs, 1H), 8.02-7.92 (m, 1H), 7.74-7.66 (m, 2H), 7.48 (d, 1H), 7.32 (s, 1H), 6.42 (s, 1H), 5.91 (d, 1H), 5.30 (dd, 1H), 3.72 (s, 3H), 3.54 (s, 3H), 3.47 (dd, 1H), 3.38-3.26 (m, 1H)

Example 22.1A tert-Butyl 2-[4-(5-chloro-2-cyanophenyl)-5-methoxy-2-oxopyridin-1(2H)-yl]-3-(5-methyl-1,2-oxazol-3-yl)propanoate (racemate)

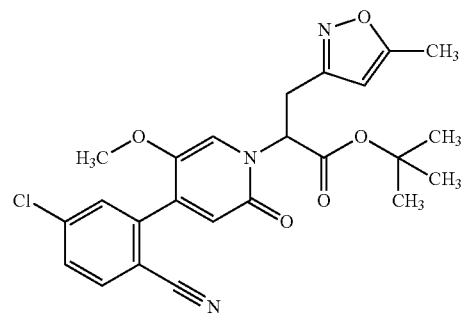 [SMILES: COc1cn(C(Cc2cc(C)on2)C(=O)OC(C)(C)C)c(=O)cc1-c1cc(Cl)ccc1C#N]

To a solution of 737 mg (1.97 mmol) of tert-butyl [4-(5-chloro-2-cyanophenyl)-5-methoxy-2-oxopyridin-1(2H)-yl]acetate in 15 ml of THF under argon at −70° C. were added 2.46 ml (2.46 mmol, 1.25 eq.) of 1 N lithium bis(trimethylsilyl)amide in THF, and the mixture was stirred for 30 min. Subsequently, 500 mg (2.76 mmol, 1.40 eq.) of 3-(bromomethyl)-5-methyl-1,2-oxazole were added, the mixture was stirred at −70° C. for 30 min and then stirred while coming to RT for 2 h. To the reaction mixture were added 10 ml of saturated aqueous ammonium chloride solution, 10 ml of water and 80 ml of ethyl acetate. The aqueous phase was extracted once with ethyl acetate, and the combined organic phases were washed with saturated aqueous sodium chloride solution, then dried and concentrated. The crude product was purified by means of normal phase flash chromatography (eluent: cyclohexane/ethyl acetate, 0-35%). Yield: 800 mg (87% of theory).

LC/MS [Method 1]: $R_t$=1.08 min; MS (ESIpos): m/z=470 (M+H)$^+$, $^1$H-NMR (400 MHz, DMSO-d$_6$): δ [ppm]=8.01-7.93 (m, 1H), 7.75-7.67 (m, 2H), 7.37 (s, 1H), 6.48 (s, 1H), 6.05-7.98 (m, 1H), 5.33 (dd, 1H), 3.57 (s, 3H), 3.55-3.38 (m, 2H), 2.32 (s, 3H), 1.40 (s, 9H)

Example 22.1B

2-[4-(5-Chloro-2-cyanophenyl)-5-methoxy-2-oxopyridin-1(2H)-yl]-3-(5-methyl-1,2-oxazol-3-yl)propanoic acid (racemate)

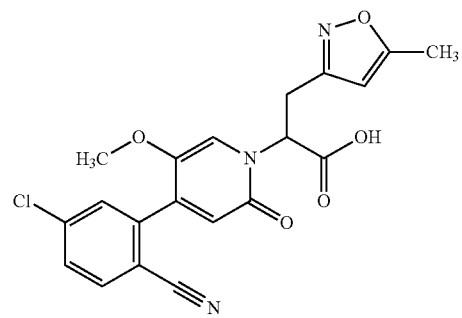 [SMILES: COc1cn(C(Cc2cc(C)on2)C(=O)O)c(=O)cc1-c1cc(Cl)ccc1C#N]

To 800 mg (1.70 mmol) of tert-butyl 2-[4-(5-chloro-2-cyanophenyl)-5-methoxy-2-oxopyridin-1(2H)-yl]-3-(5-methyl-1,2-oxazol-3-yl)propanoate (racemate) were added 17 ml of 4 N hydrogen chloride in dioxane and the mixture was stirred at RT for 24 h. The reaction mixture was concentrated, and the residue was twice admixed with THF and concentrated. Yield: 780 mg (88% purity, 97% of theory).

LC/MS [Method 1]: $R_t$=0.81 min; MS (ESIpos): m/z=414 (M+H)$^+$, $^1$H-NMR (400 MHz, DMSO-d$_6$): δ [ppm]=13.22 (bs, 1H), 8.00-7.95 (m, 1H), 7.75-7.69 (m, 2H), 7.41 (s, 1H), 6.47 (s, 1H), 5.99-5.93 (m, 1H), 5.36 (dd, 1H), 3.59-3.40 (m, 5H), 2.31 (s, 3H).

Example 23.1A 2-(2,5-Dimethoxypyridin-4-yl)-4-methylbenzonitrile

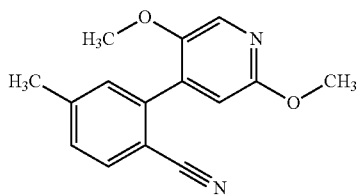

2.50 g (9.36 mmol) of diisopropyl (2,5-dimethoxypyridin-4-yl)borate, 3.88 g (28.08 mmol, 3 eq.) of potassium carbonate and 0.764 g (0.936 mmol, 0.1 eq.) of [1,1-bis(diphenylphosphino)ferrocene]palladium(II) chloride dichloromethane adduct were initially charged in a flask, which was then evacuated and filled with argon three times. 2.27 g (11.23 mmol, 1.2 eq) of 2-bromo-4-methylbenzonitrile and 68 ml of dioxane were added, argon was passed through for 2 min and the mixture was stirred at 100° C. overnight. The reaction mixture was filtered through kieselguhr and washed with dichloromethane/methanol 9:1, and the filtrate was concentrated. The crude product was purified by means of normal phase flash chromatography (eluent: cyclohexane/ethyl acetate, 0-40%). Yield: 1.72 g (71% of theory).

LC/MS [Method 1]: $R_t$=1.00 min; MS (ESIpos): m/z=255 (M+H)$^+$, $^1$H-NMR (400 MHz, DMSO-d$_6$): δ [ppm]=8.03 (s, 1H), 7.81 (d, 1H), 7.42 (d, 1H), 7.37 (s, 1H), 6.78 (s, 1H), 3.85 (s, 3H), 3.78 (s, 3H), 2.42 (s, 3H).

Example 23.1B 2-(5-Methoxy-2-oxo-1,2-dihydropyridin-4-yl)-4-methylbenzonitrile

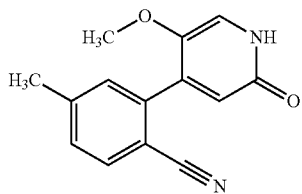 [SMILES: COc1c[nH]c(=O)cc1-c1cc(C)ccc1C#N]

To 1.72 g (6.63 mmol) of 2-(2,5-dimethoxypyridin-4-yl)-4-methylbenzonitrile and 8.49 g (53.03 mmol, 8 eq.) of pyridine hydrobromide were added 72 ml of DMF and the mixture was stirred at 100° C. for 4 h. The reaction mixture was cooled down and concentrated. The residue was stirred with 40 ml of water, filtered off with suction and washed with water. Subsequently, the residue was twice slurried in acetonitrile, concentrated and dried under high vacuum. Overall yield: 1.35 g (90% purity, 76% of theory).

LC/MS [Method 1]: $R_t$=0.63 min; MS (ESIpos): m/z=241 (M+H)$^+$, $^1$H-NMR (400 MHz, DMSO-d$_6$): δ [ppm]=7.80 (d, 1H), 7.42 (d, 1H), 7.35 (s, 1H), 7.28 (bs, 1H), 6.35 (s, 1H), 3.63 (s, 3H), 2.42 (s, 3H).

Example 23.1C tert-Butyl [4-(2-cyano-5-methylphenyl)-5-methoxy-2-oxopyridin-1(2H)-yl]acetate

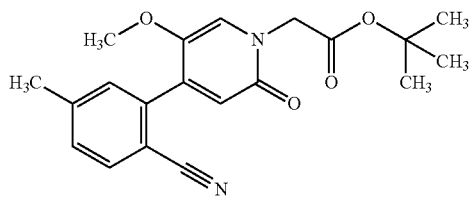 [SMILES: COc1cn(CC(=O)OC(C)(C)C)c(=O)cc1-c1cc(C)ccc1C#N]

To 1.35 g (5.06 mmol, 90% purity) of 2-(5-methoxy-2-oxo-1,2-dihydropyridin-4-yl)-4-methylbenzonitrile, 0.914 ml (6.07 mmol, 1.2 eq.) of tert-butyl bromoacetate and 1.05 g (7.59 mmol, 1.5 eq.) of potassium carbonate were added 31 ml of DMF and the mixture was stirred at 100° C. for 90 min. The reaction mixture was concentrated. The residue was dissolved in 6 ml of dichloromethane and purified by means of normal phase flash chromatography (eluent: cyclohexane/ethyl acetate, 0-70%). Yield: 1.29 g (72% of theory).

LC/MS [Method 1]: $R_t$=0.94 min; MS (ESIpos): m/z=355 (M+H)$^+$, $^1$H-NMR (400 MHz, DMSO-d$_6$): δ [ppm]=7.81 (d, 1H), 7.53 (s, 1H), 7.43 (d, 1H), 7.37 (s, 1H), 6.39 (s, 1H), 4.60 (s, 2H), 3.60 (s, 3H), 2.42 (s, 3H), 1.44 (s, 9H).

Example 23.1D tert-Butyl 2-[4-(2-cyano-2-methylphenyl)-5-methoxy-5-oxopyridin-1(2H)-yl]-3-(1-methyl-1H-pyrazol-3-yl)propanoate (racemate)

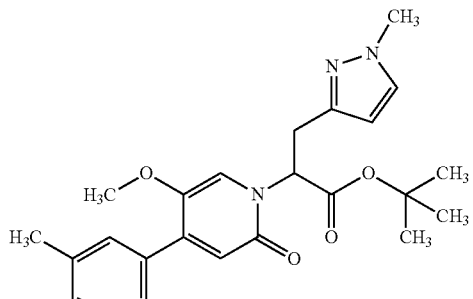

To a solution of 0.90 g (2.54 mmol) of tert-butyl [4-(2-cyano-5-methylphenyl)-5-methoxy-2-oxopyridin-1(2H)-yl] acetate in 19 ml of THF under argon at −70° C. were added 3.17 ml (3.17 mmol, 1.25 eq.) of 1 N lithium bis(trimethylsilyl)amide in THF, and the mixture was stirred for 30 min. Subsequently, 543 mg (3.56 mmol, 1.4 eq.) of a mixture of 3-(bromomethyl)-1-methyl-1H-pyrazole and 3-(chloromethyl)-1-methyl-1H-pyrazole were added, the mixture was stirred at −70° C. for 30 min and then stirred while coming to RT for 2 h. To the reaction mixture were added 15 ml of saturated aqueous ammonium chloride solution, 15 ml of water and 150 ml of ethyl acetate. The aqueous phase was extracted once with ethyl acetate, and the combined organic phases were washed once with saturated aqueous sodium chloride solution, then dried and concentrated. The crude product was purified by means of normal phase flash chromatography (eluent: dichloromethane/methanol, 0% methanol to 5% methanol). The product fractions were combined and purified by means of preparative HPLC (RP18 column, eluent: acetonitrile/water gradient with addition of 0.1% formic acid). Yield: 640 mg (58% of theory).

LC/MS [Method 1]: $R_t$=0.94 min; MS (ESIpos): m/z=449 (M+H)$^+$, $^1$H-NMR (400 MHz, DMSO-d$_6$): δ [ppm]=7.79 (d, 1H), 7.51 (d, 1H), 7.42 (d, 1H), 7.35 (s, 1H), 7.27 (s, 1H), 6.33 (s, 1H), 5.95 (d, 1H), 5.29 (dd, 1H), 3.73 (s, 3H), 3.53 (s, 3 H), 3.47-3.38 (m, 1H), 3.36-3.28 (m, 3H), 2.41 (s, 3H), 1.41 (s, 9H).

Example 23.1E

2-[4-(2-Cyano-5-methylphenyl)-5-methoxy-2-oxopyridin-1(2H)-yl]-3-(1-methyl-1H-pyrazol-3-yl) propanoic acid hydrochloride (racemate)

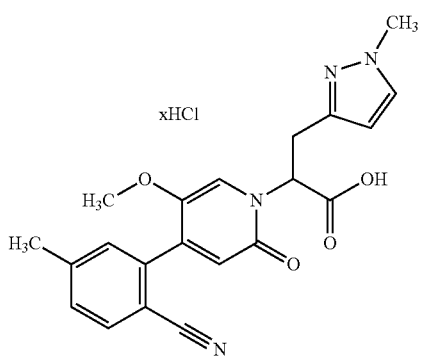 [SMILES: COc1cn(C(Cc2ccn(C)n2)C(=O)O)c(=O)cc1-c1cc(C)ccc1C#N]

To 640 mg (1.33 mmol) of tert-butyl 2-[4-(2-cyano-5-methylphenyl)-5-methoxy-2-oxopyridin-1(2H)-yl]-3-(1-methyl-1H-pyrazol-3-yl)propanoate (racemate) were added 13 ml of 4 N hydrogen chloride in dioxane and the mixture was stirred at RT overnight. The reaction mixture was concentrated and dried under high vacuum. The residue was twice admixed with THF and concentrated again. Yield: 700 mg (80% purity, 98% of theory).

LC/MS [Method 1]: $R_t$=0.71 min; MS (ESIpos): m/z=393 (M+H)$^+$, $^1$H-NMR (400 MHz, DMSO-d$_6$): δ [ppm]=7.79 (d, 1H), 7.50 (d, 1H), 7.41 (d, 1H), 7.35 (s, 1H), 7.29 (s, 1H), 6.32 (s, 1H), 5.92 (d, 1H), 5.31 (dd, 1H), 3.72 (s, 3H), 3.52 (s, 3H), 3.51-3.43 (m, 1H), 3.39-3.28 (m, 1H), 2.41 (s, 3H).

Example 24.1A tert-Butyl 2-[4-(2-cyano-2-methylphenyl)-5-methoxy-5-oxopyridin-1(2H)-yl]-4-methoxybutanoate (racemate)

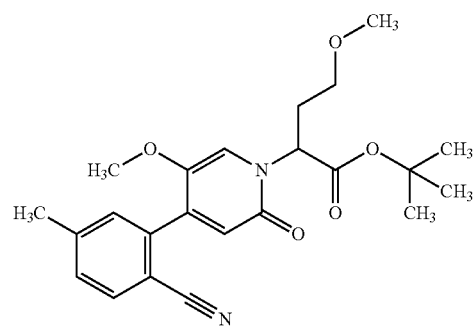 [SMILES: COCCC(C(=O)OC(C)(C)C)n1cc(OC)c(-c2cc(C)ccc2C#N)cc1=O]

0.545 g (2.70 mmol) of 2-bromo-4-methylbenzonitrile, 1.87 g (2.70 mmol, 61% purity, 1 eq.) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) and 1.12 g (8.08 mmol, 3 eq.) of potassium carbonate were initially charged in 27 ml of dioxane under argon, 66 mg (0.08 mmol, 0.03 eq) of [1,1-bis(diphenylphosphino)ferrocene]dichloropalladium dichloromethane complex were added, and the mixture was stirred at 80° C. for 16 h. The reaction mixture was cooled and filtered through kieselguhr, and the filtercake was washed with dichloromethane and acetonitrile. The filtrate was concentrated and the residue was then purified by means of normal phase flash chromatography (eluent: cyclohexane/ethyl acetate, 0-70%). Yield: 1.04 g (85% purity, 80% of theory).

LC/MS [Method 10]: $R_t$=1.86 min; MS (ESIpos): m/z=413 (M+H)$^+$, $^1$H-NMR (400 MHz, DMSO-d$_6$): δ [ppm]=7.80 (d, 1H), 7.43 (d, 1H), 7.39 (s, 1H), 7.34 (s, 1H), 6.38 (s, 1H), 5.15-5.05 (m, 1H), 3.62 (s, 3H), 3.43-3.35 (m, 1H), 3.23-3.11 (m, 4H), 2.42 (s, 3H), 2.38-2.29 (m, 2H), 1.40 (s, 9H).

Example 24.1B

2-[4-(2-Cyano-5-methylphenyl)-5-methoxy-2-oxopyridin-1(2H)-yl]-4-methoxybutanoic acid (racemate)

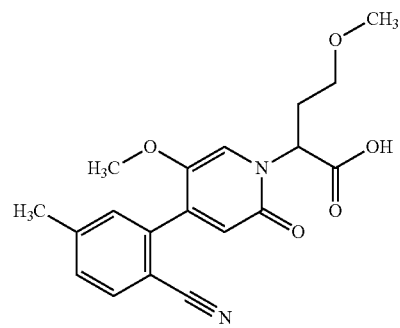

To 1.04 g (2.14 mmol, 85% purity) of tert-butyl 2-[4-(2-cyano-5-methylphenyl)-5-methoxy-5-oxopyridin-1(2H)- yl]-4-methoxybutanoate (racemate) were added 20.4 ml of 4 N hydrogen chloride in dioxane and the mixture was stirred at RT overnight. The reaction mixture was concentrated, and the residue was twice dissolved in THF, concentrated again and dried under high vacuum. Yield: 890 mg (85% purity, 99% of theory).

LC/MS [Method 10]: $R_t$=1.31 min; MS (ESIpos): m/z=357 (M+H)$^+$, $^1$H-NMR (400 MHz, DMSO-d$_6$): δ [ppm]=12.96 (s, 1H), 7.81 (d, 1H), 7.46-7.36 (m, 3H), 6.37 (s, 1H), 5.18-5.09 (m, 1H), 3.62 (s, 3H), 3.42-3.35 (m, 1H), 3.19 (s, 3H), 3.17-3.09 (m, 1H), 2.42 (s, 3H), 2.40-2.31 (m, 2H).

Example 25.1A tert-Butyl 2-[4-(5-chloro-2-cyanophenyl)-5-methoxy-2-oxopyridin-1(2H)-yl]-3-(3-methyl-1,2-oxazol-5-yl)propanoate (racemate)

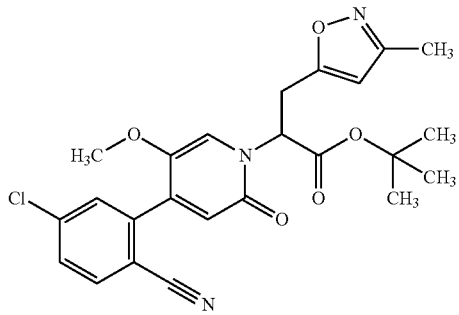 [SMILES: COc1cn(C(Cc2cc(C)no2)C(=O)OC(C)(C)C)c(=O)cc1-c1cc(Cl)ccc1C#N]

To a solution of 900 mg (2.4 mmol) of tert-butyl [4-(5-chloro-2-cyanophenyl)-5-methoxy-2-oxopyridin-1(2H)-yl]acetate in 18 ml of THF under argon at −70° C. were added 3.0 ml (3.0 mmol, 1.25 eq.) of 1 N lithium bis(trimethylsilyl)amide in THF, and the mixture was stirred for 30 min. Subsequently, 623 mg (3.4 mmol, 1.4 eq.) of 5-(bromomethyl)-3-methyl-1,2-oxazole were added, the mixture was stirred at −70° C. for 30 min and then stirred while coming to RT for 90 min. To the reaction mixture were added 15 ml of saturated aqueous ammonium chloride solution, 15 ml of water and 150 ml of ethyl acetate. The aqueous phase was extracted once with ethyl acetate, and the combined organic phases were washed with saturated aqueous sodium chloride solution, then dried and concentrated. The crude product was purified by means of normal phase flash chromatography (eluent: cyclohexane/ethyl acetate, 0-38%). Yield: 1.10 g (95% of theory).

LC/MS [Method 1]: $R_t$=1.04 min; MS (ESIpos): m/z=470 (M+H)$^+$, $^1$H-NMR (400 MHz, DMSO-d$_6$): δ [ppm]=8.03-7.93 (m, 1H), 7.76-7.67 (m, 2H), 7.37 (s, 1H), 6.50 (s, 1H), 6.05 (s, 1H), 5.36 (dd, 1H), 3.72-3.51 (m, 5H), 2.14 (s, 3H), 1.40 (s, 9H)

Example 25.1B

2-[4-(5-Chloro-2-cyanophenyl)-5-methoxy-2-oxopyridin-1(2H)-yl]-3-(3-methyl-1,2-oxazol-5-yl) propanoic acid (racemate)

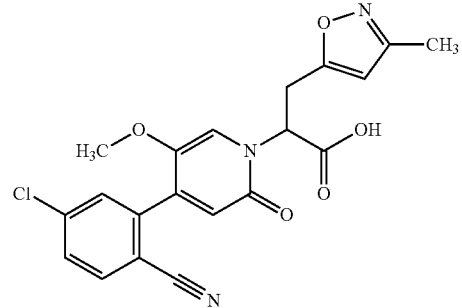 [SMILES: COc1cn(C(Cc2cc(C)no2)C(=O)O)c(=O)cc1-c1cc(Cl)ccc1C#N]

To 1.10 g (2.27 mmol) of tert-butyl 2-[4-(5-chloro-2-cyanophenyl)-5-methoxy-2-oxopyridin-1(2H)-yl]-3-(3-methyl-1,2-oxazol-5-yl)propanoate (racemate) were added 23 ml of 4 N hydrogen chloride in dioxane and the mixture was stirred at RT for 24 h. The reaction mixture was concentrated, and the residue was twice stirred in THF, concentrated again and dried under high vacuum. Yield: 1.05 g (89% purity, 99% of theory).

LC/MS [Method 1]: $R_t$=0.77 min; MS (ESIpos): m/z=414 (M+H)$^+$, $^1$H-NMR (400 MHz, DMSO-d$_6$): δ [ppm]=13.28 (bs, 1H), 8.05-7.92 (m, 1H), 7.79-7.67 (m, 2H), 7.40 (s, 1H), 6.48 (s, 1H), 5.99 (s, 1H), 5.39 (dd, 1H), 3.77-3.64 (m, 1H), 3.63-3.52 (m, 4H), 2.13 (s, 3H)

Example 26.1A 2-(Bromomethyl)-1,3-oxazole

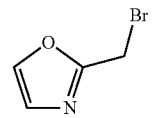

Under argon, 0.50 g (5.05 mmol) of 1,3-oxazol-2-yl-methanol and 0.91 ml (6.56 mmol, 1.3 eq.) of triethylamine were dissolved in 7.0 ml of DMF and cooled to 0° C. At this temperature, 0.508 ml (6.56 mmol, 1.3 eq.) of methanesulphonyl chloride was added dropwise and the mixture was stirred at 0° C. for 1 h. 1.23 g (14.13 mmol, 2.8 eq.) of lithium bromide were then added, and the mixture was stirred at 0° C. for 1 h. The reaction mixture was admixed with water and extracted three times with ethyl acetate. The combined organic phases were washed with saturated aqueous sodium chloride solution, dried over sodium sulphate and concentrated. The residue was purified by means of normal phase flash chromatography (eluent: dichloromethane). Yield: 450 mg (90% purity, 50% of theory)

LC/MS [Method 9]: $R_t$=2.21 min; MS (ESIneg): m/z=162 (M+H)$^+$, $^1$H-NMR (400 MHz, CDCl$_3$-d$_6$): δ [ppm]=7.68 (s, 1H), 7.13 (s, 1H), 4.63 (s, 2H).

Example 26.1B tert-Butyl 2-[4-(5-chloro-2-cyanophenyl)-5-methoxy-2-oxopyridin-1(2H)-yl]-3-(1,3-oxazol-2-yl)propanoate (racemate)

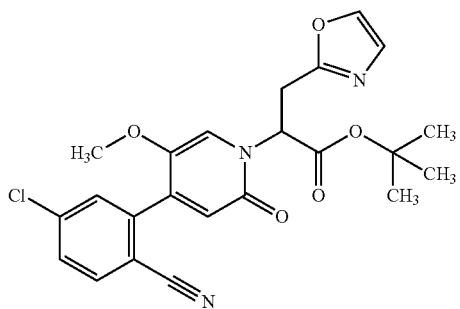 [SMILES: COc1cn(C(Cc2ncco2)C(=O)OC(C)(C)C)c(=O)cc1-c1cc(Cl)ccc1C#N]

To a solution of 642 mg (1.71 mmol) of tert-butyl [4-(5-chloro-2-cyanophenyl)-5-methoxy-2-oxopyridin-1(2H)-yl]acetate in 13 ml of THF under argon at −70° C. were added 2.14 ml (2.14 mmol, 1.25 eq.) of 1 N lithium bis(trimethylsilyl)amide in THF, and the mixture was stirred for 30 min. Subsequently, 410 mg (2.28 mmol, 90% purity, 1.33 eq.) of 2-(bromomethyl)-1,3-oxazole were added, the mixture was stirred at −70° C. for 30 min and then stirred while coming to RT for 2 h. To the reaction mixture were added 10 ml of saturated aqueous ammonium chloride solution, 10 ml of water and 80 ml of ethyl acetate. The aqueous phase was extracted once with ethyl acetate, and the combined organic phases were washed with saturated aqueous sodium chloride solution, then dried and concentrated. The crude product was purified by means of normal phase flash chromatography (eluent: cyclohexane/ethyl acetate, 0-66%). Yield: 570 mg (71% of theory).

LC/MS [Method 1]: $R_t$=1.01 min; MS (ESIpos): m/z=456 (M+H)$^+$, $^1$H-NMR (400 MHz, DMSO-d$_6$): δ [ppm]=8.01-7.95 (m, 2H), 7.75-7.67 (m, 2H), 7.43 (s, 1H), 7.14-7.11 (m, 1H), 6.49 (s, 1H), 5.45 (dd, 1H), 3.73-3.64 (m, 1H), 3.61-3.51 (m, 4H), 1.37 (s, 9H)

Example 26.1C

2-[4-(5-Chloro-2-cyanophenyl)-5-methoxy-2-oxopyridin-1(2H)-yl]-3-(1,3-oxazol-2-yl)propanoic acid (racemate)

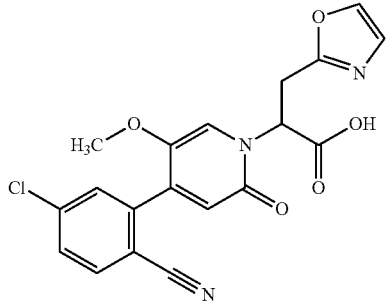 [SMILES: COc1cn(C(Cc2ncco2)C(=O)O)c(=O)cc1-c1cc(Cl)ccc1C#N]

To 570 mg (1.21 mmol) of tert-butyl 2-[4-(5-chloro-2-cyanophenyl)-5-methoxy-2-oxopyridin-1(2H)-yl]-3-(1,3-oxazol-2-yl)propanoate (racemate) were added 12 ml of 4 N hydrogen chloride in dioxane and the mixture was stirred at RT for 18 h. Another 10 ml of 4 N hydrogen chloride in dioxane were added and the mixture was stirred at RT for 3 days. The reaction mixture was concentrated, and the residue was admixed with THF and concentrated. The crude product was purified by means of preparative HPLC (RP18 column, eluent: acetonitrile/water gradient with addition of 0.1% formic acid). Yield: 400 mg (81% of theory).

LC/MS [Method 1]: $R_t$=0.72 min; MS (ESIpos): m/z=400 (M+H)$^+$, $^1$H-NMR (400 MHz, DMSO-d$_6$): δ [ppm]=13.21 (bs, 1H), 8.00-7.93 (m, 2H), 7.74-7.66 (m, 2H), 7.42 (s, 1H), 7.10 (s, 1H), 6.47 (s, 1H), 5.49-5.39 (m, 1H), 3.68-3.60 (m, 2H), 3.56 (s, 3H)

Example 27.1A

Mixture of: 4-(bromomethyl)-2-methyl-1,3-oxazole and 4-(chloromethyl)-2-methyl-1,3-oxazole

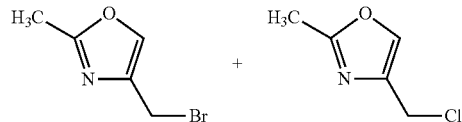

Under argon, 1.00 g (8.84 mmol) of (2-methyl-1,3-oxazol-4-yl)methanol and 1.60 ml (11.49 mmol, 1.3 eq.) of triethylamine were dissolved in 12.5 ml of DMF and cooled to 0° C. At this temperature, 0.890 ml (11.49 mmol, 1.3 eq.) of methanesulphonyl chloride was added dropwise and the mixture was stirred at 0° C. for 1 h. 2.15 g (24.75 mmol, 2.8 eq.) of lithium bromide were then added, and the mixture was stirred at 0° C. for 1 h. The reaction mixture was admixed with water and extracted three times with ethyl acetate. The combined organic phases were washed with saturated aqueous sodium chloride solution, dried over sodium sulphate and concentrated. The residue was purified by means of normal phase flash chromatography (eluent: dichloromethane). Yield: 3.00 g (38% purity, 73% of theory).

LC/MS [Method 9]: $R_t$=2.73 min; MS (ESIpos): m/z=177 (M+H)$^+$,

LC/MS [Method 9]: $R_t$=2.19 min; MS (ESIpos): m/z=133 (M+H)$^+$.

Example 27.1B tert-Butyl 2-[4-(5-chloro-2-cyanophenyl)-5-methoxy-2-oxopyridin-1(2H)-yl]-3-(2-methyl-1,3-oxazol-4-yl)propanoate (racemate)

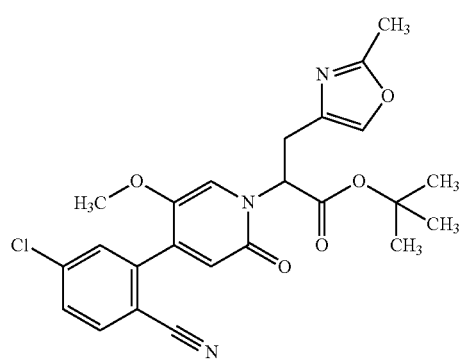 [SMILES: COc1cn(C(Cc2coc(C)n2)C(=O)OC(C)(C)C)c(=O)cc1-c1cc(Cl)ccc1C#N]

To a solution of 1.00 g (2.67 mmol) of tert-butyl [4-(5-chloro-2-cyanophenyl)-5-methoxy-2-oxopyridin-1(2H)-yl]acetate in 26 ml of THF under argon at −70° C. were added 3.34 ml (3.34 mmol, 1.25 eq.) of 1 N lithium bis(trimethylsilyl)amide in THF, and the mixture was stirred for 30 min. Subsequently, 1.09 mg (3.74 mmol, 60.5% purity, 1.4 eq.) of the mixture of 4-(bromomethyl)-2-methyl-1,3-oxazole and 4-(chloromethyl)-2-methyl-1,3-oxazole were added, the mixture was stirred at −70° C. for 30 min and then stirred while coming to RT for 2 h. To the reaction mixture were added 10 ml of saturated aqueous ammonium chloride solution, 10 ml of water and 80 ml of ethyl acetate. The aqueous phase was extracted once with ethyl acetate, and the combined organic phases were washed with saturated aqueous sodium chloride solution, then dried and concentrated. The crude product was purified by means of normal phase flash chromatography (eluent: cyclohexane/ethyl acetate, 50-100%). Yield: 1.11 g (88% of theory).

LC/MS [Method 1]: $R_t$=1.03 min; MS (ESIpos): m/z=470 (M+H)$^+$, $^1$H-NMR (400 MHz, DMSO-d$_6$): δ [ppm]=7.97 (d, 1H), 7.76-7.67 (m, 2H), 7.60 (s, 1H), 7.33 (s, 1H), 6.45 (s, 1H), 5.31 (dd, 1H), 3.57 (s, 3H), 3.36 (dd, 1H), 3.24 (dd, 1H), 2.33 (s, 3H), 1.40 (s, 9H).

Example 27.1C

2-[4-(5-Chloro-2-cyanophenyl)-5-methoxy-2-oxopyridin-1(2H)-yl]-3-(2-methyl-1,3-oxazol-4-yl)propanoic acid hydrochloride (racemate)

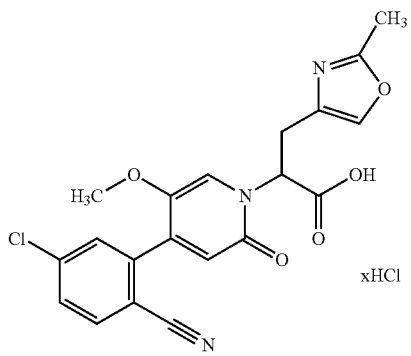 [SMILES: COc1cn(C(Cc2coc(C)n2)C(=O)O)c(=O)cc1-c1cc(Cl)ccc1C#N]

To 1.11 g (2.34 mmol) of tert-butyl 2-[4-(5-chloro-2-cyanophenyl)-5-methoxy-2-oxopyridin-1(2H)-yl]-3-(2-methyl-1,3-oxazol-4-yl)propanoate (racemate) were added 25 ml of 4 N hydrogen chloride in dioxane and the mixture was stirred at RT overnight. The reaction mixture was concentrated and lyophilized Yield: 893 mg (94% purity, 79% of theory).

LC/MS [Method 1]: $R_t$=0.79 min; MS (ESIpos): m/z=414 (M+H)$^+$, $^1$H-NMR (400 MHz, DMSO-d$_6$): δ [ppm]=8.02-7.93 (m, 1H), 7.76-7.65 (m, 2H), 7.55 (s, 1H), 7.35 (s, 1H), 6.43 (s, 1H), 5.32 (dd, 1H), 3.56 (s, 3H), 3.41 (dd, 1H), 3.23 (dd, 1H), 2.32 (s, 3H).

Example 28.1A

Mixture of: 3-(bromomethyl)-5-methyl-1,2,4-oxadiazole and 3-(chloromethyl)-5-methyl-1,2,4-oxadiazole

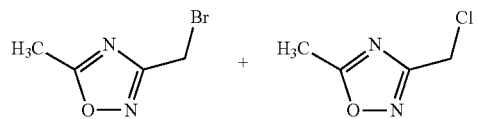

Under argon, 0.95 g (7.91 mmol) of (5-methyl-1,2,4-oxadiazol-3-yl)methanol and 1.43 ml (10.28 mmol, 1.3 eq.) of triethylamine were dissolved in 11 ml of DMF and cooled to 0° C. At this temperature, 0.796 ml (10.28 mmol, 1.3 eq.) of methanesulphonyl chloride was added dropwise and the mixture was stirred at 0° C. for 1 h. 1.92 g (22.14 mmol, 2.8 eq.) of lithium bromide were then added, and the mixture was stirred at 0° C. for 1 h. The reaction mixture was admixed with 60 ml of water and 15 g of sodium chloride and extracted four times with diethyl ether. The combined organic phases were washed with saturated aqueous sodium chloride solution, dried over sodium sulphate and concentrated. The residue was purified by means of normal phase flash chromatography (eluent: dichloromethane, then dichloromethane/methanol 20:1). Yield: 610 mg (43% of theory)

LC/MS [Method 9]: $R_t$=2.80 min; MS (ESIneg): m/z=175 (M−H)$^−$,

LC/MS [Method 9]: $R_t$=2.31 min; MS (ESIpos): m/z=133 (M+H)$^+$.

Example 28.1B tert-Butyl 2-[4-(5-chloro-2-cyanophenyl)-5-methoxy-2-oxopyridin-1(5H)-yl]-3-(2-methyl-1,2,4-oxadiazol-3-yl)propanoate (racemate)

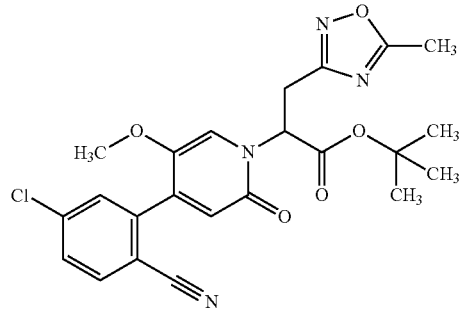 [SMILES: COc1cn(C(Cc2noc(C)n2)C(=O)OC(C)(C)C)c(=O)cc1-c1cc(Cl)ccc1C#N]

To a solution of 900 mg (2.40 mmol) of tert-butyl [4-(5-chloro-2-cyanophenyl)-5-methoxy-2-oxopyridin-1(2H)-yl]acetate in 18 ml of THF under argon at −70° C. were added 3.0 ml (3.0 mmol, 1.25 eq.) of 1 N lithium bis(trimethylsilyl)amide in THF, and the mixture was stirred for 30 min. Subsequently, 607 mg (3.36 mmol, 1.4 eq.) of a mixture of 3-(bromomethyl)-5-methyl-1,2,4-oxadiazole and 3-(chloromethyl)-5-methyl-1,2,4-oxadiazole were added, the mixture was stirred at −70° C. for 30 min and then stirred while coming to RT for 90 min. To the reaction mixture were added 15 ml of saturated aqueous ammonium chloride solution, 15 ml of water and 150 ml of ethyl acetate. The aqueous phase was extracted once more with ethyl acetate. The combined organic phases were washed with saturated aqueous sodium chloride solution, then dried and concentrated. The crude product was purified twice by means of normal phase flash chromatography (eluent: cyclohexane/ethyl acetate, 0-50%). Yield: 560 mg (49% of theory).

LC/MS [Method 1]: $R_t$=1.04 min; MS (ESIpos): m/z=471 (M+H)$^+$, $^1$H-NMR (400 MHz, DMSO-d$_6$): δ [ppm]=7.97 (d, 1H), 7.77-7.67 (m, 2H), 7.44 (s, 1H), 6.48 (s, 1H), 5.44 (dd, 1H), 3.67-3.46 (m, 5H), 2.55 (s, 3H), 1.37 (s, 9H).

Example 28.1C

2-[4-(5-Chloro-2-cyanophenyl)-5-methoxy-2-oxopyridin-1(2H)-yl]-3-(5-methyl-1,2,4-oxadiazol-3-yl)propanoic acid (racemate)

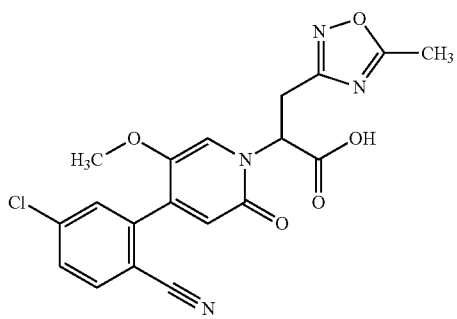 [SMILES: COc1cn(C(Cc2noc(C)n2)C(=O)O)c(=O)cc1-c1cc(Cl)ccc1C#N]

To 560 mg (1.17 mmol) of tert-butyl 2-[4-(5-chloro-2-cyanophenyl)-5-methoxy-2-oxopyridin-1(2H)-yl]-3-(5-methyl-1,2,4-oxadiazol-3-yl)propanoate (racemate) were added 11.7 ml of 4 N hydrogen chloride in dioxane and the mixture was stirred at RT for 18 h. The reaction mixture was concentrated, and the residue was twice stirred in THF, concentrated again and dried under high vacuum overnight. The crude product was purified by means of preparative HPLC (RP18 column, eluent: acetonitrile/water gradient with addition of 0.1% formic acid). Yield: 415 mg (86% of theory).

LC/MS [Method 1]: $R_t$=0.77 min; MS (ESIpos): m/z=415 (M+H)$^+$, $^1$H-NMR (400 MHz, DMSO-d$_6$): δ [ppm]=13.24 (bs, H), 8.04-7.91 (m, 1H), 7.74-7.68 (m, 2H), 7.45 (s, 1H), 6.46 (s, 1H), 5.44 (dd, 1H), 3.67-3.52 (m, 5H), 2.53 (s, 3H).

Example 29.1A

2-Bromo-4-chloro-1-(difluoromethyl)benzene

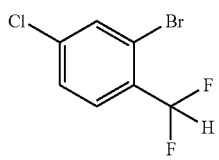 [SMILES: FC(F)c1ccc(Cl)cc1Br]

1.50 g (6.84 mmol) of 2-bromo-4-chlorobenzaldehyde were initially charged in 18 ml of dichloromethane, 1.36 ml (10.25 mmol, 1.5 eq.) of N,N-diethylaminosulphur trifluoride were added at 0° C. and the mixture was stirred at RT for 3 h. Subsequently, 80 ml of saturated aqueous sodium hydrogencarbonate solution were added dropwise and the mixture was extracted twice with dichloromethane. The combined organic phases were washed with saturated aqueous sodium chloride solution, dried over sodium sulphate and concentrated. Yield: 1.6 g (92% purity, 89% of theory).

LC/MS [Method 9]: $R_t$=3.22 min; MS (ESIpos): m/z=241 (M+H)$^+$, $^1$H-NMR (400 MHz, DMSO-d$_6$): δ [ppm]=7.95 (s, 1H), 7.72-7.61 (m, 2H), 7.13 (s, 1H)

Example 29.1B

4-[5-Chloro-2-(difluoromethyl)phenyl]-2,5-dimethoxypyridine

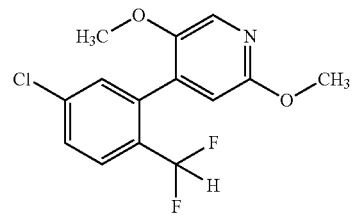 [SMILES: COc1cc(-c2cc(Cl)ccc2C(F)F)c(OC)cn1]

1.36 g (5.08 mmol) of diisopropyl (2,5-dimethoxypyridin-4-yl)borate, 2.11 g (15.24 mmol, 3 eq.) of potassium carbonate and 0.415 g (0.508 mmol, 0.1 eq.) of [1,1-bis(diphenylphosphino)ferrocene]palladium(II) chloride dichloromethane adduct were initially charged in a flask, which was then evacuated and filled with argon three times. 1.60 g (6.10 mmol, 1.2 eq) of 2-bromo-4-chloro-1-(difluoromethyl)benzene and 37 ml of dioxane were added, argon was passed through for 2 min and the mixture was stirred at 100° C. overnight. The reaction mixture was filtered through kieselguhr and washed with acetonitrile, and the filtrate was concentrated. The crude product was purified by means of normal phase flash chromatography (eluent: cyclohexane/ethyl acetate, 0-17%). Yield: 1.06 g (68% of theory).

LC/MS [Method 1]: $R_t$=1.10 min; MS (ESIpos): m/z=300 (M+H)$^+$, $^1$H-NMR (400 MHz, DMSO-d$_6$): δ [ppm]=7.99 (s, 1H), 7.75-7.62 (m, 2H), 7.43 (s, 1H), 6.74 (s, 1H), 6.68 (t, 1H), 3.84 (s, 3H), 3.75 (m, 3H).

Example 29.1C

4-[5-Chloro-2-(difluoromethyl)phenyl]-5-methoxypyridin-2(1H)-one

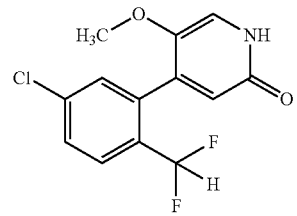 [SMILES: COc1c[nH]c(=O)cc1-c1cc(Cl)ccc1C(F)F]

To 1.06 g (3.47 mmol) of 4-[5-chloro-2-(difluoromethyl)phenyl]-2,5-dimethoxypyridine and 4.44 g (27.73 mmol, 8 eq.) of pyridine hydrobromide were added 38 ml of DMF and the mixture was stirred at 100° C. for 5 h. The reaction mixture was cooled down and concentrated, and water and ethyl acetate were added. The aqueous phase was extracted once more with ethyl acetate. The combined organic phases were washed with saturated aqueous ammonium chloride solution and with saturated aqueous sodium chloride solution, then dried and concentrated. The residue was admixed with 5 ml of dichloromethane and left to stand overnight. The crystals formed were filtered off with suction and washed with a little dichloromethane and dried. The filtrate was purified by means of normal phase flash chromatography (eluent: dichloromethane/methanol, 0-5%). Overall yield: 790 mg (79% of theory).

LC/MS [Method 1]: $R_t$=0.80 min; MS (ESIpos): m/z=286 (M+H)$^+$, $^1$H-NMR (400 MHz, DMSO-d$_6$): δ [ppm]=11.32 (bs, 1H), 7.78-7.60 (m, 2H), 7.43 (s, 1H), 7.20 (s, 1H), 6.73 (t, 1H), 6.28 (s, 1H), 3.58 (s, 3H).

Example 29.1D tert-Butyl {4-[5-chloro-2-(difluoromethyl)phenyl]-5-methoxy-2-oxopyridin-1(2H)-yl}acetate

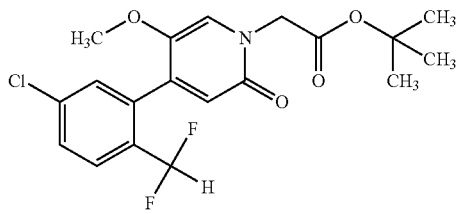 [SMILES: COc1cn(CC(=O)OC(C)(C)C)c(=O)cc1-c1cc(Cl)ccc1C(F)F]

To 0.790 g (2.71 mmol) of 4-[5-chloro-2-(difluoromethyl) phenyl]-5-methoxypyridin-2(1H)-one, 0.490 ml (3.25 mmol, 1.2 eq.) of tert-butyl bromoacetate and 0.532 g (4.07 mmol, 1.5 eq.) of potassium carbonate were added 16 ml of DMF and the mixture was stirred at 100° C. for 90 min. The reaction mixture was concentrated. The residue was admixed with ethyl acetate and water, and the aqueous phase was extracted once more with ethyl acetate. The combined organic phases were washed with saturated aqueous ammonium chloride solution and then with saturated aqueous sodium chloride solution, dried and concentrated. The crude product was purified by means of normal phase flash chromatography (eluent: cyclohexane/ethyl acetate, 0-50%). Yield: 790 mg (73% of theory).

LC/MS [Method 1]: $R_t$=1.00 min; MS (ESIpos): m/z=400 (M+H)$^+$, $^1$H-NMR (400 MHz, DMSO-d$_6$): δ [ppm]=7.77-7.61 (m, 2H), 7.53-7.42 (m, 2H), 6.76 (t, 1H), 6.35 (s, 1H), 4.70-4.50 (m, 2H), 3.56 (s, 3H), 1.45 (s, 9H).

Example 29.1E tert-Butyl 2-{4-[5-chloro-2-(difluoromethyl)phenyl]-5-methoxy-2-oxopyridin-1(2H)-yl}-3-(pyridin-2-yl) propanoate (racemate)

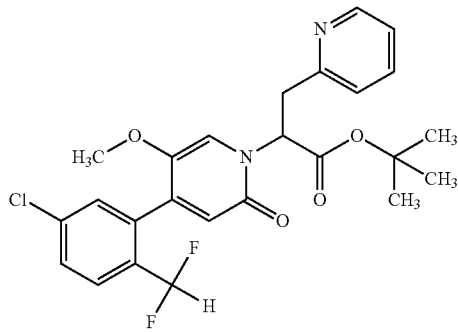 [SMILES: COc1cn(C(Cc2ccccn2)C(=O)OC(C)(C)C)c(=O)cc1-c1cc(Cl)ccc1C(F)F]

To a solution of 790 mg (1.98 mmol) of tert-butyl {4-[5-chloro-2-(difluoromethyl)phenyl]-5-methoxy-2-oxopyridin-1(2H)-yl}acetate in 15 ml of THF under argon at −70° C. were added 4.94 ml (4.94 mmol, 2.50 eq.) of 1 N lithium bis(trimethylsilyl)amide in THF, and the mixture was stirred for 15 min. Subsequently, 700 mg (2.77 mmol, 1.4 eq.) of 2-(bromomethyl)pyridine hydrobromide were added, the mixture was stirred at −70° C. for 30 min and then stirred while coming to RT for 90 min. To the reaction mixture were added 10 ml of saturated aqueous ammonium chloride solution, 10 ml of water and 70 ml of ethyl acetate. The aqueous phase was extracted once with ethyl acetate, and the combined organic phases were washed with saturated aqueous sodium chloride solution, dried and concentrated. The crude product was then purified by means of normal phase flash chromatography (eluent: cyclohexane/ ethyl acetate, 0-45%). Yield: 760 mg (77% of theory).

LC/MS [Method 1]: $R_t$=1.07 min; MS (ESIpos): m/z=491 (M+H)$^+$, $^1$H-NMR (400 MHz, DMSO-d$_6$): δ [ppm]=8.49 (d, 1H), 7.80-7.60 (m, 3H), 7.40 (s, 1H), 7.31-7.16 (m, 3H), 6.83-6.34 (m, 1H), 6.30 (s, 1H), 5.68-5.45 (m, 1H), 3.70-3.39 (m, 4H), 1.37 (s, 9H).

Example 29.1F

2-{4-[5-Chloro-2-(difluoromethyl)phenyl]-5-methoxy-2-oxopyridin-1(2H)-yl}-3-(pyridin-2-yl) propanoic acid hydrochloride (racemate)

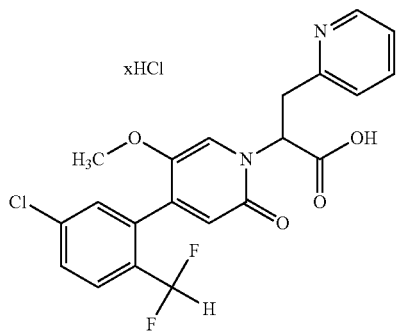 [SMILES: COc1cn(C(Cc2ccccn2)C(=O)O)c(=O)cc1-c1cc(Cl)ccc1C(F)F]

To 760 mg (1.52 mmol) of tert-butyl 2-{4-[5-chloro-2-(difluoromethyl)phenyl]-5-methoxy-2-oxopyridin-1(2H)-yl}-3-(pyridin-2-yl)propanoate (racemate) were added 15.7 ml of 4 N hydrogen chloride in dioxane and the mixture was stirred at RT for 18 h. The reaction mixture was concentrated, and the residue was twice stirred in THF, concentrated again and dried under high vacuum overnight. Yield: 800 mg (85% purity, 95% of theory).

LC/MS [Method 1]: $R_t$=0.74 min; MS (ESIpos): m/z=435 (M+H)$^+$, $^1$H-NMR (400 MHz, DMSO-d$_6$): δ [ppm]=8.90-8.70 (m, 1H), 8.50-8.35 (m, 1H), 8.00-7.78 (m, 2H), 7.77-7.57 (m, 2H), 7.57-7.34 (m, 2H), 6.90-6.50 (m, 1H), 6.40-6.19 (m, 1H), 5.84-5.40 (m, 1H), 4.09-3.92 (m, 1H), 3.82-3.68 (m, 1H), 3.63-3.53 (m, 3H).

Example 30.1A

4-{[tert-Butyl(dimethyl)silyl]oxy}but-2-yn-1-ol

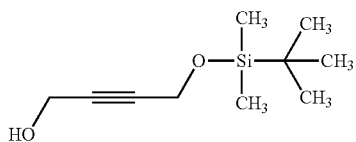

5.00 g (58.08 mmol) of but-2-yne-1,4-diol were initially charged in 62.5 ml of DMF, 2.97 g (43.56 mmol, 0.75 eq.) of 1H-imidazole and 5.25 g (34.85 mmol, 0.6 eq.) of tert-butyl(chloro)dimethylsilane were added and the mixture was stirred at RT for 24 h. The reaction mixture was admixed with 20 ml of methanol and 60 ml of water and then concentrated. The aqueous residue was extracted three times with ethyl acetate. The combined organic phases were washed with saturated aqueous sodium chloride solution, dried over sodium sulphate and concentrated. The residue was purified by means of normal phase flash chromatography (eluent: dichloromethane/methanol, 1-10%). Yield: 4.30 g (36% of theory).

LC/MS [Method 9]: $R_t$=3.74 min; MS (ESIpos): m/z=143 (M-C$_4$H$_9$)$^+$, $^1$H-NMR (400 MHz, DMSO-d$_6$): δ [ppm]=5.14 (t, 1H), 4.32 (t, 2H), 4.08 (dt, 2H), 0.90-0.85 (m, 9H), 0.11-0.06 (m, 6H).

Example 30.1B

2-[(4-{[tert-Butyl(dimethyl)silyl]oxy}but-2-yn-1-yl)oxy]-1H-isoindole-1,3(2H)-dione

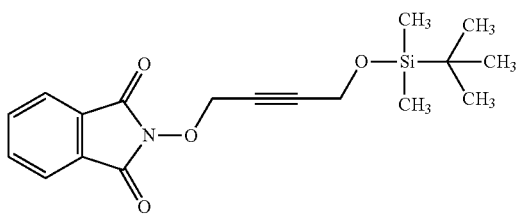 [SMILES: CC(C)(C)[Si](C)(C)OCC#CCON1C(=O)c2ccccc2C1=O]

A solution of 4.30 g (20.82 mmol) of 4-{[tert-butyl(dimethyl)silyl]oxy}but-2-yn-1-ol, 4.08 g (24.98 mmol, 1.2 eq.) of 2-hydroxy-1H-isoindole-1,3(2H)-dione and 8.19 g (31.23 mmol, 1.5 eq.) of triphenylphosphine in 40 ml of dichloromethane was cooled to 0° C., 6.13 ml (31.23 mmol, 1.5 eq.) of diisopropyl (E)-diazene-1,2-dicarboxylate were added and the mixture was stirred at 0° C. for 30 min and then for 4 h while coming to RT. The reaction mixture was concentrated and the residue was purified by means of normal phase flash chromatography (eluent: cyclohexane/ethyl acetate, 25%-50%). Yield: 7.67 g (83% purity, 88% of theory).

LC/MS [Method 1]: $R_t$=1.25 min; MS (ESIpos): m/z=346 (M+H)$^+$, $^1$H-NMR (400 MHz, DMSO-d$_6$): δ [ppm]=7.88 (s, 4H), 4.94 (t, 2H), 4.34 (t, 2H), 0.81-0.78 (m, 9H), 0.00 (s, 6H).

Example 30.1C

{[4-(Aminooxy)but-2-yn-1-yl]oxy}(tert-butyl)dimethylsilane

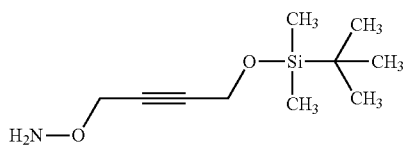

A solution of 7.67 g (18.21 mmol, 82% purity) of 2-[(4-{[tert-butyl(dimethyl)silyl]oxy}but-2-yn-1-yl)oxy]-1H-isoindole-1,3(2H)-dione in 90 ml of dichloromethane was cooled to 0° C., 8.05 ml (91.03 mmol, 55% purity, 5 eq.) of hydrazine hydrate were added and the mixture was stirred at 0° C. for 10 min. The reaction mixture was stirred at RT overnight and then diluted with 90 ml of a 5% aqueous sodium carbonate solution and extracted three times with in each case 90 ml of ethyl acetate. The combined organic phases were washed with saturated aqueous sodium chloride solution, dried over sodium sulphate and concentrated. The crude product was purified by means of normal phase flash chromatography (eluent: cyclohexane/ethyl acetate, 0-35%). Yield: 3.59 g (81% purity, 74% of theory).

LC/MS [Method 9]: $R_t$=4.24 min; MS (ESIpos): m/z=158 (M-C$_4$H$_9$)$^+$, $^1$H-NMR (400 MHz, DMSO-d$_6$): δ [ppm]=6.10 (s, 2H), 4.35 (t, 2H), 4.21 (t, 2H), 0.88-0.86 (m, 9H), 0.10-0.08 (m, 6H).

Example 30.1D 3-({[tert-Butyl(dimethyl)silyl]oxy}methyl)-4,5-dihydro-1,2-oxazole

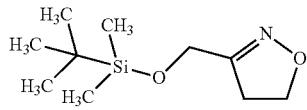

2.00 g (7.52 mmol, 81% purity) of {[4-(aminooxy)but-2-yn-1-yl]oxy}(tert-butyl)dimethylsilane were dissolved in 75 ml of dichloromethane, 116 mg (0.15 mmol, 0.02 eq.) of [(2-biphenyl)di-tert-butylphosphine]gold(I) hexafluoroantimonate-acetonitrile monoadduct were added and the mixture was stirred at RT for 30 min. Subsequently, 1.05 ml (7.52 mmol, 1 eq.) of triethylamine were added, and the mixture was filtered through silica gel and washed with dichloromethane. The filtrate was concentrated and the residue was purified by means of normal phase flash chromatography (eluent: cyclohexane/ethyl acetate, 0-10%). Yield: 1.36 g (89% purity, 75% of theory).

LC/MS [Method 9]: $R_t$=4.19 min; MS (ESIpos): m/z=158 (M-C$_4$H$_9$)$^+$, $^1$H-NMR (400 MHz, DMSO-d$_6$): δ [ppm]=4.40 (s, 2H), 4.23 (t, 2H), 3.00 (t, 2H), 0.90-0.85 (m, 9H), 0.09-0.07 (m, 6H).

Example 30.1E 4,5-Dihydro-1,2-oxazol-3-ylmethanol

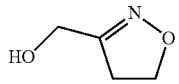

1.36 g (5.62 mmol, 89% purity) of 3-({[tert-butyl(dimethyl)silyl]oxy}methyl)-4,5-dihydro-1,2-oxazole were initially charged in 125 ml of THF, 8.43 ml (8.43 mmol, 1.5 eq.) of 1 N tetra-n-butylammonium fluoride in THF were added and the mixture was stirred at RT for 1 h. The reaction mixture was admixed with 6.3 g of silica gel and concentrated, and the residue was purified by means of normal phase flash chromatography (eluent: cyclohexane/ethyl acetate, isocratic run: 50% ethyl acetate, then 30% ethyl acetate; then dichloromethane/methanol 25%). Yield: 598 mg (81% purity, 85% of theory).

LC/MS [Method 9]: $R_t$=3.06 min; MS (ESIpos): m/z=101 (M)$^+$, $^1$H-NMR (400 MHz, DMSO-d$_6$): δ [ppm]=5.24 (t, 1H), 4.22-4.15 (m, 4H), 2.98 (t, 2H).

Example 30.1F

Mixture of: 3-(bromomethyl)-4,5-dihydro-1,2-oxazole and 3-(chloromethyl)-4,5-dihydro-1,2-oxazole

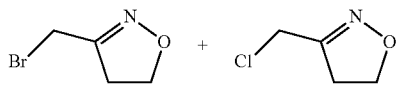 [SMILES: BrCC1=NOCC1 ; ClCC1=NOCC1]

Under argon, 598 mg (4.79 mmol, 81% purity) of 4,5-dihydro-1,2-oxazol-3-ylmethanol and 868 µl (6.23 mmol, 1.3 eq.) of triethylamine were dissolved in 8.5 ml of DMF and cooled to 0° C. At this temperature, 482 µl (6.23 mmol, 1.3 eq.) of methanesulphonyl chloride was added dropwise and the mixture was stirred at 0° C. for 1 h. 1.17 g (13.41 mmol, 2.8 eq.) of lithium bromide were then added, and the mixture was stirred at 0° C. for 1 h. The reaction mixture was admixed with water and extracted three times with ethyl acetate. The combined organic phases were washed with saturated aqueous sodium chloride solution, dried over sodium sulphate and concentrated. The residue was purified by means of normal phase flash chromatography (eluent: dichloromethane). Yield: 631 mg (77% of theory)

LC/MS [Method 9]: $R_t$=3.26 min; MS (ESIneg): m/z=162 (M-H)$^-$,

LC/MS [Method 9]: $R_t$=2.74 min; MS (ESIpos): m/z=121 (M+H)$^+$.

Example 30.1G tert-Butyl 2-[4-(5-chloro-2-cyanophenyl)-5-methoxy-2-oxopyridin-1(2H)-yl]-3-(4,5-dihydro-1,2-oxazol-3-yl)propanoate (racemate)

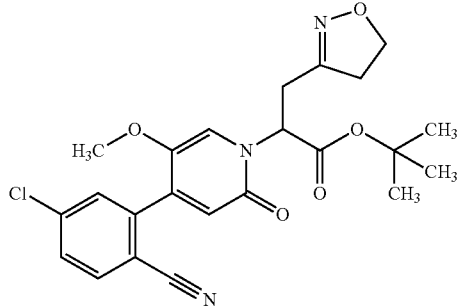 [SMILES: COc1cn(C(CC2=NOCC2)C(=O)OC(C)(C)C)c(=O)cc1-c1cc(Cl)ccc1C#N]

To a solution of 1.00 g (2.67 mmol) of tert-butyl [4-(5-chloro-2-cyanophenyl)-5-methoxy-2-oxopyridin-1(2H)-yl] acetate in 26 ml of THF under argon at −70° C. were added 3.34 ml (3.34 mmol, 1.25 eq.) of 1 N lithium bis(trimethylsilyl)amide in THF, and the mixture was stirred for 30 min. Subsequently, 638 mg (3.74 mmol, 1.4 eq.) of the mixture of 3-(bromomethyl)-4,5-dihydro-1,2-oxazole and 3-(chloromethyl)-4.5-dihydro-1,2-oxazole were added, the mixture was stirred at −70° C. for 30 min and then stirred while coming to RT for 2 h. To the reaction mixture were added 20 ml of saturated aqueous ammonium chloride solution, 20 ml of water and 150 ml of ethyl acetate. The aqueous phase was extracted once with ethyl acetate, and the combined organic phases were washed with saturated aqueous sodium chloride solution, then dried and concentrated. The crude product was purified by means of normal phase flash chromatography (eluent: cyclohexane/ethyl acetate, 50-100%). Yield: 875 mg (70% of theory).

LC/MS [Method 1]: $R_t$=1.00 min; MS (ESIpos): m/z=458 (M+H)$^+$, $^1$H-NMR (400 MHz, DMSO-d$_6$): δ [ppm]=8.03-7.95 (m, 1H), 7.75-7.70 (m, 2H), 7.46 (s, 1H), 6.51 (s, 1H), 5.38-5.30 (m, 1H), 4.22-4.06 (m, 2H), 3.63 (s, 3H), 3.25-3.18 (m, 2H), 3.08-2.96 (m, 1 H), 2.94-2.82 (m, 1H), 1.40 (s, 9H).

Example 30.1H

2-[4-(5-Chloro-2-cyanophenyl)-5-methoxy-2-oxopyridin-1(2H)-yl]-3-(4,5-dihydro-1,2-oxazol-3-yl) propanoic acid hydrochloride (racemate)

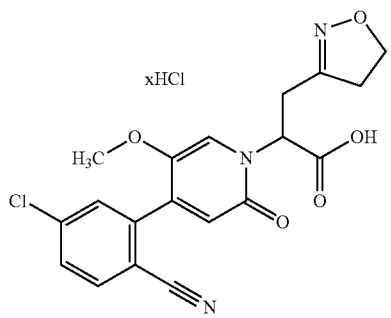 [SMILES: COc1cn(C(CC2=NOCC2)C(=O)O)c(=O)cc1-c1cc(Cl)ccc1C#N]

To 875 mg (1.87 mmol) of tert-butyl 2-[4-(5-chloro-2-cyanophenyl)-5-methoxy-2-oxopyridin-1(2H)-yl]-3-(4,5-dihydro-1,2-oxazol-3-yl)propanoate (racemate) were added 20 ml of 4 N hydrogen chloride in dioxane and the mixture was stirred at RT overnight. The reaction mixture was concentrated and lyophilized. Yield: 743 mg (94% purity, 85% of theory).

LC/MS [Method 1]: $R_t$=0.69 min; MS (ESIpos): m/z=402 (M+H)$^+$, $^1$H-NMR (400 MHz, DMSO-d$_6$): δ [ppm]=13.20 (bs, 1H), 8.03-7.95 (m, 1H), 7.76-7.69 (m, 2H), 7.51 (s, 1H), 6.50 (s, 1H), 5.37 (dd, 1H), 4.20-4.02 (m, 2H), 3.62 (s, 3H), 3.33-3.16 (m, 2H), 3.06-2.93 (m, 1H), 2.91-2.76 (m, 1H).

Example 31.1A

4-Chloro-2-(2-methoxypyridin-4-yl)benzonitrile

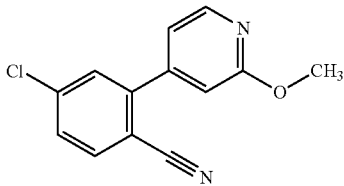 [SMILES: COc1cc(-c2cc(Cl)ccc2C#N)ccn1]

To a solution of 100 g (654 mmol) of (2-methoxypyridin-4-yl)boronic acid and 142 g (654 mmol, 1 eq.) of 2-bromo-4-chlorobenzonitrile in 2.0 l of dioxane were added 981 ml (1961 mmol, 3 eq.) of 2 N aqueous sodium carbonate solution. Argon was passed through the reaction mixture for 10 min, 53 mg (65 mmol, 0.1 eq.) of [1,1-bis(diphenylphosphino)ferrocene]dichloropalladium dichloromethane complex were added and the mixture was stirred at 85° C. for 6 h. The mixture was then stirred at RT overnight. The reaction mixture was admixed with 3 l of water and 1 l of methyl tert-butyl ether, filtered through kieselguhr and washed through with 1 l of methyl tert-butyl ether. The filtrate was separated and the aqueous phase was extracted twice with 1 l of methyl tert-butyl ether. The combined organic phases were dried over sodium sulphate and concentrated. The filtercake was washed three times with 800 ml of dichloromethane and the organic phase was dried over sodium sulphate and concentrated. Subsequently, the two residues were combined and stirred in methanol. The precipitate was filtered off with suction and washed twice with methanol. The filtrate was concentrated and dissolved together with the precipitate in dichloromethane. Subsequently, activated carbon was added and the mixture was stirred under reflux for 30 min. The reaction mixture was subjected to hot filtration through kieselguhr, and the filtrate was concentrated. The residue was stirred again in methanol, and the precipitate was filtered off with suction and washed twice with methanol. The filtrate was concentrated, and the precipitate was filtered off with suction and washed with methanol. The two precipitates were combined and dried under high vacuum overnight. The filtrate was concentrated and purified by means of flash chromatography (eluent: dichloromethane/methanol, 0-2%). The product fractions were combined, concentrated and stirred in warm methanol. The precipitate was filtered off with suction, washed with methanol and dried under high vacuum. Overall yield: 120 g (75% of theory).

LC/MS [Method 1]: $R_t$=1.02 min; MS (ESIpos): m/z=245 (M+H)$^+$, $^1$H-NMR (400 MHz, DMSO-d$_6$): δ [ppm]=8.33 (d, 1H), 8.04 (d, 1H), 7.82 (d, 1H), 7.76 (dd, 1H), 7.22 (dd, 1H), 7.07 (s, 1H), 3.92 (s, 3H).

Example 31.1B 2-(5-Bromo-2-methoxypyridin-4-yl)-4-chlorobenzonitrile

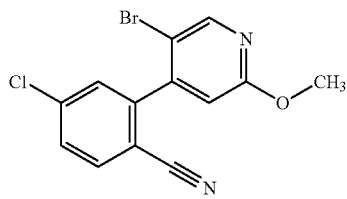 [SMILES: COc1cc(-c2cc(Cl)ccc2C#N)c(Br)cn1]

Under argon, 1.06 g (4.33 mmol) of 4-chloro-2-(2-methoxypyridin-4-yl)benzonitrile were dissolved in 400 ml of N,N-dimethylformamide, 1.16 g (6.5 mmol, 1.5 eq.) of 1-bromopyrrolidine-2,5-dione were added in portions and the mixture was stirred at 40° C. for 3 h. Subsequently, another 771 mg (4.33 mmol, 1 eq.) of 1-bromopyrrolidine-2,5-dione were added and the mixture was stirred at 40° C. for 1 h. Subsequently, another 771 mg (4.33 mmol, 1 eq.) of 1-bromopyrrolidine-2,5-dione were added and the mixture was stirred at 40° C. for 1 h. Subsequently, another 154 mg (0.87 mmol, 0.2 eq.) of 1-bromopyrrolidine-2,5-dione were added and the mixture was stirred at 40° C. overnight. The reaction mixture was added to ice-water and stirred for 10 min. The precipitate was filtered off with suction and washed repeatedly with water. The filtercake was slurried in methanol and filtered with suction, and the solids were dried under high vacuum. Yield: 1.1 g (78% of theory).

LC/MS [Method 1]: $R_t$=1.14 min; MS (ESIpos): m/z=323 (M+H)$^+$, $^1$H-NMR (400 MHz, DMSO-d$_6$): δ [ppm]=8.53 (s, 1H), 8.07 (d, 1H), 7.80 (dd, 1H), 7.75 (d, 1H), 7.09 (s, 1H), 3.92 (s, 3H).

Example 31.1C

4-Chloro-2-(2-methoxy-5-methylpyridin-4-yl)benzonitrile

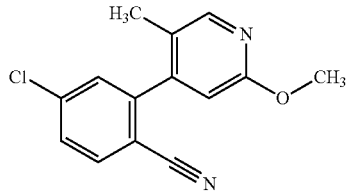 [SMILES: COc1cc(-c2cc(Cl)ccc2C#N)c(C)cn1]

Under argon, 2.00 g (6.18 mmol) of 2-(5-bromo-2-methoxypyridin-4-yl)-4-chlorobenzonitrile, 776 mg (6.18 mmol, 1 eq.) of trimethylboroxine and 3.42 g (10.5 mmol, 1.7 eq.) of caesium carbonate were initially charged, 29 ml of dioxane and 4.9 ml of water were added, the vessel was evacuated and then the mixture was stirred at 95° C. for 6 h. The reaction mixture was concentrated and the residue was admixed with 10 ml of water and 10 ml of ethyl acetate. The aqueous phase was extracted once with 10 ml of ethyl acetate, and the combined organic phases were dried over magnesium sulphate, filtered and concentrated. The residue was purified by means of normal phase flash chromatography (eluent: cyclohexane/ethyl acetate, 5-40%). Yield: 678 mg (90% purity, 38% of theory).

LC/MS [Method 1]: $R_t$=1.03 min; MS (ESIpos): m/z=259 (M+H)$^+$, $^1$H-NMR (400 MHz, DMSO-d$_6$): δ [ppm]=8.17 (s, 1H), 8.04 (d, 1H), 7.74-7.77 (m, 1H), 7.70 (d, 1H), 6.80 (s, 1H), 3.88 (s, 3H), 2.02 (s, 3H).

Example 31.1D

4-Chloro-2-(5-methyl-2-oxo-1,2-dihydropyridin-4-yl)benzonitrile

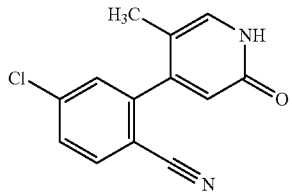 [SMILES: Cc1c[nH]c(=O)cc1-c1cc(Cl)ccc1C#N]

To 675 mg (2.61 mmol) of 4-chloro-2-(2-methoxy-5-methylpyridin-4-yl)benzonitrile and 4.18 g (26.1 mmol, 10 eq.) of pyridine hydrobromide were added 21 ml of DMF and the mixture was stirred at 100° C. under argon for 1.5 h. The reaction mixture was concentrated and the residue was admixed with 10 ml of water. The precipitated solids were filtered off with suction, washed with 100 ml of water and dried in a vacuum drying cabinet at 50° C. for 2 h. Yield: 598 mg (90% purity, 84% of theory).

LC/MS [Method 1]: $R_t$=0.70 min; MS (ESIpos): m/z=245 (M+H)$^+$, $^1$H-NMR (400 MHz, DMSO-d$_6$): δ [ppm]=11.72 (bs, 1H), 8.02 (d, 1H), 7.71-7.75 (m, 1H), 7.66-7.70 (m, 1H), 7.38 (s, 1H), 6.29 (s, 1H), 1.78 (s, 3H).

Example 31.1E tert-Butyl [4-(5-chloro-2-cyanophenyl)-5-methyl-2-oxopyridin-1(2H)-yl]acetate

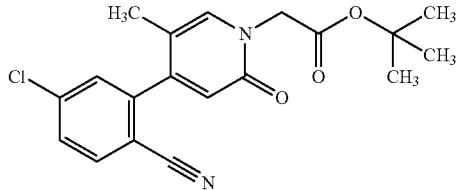 [SMILES: Cc1cn(CC(=O)OC(C)(C)C)c(=O)cc1-c1cc(Cl)ccc1C#N]

To 595 mg (2.43 mmol) of 4-chloro-(5-methyl-2-oxo-1,2-dihydropyridin-4-yl)benzonitrile, 0.440 ml (2.92 mmol, 1.2 eq.) of tert-butyl bromoacetate and 1.19 g (3.65 mmol, 1.5 eq.) of caesium carbonate were added 16 ml of DMF and the mixture was stirred at 100° C. for 15 min. The cooled reaction mixture was admixed with 20 ml of water and 20 ml of ethyl acetate, and the aqueous phase was extracted once with 20 ml of ethyl acetate. The combined organic phases were washed once with 20 ml of water and then with saturated aqueous sodium chloride solution, dried over magnesium sulphate, filtered and concentrated. The residue was purified by means of normal phase flash chromatography (eluent: cyclohexane/ethyl acetate, 88-100%). Yield: 445 mg (50% of theory).

LC/MS [Method 1]: $R_t$=1.00 min; MS (ESIpos): m/z=359 (M+H)$^+$, $^1$H-NMR (400 MHz, DMSO-d$_6$): δ [ppm]=8.03 (d, 1H), 7.75 (dd, 1H), 7.70 (d, 1H), 7.66 (s, 1H), 6.40 (s, 1H), 4.61 (s, 2H), 1.80 (s, 3H), 1.44 (s, 9H).

Example 31.1F tert-Butyl 2-[4-(5-chloro-2-cyanophenyl)-5-methyl-2-oxopyridin-1(2H)-yl]-3-(1-methyl-1H-pyrazol-3-yl)propanoate (racemate)

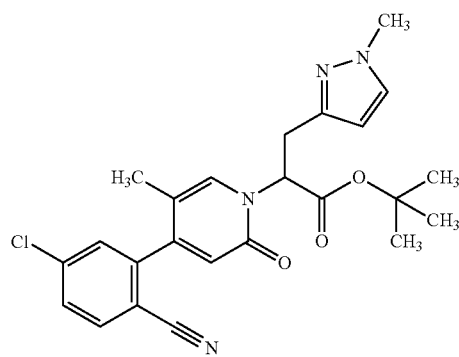 [SMILES: Cc1cn(C(Cc2ccn(C)n2)C(=O)OC(C)(C)C)c(=O)cc1-c1cc(Cl)ccc1C#N]

To a solution of 680 mg (1.90 mmol) of tert-butyl [4-(5-chloro-2-cyanophenyl)-5-methyl-2-oxopyridin-1 (2H)-yl]acetate in 8.9 ml of THF under argon at −70° C. were added 2.65 ml (2.65 mmol, 1.4 eq.) of 1 N lithium bis(trimethylsilyl)amide in THF, and the mixture was stirred for 30 min. Subsequently, 362 mg (2.37 mmol, 1.25 eq.) of a mixture of 3-(bromomethyl)-1-methyl-1H-pyrazole and 3-(chloromethyl)-1-methyl-1H-pyrazole were added, the mixture was stirred at −70° C. for 30 min and then stirred while coming to RT for 60 min. To the reaction mixture were added 10 ml of saturated aqueous ammonium chloride solution, 20 ml of water and 50 ml of ethyl acetate. The aqueous phase was extracted once more with 30 ml of ethyl acetate. The combined organic phases were washed with saturated aqueous sodium chloride solution, then dried over magnesium sulphate, filtered and concentrated. The crude product was purified by means of normal phase flash chromatography (eluent: cyclohexane/ethyl acetate, 14-100%). Yield: 493 mg (93% purity, 53% of theory).

LC/MS [Method 1]: $R_t$=1.03 min; MS (ESIpos): m/z=453 (M+H)$^+$, $^1$H-NMR (400 MHz, DMSO-d$_6$): δ [ppm]=8.01 (d, 1H), 7.71-7.75 (m, 1H), 7.68 (d, 1H), 7.56 (br. s., 1H), 7.49 (d, 1H), 6.35 (s, 1H), 5.91 (d, 1H), 5.25-5.33 (m, 1H), 3.73 (s, 2H), 3.31 (s, 3H), 1.78 (s, 3H), 1.36-1.43 (m, 9H).

Example 31.1G

2-[4-(5-Chloro-2-cyanophenyl)-5-methyl-2-oxopyridin-1(2H)-yl]-3-(1-methyl-1H-pyrazol-3-yl)propanoic acid

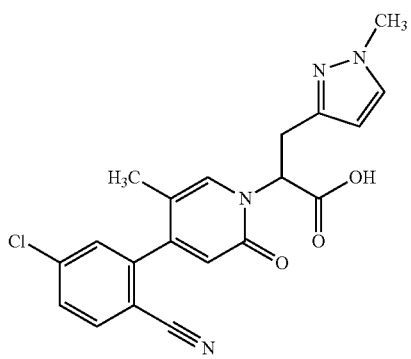 [SMILES: Cc1cn(C(Cc2ccn(C)n2)C(=O)O)c(=O)cc1-c1cc(Cl)ccc1C#N]

493 mg (1.09 mmol) of tert-butyl 2-[4-(5-chloro-2-cyanophenyl)-5-methyl-2-oxopyridin-1(2H)-yl]-3-(1-methyl-1H-pyrazol-3-yl)propanoate (racemate) were initially charged in 5.0 ml of dichloromethane and then, at 0° C., 2.52 ml (32.65 mmol) of trifluoroacetic acid were added. The mixture was stirred at 0° C. for 10 min and then brought to RT and stirring was continued at RT overnight. Then the mixture was concentrated under reduced pressure, and the residue was admixed with toluene and concentrated again. The residue thus obtained was purified by means of preparative HPLC (RP18 column, eluent: acetonitrile/water gradient with addition of 0.1% formic acid). The product fractions obtained were combined, the acetonitrile was removed under reduced pressure and the aqueous residue was extracted four times with 20 ml each time of ethyl acetate. The collected organic phases were dried over magnesium sulphate, filtered and concentrated, and the residue was dried under reduced pressure. Yield: 385 mg (90% purity, 80% of theory).

LC/MS [Method 1]: $R_t$=0.73 min; MS (ESIpos): m/z=397 (M+H)$^+$,

Example 32.1A tert-Butyl (4-bromo-5-methoxy-2-oxopyridin-1(2H)-yl)acetate

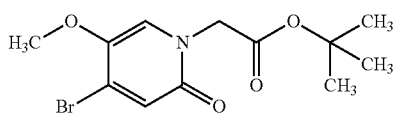 [SMILES: COc1cn(CC(=O)OC(C)(C)C)c(=O)cc1Br]

2.97 g (14.6 mmol) of 4-bromo-5-methoxypyridin-2(1H)-one and 3.02 g (21.8 mmol, 1.5 eq.) of potassium carbonate were initially charged in 66 ml of DMF, 2.63 ml (17.5 mmol, 1.2 eq.) of tert-butyl bromoacetate were added and the mixture was stirred at 50° C. for 70 min. The reaction mixture was then concentrated. 30 ml of water were added, the mixture was stirred for 5 min and filtered off with suction and the product was washed with water, suspended in acetonitrile and concentrated. The crude product was purified by means of normal phase flash chromatography (eluent: dichloromethane/methanol, 0-8%). Yield: 3.70 g (80% of theory).

LC/MS [Method 1]: $R_t$=0.78 min; MS (ESIpos): m/z=320 (M+H)$^+$, $^1$H-NMR (400 MHz, DMSO-d$_6$): δ [ppm]=7.53 (s, 1H), 6.85 (s, 1H), 4.53 (s, 2H), 3.31 (s, 3H), 1.42 (s, 9H).

Example 32.1B tert-Butyl 2-(4-bromo-5-methoxy-2-oxopyridin-1(2H)-yl)-4-methoxybutanoate (racemate)

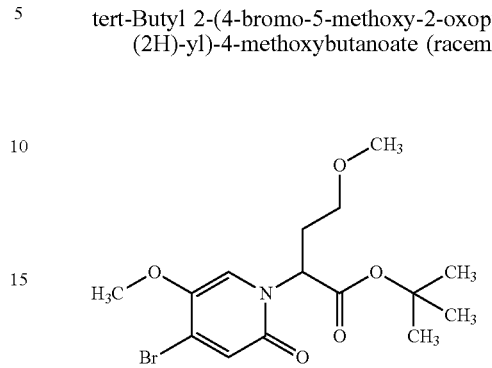

To a solution of 4.26 g (13.4 mmol) of tert-butyl (4-bromo-5-methoxy-2-oxopyridin-1(2H)-yl)acetate in 170 ml of THF under argon at −70° C. were added 18.1 ml (18.1 mmol, 1.35 eq.) of 1 N lithium bis(trimethylsilyl)amide in THF, and the mixture was stirred for 20 min. Subsequently, 2.37 ml (15.4 mmol, 1.15 eq.) of 2-methoxyethyl trifluoromethanesulphonate were added, the mixture was stirred at −70° C. for 15 min and then stirred while coming to RT for 1 h. The reaction mixture was cooled to −70° C. and another 5.4 ml (5.4 mmol, 0.4 eq.) of 1 N lithium bis(trimethylsilyl) amide in THF were added and, after 15 min, 0.72 ml (4.7 mmol, 0.35 eq.) of 2-methoxyethyl trifluoromethanesulphonate was added, and the mixture was stirred at −70° C. for 15 min and then at RT for 2 h. To the reaction mixture were added 40 ml of saturated aqueous ammonium chloride solution, 40 ml of water and 350 ml of ethyl acetate. The organic phase was washed with saturated aqueous sodium chloride solution, dried and concentrated. The crude product was then purified by means of normal phase flash chromatography (eluent: cyclohexane/ethyl acetate, 0-60%). Yield: 3.65 g (70% of theory).

LC/MS [Method 1]: $R_t$=0.94 min; MS (ESIpos): m/z=376 (M+H)$^+$, $^1$H-NMR (400 MHz, DMSO-d$_6$): δ [ppm]=7.36 (s, 1H), 6.85 (s, 1H), 5.04 (dd, 1H), 3.71 (s, 3H), 3.39-3.29 (m, 1H), 3.20-3.03 (m, 4H), 2.35-2.20 (m, 2H), 1.38 (s, 9H).

Example 32.1C tert-Butyl 4-methoxy-2-[5-methoxy-2-oxo-4-(4,4,5,5-tetramethyl-1,3,2-dioxaborolan-2-yl)pyridin-1(2H)-yl]butanoate (racemate)

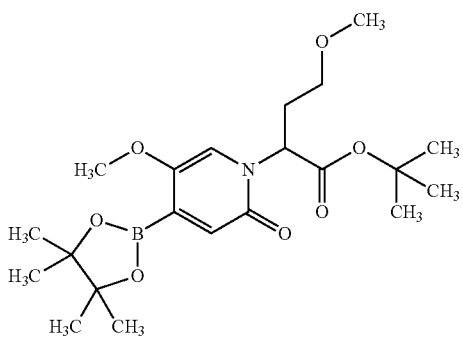 [SMILES: COCCC(C(=O)OC(C)(C)C)n1cc(OC)c(B2OC(C)(C)C(C)(C)O2)cc1=O]

3.05 g (8.1 mmol) of tert-butyl 2-(4-bromo-5-methoxy-2-oxopyridin-1(2H)-yl)-4-methoxybutanoate (racemate), 2.26 g (8.9 mmol, 1.1 eq.) of bis(pinacolato)diboron and 2.39 g (24.3 mmol, 3 eq.) of potassium acetate were initially charged in 84 ml of dioxane under argon, 199 mg (0.24 mmol, 0.03 eq) of [1,1-bis(diphenylphosphino)ferrocene]dichloropalladium dichloromethane complex were added and the mixture was stirred at 80° C. for 6 h. The reaction mixture was cooled down, filtered through kieselguhr and washed through with ethyl acetate/THF. The filtrate was concentrated, and the residue was twice admixed with THF and concentrated. Subsequently, the residue was dissolved in diethyl ether, concentrated again and dried at 40° C. under high vacuum. Yield: 4.60 g (70% purity, 94% of theory).

$^1$H-NMR (400 MHz, DMSO-$d_6$): δ [ppm]=7.09 (s, 1H), 6.49 (s, 1H), 5.00 (dd, 1H), 3.60 (s, 3H), 3.36-3.27 (m, 3H), 3.17 (s, 3H), 3.14-3.05 (m, 1H), 2.30-2.21 (m, 2H), 1.37 (s, 9H), 1.27 (s, 12H).

Example 32.1D

2-Bromo-4-(methylamino)benzonitrile

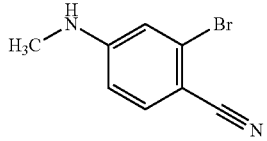

1.00 g (4.90 mmol) of 2-bromo-4-fluorobenzonitrile, 335 mg (4.96 mmol, 1.012 eq.) of methylamine hydrochloride and 1.71 ml (9.80 mmol, 2 eq.) of N,N-diisopropylethylamine were initially charged in 9.85 ml of 1-methyl-2-pyrrolidone and the mixture was heated in the microwave at 120° C. for 40 min. The cooled reaction mixture was partitioned between ethyl acetate and water, and the aqueous phase was extracted once more with ethyl acetate. The combined organic phases were washed three times with water, then with saturated aqueous sodium chloride solution, dried and concentrated. The crude product was purified by means of normal phase flash chromatography (eluent: cyclohexane/ethyl acetate, 0-40%). Yield: 660 mg (63% of theory).

LC/MS [Method 1]: $R_t$=0.82 min; MS (ESIpos): m/z=211 (M+H)$^+$, $^1$H-NMR (400 MHz, DMSO-$d_6$): δ [ppm]=7.50 (d, 1H), 7.06-6.94 (m, 1H), 6.84 (d, 1H), 6.60 (dd, 1H), 2.73 (d, 3H).

Example 32.1E tert-Butyl 2-{4-[2-cyano-5-(methylamino)phenyl]-5-methoxy-2-oxopyridin-1(2H)-yl}-4-methoxybutanoate (racemate)

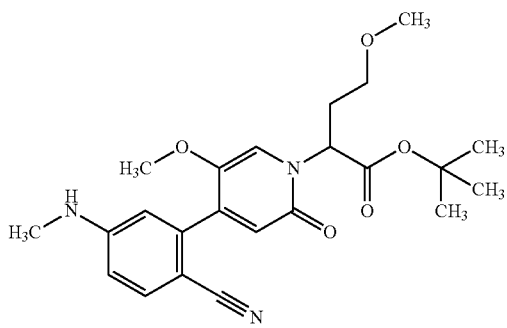 [SMILES: CNc1ccc(C#N)c(-c2cc(=O)n(C(CCOC)C(=O)OC(C)(C)C)cc2OC)c1]

To 200 mg (0.95 mmol) of 2-bromo-4-(methylamino)benzonitrile, 692 mg (0.95 mmol, 58% purity, 1 eq.) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate) and 393 mg (2.84 mmol, 3 eq.) of potassium carbonate were added 9.7 ml of DMF. For 5 min, argon was passed through the reaction mixture. 23 mg (0.03 mmol, 0.03 eq) of [1,1-bis(diphenylphosphino)ferrocene]dichloropalladium dichloromethane complex were then added, and the mixture was stirred at 80° C. overnight. The reaction mixture was filtered through kieselguhr and washed with dichloromethane, and the filtrate was concentrated. The crude product was purified by means of normal phase flash chromatography (eluent: cyclohexane/ethyl acetate, 50-100%). Yield: 354 mg (85% of theory).

LC/MS [Method 10]: $R_t$=1.69 min; MS (ESIpos): m/z=428 (M+H)$^+$, $^1$H-NMR (400 MHz, DMSO-$d_6$): δ [ppm]=7.51 (d, 1H), 7.30 (s, 1H), 6.85-6.76 (m, 1H), 6.62 (dd, 1H), 6.52 (d, 1H), 6.31 (s, 1H), 5.10 (dd, 1H), 3.62 (s, 3H), 3.42-3.34 (m, 1H), 3.23-3.12 (m, 4H), 2.74 (d, 3H), 2.39-2.26 (m, 2H), 1.40 (s, 9H).

Example 32.1F

2-{4-[2-Cyano-5-(methylamino)phenyl]-5-methoxy-2-oxopyridin-1(2H)-yl}-4-methoxybutanoic acid hydrochloride (racemate)

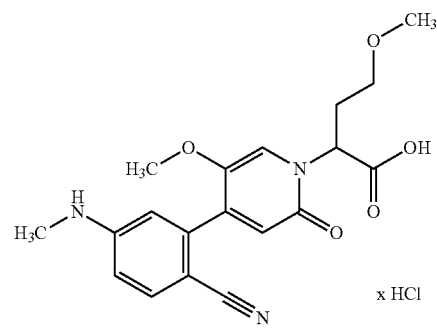

According to General Method 6B, 354 mg (0.81 mmol) of tert-butyl 2-{4-[2-cyano-5-(methylamino)phenyl]-5-methoxy-2-oxopyridin-1(2H)-yl}-4-methoxybutanoate (racemate) in 9.0 ml of hydrogen chloride in dioxane (4M) were reacted. Yield: 328 mg (98% of theory)

LC/MS [Method 10]: $R_t$=1.15 min; MS (ESIpos): m/z=372 (M+H)$^+$, $^1$H-NMR (400 MHz, DMSO-$d_6$): δ [ppm]=7.51 (d, 1H), 7.35 (s, 1H), 6.62 (dd, 1H), 6.52 (d, 1H), 6.30 (s, 1 H), 5.16-5.10 (m, 1H), 4.86 (bs) 3.61 (s, 3H), 3.41-3.33 (m, 1H), 3.19 (s, 3H), 3.17-3.09 (m, 1H), 2.74 (s, 3H), 2.40-2.29 (m, 2H).

Example 33.1A

2-Bromo-4-chloro-5-fluorobenzonitrile

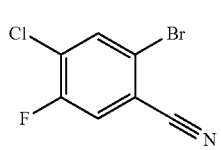 [SMILES: N#Cc1cc(F)c(Cl)cc1Br]

1.0 g (2.98 mmol) of 1-bromo-5-chloro-4-fluoro-2-iodobenzene were dissolved in 17.5 ml of DMF, and 185 mg (1.58 mmol, 0.53 eq.) of zinc cyanide were added. Argon was passed through the reaction mixture for 5 min. Subsequently, 286 mg (0.25 mmol, 0.08 eq.) of tetrakis(triphenylphosphine)palladium(0) were added and the mixture was stirred at 70° C. overnight. The mixture was heated to 90° C. and stirred at 90° C. overnight. The reaction mixture was concentrated and the residue was purified by means of normal phase flash chromatography (eluent: cyclohexane/ethyl acetate, 0-10%). The product fractions were combined and concentrated. The residue was admixed with diethyl ether, then filtered, and the filtrate was concentrated. Yield: 0.34 g (89% purity, 43% of theory).

$^1$H-NMR (400 MHz, DMSO-d$_6$): δ [ppm]=8.31 (d, 1H), 8.25 (d, 1H).

Example 33.1B tert-Butyl 2-[4-(5-chloro-2-cyano-4-fluorophenyl)-5-methoxy-2-oxopyridin-1(2H)-yl]-4-methoxybutanoate (racemate)

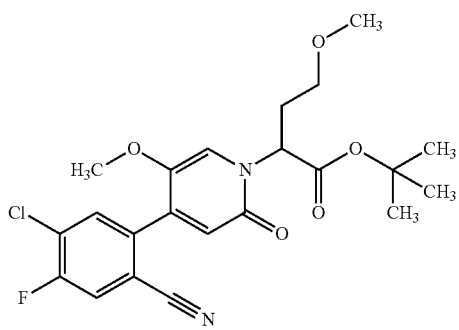 [SMILES: COCCC(C(=O)OC(C)(C)C)n1cc(OC)c(-c2cc(Cl)c(F)cc2C#N)cc1=O]

To 500 mg (0.65 mmol, 55% purity) of tert-butyl 4-methoxy-2-[5-methoxy-2-oxo-4-(4,4,5,5-tetramethyl-1,3,2-dioxaborolan-2-yl)pyridin-1(2H)-yl]butanoate (racemate), 171 mg (0.65 mmol, 89% purity) of 2-bromo-4-chloro-5-fluorobenzonitrile and 269 mg (1.95 mmol, 3 eq.) of potassium carbonate were added 6.6 ml of dioxane. Argon was passed through the reaction mixture for 5 min. Subsequently, 16 mg (0.02 mmol, 0.03 eq) of [1,1-bis(diphenylphosphino)ferrocene]dichloropalladium-dichloromethane complex were added and the mixture was stirred at 80° C. for 3 days. The reaction mixture was filtered through kieselguhr, washed with dichloromethane/acetonitrile, and the filtrate was concentrated. The crude product was purified by means of normal phase flash chromatography (eluent: cyclohexane/ethyl acetate, 0-45%). Yield: 280 mg (60% purity, 57% of theory).

LC/MS [Method 1]: R$_t$=1.05 min; MS (ESIpos): m/z=451 (M+H)$^+$, $^1$H NMR (400 MHz, DMSO-d$_6$): δ [ppm]=8.22 (d, 1H), 7.97-7.89 (m, 1H), 7.37 (s, 1H), 6.49 (s, 1H), 5.16-5.04 (m, 1H), 3.64 (s, 3H), 3.43-3.35 (m, 1H), 3.23-3.10 (m, 4H), 2.39-2.25 (m, 2H), 1.40 (s, 9H)

Example 33.1C

2-[4-(5-Chloro-2-cyano-4-fluorophenyl)-5-methoxy-2-oxopyridin-1(2H)-yl]-4-methoxybutanoic acid (racemate)

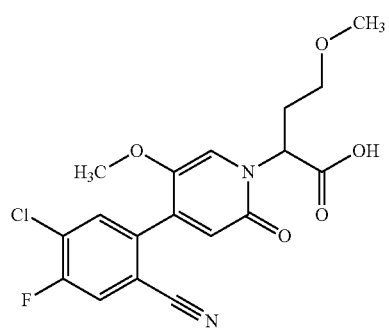 [SMILES: COCCC(C(=O)O)n1cc(OC)c(-c2cc(Cl)c(F)cc2C#N)cc1=O]

To 280 mg (0.37 mmol, 60% purity) of tert-butyl 2-[4-(5-chloro-2-cyano-4-fluorophenyl)-5-methoxy-5-oxopyridin-1(2H)-yl]-4-methoxybutanoate were added 3.64 ml of 4 N hydrogen chloride in dioxane and the mixture was stirred at RT overnight. The residue was concentrated, admixed with THF and concentrated again. The residue was dried under high vacuum. Yield: 260 mg (56% purity, 99% of theory).

LC/MS [Method 10]: R$_t$=1.44 min; MS (ESIpos): m/z=395 (M+H)$^+$, $^1$H NMR (400 MHz, DMSO-d$_6$): δ [ppm]=12.98 (bs, 1H), 8.22 (d, 1H), 7.95 (d, 1H), 7.42 (s, 1H), 6.48 (s, 1H), 5.20-5.07 (m, 1H), 3.63 (s, 3H), 3.42-3.33 (m, 1H), 3.19 (s, 3H), 3.16-3.08 (m, 1H), 2.41-2.29 (m, 2H).

Example 34.1A 2-(2,5-Dimethoxypyridin-4-yl)-4-fluorobenzonitrile

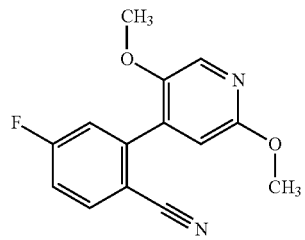 [SMILES: COc1cc(-c2cc(F)ccc2C#N)c(OC)cn1]

1.11 g (4.17 mmol) of diisopropyl (2,5-dimethoxypyridin-4-yl)borate, 1.73 g (12.50 mmol, 3 eq.) of potassium carbonate and 0.340 mg (0.417 mmol, 0.1 eq.) of [1,1-bis(diphenylphosphino)ferrocene]palladium(II) chloride dichloromethane adduct were initially charged in a flask, which was then evacuated and filled with argon three times. 1.00 g (5.00 mmol, 1.2 eq) of 2-bromo-4-fluorobenzonitrile and 40 ml of dioxane were added, argon was passed through for 2 min and the mixture was stirred at 100° C. overnight. The reaction mixture was cooled down, filtered through kieselguhr and washed with acetonitrile, and the filtrate was concentrated. The crude product was purified by means of normal phase flash chromatography (eluent: cyclohexane/ethyl acetate, 5-25%). Yield: 0.75 g (67% of theory).

LC/MS [Method 1]: $R_t$=0.96 min; MS (ESIpos): m/z=259 (M+H)$^+$, $^1$H-NMR (400 MHz, DMSO-d$_6$): δ [ppm]=8.10-8.01 (m, 2H), 7.55-7.46 (m, 2H), 6.86 (s, 1H), 3.86 (s, 3H), 3.80 (s, 3H).

Example 34.1B

4-Fluoro-2-(5-methoxy-2-oxo-1,2-dihydropyridin-4-yl)benzonitrile

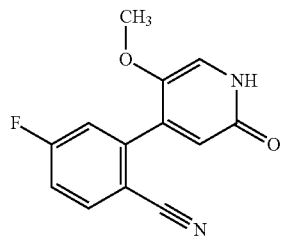 [SMILES: COc1c[nH]c(=O)cc1-c1cc(F)ccc1C#N]

747 mg (2.78 mmol) of 2-(2,5-dimethoxypyridin-4-yl)-4-fluorobenzonitrile were initially charged in 14 ml of DMF, 889 mg (5.55 mmol, 2 eq.) of pyridine hydrobromide were added, and the mixture was stirred at 120° C. for 7 h and then at 100° C. overnight. The reaction mixture was concentrated, admixed with water and extracted three times with ethyl acetate. The combined organic phases were washed with saturated aqueous sodium chloride solution, dried over sodium sulphate and concentrated. The residue was purified by means of normal phase flash chromatography (eluent: dichloromethane/methanol, 0-5%). Overall yield: 480 mg (71% of theory).

LC/MS [Method 1]: $R_t$=0.62 min; MS (ESIpos): m/z=245 (M+H)$^+$, $^1$H-NMR (400 MHz, DMSO-d$_6$): δ [ppm]=11.40 (bs, 1H), 8.07-7.98 (m, 1H), 7.54-7.45 (m, 2H), 7.30 (bs, 1H), 6.42 (s, 1H), 3.64 (s, 3H).

Example 34.1C tert-Butyl [4-(2-cyano-5-fluorophenyl)-5-methoxy-2-oxopyridin-1(2H)-yl]acetate

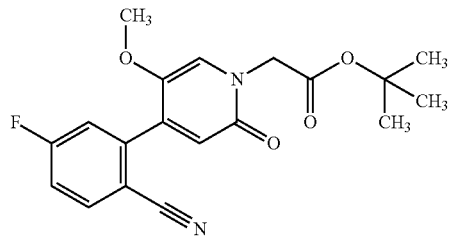 [SMILES: COc1cn(CC(=O)OC(C)(C)C)c(=O)cc1-c1cc(F)ccc1C#N]

To 480 mg (1.97 mmol) of 4-fluoro-(5-methoxy-2-oxo-1,2-dihydropyridin-4-yl)benzonitrile, 0.355 ml (2.36 mmol, 1.2 eq.) of tert-butyl bromoacetate and 407 mg (2.95 mmol, 1.5 eq.) of potassium carbonate were added 10 ml of DMF and the mixture was stirred at 100° C. for 45 min. The reaction mixture was concentrated. The residue was admixed with ethyl acetate and water, and the aqueous phase was extracted once more with ethyl acetate. The combined organic phases were washed with saturated aqueous sodium chloride solution, dried over sodium sulphate and concentrated. The crude product was purified by means of normal phase flash chromatography (eluent: dichloromethane/methanol, 0-5%). Yield: 459 mg (65% of theory).

LC/MS [Method 1]: $R_t$=0.91 min; MS (ESIpos): m/z=359 (M+H)$^+$, $^1$H-NMR (400 MHz, DMSO-d$_6$): δ [ppm]=8.05 (dd, 1H), 7.60-7.44 (m, 3H), 6.48 (s, 1H), 4.61 (s, 2H), 3.62 (s, 3H), 1.44 (s, 9H).

Example 34.1D tert-Butyl 2-[4-(2-cyano-2-fluorophenyl)-5-methoxy-5-oxopyridin-1(2H)-yl]-3-(1-methyl-1H-pyrazol-3-yl)propanoate (racemate)

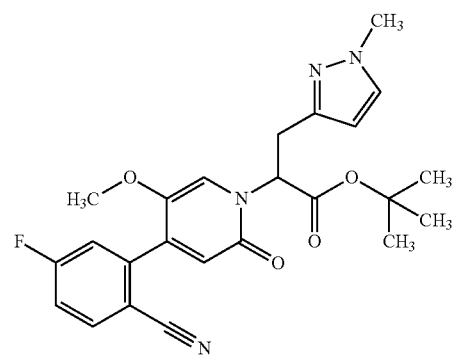 [SMILES: COc1cn(C(Cc2ccn(C)n2)C(=O)OC(C)(C)C)c(=O)cc1-c1cc(F)ccc1C#N]

To a solution of 459 mg (1.28 mmol) of tert-butyl [4-(2-cyano-5-fluorophenyl)-5-methoxy-2-oxopyridin-1 (2H)-yl]acetate in 10 ml of THF under argon at −70° C. were added 1.60 ml (1.60 mmol, 1.25 eq.) of 1 N lithium bis(trimethylsilyl)amide in THF, and the mixture was stirred for 30 min. Subsequently, 402 mg (1.47 mmol, 64% purity, 1,148 eq.) of 3-(bromomethyl)-1-methyl-1H-pyrazole were added, the mixture was stirred at −70° C. for 30 min and then stirred while coming to RT for 2 h. To the reaction mixture were added 10 ml of saturated aqueous ammonium chloride solution, 10 ml of water and 80 ml of ethyl acetate. The aqueous phase was extracted once with ethyl acetate, and the combined organic phases were washed once with saturated aqueous sodium chloride solution, dried and concentrated. The crude product was purified by means of normal phase flash chromatography (eluent: dichloromethane/methanol, 0-5%). The product fractions were combined and the residue was purified again by means of normal phase flash chromatography (eluent: cyclohexane/ethyl acetate, 50-100%). Yield: 379 mg (64% of theory).

LC/MS [Method 1]: $R_t$=0.94 min; MS (ESIpos): m/z=453 (M+H)$^+$, $^1$H-NMR (400 MHz, DMSO-d$_6$): δ [ppm]=8.08-7.98 (m, 1H), 7.55-7.43 (m, 3H), 7.31 (s, 1H), 6.43 (s, 1H), 5.96 (d, 1H), 5.30 (dd, 1H), 3.73 (s, 3H), 3.55 (s, 3H), 3.48-3.37 (m, 1H), 3.37-3.27 (m, 1H), 1.41 (s, 9H).

Example 34.1E

2-[4-(2-Cyano-5-fluorophenyl)-5-methoxy-2-oxopyridin-1(2H)-yl]-3-(1-methyl-1H-pyrazol-3-yl)propanoic acid (racemate)

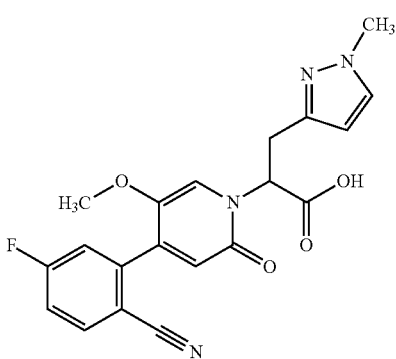 [SMILES: COc1cn(C(Cc2ccn(C)n2)C(=O)O)c(=O)cc1-c1cc(F)ccc1C#N]

According to General Method 6B, 378 mg (0.814 mmol) of tert-butyl 2-[4-(2-cyano-5-fluorophenyl)-5-methoxy-2-oxopyridin-1(2H)-yl]-3-(1-methyl-1H-pyrazol-3-yl)propanoate (racemate) in 8.0 ml of hydrogen chloride in dioxane (4 M) were reacted. Yield: 338 mg (95% purity, 99% of theory)

LC/MS [Method 1]: $R_t$=0.70 min; MS (ESIpos): m/z=397 (M+H)$^+$, $^1$H-NMR (400 MHz, DMSO-d$_6$): δ [ppm]=8.03 (dd, 1H), 7.55-7.45 (m, 3H), 7.33 (s, 1H), 6.41 (s, 1H), 5.91 (d, 1H), 5.31 (dd, 1H), 3.72 (s, 3H), 3.54 (s, 3H), 3.52-3.42 (m, 1H), 3.38-3.30 (m, 1H).

Example 35.1A

4-Chloro-2-fluoro-6-(4,4,5,5-tetramethyl-1,3,2-dioxaborolan-2-yl)benzonitrile

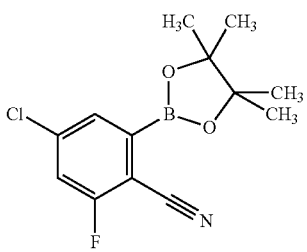 [SMILES: CC1(C)OB(c2cc(Cl)cc(F)c2C#N)OC1(C)C]

To 1500 mg (9.64 mmol) of 4-chloro-2-fluorobenzonitrile, 2.80 ml (19.29 mmol, 2 eq.) of 4,4,5,5-tetramethyl-1,3,2-dioxaborolane, 96 mg (0.145 mmol, 0.015 eq.) of methoxy(1,5-cyclooctadiene)-iridium(I) dimer and 107 mg (0.289 mmol, 0.03 eq.) of 4,4-di-tert-butyl-2,2-dipyridyl were added 20 ml of THF. Argon was passed through the reaction mixture for 5 min and then it was stirred under a gentle argon stream at 50° C. overnight. Subsequently, the reaction mixture was concentrated and the residue was purified by means of silica gel chromatography (eluent: cyclohexane/ethyl acetate, 8-80%). The product fractions were combined and the residue was stirred with 10 ml of diethyl ether. The precipitate was filtered off and washed twice with 1 ml each time of diethyl ether, and the filtrate was concentrated and dried under high vacuum. Yield: 2.68 g (60% purity, 59% of theory).

LC/MS [Method 9]: $R_t$=5.63 min; MS (ESIpos): m/z=281 (M+H)$^+$,

Example 35.1B tert-Butyl 2-[4-(5-chloro-2-cyano-3-fluorophenyl)-5-methoxy-2-oxopyridin-1(2H)-yl]-4-methoxybutanoate (racemate)

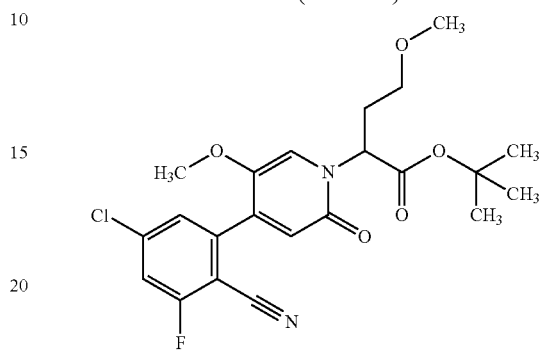

To 200 mg (0.505 mmol, 95% purity) of tert-butyl-2-(4-bromo-5-methoxy-2-oxopyridin-1(2H)-yl)-4-methoxybutanoate (racemate), 237 mg (0.505 mmol, 60% purity, 1 eq.) of 4-chloro-2-fluoro-6-(4,4,5,5-tetramethyl-1,3,2-dioxaborolan-2-yl)benzonitrile and 209 mg (1.515 mmol, 3 eq.) of potassium carbonate were added 5.1 ml of DMF. Argon was passed through the reaction mixture for 5 min. Subsequently, 12 mg (0.015 mmol, 0.03 eq) of [1,1-bis(diphenylphosphino)ferrocene]dichloropalladium dichloromethane complex were added, and the mixture was stirred at 80° C. for one day. The reaction mixture was filtered through kieselguhr and washed with acetonitrile/dichloromethane, and the filtrate was concentrated. The crude product was purified by means of normal phase flash chromatography (eluent: cyclohexane/ethyl acetate, 0-45%). Yield: 153 mg (70% purity, 47% of theory).

LC/MS [Method 10]: $R_t$=1.97 min; MS (ESIpos): m/z=451 (M+H)$^+$, $^1$H-NMR (400 MHz, DMSO-d$_6$): δ [ppm]=7.93 (d, 1H), 7.65 (s, 1H), 7.40 (s, 1H), 6.53 (s, 1H), 5.17-5.05 (m, 1H), 3.65 (s, 3H), 3.43-3.34 (m, 1H), 3.22-3.10 (m, 4H), 2.39-2.24 (m, 2H), 1.40 (s, 9H).

Example 35.1C

2-[4-(5-Chloro-2-cyano-3-fluorophenyl)-5-methoxy-2-oxopyridin-1(2H)-yl]-4-methoxybutanoic acid (racemate)

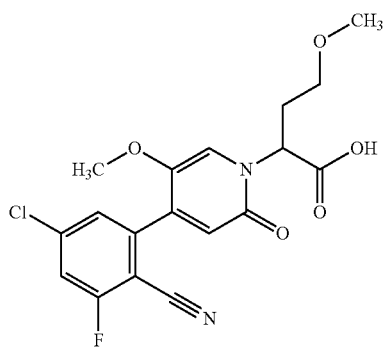 [SMILES: COCCC(C(=O)O)n1cc(OC)c(-c2cc(Cl)cc(F)c2C#N)cc1=O]

According to General Method 6B, 153 mg (0.238 mmol, 70% purity) of tert-butyl 2-[4-(5-chloro-2-cyano-3-fluorophenyl)-5-methoxy-2-oxopyridin-1(2H)-yl]-4-methoxybutanoate (racemate) in 2.3 ml of hydrogen chloride in dioxane (4 M) were reacted. Yield: 150 mg (62% purity, 99% of theory)

LC/MS [Method 10]: $R_t$=1.46 min; MS (ESIpos): m/z=395 (M+H)$^+$, $^1$H-NMR (400 MHz, DMSO-d$_6$): δ [ppm]=13.01 (bs, 1H), 7.94 (dd, 1H), 7.66 (d, 1H), 7.45 (s, 1H), 6.52 (s, 1H), 5.20-5.07 (m, 1H), 3.57 (s, 3H), 3.42-3.34 (m, 1H), 3.19 (s, 3H), 3.17-3.08 (m, 1H), 2.40-2.31 (m, 2H).

Example 36.1A

4-Chloro-2-(5-cyclopropyl-2-methoxypyridin-4-yl)benzonitrile

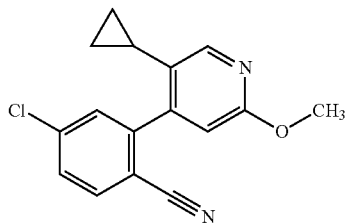 [SMILES: COc1cc(-c2cc(Cl)ccc2C#N)c(C2CC2)cn1]

Under argon, 500 mg (1.50 mmol) of 2-(5-bromo-2-methoxypyridin-4-yl)-4-chlorobenzonitrile, 0.262 ml (1.80 mmol, 1.2 eq.) of cyclopropylboronic acid, 1050 mg (4.95 mmol, 3.3 eq.) of potassium phosphate, 42 mg (0.15 mmol, 0.1 eq.) of tricyclohexylphosphine and 17 mg (0.075 mmol, 0.05 eq.) of palladium(II) acetate were initially charged in a flask, which was then evacuated and filled with argon three times. 15 ml of degassed toluene and 0.75 ml of water were added and the mixture was stirred at 100° C. overnight. The reaction mixture was cooled down to RT, filtered through Celite and washed through with ethyl acetate. The filtrate was concentrated and the residue was purified by means of silica gel chromatography (eluent: cyclohexane/ethyl acetate, 5-60%). Yield: 0.75 g (67% of theory).

LC/MS [Method 1]: $R_t$=1.14 min; MS (ESIpos): m/z=323 (M+H)$^+$, $^1$H-NMR (400 MHz, DMSO-d$_6$): δ [ppm]=8.07-7.99 (m, 2H), 7.79-7.71 (m, 2H), 6.79 (s, 1H), 3.87 (s, 3H), 1.55-1.45 (m, 1H), 0.72-0.66 (m, 2H), 0.64-0.57 (m, 2H).

Example 36.1B

4-Chloro-2-(5-cyclopropyl-2-oxo-1,2-dihydropyridin-4-yl)benzonitrile

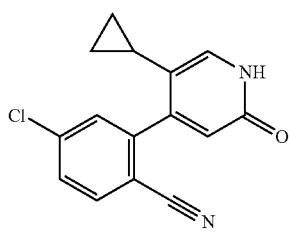 [SMILES: N#Cc1ccc(Cl)cc1-c1cc(=O)[nH]cc1C1CC1]

To 550 mg (1.93 mmol) of 4-chloro-2-(5-cyclopropyl-2-methoxypyridin-4-yl)benzonitrile and 3.09 g (19.3 mmol, 10 eq.) of pyridine hydrobromide were added 16 ml of DMF and the mixture was stirred at 100° C. under argon for 2 h.

The reaction mixture was concentrated and the residue was admixed with 20 ml of water. The precipitated solids were filtered off, washed with 100 ml of water and dried in a vacuum drying cabinet at 50° C. for 2 h. Yield: 495 mg (91% purity, 86% of theory).

LC/MS [Method 1]: $R_t$=0.79 min; MS (ESIpos): m/z=271 (M+H)$^+$, $^1$H-NMR (400 MHz, DMSO-d$_6$): δ [ppm]=11.74 (bs, 1H), 8.02 (d, 1H), 7.75-7.71 (m, 2H), 7.18 (s, 1H), 6.29 (s, 1H), 1.32-1.21 (m, 1H), 0.54-0.47 (m, 2H), 0.47-0.40 (m, 2H).

Example 36.1C tert-Butyl [4-(5-chloro-2-cyanophenyl)-5-cyclopropyl-2-oxopyridin-1(2H)-yl]acetate

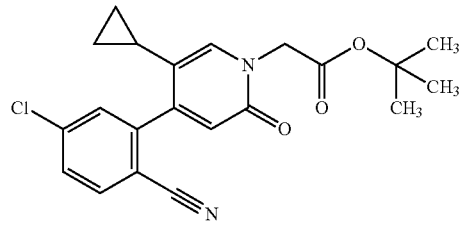 [SMILES: CC(C)(C)OC(=O)Cn1cc(C2CC2)c(-c2cc(Cl)ccc2C#N)cc1=O]

490 mg (1.81 mmol) of 4-chloro-2-(5-cyclopropyl-2-oxo-1,2-dihydropyridin-4-yl)benzonitrile and 375 mg (2.72 mmol, 1.5 eq.) of potassium carbonate were initially charged in 10 ml of DMF, 0.327 ml (2.17 mmol, 1.2 eq.) of tert-butyl bromoacetate was added and the mixture was stirred at 60° C. for 1.5 h. The cooled reaction mixture was partitioned between 20 ml of ethyl acetate and 20 ml of water, and the aqueous phase was extracted once more with 20 ml of ethyl acetate. The combined organic phases were washed once with 20 ml of water, then with saturated aqueous sodium chloride solution, dried over magnesium sulphate, filtered and concentrated. The residue was purified by means of silica gel chromatography (eluent: cyclohexane/ethyl acetate 88-100%). Yield: 431 mg (61% of theory).

LC/MS [Method 1]: $R_t$=1.07 min; MS (ESIpos): m/z=385 (M+H)$^+$, $^1$H-NMR (400 MHz, DMSO-d$_6$): δ [ppm]=8.03 (d, 1H), 7.77-7.72 (m, 2H), 7.57 (s, 1H), 6.39 (s, 1H), 4.60 (s, 2H), 1.43 (s, 9H), 1.36-1.27 (m, 1H), 0.59-0.52 (m, 2H), 0.47-0.41 (m, 2H).

Example 36.1D tert-Butyl 2-[4-(5-chloro-2-cyanophenyl)-5-cyclopropyl-2-oxopyridin-1(2H)-yl]-3-(1-methyl-1H-pyrazol-3-yl)propanoate (racemate)

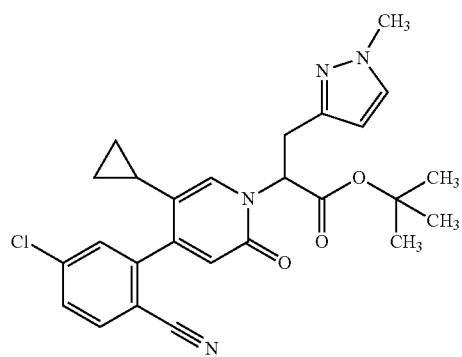 [SMILES: Cn1ccc(CC(C(=O)OC(C)(C)C)n2cc(C3CC3)c(-c3cc(Cl)ccc3C#N)cc2=O)n1]

To a solution of 430 mg (1.12 mmol) of tert-butyl [4-(5-chloro-2-cyanophenyl)-5-cyclopropyl-2-oxopyridin-1 (2H)-yl]acetate in 5.2 ml of THF under argon at −70° C. were added 1.56 ml (1.56 mmol, 1.4 eq.) of 1 N lithium bis(trimethylsilyl)amide in THF, and the mixture was stirred for 30 min. Subsequently, 208 mg (1.45 mmol, 1.3 eq.) of a mixture of 3-(bromomethyl)-1-methyl-1H-pyrazole and 3-(chloromethyl)-1-methyl-1H-pyrazole were added, the mixture was stirred at −70° C. for 30 min and then stirred while coming to RT for 1.5 h. The reaction mixture was stirred with 10 ml of saturated aqueous ammonium chloride solution, and 20 ml of water and 50 ml of ethyl acetate were added. The aqueous phase was extracted once with 30 ml of ethyl acetate. The combined organic phases were washed with saturated aqueous sodium chloride solution, then dried over magnesium sulphate, filtered and concentrated. The residue was purified by silica gel chromatography (eluent: cyclohexane/ethyl acetate 16-100%). Yield: 243 mg (95% purity, 43% of theory).

LC/MS [Method 1]: $R_t$=1.06 min; MS (ESIpos): m/z=479 (M+H)$^+$, $^1$H-NMR (400 MHz, DMSO-d$_6$): δ [ppm]=8.01 (d, 1H), 7.75-7.69 (m, 2H), 7.49 (d, 1H), 7.25 (s, 1H), 6.34 (s, 1H), 5.89 (d, 1H), 5.26-5.17 (m, 1H), 3.72 (s, 3H), 1.99 (s, 2H), 1.40 (s, 9H), 1.30-1.22 (m, 1H), 0.55-0.46 (m, 2H), 0.36-0.23 (m, 2H).

Example 36.1E

2-[4-(5-Chloro-2-cyanophenyl)-5-cyclopropyl-2-oxopyridin-1(2H)-yl]-3-(1-methyl-1H-pyrazol-3-yl)propanoic acid (racemate)

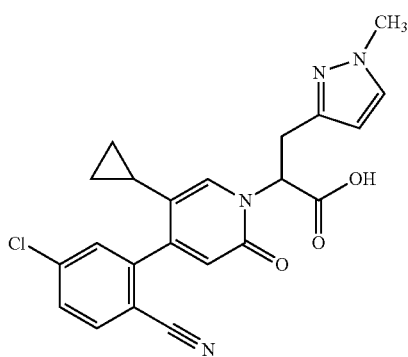 [SMILES: Cn1ccc(CC(C(=O)O)n2cc(C3CC3)c(-c3cc(Cl)ccc3C#N)cc2=O)n1]

According to General Method 6A, 237 mg (0.495 mmol) of tert-butyl 2-[4-(5-chloro-2-cyanophenyl)-5-cyclopropyl-2-oxopyridin-1(2H)-yl]-3-(1-methyl-1H-pyrazol-3-yl)propanoate (racemate) were reacted with 1.4 ml of TFA. Yield: 170 mg (79% of theory)

LC/MS [Method 1]: $R_t$=0.80 min; MS (ESIpos): m/z=423 (M+H)$^+$, $^1$H-NMR (400 MHz, DMSO-d$_6$): δ [ppm]=13.01 (bs, 1H), 8.01 (d, 1H), 7.76-7.69 (m, 2H), 7.46 (d, 1H), 7.25 (s, 1H), 6.32 (s, 1H), 5.83 (d, 1H), 5.29-5.16 (m, 1H), 3.71 (s, 3H), 3.46-3.36 (m, 1H), 1.31-1.22 (m, 1H), 0.55-0.45 (m, 2H), 0.34-0.23 (m, 2H).

Example 37.1A tert-Butyl 2-[4-(5-chloro-2-fluorophenyl)-5-methoxy-2-oxopyridin-1(2H)-yl]-3-(1,3-oxazol-2-yl)propanoate (racemate)

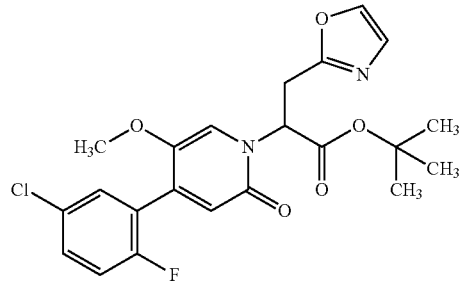 [SMILES: COc1cn(C(Cc2ncco2)C(=O)OC(C)(C)C)c(=O)cc1-c1cc(Cl)ccc1F]

To a solution of 691 mg (1.88 mmol) of tert-butyl [4-(5-chloro-2-fluorophenyl)-5-methoxy-2-oxopyridin-1(2H)-yl]acetate in 14 ml of THF under argon at −70° C. were added 2.35 ml (2.35 mmol, 1.25 eq.) of 1 N lithium bis(trimethylsilyl)amide in THF, and the mixture was stirred for 30 min. Subsequently, 450 mg (2.50 mmol, 90% purity, 1.33 eq.) of 2-(bromomethyl)-1,3-oxazole were added, the mixture was stirred at −70° C. for 30 min and then stirred while coming to RT for 2 h. To the reaction mixture were added 15 ml of saturated aqueous ammonium chloride solution, 15 ml of water and 150 ml of ethyl acetate. The aqueous phase was extracted once with ethyl acetate, and the combined organic phases were washed with saturated aqueous sodium chloride solution, dried and concentrated. The crude product was purified twice by means of normal phase flash chromatography (eluent: cyclohexane/ethyl acetate, 0-50%). Yield: 480 mg (57% of theory).

LC/MS [Method 1]: $R_t$=1.05 min; MS (ESIpos): m/z=449 (M+H)$^+$, $^1$H-NMR (400 MHz, DMSO-d$_6$): δ [ppm]=8.02 (s, 1H), 7.54 (ddd, 1H), 7.48 (dd, 1H), 7.38 (s, 1H), 7.37-7.31 (m, 1H), 7.14 (s, 1H), 6.42 (s, 1H), 5.45 (dd, 1H), 3.73-3.64 (m, 1H), 3.60-3.48 (m, 4H), 1.36 (s, 9H).

Example 37.1B

2-[4-(5-Chloro-2-fluorophenyl)-5-methoxy-2-oxopyridin-1(2H)-yl]-3-(1,3-oxazol-2-yl)propanoic acid (racemate)

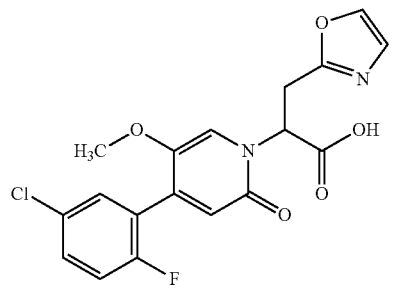 [SMILES: COc1cn(C(Cc2ncco2)C(=O)O)c(=O)cc1-c1cc(Cl)ccc1F]

According to General Method 6B, 480 mg (1.07 mmol) of tert-butyl 5-[4-(2-chloro-2-fluorophenyl)-5-methoxy-2-oxopyridin-1(2H)-yl]-3-(1,3-oxazol-2-yl)propanoate (racemate) in 10.8 ml of hydrogen chloride in dioxane (4 M) were reacted. Then 50 ml of diethyl ether were added, and the mixture was concentrated and dried under high vacuum. This procedure was repeated once. Yield: 470 mg (80% purity, 90% of theory)

LC/MS [Method 1]: $R_t$=0.74 min; MS (ESIpos): m/z=393 $(M+H)^+$.

Example 38.1A

4-[5-Chloro-2-(trifluoromethyl)phenyl]-2,5-dimethoxypyridine

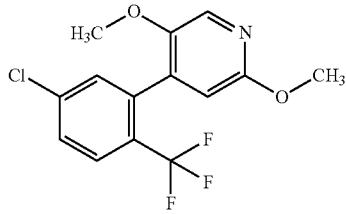 [SMILES: COc1cc(-c2cc(Cl)ccc2C(F)(F)F)c(OC)cn1]

3.00 g (16.40 mmol) of (2,5-dimethoxypyridin-4-yl)boric acid, 5.11 g (19.68 mmol, 1.2 eq.) of 2-bromo-4-chloro-1-(trifluoromethyl)benzene, 6.80 g (49.19 mmol, 3 eq.) of potassium carbonate and 1.34 g (1.64 mmol, 0.1 eq.) of [1,1-bis(diphenylphosphino)ferrocene]palladium(II) chloride dichloromethane adduct were initially charged in a flask, which was then filled with argon. 150 ml of dioxane were added, argon was passed through for 2 min and the mixture was stirred at 110° C. overnight. The reaction mixture was filtered through kieselguhr and washed with dioxane, and the filtrate was concentrated. The crude product was purified by means of normal phase flash chromatography (eluent: cyclohexane/ethyl acetate, 20-50%). Yield: 2.57 g (49% of theory).

LC/MS [Method 1]: $R_t$=1.18 min; MS (ESIpos): m/z=318 $(M+H)^+$, $^1$H-NMR (400 MHz, DMSO-$d_6$): δ [ppm]=7.97 (s, 1H), 7.86 (d, 1H), 7.72 (dd, 1H), 7.51 (d, 1H), 6.71 (s, 1H), 3.83 (s, 3H), 3.72 (s, 3H).

Example 38.1B

4-[5-Chloro-2-(trifluoromethyl)phenyl]-5-methoxypyridin-2(1H)-one

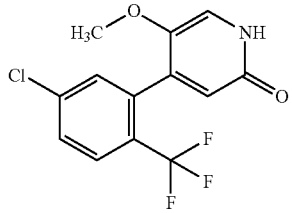 [SMILES: COc1c[nH]c(=O)cc1-c1cc(Cl)ccc1C(F)(F)F]

2.67 mg (8.31 mmol) of 4-[5-chloro-2-(trifluoromethyl) phenyl]-2,5-dimethoxypyridine were initially charged in 40 ml of DMF, 2.66 g (16.61 mmol, 2 eq.) of pyridine hydrobromide were added, and the mixture was stirred at 120° C. overnight. The reaction mixture was concentrated, ethyl acetate and water were added and the aqueous phase was extracted twice with ethyl acetate. The combined organic phases were washed once with saturated aqueous sodium hydrogencarbonate solution, then with saturated aqueous sodium chloride solution, dried over sodium sulphate and concentrated. The residue was purified by means of normal phase flash chromatography (eluent: dichloromethane/methanol, 2-5%). Yield: 2.13 g (93% purity, 79% of theory).

LC/MS [Method 1]: $R_t$=0.81 min; MS (ESIpos): m/z=304 $(M+H)^+$, $^1$H-NMR (400 MHz, DMSO-$d_6$): δ [ppm]=11.32 (bs, 1H), 7.84 (d, 1H), 7.74-7.68 (m, 1H), 7.51 (d, 1H), 7.16 (s, 1H), 6.25 (s, 1H), 3.56 (s, 3H).

Example 38.1C tert-Butyl {4-[5-chloro-2-(trifluoromethyl)phenyl]-5-methoxy-2-oxopyridin-1(2H)-yl}acetate

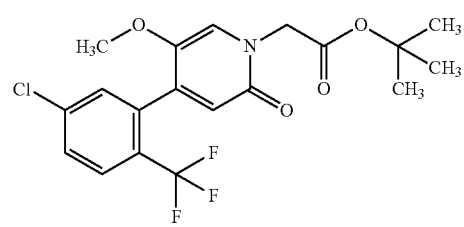 [SMILES: COc1cn(CC(=O)OC(C)(C)C)c(=O)cc1-c1cc(Cl)ccc1C(F)(F)F]

According to General Method 4A, 2.13 g (6.52 mmol, 93% purity) of 4-[5-chloro-2-(trifluoromethyl)phenyl]-5-methoxypyridin-2(1H)-one were reacted with 1.18 ml (7.83 mmol, 1.2 eq.) of tert-butyl bromoacetate at 100° C. Yield: 2.21 g (80% of theory)

LC/MS [Method 1]: $R_t$=1.07 min; MS (ESIpos): m/z=418 $(M+H)^+$, $^1$H-NMR (400 MHz, DMSO-$d_6$): δ [ppm]=7.85 (d, 1H), 7.72 (d, 1H), 7.53 (d, 1H), 7.45 (s, 1H), 6.32 (s, 1H), 4.58 (s, 2H), 3.54 (s, 3H), 1.44 (s, 9H).

Example 38.1D tert-Butyl 2-{4-[5-chloro-2-(trifluoromethyl)phenyl]-5-methoxy-2-oxopyridin-1(2H)-yl}-3-(pyridin-2-yl)propanoate (racemate)

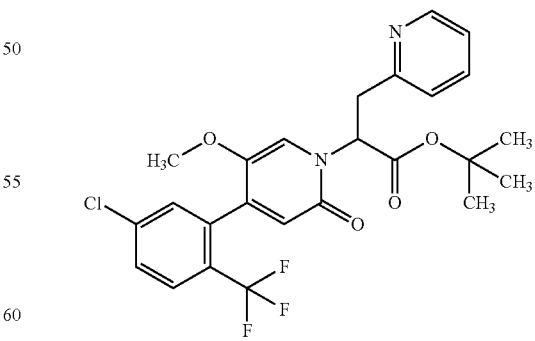

To a solution of 687 mg (1.63 mmol) of tert-butyl {4-[5-chloro-2-(trifluoromethyl)phenyl]-5-methoxy-2-oxopyridin-1(2H)-yl}acetate in 14 ml of THF under argon at −70° C. were added 4.07 ml (4.07 mmol, 2.5 eq.) of 1 N lithium bis(trimethylsilyl)amide in THF, and the mixture was stirred for 15 min. Subsequently, 588 mg (2.28 mmol, 1.4 eq.) of 2-(bromomethyl)pyridine hydrobromide were added, the mixture was stirred at −70° C. for 30 min and then stirred while coming to RT overnight. The reaction mixture was cooled to −70° C., 3.30 ml (3.30 mmol, 2 eq.) of 1 N lithium bis(trimethylsilyl)amide in THF were added and the mixture was stirred for 15 min. Subsequently, 418 mg (1.63 mmol, 1.0 eq.) of 2-(bromomethyl)pyridine hydrobromide were added, and the mixture was stirred while coming gradually to RT for 2 h. To the reaction mixture were added 20 ml of saturated aqueous ammonium chloride solution, then 20 ml of water and 22 ml of ethyl acetate. The organic phase was washed with a mixture of saturated aqueous sodium chloride solution and water (1:1), dried and concentrated. The crude product was purified by means of normal phase flash chromatography (eluent: cyclohexane/ethyl acetate, 0-60%). Yield: 716 mg (95% purity, 82% of theory).

LC/MS [Method 1]: $R_t$=1.03 min; MS (ESIpos): m/z=509 (M+H)$^+$, $^1$H-NMR (400 MHz, DMSO-d$_6$): δ [ppm]=8.52-8.46 (m, 1H), 7.82 (d, 1H), 7.73-7.62 (m, 2H), 7.48-7.44 (m, 1H), 7.25-7.14 (m, 3H), 6.25 (d, 1H), 5.59-5.46 (m, 1H), 3.66-3.50 (m, 2H), 1.42-1.35 (m, 9H).

Example 38.1E

2-{4-[5-Chloro-2-(trifluoromethyl)phenyl]-5-methoxy-2-oxopyridin-1(2H)-yl}-3-(pyridin-2-yl)propanoic acid (mixture of racemic diastereomers)

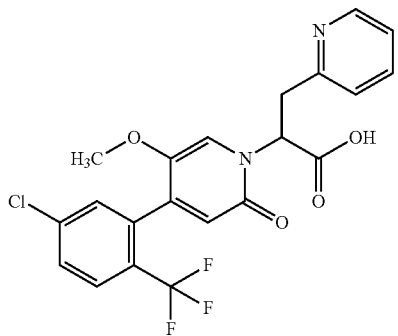 [SMILES: COc1cn(C(Cc2ccccn2)C(=O)O)c(=O)cc1-c1cc(Cl)ccc1C(F)(F)F]

According to General Method 6B, 711 mg (1.33 mmol, 95% purity) of tert-butyl 2-{4-[5-chloro-2-(trifluoromethyl)phenyl]-5-methoxy-2-oxopyridin-1(2H)-yl}-3-(pyridin-2-yl)propanoate (racemate) in 13 ml of hydrogen chloride in dioxane (4 M) were reacted. Yield: 614 mg (91% of theory)

LC/MS [Method 1]: $R_t$=0.73 min; MS (ESIpos): m/z=453 (M+H)$^+$, $^1$H-NMR (400 MHz, DMSO-d$_6$): δ [ppm]=8.85-8.77 (m, 2H), 8.38 (bs, 2H), 7.92-7.75 (m, 6H), 7.74-7.67 (m, 2H), 7.55-7.49 (m, 2H), 7.47-7.35 (m, 2H), 6.29 (s, 1H), 6.25 (s, 1H), 5.80-5.70 (m, 1H), 5.63-5.52 (m, 1H), 4.06-3.91 (m, 2H), 3.87-3.74 (m, 2H), 3.53 (s, 3 H), 3.44 (s, 3H).

Example 39.1A tert-Butyl 2-{4-[5-chloro-2-(trifluoromethyl)phenyl]-5-methoxy-2-oxopyridin-1(2H)-yl}-3-(3-methyl-1,2-oxazol-5-yl)propanoate (mixture of racemic diastereomers)

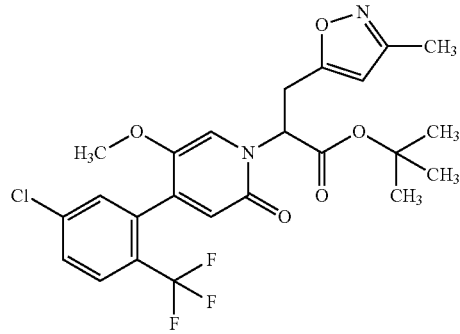 [SMILES: COc1cn(C(Cc2cc(C)no2)C(=O)OC(C)(C)C)c(=O)cc1-c1cc(Cl)ccc1C(F)(F)F]

To a solution of 687 mg (1.63 mmol) of tert-butyl {4-[5-chloro-2-(trifluoromethyl)phenyl]-5-methoxy-2-oxopyridin-1(2H)-yl}acetate in 14 ml of THF under argon at −70° C. were added 1.87 ml (1.87 mmol, 1.15 eq.) of 1 N lithium bis(trimethylsilyl)amide in THF, and the mixture was stirred for 30 min. Subsequently, 422 mg (2.28 mmol, 95% purity, 1.4 eq.) of 5-(bromomethyl)-3-methyl-1,2-oxazole were added, the mixture was stirred at −70° C. for 30 min and then stirred while coming to RT overnight. To the reaction mixture were added 20 ml of saturated aqueous ammonium chloride solution, then 20 ml of water and 200 ml of ethyl acetate. The organic phase was washed with a mixture of saturated aqueous sodium chloride solution and water (1:1), dried and concentrated. The crude product was purified by means of normal phase flash chromatography (eluent: cyclohexane/ethyl acetate, 20-50%). Yield: 673 mg (78% of theory).

LC/MS [Method 1]: $R_t$=1.17 min; MS (ESIpos): m/z=513 (M+H)$^+$, $^1$H-NMR (400 MHz, DMSO-d$_6$): δ [ppm]=7.87-7.80 (m, 2H), 7.75-7.68 (m, 2H), 7.55-7.50 (m, 2H), 7.30 (s, 1H), 7.20 (s, 1H), 6.35-6.30 (m, 2H), 6.10 (s, 1H), 5.98 (s, 1H), 5.36 (dd, 1H), 5.29 (dd, 1H), 3.73-3.57 (m, 3H), 3.56-3.42 (m, 7H), 2.14 (s, 3H), 2.17 (s, 3H), 1.41 (s, 9H), 1.38 (s, 9H).

Example 39.1B

2-{4-[5-Chloro-2-(trifluoromethyl)phenyl]-5-methoxy-2-oxopyridin-1(2H)-yl}-3-(3-methyl-1,2-oxazol-5-yl)propanoic acid (mixture of racemic diastereomers)

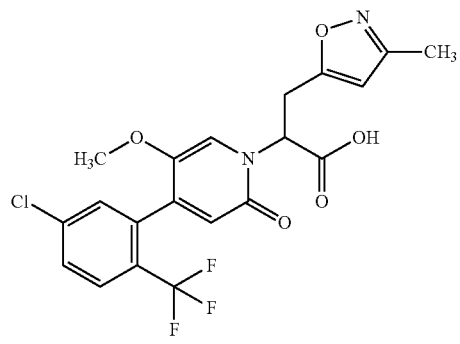 [SMILES: COc1cn(C(Cc2cc(C)no2)C(=O)O)c(=O)cc1-c1cc(Cl)ccc1C(F)(F)F]

According to General Method 6A, 668 mg (1.26 mmol) of tert-butyl 2-{4-[5-chloro-2-(trifluoromethyl)phenyl]-5-methoxy-2-oxopyridin-1(2H)-yl}-3-(3-methyl-1,2-oxazol- 5-yl)propanoate (racemate) in 14 ml of dichloromethane were reacted with 7 ml (90.9 mmol) of TFA. Yield: 441 mg (75% of theory)

LC/MS [Method 1]: $R_t$=0.90 min; MS (ESIpos): m/z=457 (M+H)+, $^1$H-NMR (400 MHz, DMSO-d$_6$): δ [ppm]=13.22 (bs, 2H), 7.87-7.80 (m, 2H), 7.75-7.68 (m, 2H), 7.58-7.49 (m, 2H), 7.31 (s, 1H), 7.23 (s, 1H), 6.30 (s, 2H), 6.00 (s, 1H), 5.92 (s, 1H), 5.49 (dd, 1H), 5.26 (dd, 1H), 3.76-3.64 (m, 2H), 3.63-3.54 (m, 1H), 3.53-3.41 (m, 7H), 2.14 (s, 3H), 2.12 (s, 3H).

Working Examples

General Method 1: Amide Coupling using T3P/Pyridine

A solution of the appropriate carboxylic acid or carboxylic acid hydrochloride (1 eq.) and the appropriate amine or amine hydrochloride (1.1-1.9 eq.) in pyridine (about 0.1 M) was heated to 60° C., and T3P (50% in ethyl acetate, 1.5-15 eq.) was added dropwise. Alternatively, T3P was added at RT and the mixture was then stirred at RT or heated to 50 to 90° C. After 1 to 20 h, the reaction mixture was cooled to RT and either purified directly by means of preparative HPLC (water-acetonitrile gradient or water-methanol gradient) or admixed with water and ethyl acetate. The aqueous phase was extracted with ethyl acetate. The combined organic phases were washed with aqueous buffer solution (pH=5), with saturated aqueous sodium hydrogencarbonate solution and with saturated aqueous sodium chloride solution, dried over sodium sulphate and concentrated under reduced pressure. The crude product was then optionally purified either by means of normal phase chromatography (eluent: cyclohexane/ethyl acetate mixtures or dichloromethane/methanol mixtures) or preparative RP-HPLC (water/acetonitrile gradient or water/methanol gradient).

General Method 2: Amide Coupling with HATU/DIEA

To a solution of the appropriate carboxylic acid (1.0 eq.) in dimethylformamide (7-15 ml/mmol) under argon and at RT were added the amine (1.1 eq.), N,N-diisopropylethylamine (2.2 eq.) and a solution of HATU (1.2 eq.) in a little dimethylformamide. The reaction mixture was stirred at RT. After addition of water/ethyl acetate and phase separation, the organic phase was washed with water and with saturated aqueous sodium chloride solution, dried (sodium sulphate or magnesium sulphate), filtered and concentrated under reduced pressure. The crude product was then purified either by means of normal phase chromatography (eluent: cyclohexane/ethyl acetate mixtures or dichloromethane/methanol mixtures) or preparative RP-HPLC (water/acetonitrile gradient or water/methanol gradient).

The following Examples 1 to 14 were prepared according to General Method 1:

| Ex. | IUPAC name/structure | Yield | Analysis |
|---|---|---|---|
| 1 | 5-({2-[4-(5-Chloro-2-cyanophenyl)-5-methoxy-2-oxopyridin-1(2H)-yl]butanoyl}amino)pyridine-2-carboxamide (racemate)<br>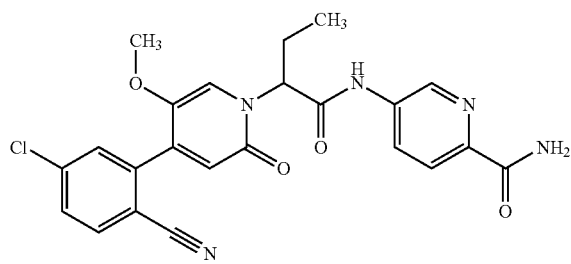<br>Prepared from: 50 mg (0.14 mmol) of 2-[4-(5-chloro-2-cyanophenyl)-5-methoxy-2-oxopyridin-1(2H)-yl]butanoic acid (racemate), 31 mg (92% purity, 0.21 mmol) 5-aminopyridine-2-carboxamide and equimolar amounts of the other reagents | 48 mg, 93% purity 69% of theory | MS (ESI): m/z = 466 [M + H]+ LC/MS (Method 1): $R_t$ = 0.87 min. $^1$H-NMR (400 MHz, DMSO-(d$_6$) δ ppm 10.95 (s, 1H), 8.85 (d, 1H), 8.22 (dd, 1H), 8.05-7.96 (m, 3H), 7.78-7.67 (m, 2H), 7.60-7.46 (m, 2H), 6.55 (s, 1H), 5.63 (dd, 1H), 3.69 (s, 3H), 2.29-2.10 (m, 2H), 0.91 (t, 3H) |
| 2 | 5-({2-[4-(5-Chloro-2-cyanophenyl)-5-methoxy-2-oxo-pyridin-1(2H)-yl]butanoyl}amino)-N-methylpyridine-2-carboxamide (racemate)<br>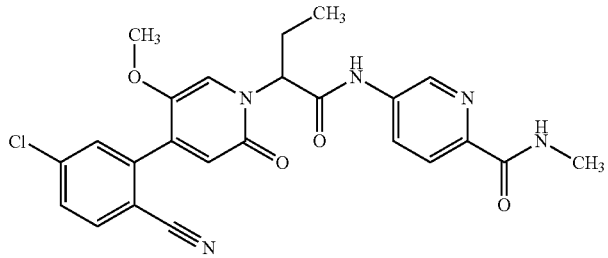<br>Prepared from: 31 mg (0.09 mmol) of 2-[4-(5-chloro-2-cyanophenyl)-5-methoxy-2-oxopyridin-1(2H)-yl]butanoic acid (racemate), 13 mg (0.09 mmol) 5-amino-N-methylpyridine-2-carboxamide and equimolar amounts of the other reagents | 29 mg 70% of theory | MS (ESI): m/z = 480 [M + H]+ LC/MS (Method 1): $R_t$ = 0.87 min. $^1$H-NMR (400 MHz, DMSO-d$_6$) δ ppm 10.93 (s, 1H), 8.87 (d, 1H), 8.68-8.62 (m, 1H), 8.20 (dd, 1H), 8.05-7.97 (m, 2H), 7.79-7.69 (m, 2H), 7.49 (s, 1H), 6.55 (s, 1H), 5.62 (dd, 1H), 3.69 (s, 3H), 2.80 (d, 3H), 2.29-2.12 (m, 2H), 0.92 (t, 3H) |

| Ex. | IUPAC name/structure | Yield | Analysis |
|---|---|---|---|
| 3 | 5-({2-[5-Chloro-4-(5-chloro-2-cyanophenyl)-2-oxo-pyridin-1(2H)-yl]-4-methoxybutanoyl}amino)-pyridine-2-carboxamide (racemate)<br>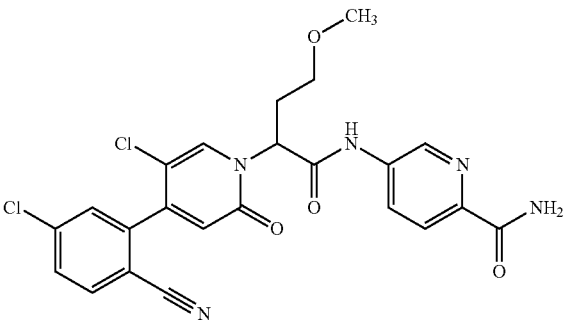<br>Prepared from: 50 mg (0.13 mmol) of 2-[5-chloro-4-(5-chloro-2-cyanophenyl)-2-oxopyridin-1(2H)-yl]-4-methoxybutanoic acid (racemate), 27 mg (0.19 mmol) of 5 aminopyridine-2-carboxamide and equimolar amounts of the other reagents | 21 mg 32% of theory | MS (ESI): m/z = 500 [M + H]$^+$<br>LC/MS (Method 1): R$_t$ = 0.90 min.<br>$^1$H-NMR (400 MHz, DMSO-d$_6$) δ ppm 10.96 (bs, 1H), 8.86 (d, 1H), 8.23 (s, 1H), 8.20 (dd, 1H), 8.09-7.99 (m, 3H), 7.86-7.75 (m, 2H), 7.55-7.50 (m, 1H), 6.68 (s, 1H), 5.82-5.74 (m, 1H), 3.47-3.39 (m, 1H), 3.28-3.23 (m, 1H), 3.20 (s, 3H), 2.48-2.41 (d, 2H) |
| 4 | 5-({2-[5-Chloro-4-(5-chloro-2-cyanophenyl)-2-oxopyridin-1(2H)-yl]-3-[(2S)-tetrahydro-2H-pyran-2-yl]propanoyl}amino)pyridine-2-carboxamide (diastereomer mixture)<br>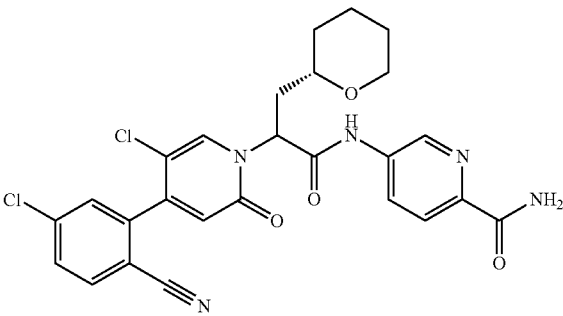<br>Prepared from: 50 mg (0.12 mmol) of 2-[5-chloro-4-(5-chloro-2-cyanophenyl)-2-oxopyridin-1(2H)-yl]-3-[(2S)-tetrahydro-2H-pyran-2-yl]propanoic acid (diastereomer mixture), 25 mg (0.18 mmol) of 5-aminopyridine-2-carboxamide and equimolar amounts of the other reagents | 42 mg 65% of theory | MS (ESI): m/z = 540 [M + H]$^+$<br>LC/MS (Method 1): R$_t$ = 0.99 min.<br>$^1$H-NMR (400 MHz, DMSO-d$_6$) δ ppm 10.93 (bs, 1H), 8.90-8.82 (m, 1H), 8.27-8.16 (m, 2H), 8.11-7.97 (m, 3H), 7.86-7.75 (m, 2H), 7.57-7.47 (m, 2H), 6.67 (s, 1H), 5.89-5.71 (m, 1H), 3.90-3.75 (m, 1H), 3.27-3.00 (m, 2H), 2.46-2.17 (m, 2H), 1.82-1.67 (m, 1H), 1.67-1.53 (m, 1H), 1.50-1.18 (m, 4H) |

| Ex. | IUPAC name/structure | Yield | Analysis |
|---|---|---|---|
| 5 | 5-({2-[5-Chloro-4-(5-chloro-2-cyanophenyl)-2-oxopyridin-1(2H)-yl]-3-[(2S)-tetrahydro-2H-pyran-2-yl]propanoyl}amino)-N-methylpyridine-2-carboxamide (diastereomer mixture)<br>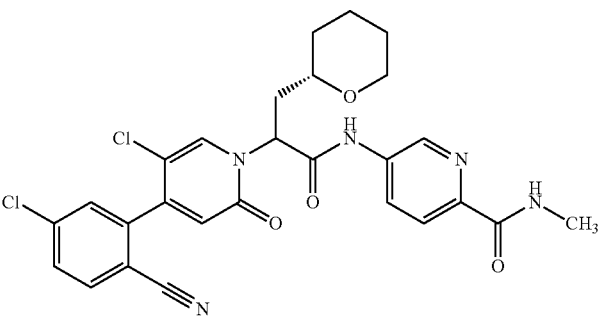<br>Prepared from: 50 mg (0.12 mmol) of 2-[5-chloro-4-(5-chloro-2-cyanophenyl)-2-oxopyridin-1(2H)-yl]-3-[(2S)-tetrahydro-2H-pyran-2-yl]propanoic acid (diastereomer mixture), 31 mg (86% purity, 0.18 mmol) of 5-amino-N-methylpyridine-2-carboxamide and equimolar amounts of the other reagents | 39 mg, 59% of theory | MS (ESI): m/z = 554 [M + H]$^+$<br>LC/MS (Method 3): R$_t$ = 2.29 min.<br>$^1$H-NMR (400 MHz, DMSO-d$_6$) δ ppm 10.92 (bs, 1H), 8.92-8.83 (m, 1H), 8.70-8.63 (m, 1H), 8.24-8.15 (m, 2H), 8.09-7.97 (m, 2H), 7.86-7.72 (m, 2H), 6.67 (s, 1H), 5.87-5.71 (m, 1H), 3.90-3.74 (m, 1H), 3.29-3.00 (m, 2H), 2.80 (d, 3H), 2.48-2.18 (m, 2H), 1.80-1.70 (m, 1H), 1.64-1.56 (m, 1H), 1.48-1.19 (m, 4H) |
| 6 | 5-({2-[4-(5-Chloro-2-cyanophenyl)-5-methoxy-2-oxopyridin-1(2H)-yl]-3-(pyridin-2-yl)propanoyl}amino)pyridine-2-carboxamide (racemate)<br>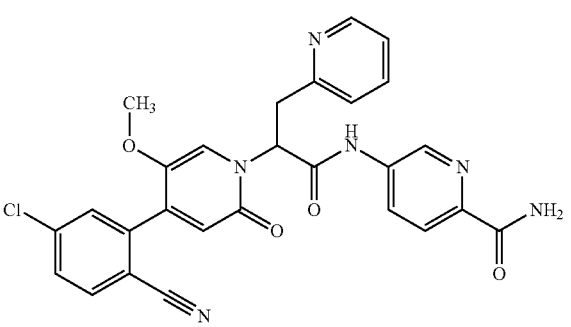<br>Prepared from: 150 mg (0.34 mmol) of 2-[4-(5-chloro-2-cyanophenyl)-5-methoxy-2-oxopyridin-1(2H)-yl]-3-(pyridin-2-yl)propanoic acid (racemate), 70 mg (0.50 mmol) of 5-aminopyridine-2-carboxamide and equimolar amounts of the other reagents | 59 mg, 86% purity 29% of theory | MS (ESI): m/z = 529 [M + H]$^+$<br>LC/MS (Method 1): R$_t$ = 0.79 min.<br>$^1$H-NMR (400 MHz, DMSO-d$_6$) δ ppm 11.01 (s, 1H), 8.86 (d, 1H), 8.53-8.45 (m, 1H), 8.22 (dd, 1H), 8.06-7.99 (m, 2H), 7.99-7.93 (m, 1H), 7.75-7.64 (m, 3H), 7.57-7.49 (m, 2H), 7.35 (d, 1H), 7.26-7.18 (m, 1H), 6.43 (s, 1H), 6.13 (dd, 1H), 3.76-3.69 (m, 2H), 3.62 (s, 3H) |

-continued

| Ex. | IUPAC name/structure | Yield | Analysis |
|---|---|---|---|
| 7 | 5-({2-[4-(5-Chloro-2-cyanophenyl)-5-(difluoromethoxy)-2-oxopyridin-1(2H)-yl]-3-(pyridin-2-yl)propanoyl}amino)pyridine-2-carboxamide (racemate)<br>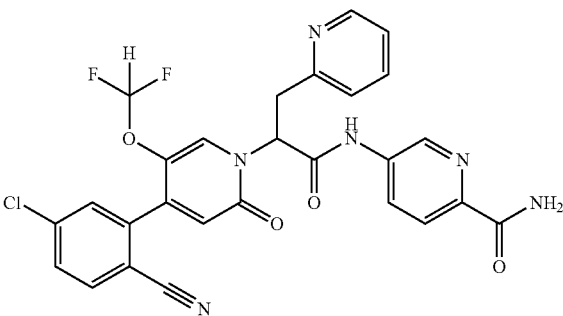<br>Prepared from: 90 mg (86% purity, 0.14 mmol) of 2-[4-(5-chloro-2-cyanophenyl)-5-(difluoromethoxy)-2-oxopyridin-1(2H)-yl]-3-(pyridin-2-yl)propanoic acid-trifluoroacetic acid (racemate), 29 mg (0.21 mmol) of 5-aminopyridine-2-carboxamide and equimolar amounts of the other reagents | 16 mg 51% of theory | MS (ESI): m/z = 565 [M + H]$^+$<br>LC/MS (Method 1):<br>$R_t$ = 0.84 min.<br>$^1$H-NMR (400 MHz, DMSO-d$_6$) δ ppm 11.10 (s, 1H), 8.84 (d, 1H), 8.50-8.45 (m, 1H), 8.22 (dd, 1H), 8.10 (s, 1H), 8.05-7.99 (m, 3H), 7.75 (dd, 1H), 7.73-7.66 (m, 2H), 7.56-7.51 (m, 1H), 7.34 (d, 1H), 7.27-7.17 (m, 1H), 6.76 (t, 1H), 6.54 (s, 1H), 6.16 (dd, 1H), 3.74-3.67 (m, 2H) |
| 8 | 5-({2-[4-(5-Chloro-2-cyanophenyl)-5-methoxy-2-oxopyridin-1(2H)-yl]-3-(pyridin-3-yl)propanoyl}amino)pyridine-2-carboxamide (racemate)<br>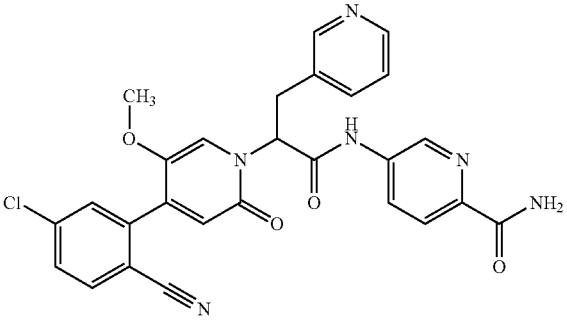<br>Prepared from: 55 mg (88% purity, 0.11 mmol) of 2-[4-(5-chloro-2-cyanophenyl)-5-methoxy-2-oxopyridin-1(2H)-yl]-3-(pyridin-3-yl)propanoic acid hydrochloride (racemate), 23 mg (0.16 mmol) of 5-aminopyridine-2-carboxamide and equimolar amounts of the other reagents | 43 mg 73% of theory | MS (ESI): m/z = 529 [M + H]$^+$<br>LC/MS (Method 1):<br>$R_t$ = 0.69 min.<br>$^1$H-NMR (400 MHz, DMSO-d$_6$) δ ppm 10.94 (s, 1H), 8.83 (d, 1H), 8.52 (d, 1H), 8.40 (dd, 1H), 8.22 (dd, 1H), 8.06-7.95 (m, 3H), 7.72 (dd, 1H), 7.65 (d, 1H), 7.63-7.58 (m, 2H), 7.56-7.51 (m, 1H), 7.27 (dd, 1H), 6.44 (s, 1H), 6.00 (dd, 1H), 3.68 (s, 3H), 3.63-3.55 (m, 2H) |

| Ex. | IUPAC name/structure | Yield | Analysis |
|---|---|---|---|
| 9 | 5-({2-[4-(5-Chloro-2-cyanophenyl)-5-methoxy-2-oxopyridin-1(2H)-yl]-3-(pyridin-4-yl)propanoyl}amino)pyridine-2-carboxamide (racemate)<br><br>Prepared from: 50 mg (93% purity, 0.10 mmol) of 2-[4-(5-chloro-2-cyanophenyl)-5-methoxy-2-oxopyridin-1(2H)-yl]-3-(pyridin-4-yl)propanoic acid hydrochloride (racemate), 22 mg (0.16 mmol) of 5-aminopyridine-2-carboxamide and equimolar amounts of the other reagents | 25 mg 46% of theory | MS (ESI): m/z = 529 [M + H]$^+$<br>LC/MS (Method 1): R$_t$ = 0.65 min.<br>$^1$H-NMR (400 MHz, DMSO-d$_6$) δ ppm 10.96 (s, 1H), 8.84 (d, 1H), 8.44 (d, 2H), 8.22 (dd, 1H), 8.08-7.95 (m, 3H), 7.72 (dd, 1H), 7.66 (d, 1H), 7.61-7.51 (m, 2H), 7.27 (d, 2H), 6.44 (s, 1H), 6.03 (dd, 1H), 3.70-3.52 (m, 5H) |
| 10 | 5-({2-[5-Chloro-4-(5-chloro-2-cyanophenyl)-2-oxopyridin-1(2H)-yl]-3-(1,3-oxazol-4-yl)propanoyl}-amino)pyridine-2-carboxamide (racemate)<br><br>Prepared from: 50 mg (0.12 mmol) of 2-[5-chloro-4-(5-chloro-2-cyanophenyl)-2-oxopyridin-1(2H)-yl]-3-(1,3-oxazol-4-yl)propanoic acid (racemate), 30 mg (0.21 mmol) of 5-aminopyridine-2-carboxamide and equimolar amounts of the other reagents | 32 mg 48% of theory | MS (ESI): m/z = 523 [M + H]$^+$<br>LC/MS (Method 1): R$_t$ = 0.80 min.<br>$^1$H-NMR (400 MHz, DMSO-d$_6$) δ ppm 11.07 (bs, 1H), 8.85 (d, 1H), 8.32-8.25 (m, 2H), 8.21 (dd, 1H), 8.07-7.99 (m, 3H), 7.86-7.70 (m, 3H), 7.57-7.50 (m, 1H), 6.62 (s, 1H), 5.97 (dd, 1H), 3.59 (dd, 1H), 3.45 (dd, 1H) |
| 11 | 5-({2-[4-(5-Chloro-2-cyanophenyl)-5-methoxy-2-oxopyridin-1(2H)-yl]-3-(1,3-oxazol-4-yl)propanoyl}-amino)pyridine-2-carboxamide (racemate)<br><br>Prepared from: 50 mg (0.12 mmol) of 2-[4-(5-chloro-2-cyanophenyl-5-methoxy-2-oxopyridin-1(2H)-yl]-3-(1,3-oxzol-4-yl)propanoic acid (racemate), 30 mg (0.21 mmol) of 5-aminopyridine-2-carboxamide and equimolar amounts of the other reagents | 40 mg 62% of theory | MS (ESI): m/z = 519 [M + H]$^+$<br>LC/MS (Method 1): R$_t$ = 0.74 min.<br>$^1$H-NMR (400 MHz, DMSO-d$_6$) δ ppm 10.99 (s, 1H), 8.85 (d, 1H), 8.29-8.31 (m, 1H), 8.23 (dd, 1H), 8.06-7.95 (m, 3H), 7.82 (s, 1H), 7.76-7.68 (m, 2H), 7.58-7.47 (m, 2H), 6.47 (s, 1H), 5.96 (dd, 1H), 3.67 (s, 3H), 3.57 (dd, 1H), 3.44 (dd, 1H) |

| Ex. | IUPAC name/structure | Yield | Analysis |
|---|---|---|---|
| 12 | 5-({2-[4-(5-Chloro-2-cyanophenyl)-5-(difluoromethoxy)-2-oxopyridin-1(2H)-yl]-3-(1,3-oxazol-5-yl)propanoyl}amino)pyridine-2-carboxamide (racemate)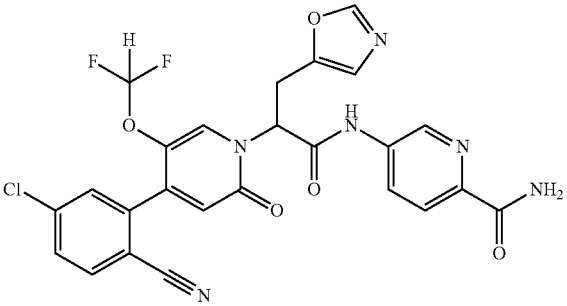Prepared from: 40 mg (0.09 mmol) of 2-[4-(5-chloro-2-cyanophenyl-5-(difluoromethoxy)-2-oxopyridin-1(2H)-yl]-3-(1,3-oxazol-5-yl)propanoic acid (racemate), 22 mg (0.16 mmol) of 5-aminopyridine-2-carboxamide and equimolar amounts of the other reagents | 18 mg 35% of theory | MS (ESI): m/z = 555 [M + H]$^+$ LC/MS (Method 8): R$_t$ = 1.03 min. $^1$H-NMR (400 MHz, DMSO-d$_6$) δ ppm 11.06 (s, 1H), 8.82 (d, 1H), 8.24 (s, 1H), 8.21 (dd, 1H), 8.13 (s, 1H), 8.07-8.00 (m, 3 H), 7.79-7.73 (m, 2H), 7.57-7.51 (m, 1H), 6.91 (s, 1H), 6.82 (t, 1H), 6.62 (s, 1H), 5.97 (dd, 1H), 3.75 (dd, 1H), 3.66 (dd, 1H) |
| 13 | 5-({2-[4-(5-Chloro-2-fluorophenyl)-5-methoxy-2-oxopyridin-1(2H)-yl]-3-(pyridin-2-yl)propanoyl}amino)pyridine-2-carboxamide (racemate)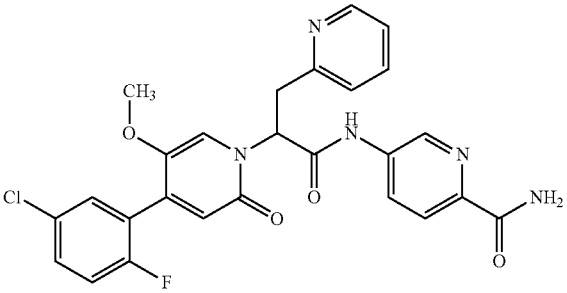Prepared from: 70 mg (75% purity, 0.12 mmol) of 2-[4-(5-chloro-2-fluorophenyl)-5-methoxy-2-oxopyridin-1(2H)-yl]-3-(pyridin-2-yl)propanoic acid hydrochloride (racemate), 24.8 mg (0.18 mmol) of 5-aminopyridine-2-carboxamide and equimolar amounts of the other reagents | 2.5 mg 4% of theory | MS (ESI): m/z = 522 [M + H]$^+$ LC/MS (Method 8): R$_t$ = 1.07 min. $^1$H-NMR (400 MHz, DMSO-d$_6$) δ ppm 10.99 (s, 1H), 8.86 (d, 1H), 8.50 (d, 1H), 8.21 (dd, 1H), 8.04-7.99 (m, 2H), 7.72 (td, 1H), 7.57-7.49 (m, 2H), 7.47 (s, 1H), 7.44 (dd, 1H), 7.38 (d, 1H), 7.33 (dd, 1H), 7.24 (dd, 1H), 6.37 (s, 1H), 6.13 (dd, 1H), 3.75-3.68 (m, 2H), 3.59 (s, 3H) |
| 14 | 5-({2-[4-(5-Chloro-2-fluorophenyl)-5-methoxy-2-oxopyridin-1(2H)-yl]-3-(3-methyl-1,2-oxazol-5-yl)propanoyl}amino)pyridine-2-carboxamide (racemate)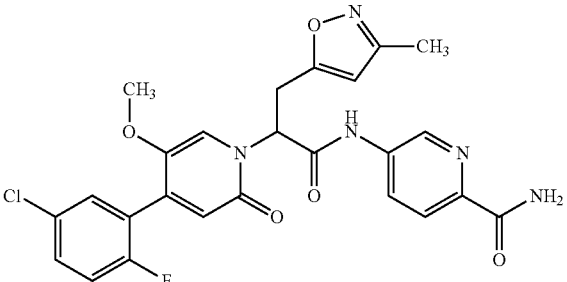Prepared from: 60 mg (90% purity, 0.13 mmol) of 2-[4-(5-chloro-2-fluorophenyl)-5-methoxy-2-oxopyridin-1(2H)-yl]-3-(3-methyl-1,2-oxazol-5-yl)propanoic acid (racemate), 28 mg (0.20 mmol) of 5-aminopyridine-2-carboxamide and equimolar amounts of the other reagents | 30 mg, 43% of theory | MS (ESI): m/z = 526 [M + H]$^+$ LC/MS (Method 1): R$_t$ = 0.88 min. $^1$H-NMR (400 MHz, DMSO-d$_6$) δ ppm 10.91 (s, 1H), 8.84 (d, 1H), 8.20 (dd, 1H), 8.08-7.97 (m, 2H), 7.58-7.51 (m, 2H), 7.51-7.45 (m, 2H), 7.36 (dd, 1H), 6.45 (s, 1H), 6.13 (s, 1H), 5.97 (dd, 1H), 3.83 (dd, 1H), 3.69 (dd, 1H), 3.64 (s, 3H), 2.16 (s, 3H) |

The following Examples 15 to 17 were prepared according to General Method 2:

| Ex. | IUPAC name/structure | Yield | Analysis |
|-----|----------------------|-------|----------|
| 15 | 5-({2-[5-Chloro-4-(5-chloro-2-cyanophenyl)-2-oxopyridin-1(2H)-yl]-4-methoxybutanoyl}amino)-N-methylpyridine-2-carboxamide (racemate)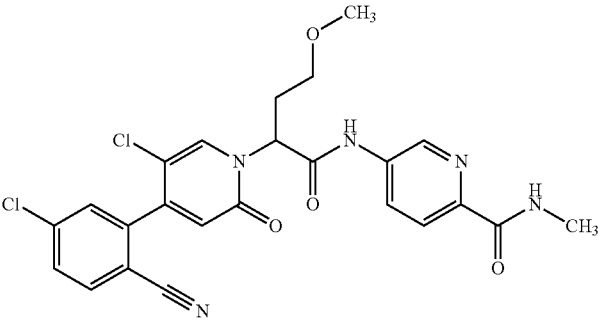Prepared from: 85 mg (90% purity, 0.20 mmol) of 2-[5-chloro-4-(5-chloro-2-cyanophenyl)-2-oxopyridin-1(2H)-yl]-4-methoxybutanoic acid (racemate), 71 mg (86% purity, 0.40 mmol) of 5-amino-N-methylpyridine-2-carboxamide and equimolar amounts of the other reagents | 42 mg 41% of theory | MS (ESI): m/z = 514 $[M + H]^+$<br>LC/MS (Method 1):<br>$R_t$ = 0.93 min.<br>$^1$H-NMR (400 MHz, DMSO-$d_6$) δ ppm 10.95 (bs, 1H), 8.88 (d, 1H), 8.71-8.63 (m, 1H), 8.23 (s, 1H), 8.18 (dd, 1H), 8.07 (d, 1H), 8.01 (d, 1H), 7.86-7.74 (m, 2H), 6.68 (s, 1H), 5.83-5.69 (m, 1H), 3.43 (dt, 1H), 3.26 (dt, 1H), 3.20 (s, 3H), 2.80 (d, 3H), 2.48-2.39 (m, 2H) |
| 16 | 5-({2-[5-Chloro-4-(5-chloro-2-cyanophenyl)-2-oxopyridin-1(2H)-yl]-3-(1,3-oxazol-5-yl)propanoyl}-amino)pyridine-2-carboxamide (racemate)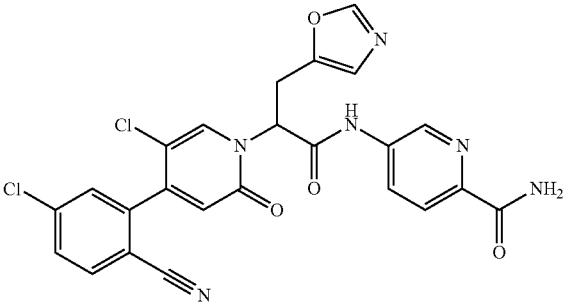Prepared from: 50 mg (85% purity, 0.11 mmol) of 2-[5-chloro-4-(5-chloro-2-cyanophenyl)-2-oxopyridin-1(2H)-yl]-3-(1,3-oxazol-5-yl)propanoic acid (racemate), 25 mg (0.18 mmol) of 5-aminopyridine-2-carboxamide and equimolar amounts of the other reagents | 13 mg 22% of theory | MS (ESI): m/z = 523 $[M + H]^+$<br>LC/MS (Method 1):<br>$R_t$ = 0.78 min.<br>$^1$H-NMR (400 MHz, DMSO-$d_6$) δ ppm 11.03 (bs, 1H), 8.83 (d, 1H), 8.33 (s, 1H), 8.26-8.22 (m, 1H), 8.19 (dd, 1H), 8.10-7.95 (m, 3H), 7.83-7.69 (m, 2H), 7.57-7.50 (m, 1H), 6.91 (s, 1H), 6.66 (s, 1H), 6.03-5.86 (m, 1H), 3.79 (dd, 1H), 3.69 (dd, 1H) |

| Ex. | IUPAC name/structure | Yield | Analysis |
|---|---|---|---|
| 17 | 5-({2-[4-(5-Chloro-2-cyanphenyl)-5-methoxy-2-oxopyridin-1(2H)-yl]-3-(1,3-oxazol-5-yl)propanoyl}amino)pyridine-2-carboxamide (racemate)<br>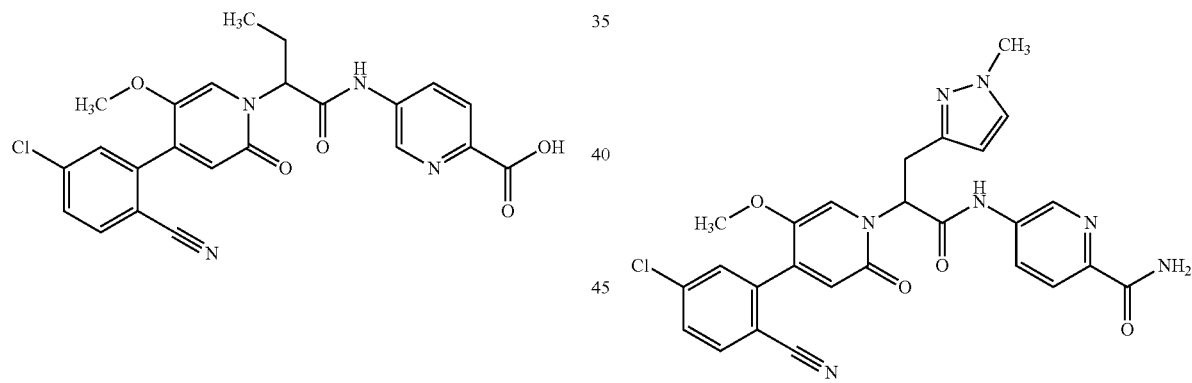<br>Prepared from: 50 mg (80% purity, 0.10 mmol) of 2-[4-(5-chloro-2-cyanophenyl)-5-methoxy-2-oxopyridin-1(2H)-yl]-3-1,3-oxazol-5-yl)propanoic acid (racemate), 26 mg (0.18 mmol) of 5-aminopyridine-2-carboxamide and equimolar amounts of the other reagents | 10 mg 19% of theory | MS (ESI): m/z = 519 [M + H]+<br>LC/MS (Method 8): $R_t$ = 0.98 min.<br>$^1$H-NMR (400 MHz, DMSO-$d_6$) δ ppm 10.95 (s, 1H), 8.84 (d, 1H), 8.27-8.18 (m, 2H), 8.05-7.97 (m, 3H), 7.77-7.67 (m, 2H), 7.59-7.48 (m, 2H), 6.91 (s, 1H), 6.51 (s, 1H), 5.95 (dd, 1H), 3.78 (dd, 1H), 3.70-3.62 (m, 4H) |

Example 18

5-({2-[4-(5-Chloro-2-cyanophenyl)-5-methoxy-2-oxopyridin-1(2H)-yl]butanoyl}amino)pyridine-2-carboxylic acid (racemate)

To a solution of 195 mg (0.37 mmol) of tert-butyl 5-({2-[4-(5-chloro-2-cyanophenyl)-5-methoxy-2-oxopyridin-1(2H)-yl]butanoyl}amino)pyridine-2-carboxylate (racemate) in 9 ml of dichloromethane were added 4.5 ml (58.4 mmol, 157 eq.) of trifluoroacetic acid and the mixture was stirred for 10 min. Subsequently, the solution was allowed to warm up to room temperature and stirred for 6 h. The reaction mixture was concentrated under reduced pressure. The crude product was purified by means of preparative HPLC (water/acetonitrile/0.1% formic acid gradient). Yield: 145 mg (83% of theory)

LC/MS [Method 1]: $R_t$=0.82 min; MS (ESIpos): m/z=467 (M+H)+, $^1$H-NMR (400 MHz, DMSO-$d_6$): δ [ppm]=13.0 (br. s, 1H), 11.01 (s, 1H), 8.90 (d, 1H), 8.24 (dd, 1H), 8.05 (d, 1H), 8.00 (d, 1H), 7.76-7.71 (m, 2H), 7.49 (s, 1H), 6.55 (s, 1H), 5.63 (dd, 1H), 3.69 (s, 3H), 2.29-2.12 (m, 2H), 0.92 (t, 3H).

Example 19

5-({2-[4-(5-Chloro-2-cyanophenyl)-5-methoxy-2-oxopyridin-1(2H)-yl]-3-(1-methyl-1H-pyrazol-3-yl)propanoyl}amino)pyridine-2-carboxamide (racemate)

According to General Method 1, 50 mg (0.121 mmol) of 2-[4-(5-chloro-2-cyanophenyl)-5-methoxy-2-oxopyridin-1(2H)-yl]-3-(1-methyl-1H-pyrazol-3-yl)propanoic acid (racemate) and 25 mg (0.182 mmol) of 5-aminopyridine-2-carboxamide in 1.0 ml of pyridine were reacted. Yield: 33 mg (51% of theory).

LC/MS [Method 1]: $R_t$=0.79 min; MS (ESIpos): m/z=532 (M+H)+, $^1$H-NMR (400 MHz, DMSO-$d_6$): δ [ppm]=10.97 (s, 1H), 8.85 (d, 1H), 8.22 (dd, 1H), 8.05-7.95 (m, 3H), 7.75-7.68 (m, 2H), 7.59 (s, 1H), 7.55-7.49 (m, 2H), 6.46 (s, 1H), 6.00 (d, 1H), 5.89 (dd, 1H), 3.74 (s, 3H), 3.67 (s, 3H), 3.55-3.43 (m, 2H)

Example 20

5-({2-[4-(5-Chloro-2-cyanophenyl)-5-methoxy-2-oxopyridin-1(2H)-yl]-3-(1-methyl-1H-pyrazol-3-yl)propanoyl}amino)-N-methylpyridine-2-carboxamide (racemate)

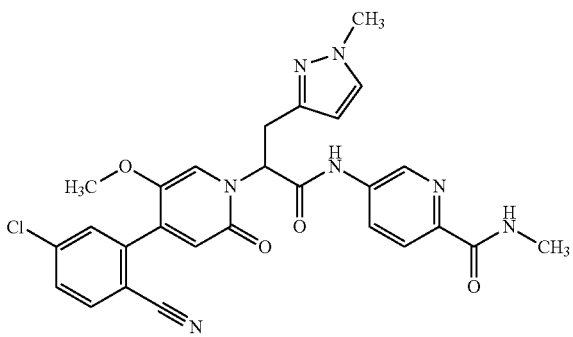 [SMILES: CNC(=O)c1ccc(NC(=O)C(Cc2ccn(C)n2)n2cc(OC)c(-c3cc(Cl)ccc3C#N)cc2=O)cn1]

According to General Method 1, 45 mg (0.102 mmol, 94% purity) of 2-[4-(5-chloro-2-cyanophenyl)-5-methoxy-2-oxopyridin-1(2H)-yl]-3-(1-methyl-1H-pyrazol-3-yl)propanoic acid (racemate) and 23 mg (0.154 mmol, 1.5 eq) of 5-amino-N-methylpyridine-2-carboxamide in 0.84 ml of pyridine were reacted. Yield: 42 mg (75% of theory).

LC/MS [Method 1]: $R_t$=0.81 min; MS (ESIpos): m/z=546 (M+H)$^+$, $^1$H-NMR (400 MHz, DMSO-$d_6$): δ [ppm]=10.96 (s, 1H), 8.88 (d, 1H), 8.70-8.62 (m, 1H), 8.20 (dd, 1H), 8.04-7.95 (m, 2H), 7.74-7.67 (m, 2H), 7.58 (s, 1H), 7.52 (d, 1H), 6.46 (s, 1H), 6.00 (d, 1H), 5.88 (dd, 1H), 3.73 (s, 3H), 3.67 (s, 3H), 3.57-3.43 (m, 2H), 2.80 (d, 3H)

Example 21

5-({2-[4-(5-Chloro-2-cyanophenyl)-5-methoxy-2-oxopyridin-1(2H)-yl]-3-(pyridin-4-yl)propanoyl}amino)pyridine-2-carboxamide (enantiomer 2)

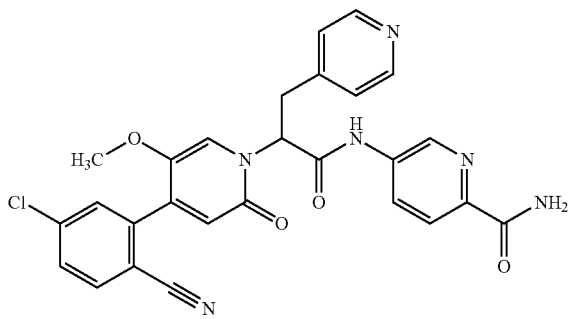 [SMILES: COc1cn(C(Cc2ccncc2)C(=O)Nc2ccc(C(N)=O)nc2)c(=O)cc1-c1cc(Cl)ccc1C#N]

Enantiomer separation of 96 mg of 5-({2-[4-(5-chloro-2-cyanophenyl)-5-methoxy-2-oxopyridin-1(2H)-yl]-3-(pyridin-4-yl)propanoyl}amino)pyridine-2-carboxamide (racemate) gave 32 mg of the Example 21 title compound (enantiomer 2), chiral HPLC: $R_t$=7.80 min, 100% ee., and 37 mg of enantiomer 1 (chiral HPLC: $R_t$=4.80 min).

Separation method: column: Daicel Chiralcel OD-H, 5 μm 250 mm×20 mm; eluent: 70% carbon dioxide/30% ethanol; temperature: 40° C.; flow rate: 80 ml/min; pressure: 100 bar; UV detection: 210 nm.

Analysis: column: Daicel Chiralcel OD-H 5 μm 250 mm×4.6 mm; eluent: 60% carbon dioxide, 40% ethanol; flow rate: 3 ml/min; UV detection: 210 nm.

LC/MS [Method 1]: $R_t$=0.63 min; MS (ESIpos): m/z=529 (M+H)$^+$, $^1$H-NMR (400 MHz, DMSO-$d_6$): δ [ppm]=10.96 (s, 1H), 8.84 (d, 1H), 8.51 (d, 2H), 8.22 (dd, 1H), 8.04 (d, 2H), 7.98 (d, 1H), 7.72 (dd, 1H), 7.66 (d, 1H), 7.58 (s, 1H), 7.54 (bs, 1H), 7.38 (d, 2H), 6.44 (s, 1H), 6.05 (dd, 1H), 3.75-3.59 (m, 5H).

Example 22

5-({2-[4-(5-Chloro-2-cyanophenyl)-5-methoxy-2-oxopyridin-1(2H)-yl]-3-(1,3-oxazol-5-yl)propanoyl}amino)pyridine-2-carboxamide (enantiomer 2)

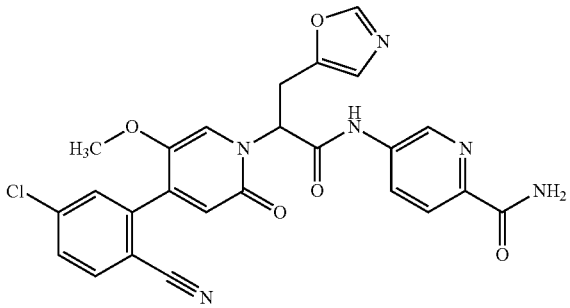 [SMILES: COc1cn(C(Cc2cnco2)C(=O)Nc2ccc(C(N)=O)nc2)c(=O)cc1-c1cc(Cl)ccc1C#N]

Enantiomer separation of 95 mg of 5-({2-[4-(5-chloro-2-cyanophenyl)-5-methoxy-2-oxopyridin-1(2H)-yl]-3-(1,3-oxazol-5-yl)propanoyl}amino)pyridine-2-carboxamide (racemate) gave 42 mg of the Example 22 title compound (enantiomer 2), chiral HPLC: $R_t$=5.57 min, 100% ee., and 46 mg of enantiomer 1 (chiral HPLC: $R_t$=3.37 min).

Separation method: column: Chiralcel OD, 20 μm 250 mm×30 mm; eluent: 65% carbon dioxide/35% methanol; temperature: 30° C.; flow rate: 100 ml/min; pressure: 100 bar; UV detection: 210 nm.

Analysis: column: Daicel Chiralpak OD-H 5 μm 250 mm×4.6 mm; eluent: 70% carbon dioxide, 30% methanol; flow rate: 3 ml/min; UV detection: 210 nm.

LC/MS [Method 1]: $R_t$=0.76 min; MS (ESIpos): m/z=519 (M+H)$^+$, $^1$H-NMR (400 MHz, DMSO-$d_6$): δ [ppm]=10.95 (s, 1H), 8.84 (d, 1H), 8.26-8.18 (m, 2H), 8.06-7.96 (m, 3H), 7.76-7.67 (m, 2H), 7.59-7.49 (m, 2H), 6.91 (s, 1H), 6.51 (s, 1H), 5.95 (dd, 1H), 3.83-3.72 (m, 1H), 3.71-3.61 (m, 4H)

Example 23

5-({2-[4-(5-Chloro-2-cyanophenyl)-5-methoxy-2-oxopyridin-1(2H)-yl]-3-(pyridin-2-yl)propanoyl}amino)pyridine-2-carboxamide (enantiomer 2)

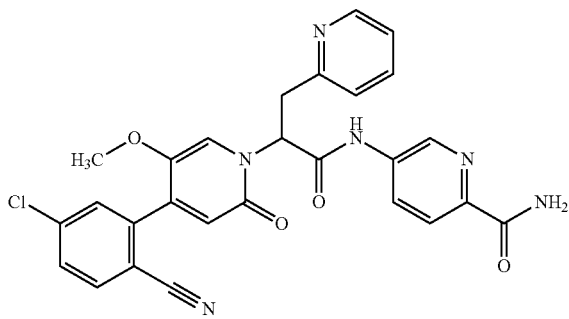 [SMILES: COc1cn(C(Cc2ccccn2)C(=O)Nc2ccc(C(N)=O)nc2)c(=O)cc1-c1cc(Cl)ccc1C#N]

Enantiomer separation of 59 mg of 5-({2-[4-(5-chloro-2-cyanophenyl)-5-methoxy-2-oxopyridin-1(2H)-yl]-3-(pyridin-2-yl)propanoyl}amino)pyridine-2-carboxamide (racemate) gave 16 mg of the Example 23 title compound (enantiomer 2), chiral HPLC: $R_t$=14.5 min, 100% ee., and 9 mg of enantiomer 1 (chiral HPLC: $R_t$=10.8 min).

Separation method: column: Chiralcel AD-H, 5 μm 250 mm×20 mm; eluent: 60% carbon dioxide/40% ethanol; temperature: 40° C.; flow rate: 80 ml/min; pressure: 100 bar; UV detection: 210 nm.

Analysis: column: Daicel AD-H 5 μm 250 mm×4.6 mm; eluent: 60% carbon dioxide, 40% ethanol; flow rate: 3 ml/min; UV detection: 210 nm.

LC/MS [Method 1]: $R_t$=0.79 min; MS (ESIpos): m/z=529 (M+H)$^+$, $^1$H-NMR (400 MHz, DMSO-d$_6$): δ [ppm]=11.01 (bs, 1H), 8.86 (d, 1H), 8.51-8.47 (m, 1H), 8.22 (dd, 1H), 8.05-7.99 (m, 2H), 7.96 (d, 1H), 7.73-7.64 (m, 3H), 7.58-7.49 (m, 2H), 7.35 (d, 1H), 7.22 (dd, 1H), 6.43 (s, 1H), 6.13 (t, 1H), 3.72 (d, 2H), 3.62 (s, 3H)

Example 24

5-({2-[4-(5-Chloro-2-cyanophenyl)-5-methoxy-2-oxopyridin-1(2H)-yl]-4-methoxybutanoyl}amino)pyridine-2-carboxamide (racemate)

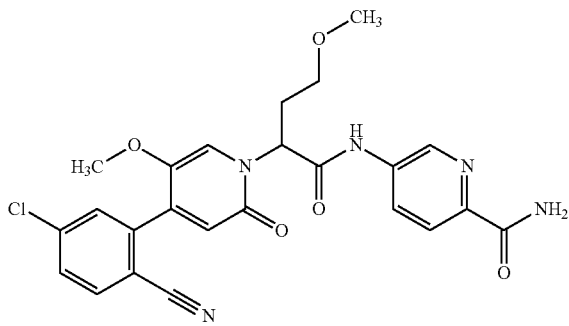 [SMILES: COCCC(C(=O)Nc1ccc(C(N)=O)nc1)n1cc(OC)c(-c2cc(Cl)ccc2C#N)cc1=O]

According to General Method 1, 50 mg (0.121 mmol, 91% purity) of 2-[4-(5-chloro-2-cyanophenyl)-5-methoxy-2-oxopyridin-1(2H)-yl]-4-methoxybutanoic acid (racemate) and 25 mg (0.182 mmol) of 5-aminopyridine-2-carboxamide in 1.0 ml of pyridine were reacted. Yield: 44 mg (73% of theory).

LC/MS [Method 1]: $R_t$=0.79 min; MS (ESIpos): m/z=496 (M+H)$^+$, $^1$H-NMR (400 MHz, DMSO-d$_6$): δ [ppm]=10.89 (s, 1H), 8.86 (d, 1H), 8.23 (dd, 1H), 8.05-7.96 (m, 3H), 7.77-7.70 (m, 2H), 7.55-7.48 (m, 2H), 6.54 (s, 1H), 5.75 (dd, 1H), 3.69 (s, 3H), 3.46-3.37 (m, 1H), 3.30-3.24 (m, 1H), 3.21 (s, 3H), 2.50-2.38 (m, 2H)

Example 25

5-({2-[4-(5-Chloro-2-cyanophenyl)-5-methoxy-2-oxopyridin-1(2H)-yl]-4-methoxybutanoyl}amino)pyridine-2-carboxamide (enantiomer 2)

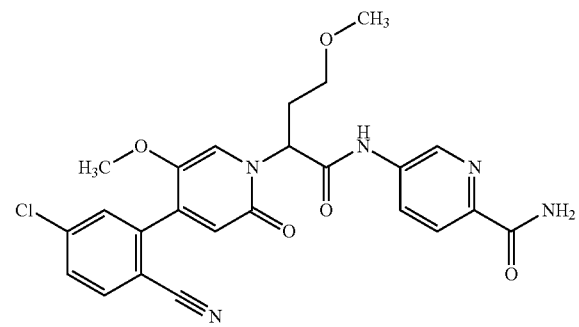 [SMILES: COCCC(C(=O)Nc1ccc(C(N)=O)nc1)n1cc(OC)c(-c2cc(Cl)ccc2C#N)cc1=O]

Enantiomer separation of 285 mg of 5-({2-[4-(5-chloro-2-cyanophenyl)-5-methoxy-2-oxopyridin-1(2H)-yl]-4-methoxybutanoyl}amino)pyridine-2-carboxamide (racemate) gave 117 mg of the Example 25 title compound (enantiomer 2), chiral HPLC: $R_t$=18.8 min, 97.3% ee., and 114 mg of enantiomer 1 (chiral HPLC: $R_t$=16.8 min).

Separation method: column: Daicel Chiralcel OD-H, 5 μm 250 mm×20 mm; eluent: 86% carbon dioxide/14% methanol; temperature: 40° C.; flow rate: 80 ml/min; pressure: 100 bar; UV detection: 210 nm.

Analysis: column: Daicel OD-H 5 μm 250 mm×4.6 mm; eluent: 80% carbon dioxide, 20% ethanol; flow rate: 3 ml/min; UV detection: 210 nm.

Example 26

5-({2-[4-(5-Chloro-2-cyanophenyl)-5-methoxy-2-oxopyridin-1(2H)-yl]-4-methoxybutanoyl}amino)-N-methylpyridine-2-carboxamide (racemate)

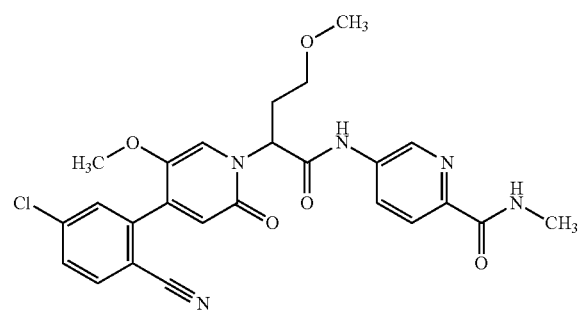 [SMILES: CNC(=O)c1ccc(NC(=O)C(CCOC)n2cc(OC)c(-c3cc(Cl)ccc3C#N)cc2=O)cn1]

According to General Method 1, 100 mg (0.252 mmol, 95% purity) of 2-[4-(5-chloro-2-cyanophenyl)-5-methoxy-2-oxopyridin-1(2H)-yl]-4-methoxybutanoic acid (racemate) and 58 mg (0.378 mmol) of 5-amino-N-methylpyridine-2-carboxamide in 2.0 ml of pyridine were reacted. Yield: 124 mg (96% of theory).

LC/MS [Method 10]: $R_t$=1.55 min; MS (ESIpos): m/z=510 (M+H)$^+$, $^1$H-NMR (400 MHz, DMSO-d$_6$): δ [ppm]=10.87 (s, 1H), 8.88 (d, 1H), 8.69-8.62 (m, 1H), 8.21 (dd, 1H), 8.03-7.96 (m, 2H), 7.76-7.70 (m, 2H), 7.51 (s, 1H), 6.53 (s, 1H), 5.74 (dd, 1H), 3.69 (s, 3H), 3.46-3.37 (m, 1H), 3.30-3.24 (m, 1H), 3.21 (s, 3H), 2.80 (d, 3H), 2.49-2.39 (m, 2H)

Example 27

5-({2-[4-(5-Chloro-2-cyanophenyl)-5-methoxy-2-oxopyridin-1(2H)-yl]-4-methoxybutanoyl}amino)-N-methylpyridine-2-carboxamide (enantiomer 2)

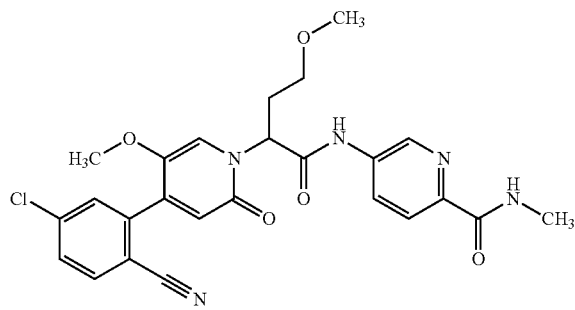 [SMILES: CNC(=O)c1ccc(NC(=O)C(CCOC)n2cc(OC)c(-c3cc(Cl)ccc3C#N)cc2=O)cn1]

Enantiomer separation of 120 mg of 5-({2-[4-(5-chloro-2-cyanophenyl)-5-methoxy-2-oxopyridin-1(2H)-yl]-4-methoxybutanoyl}amino)-N-methylpyridine-2-carboxamide (racemate) gave 23 mg of the Example 27 title compound (enantiomer 2), chiral HPLC: $R_t$=8.2 min, 99% ee., and 12 mg of enantiomer 1 (chiral HPLC: $R_t$=6.8 min).

Separation method: column: Daicel Chiralcel OD-H, 5 µm 250 mm×20 mm; eluent: 82% carbon dioxide/18% methanol; temperature: 40° C.; flow rate: 80 ml/min; pressure: 100 bar; UV detection: 210 nm.

Analysis: column: Daicel OD-H 5 µm 250 mm×4.6 mm; eluent: 80% carbon dioxide, 20% methanol; flow rate: 3 ml/min; UV detection: 210 nm.

Example 28

5-({2-[4-(5-Chloro-2-cyanophenyl)-5-methoxy-2-oxopyridin-1(2H)-yl]-3-(5-methyl-1,2-oxazol-3-yl)propanoyl}amino)pyridine-2-carboxamide (racemate)

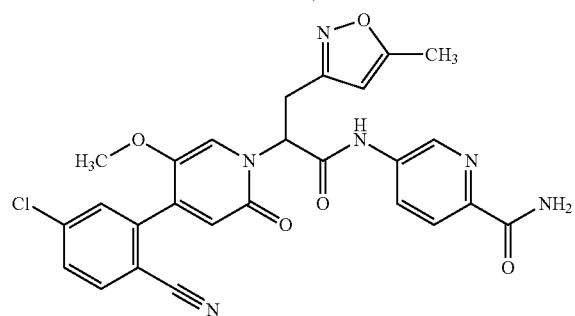

According to General Method 1, 50 mg (0.106 mmol, 88% purity) of 2-[4-(5-chloro-2-cyanophenyl)-5-methoxy-2-oxopyridin-1(2H)-yl]-3-(5-methyl-1,2-oxazol-3-yl)propanoic acid (racemate) and 22 mg (0.159 mmol) of 5-aminopyridine-2-carboxamide in 1.0 ml of pyridine were reacted. Yield: 36 mg (64% of theory).

LC/MS [Method 1]: $R_t$=0.87 min; MS (ESIpos): m/z=533 (M+H)$^+$, $^1$H-NMR (400 MHz, DMSO-d$_6$): δ [ppm]=10.95 (s, 1H), 8.85 (d, 1H), 8.22 (dd, 1H), 8.05-8.01 (m, 2H), 7.99 (d, 1H), 7.75-7.70 (m, 2H), 7.56 (s, 1H), 7.53 (bs, 1H), 6.51 (s, 1H), 5.98 (s, 1H), 5.95 (dd, 1H), 3.70-3.61 (m, 4H), 3.61-3.53 (m, 1H), 2.33 (s, 3H)

Example 29

5-({2-[4-(2-Cyano-5-methylphenyl)-5-methoxy-2-oxopyridin-1(2H)-yl]-3-(1-methyl-1H-pyrazol-3-yl)propanoyl}amino)-N-methylpyridine-2-carboxamide (racemate)

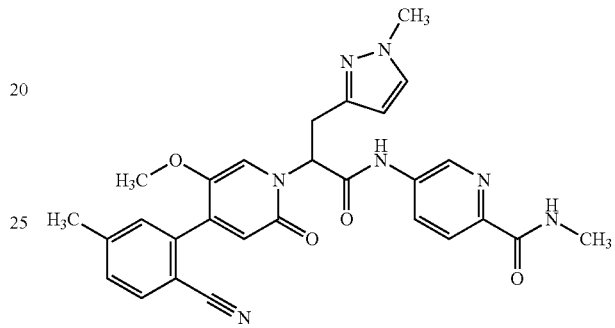

According to General Method 1, 50 mg (0.093 mmol, 80% purity) of 2-[4-(2-cyano-5-methylphenyl)-5-methoxy-2-oxopyridin-1(2H)-yl]-3-(1-methyl-1H-pyrazol-3-yl)propanoic acid hydrochloride (racemate) and 22 mg (0.140 mmol) of 5-amino-N-methylpyridine-2-carboxamide in 0.8 ml of pyridine were reacted. Yield: 38 mg (78% of theory).

LC/MS [Method 1]: $R_t$=0.78 min; MS (ESIpos): m/z=526 (M+H)$^+$, $^1$H-NMR (400 MHz, DMSO-d$_6$): δ [ppm]=10.95 (s, 1H), 8.88 (d, 1H), 8.66 (q, 1H), 8.21 (dd, 1H), 8.01 (d, 1H), 7.80 (d, 1H), 7.57-7.50 (m, 2H), 7.43 (d, 1H), 7.36 (s, 1H), 6.36 (s, 1H), 6.00 (d, 1H), 5.88 (dd, 1H), 3.74 (s, 3H), 3.65 (s, 3H), 3.57-3.43 (m, 2H), 2.80 (d, 3H), 2.41 (s, 3H)

Example 30

5-({2-[4-(2-Cyano-5-methylphenyl)-5-methoxy-2-oxopyridin-1(2H)-yl]-3-(1-methyl-1H-pyrazol-3-yl)propanoyl}amino)pyridine-2-carboxamide (racemate)

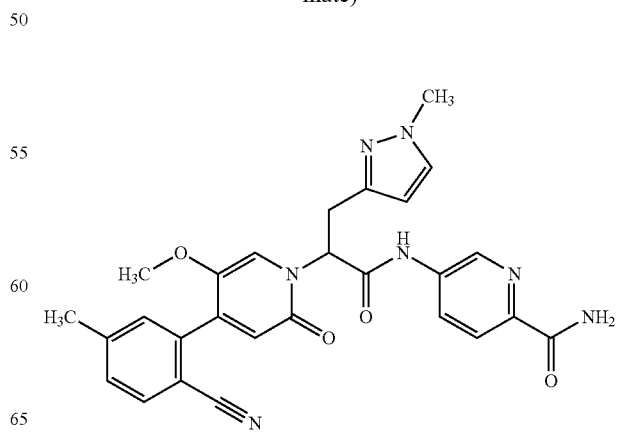

According to General Method 1, 50 mg (0.093 mmol, 80% purity) of 2-[4-(2-cyano-5-methylphenyl)-5-methoxy-2-oxopyridin-1(2H)-yl]-3-(1-methyl-1H-pyrazol-3-yl)propanoic acid hydrochloride (racemate) and 19 mg (0.140 mmol) of 5-aminopyridine-2-carboxamide in 0.8 ml of pyridine were reacted. Yield: 35 mg (73% of theory).

LC/MS [Method 1]: $R_t$=0.75 min; MS (ESIpos): m/z=512 (M+H)+, $^1$H-NMR (400 MHz, DMSO-$d_6$): δ [ppm]=10.96 (s, 1H), 8.86 (d, 1H), 8.22 (dd, 1H), 8.06-7.97 (m, 2H), 7.80 (d, 1H), 7.58-7.47 (m, 3H), 7.43 (d, 1H), 7.36 (s, 1H), 6.36 (s, 1H), 6.00 (d, 1H), 5.89 (dd, 1H), 3.74 (s, 3H), 3.65 (s, 3H), 3.56-3.42 (m, 2 H), 2.41 (s, 3H)

Example 31

5-({2-[4-(5-Chloro-2-cyanophenyl)-5-methoxy-2-oxopyridin-1(2H)-yl]-3-(1-methyl-1H-pyrazol-3-yl)propanoyl}amino)-3-fluoropyridine-2-carboxamide (racemate)

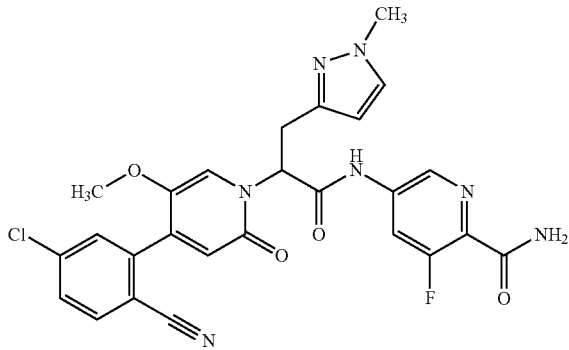 [SMILES: COc1cn(C(Cc2ccn(C)n2)C(=O)Nc2cnc(C(N)=O)c(F)c2)c(=O)cc1-c1cc(Cl)ccc1C#N]

According to General Method 1, 40 mg (0.091 mmol, 94% purity) of 2-[4-(5-chloro-2-methylphenyl)-5-methoxy-2-oxopyridin-1(2H)-yl]-3-(1-methyl-1H-pyrazol-3-yl)propanoic acid (racemate) and 26 mg (0.137 mmol) of 5-amino-3-fluoropyridine-2-carboxamide hydrochloride in 0.8 ml of pyridine were reacted. Yield: 35 mg (70% of theory).

LC/MS [Method 1]: $R_t$=0.82 min; MS (ESIpos): m/z=550 (M+H)+, $^1$H-NMR (400 MHz, DMSO-$d_6$): δ [ppm]=11.14 (s, 1H), 8.63 (s, 1H), 8.11 (dd, 1H), 7.98 (d, 1H), 7.93 (bs, 1H), 7.75-7.67 (m, 2H), 7.58-7.50 (m, 3H), 6.47 (s, 1H), 5.99 (d, 1H), 5.86 (dd, 1H), 3.74 (s, 3H), 3.66 (s, 3H), 3.57-3.43 (m, 2H)

Example 32

5-({2-[4-(5-Chloro-2-cyanophenyl)-5-methoxy-2-oxopyridin-1(2H)-yl]-3-(1,3-oxazol-3-yl)propanoyl}amino)-N-methylpyridine-2-carboxamide (racemate)

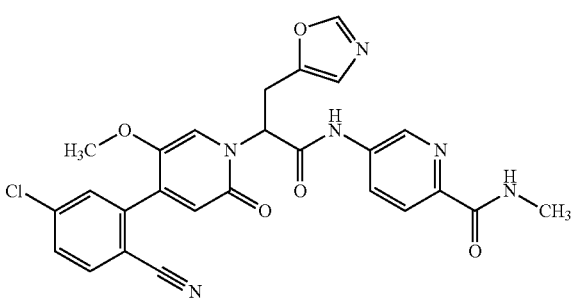 [SMILES: CNC(=O)c1ccc(NC(=O)C(Cc2cnco2)n2cc(OC)c(-c3cc(Cl)ccc3C#N)cc2=O)cn1]

According to General Method 1, 50 mg (0.115 mmol) of 2-[4-(5-chloro-2-cyanophenyl)-5-methoxy-2-oxopyridin-1(2H)-yl]-3-(1,3-oxazol-5-yl)propanoic acid hydrochloride (racemate) and 27 mg (0.172 mmol) of 5-amino-N-methylpyridine-2-carboxamide in 1.0 ml of pyridine were reacted. Yield: 53 mg (87% of theory).

LC/MS [Method 1]: $R_t$=0.82 min; MS (ESIpos): m/z=533 (M+H)+, $^1$H-NMR (400 MHz, DMSO-$d_6$): δ [ppm]=10.93 (s, 1H), 8.86 (d, 1H), 8.70-8.63 (m, 1H), 8.23 (s, 1H), 8.21 (dd, 1H), 8.02 (d, 1H), 7.99 (d, 1H), 7.75-7.78 (m, 2H), 7.55 (s, 1H), 6.90 (s, 1H), 6.50 (s, 1H), 5.94 (dd, 1H), 3.83-3.72 (m, 1H), 3.71-3.62 (m, 4H), 2.80 (d, 3H)

Example 33

5-({2-[4-(2-Cyano-5-methylphenyl)-5-methoxy-2-oxopyridin-1(2H)-yl]-4-methoxybutanoyl}amino)pyridine-2-carboxamide (racemate)

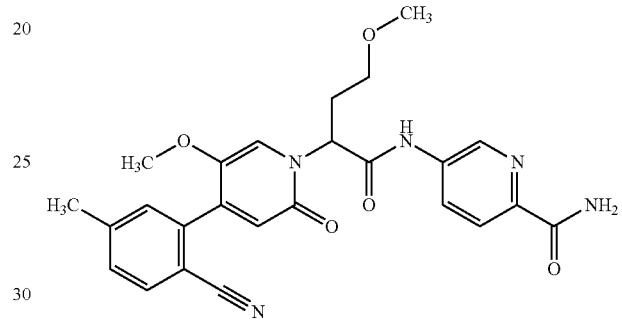

According to General Method 1, 40 mg (0.108 mmol) of 2-[4-(2-cyano-5-methylphenyl)-5-methoxy-2-oxopyridin-1(2H)-yl]-4-methoxybutanoic acid (racemate) and 22 mg (0.162 mmol) of 5-aminopyridine-2-carboxamide in 1.0 ml of pyridine were reacted. Yield: 43 mg (83% of theory).

LC/MS [Method 1]: $R_t$=0.78 min; MS (ESIpos): m/z=476 (M+H)+, $^1$H-NMR (400 MHz, DMSO-$d_6$): δ [ppm]=10.87 (s, 1H), 8.86 (d, 1H), 8.23 (dd, 1H), 8.05-7.98 (m, 2H), 7.82 (d, 1H), 7.52 (bs, 1H), 7.48 (s, 1H), 7.44 (d, 1H), 7.40 (s, 1H), 7.28-7.21 (m, 1H), 7.20-7.12 (m, 2H), 6.43 (s, 1H), 5.74 (dd, 1H), 3.67 (s, 3H), 3.46-3.37 (m, 1H), 3.30-3.24 (m, 1H), 3.21 (s, 3H), 2.48-2.36 (m, 5H).

Example 34

5-({2-[4-(2-Cyano-5-methylphenyl)-5-methoxy-2-oxopyridin-1(2H)-yl]-4-methoxybutanoyl}amino)pyridine-2-carboxamide (enantiomer 2)

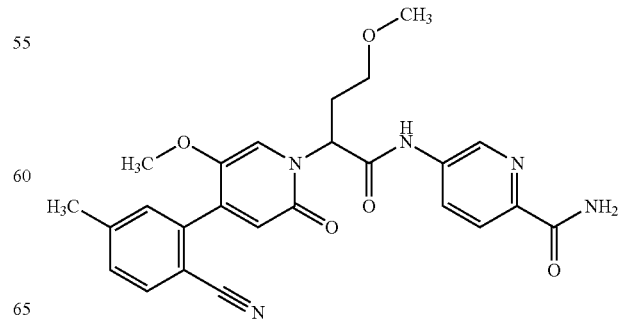

Enantiomer separation of 80 mg of 5-({2-[4-(2-cyano-5-methylphenyl)-5-methoxy-2-oxopyridin-1(2H)-yl]-4-methoxybutanoyl}amino)pyridine-2-carboxamide (racemate) gave 28 mg of the Example 34 title compound (enantiomer 2), chiral HPLC: $R_t$=31 min, 99% ee., and 31 mg of enantiomer 1 (chiral HPLC: $R_t$=22 min).

Separation method: column: Daicel Chiralpak AZ-H, 5 μm 250 mm×30 mm; eluent: 75% carbon dioxide/25% ethanol; temperature: 40° C.; flow rate: 100 ml/min; pressure: 100 bar; UV detection: 210 nm.

Analysis: column: Daicel AZ-H 5 μm 250 mm×4.6 mm; eluent: 70% carbon dioxide, 30% ethanol; flow rate: 3 ml/min; UV detection: 210 nm.

LC/MS [Method 1]: $R_t$=0.78 min; MS (ESIpos): m/z=476 (M+H)$^+$, $^1$H-NMR (400 MHz, DMSO-d$_6$): δ [ppm]=10.87 (s, 1H), 8.86 (d, 1H), 8.23 (dd, 1H), 8.05-7.98 (m, 2H), 7.82 (d, 1H), 7.52 (bs, 1H), 7.48 (s, 1H), 7.44 (d, 1H), 7.40 (s, 1H), 7.28-7.21 (m, 1H), 7.20-7.12 (m, 2H), 6.43 (s, 1H), 5.74 (dd, 1H), 3.67 (s, 3H), 3.46-3.37 (m, 1H), 3.30-3.24 (m, 1H), 3.21 (s, 3H), 2.48-2.36 (m, 5H).

Example 35

5-({2-[4-(5-Chloro-2-cyanophenyl)-5-methoxy-2-oxopyridin-1(2H)-yl]-3-(3-methyl-1,2-oxazol-5-yl)propanoyl}amino)pyridine-2-carboxamide (racemate)

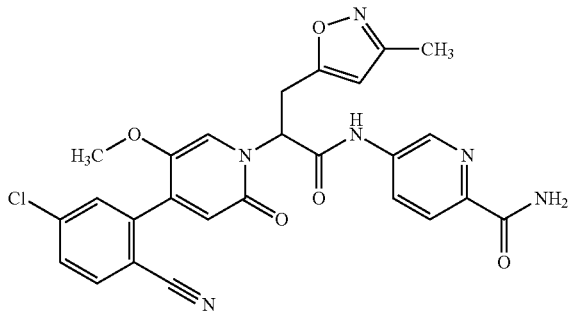 [SMILES: COc1cn(C(Cc2cc(C)no2)C(=O)Nc2ccc(C(N)=O)nc2)c(=O)cc1-c1cc(Cl)ccc1C#N]

60 mg (0.129 mmol, 89% purity) of 2-[4-(5-chloro-2-cyanophenyl)-5-methoxy-2-oxopyridin-1(2H)-yl]-3-(3-methyl-1,2-oxazol-5-yl)propanoic acid (racemate) and 27 mg (0.194 mmol, 1.5 eq.) of 5-aminopyridine-2-carboxamide were initially charged in 1.0 ml of pyridine, 123 μl (0.516 mmol, 50% in ethyl acetate, 4.0 eq.) of T3P were added and the mixture was stirred at 50° C. for 2 h. The reaction mixture was cooled, 4 ml of water and 4 ml of saturated aqueous sodium hydrogencarbonate solution were added and the mixture was stirred for 10 min. The suspension was filtered with suction and washed with water and three times with 2 ml each time of acetonitrile, and then the filtrate was lyophilized Yield: 51 mg (73% of theory).

LC/MS [Method 1]: $R_t$=0.83 min; MS (ESIpos): m/z=533 (M+H)$^+$, $^1$H-NMR (400 MHz, DMSO-d$_6$): δ [ppm]=10.94 (s, 1H), 8.84 (d, 1H), 8.22 (dd, 1 H), 8.07-8.01 (m, 2 H), 7.99 (d, 1H), 7.75-7.68 (m, 2H), 7.58-7.50 (m, 2H), 6.52 (s, 1H), 6.03 (s, 1H), 5.99 (dd, 1H), 3.88 (dd, 1H), 3.74-3.63 (m, 4H), 2.14 (s, 3H)

Example 36

5-({2-[4-(5-Chloro-2-cyanophenyl)-5-methoxy-2-oxopyridin-1(2H)-yl]-3-(1,3-oxazol-2-yl)propanoyl}amino)pyridine-2-carboxamide (racemate)

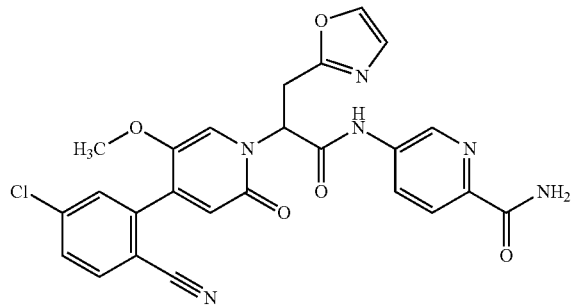 [SMILES: COc1cn(C(Cc2ncco2)C(=O)Nc2ccc(C(N)=O)nc2)c(=O)cc1-c1cc(Cl)ccc1C#N]

40 mg (0.098 mmol) of 2-[4-(5-chloro-2-cyanophenyl)-5-methoxy-2-oxopyridin-1(2H)-yl]-3-(1,3-oxazol-2-yl)propanoic acid (racemate) and 20 mg (0.147 mmol, 1.5 eq.) of 5-aminopyridine-2-carboxamide were initially charged in 0.8 ml of pyridine, 93 μl (0.392 mmol, 50% in ethyl acetate, 4.0 eq.) of T3P were added and the mixture was stirred at 50° C. for 2 h. The reaction mixture was cooled, 6 ml of saturated aqueous sodium hydrogencarbonate solution were added and the mixture was stirred for 15 min. The crystals formed were filtered off with suction and washed with water, 500 μl of isopropanol and then pentane. The residue was dried under high vacuum. Yield: 29 mg (57% of theory).

LC/MS [Method 1]: $R_t$=0.79 min; MS (ESIpos): m/z=519 (M+H)$^+$, $^1$H-NMR (400 MHz, DMSO-d$_6$): δ [ppm]=10.91 (s, 1H), 8.84 (d, 1H), 8.20 (dd, 1H), 8.07-7.95 (m, 4H), 7.73 (dd, 1H), 7.68 (d, 1H), 7.52 (s, 2H), 7.12 (s, 1H), 6.51 (s, 1H), 6.00 (t, 1H), 3.78 (d, 2H), 3.64 (s, 3H)

Example 37

5-({2-[4-(5-Chloro-2-cyanophenyl)-5-methoxy-2-oxopyridin-1(2H)-yl]-3-(1,3-oxazol-5-yl)propanoyl}amino)-3-fluoropyridine-2-carboxamide (racemate)

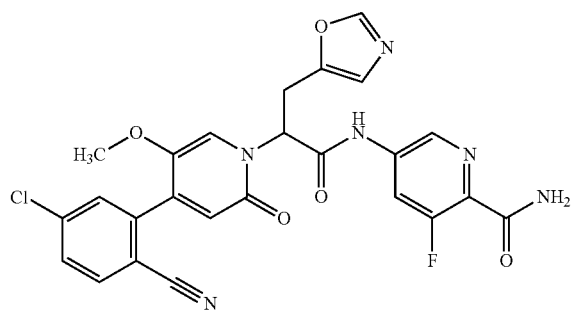 [SMILES: COc1cn(C(Cc2cnco2)C(=O)Nc2cnc(C(N)=O)c(F)c2)c(=O)cc1-c1cc(Cl)ccc1C#N]

According to General Method 1, 30 mg (0.060 mmol, 80% purity) of 2-[4-(5-chloro-2-methylphenyl)-5-methoxy-2-oxopyridin-1(2H)-yl]-3-(1,3-oxazol-3-yl)propanoic acid (racemate) and 20 mg (0.102 mmol) of 5-amino-3-fluoropyridine-2-carboxamide hydrochloride in 0.6 ml of pyridine were reacted. Yield: 10 mg (31% of theory).

LC/MS [Method 1]: $R_t$=0.75 min; MS (ESIpos): m/z=537 (M+H)$^+$, $^1$H-NMR (400 MHz, DMSO-d$_6$): δ [ppm]=11.11 (s, 1H), 8.62 (s, 1H), 8.24 (s, 1H), 8.11 (dd, 1H), 7.99 (d, 1H), 7.93 (bs, 1H), 7.75-7.68 (m, 2H), 7.56 (bs, 1H), 7.53 (s, 1H), 6.91 (s, 1H), 6.51 (s, 1H), 5.90 (dd, 1H), 3.82-3.72 (m, 1H), 3.71-3.61 (m, 4H)

Example 38

5-({2-[4-(5-Chloro-2-cyanophenyl)-5-methoxy-2-oxopyridin-1(2H)-yl]-3-(2-methyl-1,3-oxazol-4-yl) propanoyl}amino)-N-methylpyridine-2-carboxamide (racemate)

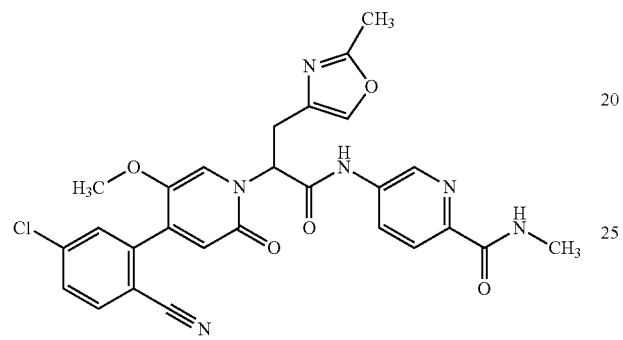

According to General Method 1, 50 mg (0.104 mmol, 94% purity) of 2-[4-(5-chloro-2-cyanophenyl)-5-methoxy-2-oxopyridin-1(2H)-yl]-3-(2-methyl-1,3-oxazol-4-yl)propanoic acid hydrochloride (racemate) and 24 mg (0.157 mmol) of 5-amino-N-methylpyridine-2-carboxamide in 0.8 ml of pyridine were reacted. Yield: 45 mg (79% of theory).

LC/MS [Method 1]: $R_t$=0.83 min; MS (ESIpos): m/z=547 (M+H)$^+$, $^1$H-NMR (400 MHz, DMSO-d$_6$): δ [ppm]=10.95 (s, 1H), 8.87 (d, 1H), 8.66 (q, 1H), 8.21 (dd, 1H), 8.05-7.95 (m, 2H), 7.75-7.68 (m, 2H), 7.64 (s, 1H), 7.54 (s, 1H), 6.48 (s, 1H), 5.90 (dd, 1H), 3.67 (s, 3H), 3.49 (dd, 1H), 3.36 (dd, 1H), 2.80 (d, 3H), 2.34 (s, 3H)

Example 39

5-({2-[4-(5-Chloro-2-cyanophenyl)-5-methoxy-2-oxopyridin-1(2H)-yl]-3-(2-methyl-1,3-oxazol-4-yl) propanoyl}amino)pyridine-2-carboxamide (racemate)

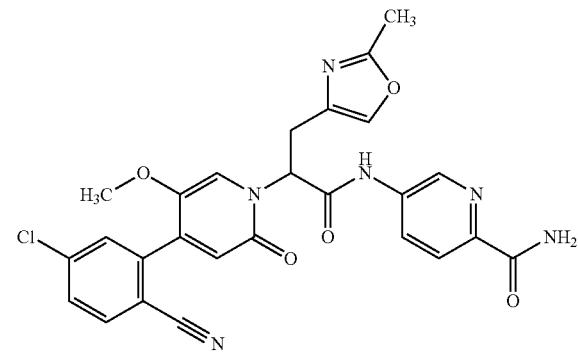 [SMILES: COc1cn(C(Cc2coc(C)n2)C(=O)Nc2ccc(C(N)=O)nc2)c(=O)cc1-c1cc(Cl)ccc1C#N]

According to General Method 1, 50 mg (0.104 mmol, 94% purity) of 2-[4-(5-chloro-2-cyanophenyl)-5-methoxy-2-oxopyridin-1(2H)-yl]-3-(2-methyl-1,3-oxazol-4-yl)propanoic acid hydrochloride (racemate) and 22 mg (0.157 mmol) of 5-aminopyridine-2-carboxamide in 0.8 ml of pyridine were reacted. Yield: 40 mg (72% of theory).

LC/MS [Method 1]: $R_t$=0.80 min; MS (ESIpos): m/z=533 (M+H)$^+$, $^1$H-NMR (400 MHz, DMSO-d$_6$): δ [ppm]=10.96 (s, 1H), 8.85 (d, 1H), 8.22 (dd, 1H), 8.05-7.96 (m, 3H), 7.74-7.69 (m, 2H), 7.64 (s, 1H), 7.57-7.50 (m, 2H), 6.48 (s, 1H), 5.91 (dd, 1H), 3.67 (s, 3H), 3.49 (dd, 1H), 3.36 (dd, 1H), 2.34 (s, 3H)

Example 40

5-({2-[4-(5-Chloro-2-cyanophenyl)-5-methoxy-2-oxopyridin-1(2H)-yl]-3-(5-methyl-1,2,4-oxadiazol-3-yl)propanoyl}amino)pyridine-2-carboxamide (racemate)

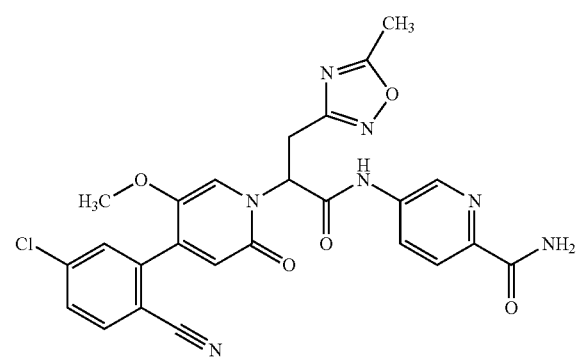 [SMILES: COc1cn(C(Cc2noc(C)n2)C(=O)Nc2ccc(C(N)=O)nc2)c(=O)cc1-c1cc(Cl)ccc1C#N]

50 mg (0.121 mmol) of 2-[4-(5-chloro-2-cyanophenyl)-5-methoxy-2-oxopyridin-1(2H)-yl]-3-(5-methyl-1,2,4-oxadiazol-3-yl)propanoic acid (racemate) and 25 mg (0.181 mmol, 1.5 eq.) of 5-aminopyridine-2-carboxamide were initially charged in 1.0 ml of pyridine, 114 µl (0.482 mmol, 50% in ethyl acetate, 4.0 eq.) of T3P were added and the mixture was stirred at 50° C. for 1.5 h. The reaction mixture was cooled, 4 ml of water and 4 ml of saturated aqueous sodium hydrogencarbonate solution were added and the mixture was stirred for 10 min. The suspension was filtered with suction and washed with water and three times with 2 ml each time of acetonitrile, and then the filtrate was lyophilized Yield: 51 mg (80% of theory).

LC/MS [Method 1]: $R_t$=0.81 min; MS (ESIpos): m/z=534 (M+H)$^+$, $^1$H-NMR (400 MHz, DMSO-d$_6$): δ [ppm]=10.90 (s, 1H), 8.85 (d, 1H), 8.21 (dd, 1H), 8.05-8.00 (m 2H), 7.98 (d, 1H), 7.75-7.67 (m, 2H), 7.56-7.50 (m, 2H), 6.51 (s, 1H), 5.98 (dd, 1H), 3.80-3.62 (m, 5H), 2.53 (s, 3H)

Example 41

5-{[2-{4-[5-Chloro-2-(difluoromethyl)phenyl]-5-methoxy-2-oxopyridin-1(2H)-yl}-3-(pyridin-2-yl)propanoyl]amino}pyridine-2-carboxamide (racemate)

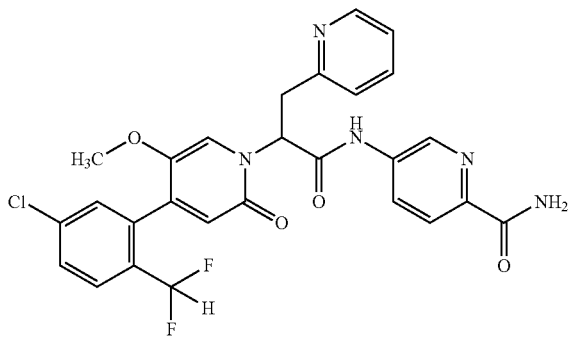

According to General Method 1, 70 mg (0.126 mmol, 85% purity) of 2-{4-[5-chloro-2-(difluoromethyl)phenyl]-5-methoxy-2-oxopyridin-1(2H)-yl}-3-(pyridin-2-yl)propanoic acid hydrochloride (racemate) and 26 mg (0.189 mmol) of 5-aminopyridine-2-carboxamide in 1.0 ml of pyridine were reacted. Yield: 4 mg (6% of theory).

LC/MS [Method 1]: $R_t$=0.85 min; MS (ESIpos): m/z=554 (M+H)$^+$, $^1$H-NMR (400 MHz, DMSO-d$_6$): δ [ppm]=10.92 (bs, 1H), 8.82 (bs, 1H), 8.49 (d, 1H), 8.21 (dd, 1H), 8.07-7.92 (m, 2H), 7.75-7.60 (m, 3H), 7.58-7.30 (m, 4H), 7.23 (dd, 1 H), 6.90-6.38 (m, 1H), 6.28 (bs, 1H), 6.08 (bs, 1H), 3.76-3.50 (m, 5H).

Example 42

5-({2-[4-(5-Chloro-2-cyanophenyl)-5-methoxy-2-oxopyridin-1(2H)-yl]-3-(4,5-dihydro-1,2-oxazol-3-yl)propanoyl}amino)-N-methylpyridine-2-carboxamide (racemate)

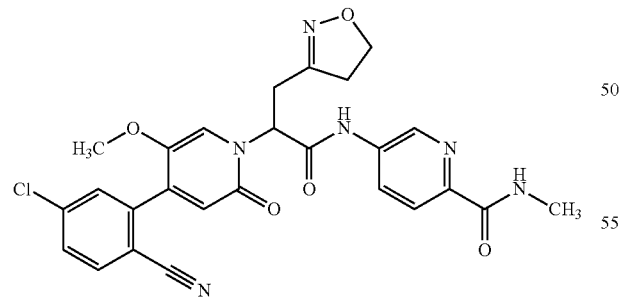

According to General Method 1, 50 mg (0.107 mmol, 94% purity) of 2-[4-(5-chloro-2-cyanophenyl)-5-methoxy-2-oxopyridin-1(2H)-yl]-3-(4,5-dihydro-1,2-oxazol-3-yl)propanoic acid hydrochloride (racemate) and 25 mg (0.161 mmol) of 5-amino-N-methylpyridine-2-carboxamide in 1.0 ml of pyridine were reacted Yield: 53 mg (93% of theory).

LC/MS [Method 1]: $R_t$=0.80 min; MS (ESIpos): m/z=535 (M+H)$^+$, $^1$H-NMR (400 MHz, DMSO-d$_6$): δ [ppm]=10.93 (s, 1H), 8.86 (d, 1H), 8.67 (q, 1H), 8.21 (dd, 1H), 8.05-7.96 (m, 2H), 7.76-7.70 (m, 2H), 7.51 (s, 1H), 6.56 (s, 1H), 5.93 (dd, 1H), 4.22-4.07 (m, 2H), 3.68 (s, 3H), 3.40-3.25 (m, 2H), 2.97 (t, 2H), 2.80 (d, 3H)

Example 43

5-({2-[4-(5-Chloro-2-cyanophenyl)-5-methyl-2-oxopyridin-1(2H)-yl]-3-(1-methyl-1H-pyrazol-3-yl)propanoyl}amino)-N-methylpyridine-2-carboxamide (racemate)

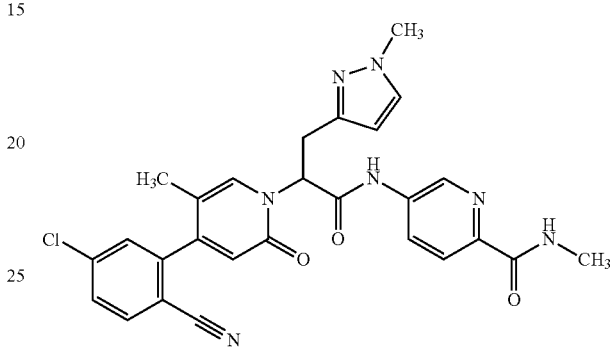

According to General Method 1, 75 mg (0.189 mmol) of 2-[4-(5-chloro-2-cyanophenyl)-5-methyl-2-oxopyridin-1(2H)-yl]-3-(1-methyl-1H-pyrazol-3-yl)propanoic acid (racemate) and 43 mg (0.283 mmol) of 5-amino-N-methylpyridine-2-carboxamide in 1.0 ml of pyridine were reacted. Yield: 44 mg (43% of theory).

LC/MS [Method 1]: $R_t$=0.83 min; MS (ESIpos): m/z=530 (M+H)$^+$, $^1$H-NMR (400 MHz, DMSO-d$_6$): δ [ppm]=11.00 (s, 1H), 8.88 (d, 1H), 8.70-8.63 (m, 1H), 8.21-8.15 (m, 1H), 8.05-7.97 (m, 2H), 7.90 (s, 1H), 7.77-7.72 (m, 1H), 7.70 (s, 1H), 7.53-7.47 (m, 1H), 6.37 (s, 1H), 5.98-5.90 (m, 2H), 3.73 (s, 3H), 3.49-3.39 (m, 2H), 2.80 (d, 3H), 1.87 (s, 3H).

Example 44

5-({2-[4-(5-Chloro-2-cyanophenyl)-5-methoxy-2-oxopyridin-1(2H)-yl]-3-(pyridin-4-yl)propanoyl}amino)pyridine-2-carboxamide (enantiomer 1)

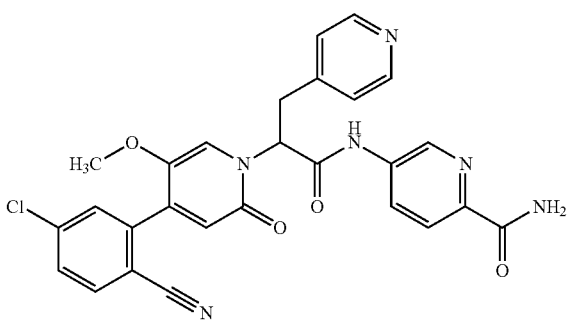 [SMILES: COc1cn(C(Cc2ccncc2)C(=O)Nc2ccc(C(N)=O)nc2)c(=O)cc1-c1cc(Cl)ccc1C#N]

Enantiomer separation of 96 mg of 5-({2-[4-(5-chloro-2-cyanophenyl)-5-methoxy-2-oxopyridin-1(2H)-yl]-3-(pyridin-4-yl)propanoyl}amino)pyridine-2-carboxamide (racemate) gave 37 mg of the Example 44 title compound (enantiomer 1), chiral HPLC: $R_t$=4.80 min, 100% ee., and 32 mg of enantiomer 2 (chiral HPLC: $R_t$=8.0 min).

Separation method: column: Daicel Chiralcel OD-H, 5 μm 250 mm×20 mm; eluent: 70% carbon dioxide/30% ethanol; temperature: 40° C.; flow rate: 80 ml/min; pressure: 100 bar; UV detection: 210 nm.

Analysis: column: Daicel OD-H 5 μm 250 mm×4.6 mm; eluent: 60% carbon dioxide, 40% ethanol; flow rate: 3 ml/min; UV detection: 210 nm.

LC/MS [Method 1]: $R_t$=0.62 min; MS (ESIpos): m/z=529 (M+H)$^+$, $^1$H-NMR (400 MHz, DMSO-d$_6$): δ [ppm]=10.95 (s, 1H), 8.84 (d, 1H), 8.44 (d, 2H), 8.22 (dd, 1H), 8.07-7.94 (m, 2H), 7.97 (d, 1H), 7.71 (dd, 1H), 7.66 (d, 1H), 7.58 (s, 1H), 7.54 (bs, 1H), 7.27 (d, 2H), 6.44 (s, 1H), 6.03 (dd, 1H), 3.72-3.52 (m, 5H).

Example 45

5-[(2-{4-[2-Cyano-5-(methylamino)phenyl]-5-methoxy-2-oxopyridin-1(2H)-yl}-4-methoxybutanoyl)amino]-N-methylpyridine-2-carboxamide (racemate)

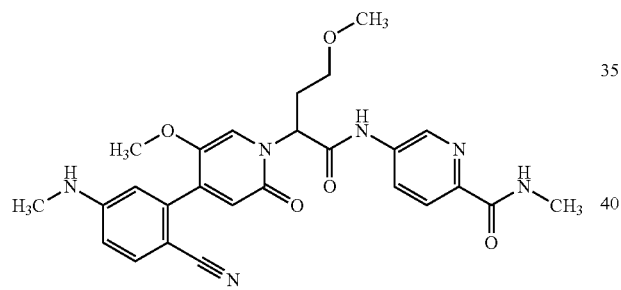

According to General Method 1, 50 mg (0.121 mmol) of 2-{4-[2-cyano-5-(methylamino)phenyl]-5-methoxy-2-oxopyridin-1(2H)-yl}-4-methoxybutanoic acid hydrochloride (racemate) and 28 mg (0.182 mmol) of 5-amino-N-methylpyridine-2-carboxamide in 1.0 ml of pyridine were reacted. Yield: 45 mg (74% of theory).

LC/MS [Method 10]: $R_t$=1.35 min; MS (ESIpos): m/z=505 (M+H)$^+$, $^1$H-NMR (400 MHz, DMSO-d$_6$): δ [ppm]=10.85 (s, 1H), 8.88 (d, 1H), 8.66 (q, 1H), 8.21 (dd, 1H), 8.00 (d, 1H), 7.52 (d, 1H), 7.44 (s, 1H), 6.82 (q, 1H), 6.63 (dd, 1H), 6.53 (d, 1H), 6.36 (s, 1H), 5.72 (dd, 1H), 3.67 (s, 3H), 3.45-3.37 (m, 1H), 3.30-3.24 (m, 1H), 3.21 (s, 3H), 2.80 (d, 3H), 2.74 (d, 3H), 2.48-2.30 (m, 2H).

Example 46

5-({2-[4-(5-Chloro-2-cyano-4-fluorophenyl)-5-methoxy-2-oxopyridin-1(2H)-yl]-4-methoxybutanoyl}amino)-N-methylpyridine-2-carboxamide (racemate)

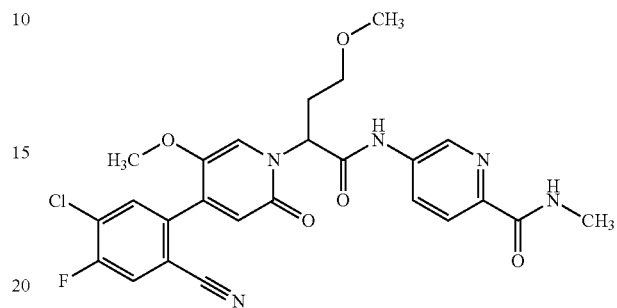

According to General Method 1, 65 mg (0.092 mmol, 56% purity) of 2-[4-(5-chloro-2-cyano-4-fluorophenyl)-5-methoxy-2-oxopyridin-1(2H)-yl]-4-methoxybutanoic acid (racemate) and 21 mg (0.138 mmol) of 5-amino-N-methylpyridine-2-carboxamide in 1.0 ml of pyridine were reacted. Yield: 47 mg (97% of theory).

LC/MS [Method 1]: $R_t$=0.86 min; MS (ESIpos): m/z=528 (M+H)$^+$, $^1$H-NMR (400 MHz, DMSO-d$_6$): δ [ppm]=10.87 (s, 1H), 8.88 (d, 1H), 8.66 (q, 1H), 8.26-8.18 (m, 2H), 8.00 (d, 1H), 7.94 (d, 1H), 7.51 (s, 1H), 6.55 (s, 1H), 5.74 (dd, 1H), 3.69 (s, 3H), 3.45-3.37 (m, 1H), 3.29-3.24 (m, 1H), 3.21 (s, 3H), 2.80 (d, 3H), 2.48-2.36 (m, 2H).

Example 47

5-({2-[4-(5-Chloro-2-cyano-4-fluorophenyl)-5-methoxy-2-oxopyridin-1(2H)-yl]-4-methoxybutanoyl}amino)pyridine-2-carboxamide (racemate)

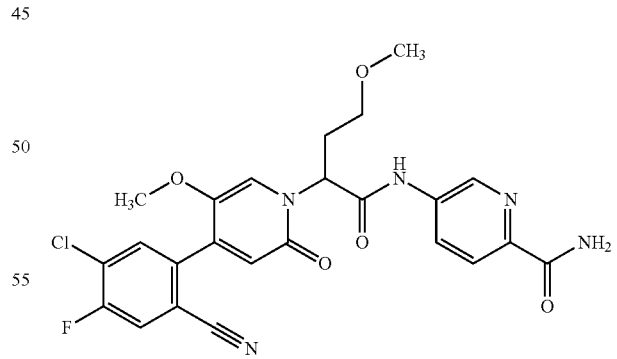

According to General Method 1, 65 mg (0.092 mmol, 56% purity) of 2-[4-(5-chloro-2-cyano-4-fluorophenyl)-5-methoxy-2-oxopyridin-1(2H)-yl]-4-methoxybutanoic acid (racemate) and 19 mg (0.138 mmol) of 5-aminopyridine-2-carboxamide in 1.0 ml of pyridine were reacted Yield: 35 mg (75% of theory).

LC/MS [Method 1]: $R_t$=0.82 min; MS (ESIpos): m/z=514 (M+H)$^+$,

¹H-NMR (400 MHz, DMSO-d₆): δ [ppm]=10.89 (s, 1H), 8.86 (d, 1H), 8.27-8.19 (m, 2H), 8.05-7.98 (d, 2H), 7.94 (d, 1H), 7.56-7.48 (m, 2H), 6.55 (s, 1H), 5.75 (dd, 1H), 3.69 (s, 3H), 3.46-3.37 (m, 1H), 3.31-3.23 (m, 1H), 3.21 (s, 3H), 2.48-2.36 (m, 2H).

Example 48

5-({2-[4-(2-Cyano-5-fluorophenyl)-5-methoxy-2-oxopyridin-1(2H)-yl]-3-(1-methyl-1H-pyrazol-3-yl)propanoyl}amino)pyridine-2-carboxamide (racemate)

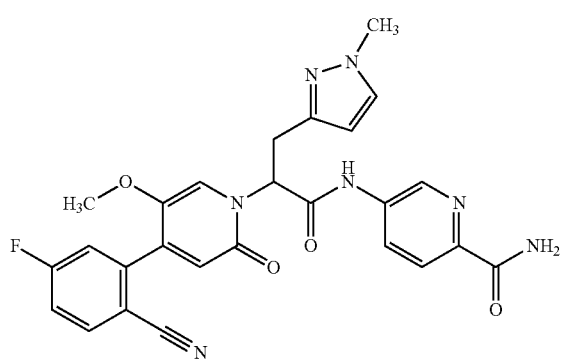 [SMILES: COc1cn(C(Cc2ccn(C)n2)C(=O)Nc2ccc(C(N)=O)nc2)c(=O)cc1-c1cc(F)ccc1C#N]

According to General Method 1, 50 mg (0.119 mmol, 94% purity) of 2-[4-(2-cyano-5-fluorophenyl)-5-methoxy-2-oxopyridin-1(2H)-yl]-3-(1-methyl-1H-pyrazol-3-yl)propanoic acid (racemate) and 25 mg (0.178 mmol) of 5-aminopyridine-2-carboxamide in 1.0 ml of pyridine were reacted. Yield: 33 mg (54% of theory).

LC/MS [Method 1]: $R_t$=0.74 min; MS (ESIpos): m/z=516 (M+H)⁺,

¹H-NMR (400 MHz, DMSO-d₆): δ [ppm]=10.97 (s, 1H), 8.85 (d, 1H), 8.22 (dd, 1H), 8.08-7.99 (m, 3H), 7.59 (s, 1H), 7.56-7.47 (m, 4H), 6.45 (s, 1H), 6.00 (d, 1H), 5.89 (dd, 1H), 3.74 (s, 3H), 3.67 (s, 3H), 3.57-3.43 (m, 2H).

Example 49

5-({2-[4-(2-Cyano-5-fluorophenyl)-5-methoxy-2-oxopyridin-1(2H)-yl]-3-(1-methyl-1H-pyrazol-3-yl)propanoyl}amino)-N-methylpyridine-2-carboxamide (racemate)

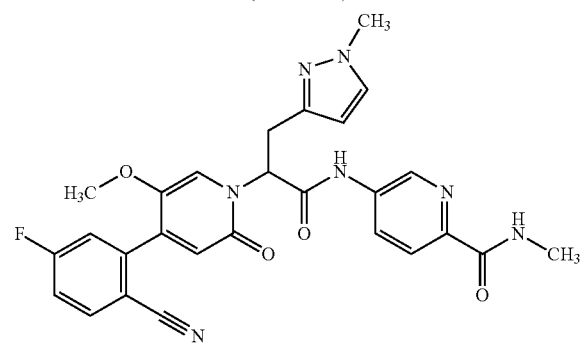

According to General Method 1, 50 mg (0.119 mmol, 94% purity) of 2-[4-(2-cyano-5-fluorophenyl)-5-methoxy-2-oxopyridin-1(2H)-yl]-3-(1-methyl-1H-pyrazol-3-yl)propanoic acid (racemate) and 27 mg (0.178 mmol) of 5-amino-N-methylpyridine-2-carboxamide in 1.0 ml of pyridine were reacted. Yield: 43 mg (68% of theory).

LC/MS [Method 1]: $R_t$=0.80 min; MS (ESIpos): m/z=529 (M+H)⁺,

¹H-NMR (400 MHz, DMSO-d₆): δ [ppm]=10.96 (s, 1H), 8.88 (d, 1H), 8.66 (q, 1H), 8.20 (dd, 1H), 8.10-7.98 (m, 2H), 7.58 (s, 1H), 7.55-7.45 (m, 3H), 6.45 (s, 1H), 6.00 (d, 1H), 5.88 (dd, 1H), 3.74 (s, 3H), 3.67 (s, 3H), 3.57-3.42 (m, 2H), 2.80 (d, 3H).

Example 50

5-({2-[4-(5-Chloro-2-cyano-3-fluorophenyl)-5-methoxy-2-oxopyridin-1(2H)-yl]-4-methoxybutanoyl}amino)pyridine-2-carboxamide (racemate)

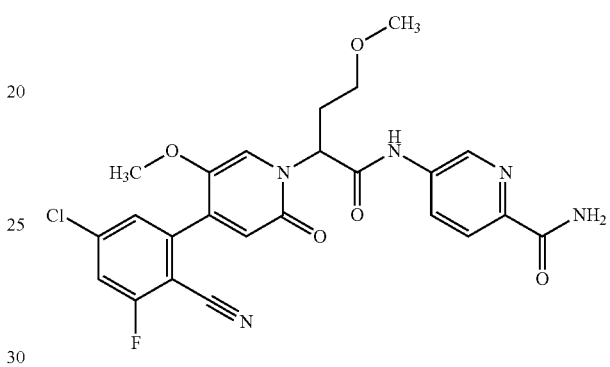

According to General Method 1, 51 mg (0.080 mmol, 62% purity) of 2-[4-(5-chloro-2-cyano-3-fluorophenyl)-5-methoxy-2-oxopyridin-1(2H)-yl]-4-methoxybutanoic acid (racemate) and 17 mg (0.120 mmol) of 5-aminopyridine-2-carboxamide in 1.0 ml of pyridine were reacted. Yield: 33 mg (54% of theory).

LC/MS [Method 1]: $R_t$=0.83 min; MS (ESIpos): m/z=514 (M+H)⁺,

¹H-NMR (400 MHz, DMSO-d₆): δ [ppm]=10.88 (s, 1H), 8.85 (d, 1H), 8.23 (dd, 1H), 8.04-7.98 (m, 2H), 7.95 (dd, 1H), 7.67-7.64 (m, 1H), 7.55-7.49 (m, 2H), 6.58 (s, 1H), 5.75 (dd, 1H), 3.70 (s, 3H), 3.46-3.38 (m, 1H), 3.31-3.24 (m, 1H), 3.21 (s, 3H), 2.48-2.40 (m, 2H).

Example 51

5-({2-[4-(5-Chloro-2-cyanophenyl)-5-cyclopropyl-2-oxopyridin-1(2H)-yl]-3-(1-methyl-1H-pyrazol-3-yl)propanoyl}amino)-N-methylpyridine-2-carboxamide (racemate)

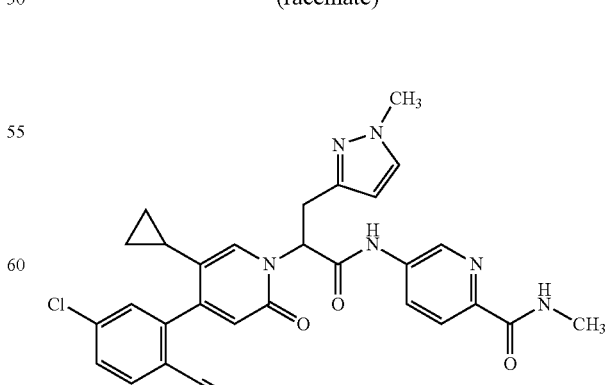

According to General Method 1, 60 mg (0.142 mmol) of 2-[4-(5-chloro-2-cyanophenyl)-5-cyclopropyl-2-oxopyridin-1(2H)-yl]-3-(1-methyl-1H-pyrazol-3-yl)propanoic acid (racemate) and 32 mg (0.213 mmol) of 5-amino-N-methyl-pyridine-2-carboxamide in 0.75 ml of pyridine were reacted. Yield: 49 mg (95% purity, 59% of theory).

LC/MS [Method 1]: $R_t$=0.91 min; MS (ESIpos): m/z=556 (M+H)+, $^1$H-NMR (400 MHz, DMSO-$d_6$): δ [ppm]=10.96 (bs, 1H), 8.87 (d, 1H), 8.71-8.62 (m, 1H), 8.20 (dd, 1H), 8.04-7.98 (m, 2H), 7.76-7.70 (m, 2H), 7.58 (s, 1H), 7.53-7.47 (m, 1H), 6.35 (s, 1H), 5.96-5.90 (m, 1H), 5.89-5.80 (m, 1H), 3.72 (s, 3H), 3.48-3.41 (m, 2H), 2.80 (d, 3H), 1.42-1.31 (m, 1H), 0.63-0.48 (m, 3H), 0.38-0.28 (m, 1H).

Example 52

5-({2-[4-(5-Chloro-2-fluorophenyl)-5-methoxy-2-oxopyridin-1(2H)-yl]-3-(1,3-oxazol-2-yl)propanoyl}amino)pyridine-2-carboxamide (racemate)

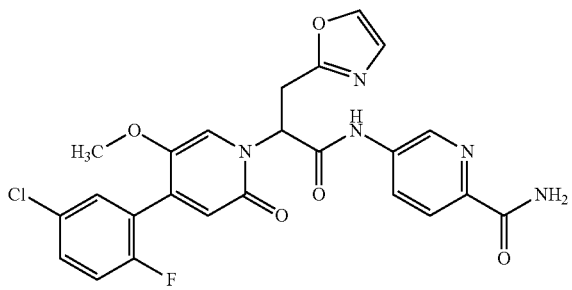 [SMILES: COc1cn(C(Cc2ncco2)C(=O)Nc2ccc(C(N)=O)nc2)c(=O)cc1-c1cc(Cl)ccc1F]

According to General Method 1, 60 mg (0.122 mmol, 80% purity) of 2-[4-(5-chloro-2-fluorophenyl)-5-methoxy-2-oxopyridin-1(2H)-yl]-3-(1,3-oxazol-2-yl)propanoic acid (racemate) and 25 mg (0.183 mmol) of 5-aminopyridine-2-carboxamide in 1.0 ml of pyridine were reacted. Yield: 14 mg (23% of theory).

LC/MS [Method 1]: $R_t$=0.80 min; MS (ESIpos): m/z=512 (M+H)+, $^1$H-NMR (400 MHz, DMSO-$d_6$): δ [ppm]=10.88 (s, 1H), 8.84 (d, 1H), 8.19 (dd, 1H), 8.06-7.98 (m, 3H), 7.57-7.50 (m, 2H), 7.49-7.43 (m, 2H), 7.38-7.33 (m, 1H), 7.13 (d, 1H), 6.44 (s, 1H), 5.99 (dd, 1H), 3.81-3.70 (m, 2H), 3.62 (s, 3H).

Example 53

5-{[2-{4-[5-Chloro-2-(trifluoromethyl)phenyl]-5-methoxy-2-oxopyridin-1(2H)-yl}-3-(pyridin-2-yl)propanoyl]amino}pyridine-2-carboxamide (mixture of racemic diastereomers)

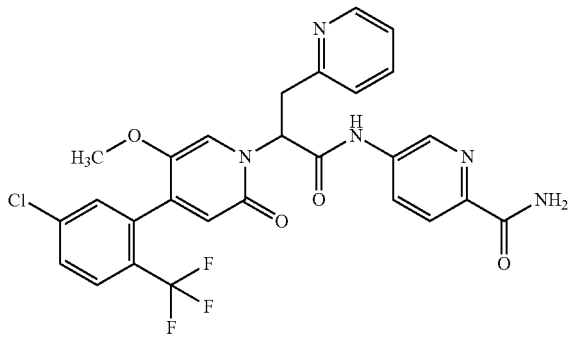 [SMILES: COc1cn(C(Cc2ccccn2)C(=O)Nc2ccc(C(N)=O)nc2)c(=O)cc1-c1cc(Cl)ccc1C(F)(F)F]

According to General Method 1, 75 mg (0.147 mmol) of 2-{4-[5-chloro-2-(trifluoromethyl)phenyl]-5-methoxy-2-oxopyridin-1(2H)-yl}-3-(pyridin-2-yl)propanoic acid hydrochloride (racemate) and 31 mg (0.221 mmol) of 5-aminopyridine-2-carboxamide in 1.5 ml of pyridine were reacted. Yield: 11 mg (13% of theory).

LC/MS [Method 1]: $R_t$=0.85 min; MS (ESIpos): m/z=572 (M+H)+, $^1$H-NMR (400 MHz, DMSO-$d_6$): δ [ppm]=11.15-10.81 (two s around 11.08 and 10.88, 2H), 8.91-8.80 (m, 2H), 8.53-8.43 (m, 2H), 8.26-8.20 (m, 2H), 8.05-7.98 (m, 4H), 7.87-7.64 (m, 7H), 7.56-7.46 (m, 4H), 7.42-7.19 (m, 6H), 6.29-5.98 (m, 4H), 3.77-3.63 (m, 4H), 3.60-3.47 (two s around 3.57 and 3.51, 6H).

Example 54

5-{[2-{4-[5-Chloro-2-(trifluoromethyl)phenyl]-5-methoxy-2-oxopyridin-1(2H)-yl}-3-(3-methyl-1,2-oxazolyl)propanoyl]amino}pyridine-2-carboxamide (mixture of racemic diastereomers)

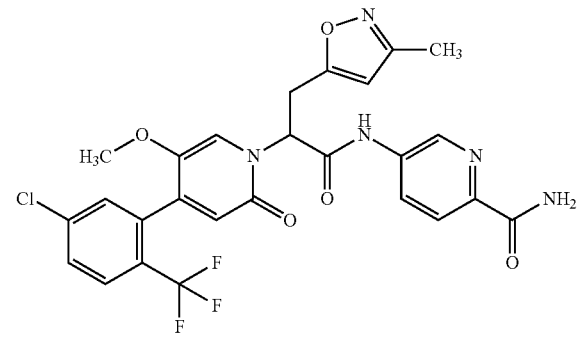 [SMILES: COc1cn(C(Cc2cc(C)no2)C(=O)Nc2ccc(C(N)=O)nc2)c(=O)cc1-c1cc(Cl)ccc1C(F)(F)F]

According to General Method 1, 50 mg (0.108 mmol) of 2-{4-[5-chloro-2-(trifluoromethyl)phenyl]-5-methoxy-2-oxopyridin-1(2H)-yl}-3-(3-methyl-1,2-oxazol-5-yl)propanoic acid (racemate) and 22 mg (0.162 mmol) of 5-aminopyridine-2-carboxamide in 1.0 ml of pyridine were reacted. Yield: 48 mg (75% of theory).

LC/MS [Method 1]: $R_t$=0.91 min; MS (ESIpos): m/z=576 (M+H)+, $^1$H-NMR (400 MHz, DMSO-$d_6$): δ [ppm]=11.02 (s, 1H), 10.78 (s, 1H), 8.88-8.80 (m, 2H), 8.25-8.19 (m, 2H), 8.07-8.00 (m, 4H), 7.87-7.81 (m, 2H), 7.75-7.69 (m, 2H), 7.59-7.51 (m, 3H), 7.51-7.49 (m, 2H), 7.39 (s, 1H), 6.35 (s, 1 H), 6.32 (s, 1H), 6.12-6.05 (m, 2H), 5.94 (s, 1H), 5.89-5.82 (m, 1H), 3.95-3.76 (m, 2H), 3.73-3.62 (m, 2H), 3.61 (s, 3H), 3.56 (s, 3H), 2.17 (s, 3H), 2.13 (s, 3H).

B) Assessment of Physiological Efficacy

The suitability of the compounds according to the invention for treating thromboembolic disorders can be demonstrated in the following assay systems:

a) Test Descriptions (In Vitro)

a.1) Measurement of FXIa Inhibition

The factor XIa inhibition of the substances according to the invention is determined using a biochemical test system which utilizes the reaction of a peptidic factor XIa substrate to determine the enzymatic activity of human factor XIa. Here, factor XIa cleaves from the peptic factor XIa substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 μM to 0.0078 μM; resulting final concentrations in the test: 50 μM to 0.00013 μM). 1 μl of the diluted substance solutions is placed into each of the wells of white microtitre plates from Greiner (384 wells). 20 μl of assay buffer (50 mM of Tris/HCl pH 7.4; 100 mM of sodium chloride; 5 mM of calcium chloride; 0.1% of bovine serum albumin) and 20 μl of factor XIa from Kordia (0.45 nM in assay buffer) are then added successively. After 15 mM of incubation, the enzyme reaction is started by addition of 20 μl of the factor XIa substrate Boc-Glu(OBzl)-Ala-Arg-AMC dissolved in assay buffer (10 μM in assay buffer) from Bachem, the mixture is incubated at room temperature (22° C.) for 30 min and fluorescence is then measured (excitation: 360 nm, emission: 460 nm). The measured emissions of the test batches with test substance are compared to those of control batches without test substance (only dimethyl sulphoxide instead of test substance in dimethyl sulphoxide), and $IC_{50}$ values are calculated from the concentration/activity relationships. Activity data from this test are listed in Table A below:

TABLE A

| Example No. | $IC_{50}$ [nM] | Example No. | $IC_{50}$ [nM] |
| --- | --- | --- | --- |
| 1 | 20 | 2 | 20 |
| 3 | 29 | 4 | 16 |
| 5 | 12 | 6 | 20 |
| 7 | 160 | 8 | 11 |
| 9 | 9 | 10 | 210 |
| 11 | 48 | 12 | 210 |
| 13 | 220 | 14 | 390 |
| 15 | 23 | 16 | 32 |
| 17 | 22 | 18 | 26 |
| 19 | 4.6 | 20 | 5.1 |
| 21 | 5.8 | 22 | 6.0 |
| 23 | 7.1 | 24 | 7.4 |
| 25 | 5.7 | 26 | 8.0 |
| 27 | 5.6 | 28 | 8.6 |
| 29 | 10 | 30 | 20 |
| 31 | 11 | 32 | 12 |
| 33 | 32 | 34 | 14 |
| 35 | 19 | 36 | 19 |
| 37 | 23 | 38 | 23 |
| 39 | 30 | 40 | 24 |
| 41 | 40 | 42 | 51 |
| 43 | 55 | 44 | 100 |
| 45 | 120 | 46 | 150 |
| 47 | 220 | 48 | 150 |
| 49 | 160 | 50 | 190 |
| 51 | 200 | 52 | 300 |
| 53 | 380 | 54 | 430 | a.2) Determination of the Selectivity

To demonstrate the selectivity of the substances with respect to FXIa inhibition, the test substances are examined for their inhibition of other human serine proteases, such as factor Xa, trypsin and plasmin. To determine the enzymatic activity of factor Xa (1.3 nmol/l from Kordia), trypsin (83 mU/ml from Sigma) and plasmin (0.1 μg/ml from Kordia), these enzymes are dissolved (50 mmol/l of Tris buffer [C,C,C-tris(hydroxymethyl)aminomethane], 100 mmol/l of NaCl, 0.1% BSA [bovine serum albumin], 5 mmol/l of calcium chloride, pH 7.4) and incubated for 15 min with test substance in various concentrations in dimethyl sulphoxide and also with dimethyl sulphoxide without test substance. The enzymatic reaction is then started by addition of the appropriate substrates (5 μmol/l of Boc-Ile-Glu-Gly-Arg-AMC from Bachem for factor Xa and trypsin, 5 50 μmol/l of MeOSuc-Ala-Phe-Lys-AMC from Bachem for plasmin). After an incubation time of 30 mM at 22° C., fluorescence is measured (excitation: 360 nm, emission: 460 nm). The measured emissions of the test mixtures with test substance are compared to the control mixtures without test substance (only dimethyl sulphoxide instead of test substance in dimethyl sulphoxide) and $IC_{50}$ values are calculated from the concentration/activity relationships.

a.3) Thrombin Generation Assay (Thrombogram)

The effect of the test substances on the thrombogram (thrombin generation assay according to Hemker) is determined in vitro in human plasma (Octaplas® from Octapharma).

In the thrombin generation assay according to Hemker, the activity of thrombin in coagulating plasma is determined by measuring the fluorescent cleavage products of the substrate I-1140 (Z-Gly-Gly-Arg-AMC, Bachem). The reactions are carried out in the presence of varying concentrations of test substance or the corresponding solvent. To start the reaction, reagents from Thrombinoscope (30 pM or 0.1 pM recombinant tissue factor, 24 μM phospholipids in HEPES) are used. In addition, a thrombin calibrator from Thrombinoscope is used whose amidolytic activity is required for calculating the thrombin activity in a sample containing an unknown amount of thrombin. The test is carried out according to the manufacturer's instructions (Thrombinoscope BV): 4 μl of test substance or of the solvent, 76 μl of plasma and 20 μl of PPP reagent or thrombin calibrator are incubated at 37° C. for 5 min. After addition of 20 μl of 2.5 mM thrombin substrate in 20 mM Hepes, 60 mg/ml of BSA, 102 mM of calcium chloride, the thrombin generation is measured every 20 s over a period of 120 min. Measurement is carried out using a fluorometer (Fluoroskan Ascent) from Thermo Electron fitted with a 390/460 nm filter pair and a dispenser.

Using the Thrombinoscope software, the thrombogram is calculated and represented graphically. The following parameters are calculated: lag time, time to peak, peak, ETP (endogenous thrombin potential) and start tail.

a.4) Determination of Anticoagulatory Activity

The anticoagulatory activity of the test substances is determined in vitro in human plasma and rat plasma. To this end, blood is drawn off in a mixing ratio of sodium citrate/blood of 1:9 using a 0.11 molar sodium citrate solution as receiver. Immediately after the blood has been drawn off, it is mixed thoroughly and centrifuged at about 4000 g for 15 minutes. The supernatant is pipetted off.

The prothrombin time (PT, synonyms: thromboplastin time, quick test) is determined in the presence of varying concentrations of test substance or the corresponding solvent using a commercial test kit (Neoplastin® from Boehringer Mannheim or Hemoliance® RecombiPlastin from Instrumentation Laboratory). The test compounds are incubated with the plasma at 37° C. for 3 minutes. Coagulation is then started by addition of thromboplastin, and the time when coagulation occurs is determined. The concentration of test substance which effects a doubling of the prothrombin time is determined.

The activated partial thromboplastin time (APTT) is determined in the presence of varying concentrations of test substance or the corresponding solvent using a commercial test kit (PTT reagent from Roche). The test compounds are incubated with the plasma and the PTT reagent (cephalin, kaolin) at 37° C. for 3 minutes. Coagulation is then started by addition of 25 mM calcium chloride, and the time when coagulation occurs is determined. The concentration of test substance which effects an extension by 50% or a doubling of the APTT is determined.

a.5) Determination of the Plasma Kallikrein Activity

To determine the plasma kallikrein inhibition of the substances according to the invention, a biochemical test system is used which utilizes the reaction of a peptidic plasma kallikrein substrate to determine the enzymatic activity of human plasma kallikrein. Here, plasma kallikrein cleaves from the peptic plasma kallikrein substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 µM to 0.0078 µM; resulting final concentrations in the test: 50 µM to 0.00013 µM). 1 µl of the diluted substance solutions is placed into each of the wells of white microtitre plates from Greiner (384 wells). 20 µl of assay buffer (50 mM Tris/HCl pH 7.4; 100 mM sodium chloride solution; 5 mM of calcium chloride solution; 0.1% of bovine serum albumin) and 20 µl of plasma kallikrein from Kordia (0.6 nM in assay buffer) are then added successively. After 15 min of incubation, the enzyme reaction is started by addition of 20 µl of the substrate H-Pro-Phe-Arg-AMC dissolved in assay buffer (10 µM in assay buffer) from Bachem, the mixture is incubated at room temperature (22° C.) for 30 min and fluorescence is then measured (excitation: 360 nm, emission: 460 nm). The measured emissions of the test batches with test substance are compared to those of control batches without test substance (only dimethyl sulphoxide instead of test substance in dimethyl sulphoxide), and $IC_{50}$ values are calculated from the concentration/activity relationships.

TABLE B

| Example No. | $IC_{50}$ [nM] | Example No. | $IC_{50}$ [nM] |
|---|---|---|---|
| 1 | 22 | 2 | 16 |
| 3 | 100 | 4 | 140 |
| 5 | 120 | 6 | 22 |
| 7 | 490 | 8 | 6 |
| 9 | 8 | 10 | 470 |
| 11 | 52 | 12 | 640 |
| 13 | 250 | 14 | 160 |
| 15 | 53 | 16 | 89 |
| 17 | 24 | 18 | 110 |
| 19 | 4.3 | 20 | 3.1 |
| 21 | 4.0 | 22 | 6.5 |
| 23 | 7.0 | 24 | 8.6 |
| 25 | 6.2 | 26 | 6.9 |
| 27 | 6.2 | 28 | 4.6 |
| 29 | 8.2 | 30 | 17 |
| 31 | 61 | 32 | 11 |
| 33 | 39 | 34 | 19 |
| 35 | 93 | 36 | 14 |
| 37 | 14 | 38 | 16 |
| 39 | 27 | 40 | 23 |
| 41 | 62 | 42 | 30 |
| 43 | 65 | 44 | 760 |
| 45 | 360 | 46 | 110 |
| 47 | 180 | 48 | 120 |
| 49 | 130 | 50 | 1100 |
| 51 | 80 | 52 | 310 |
| 53 | 400 | 54 | 200 | a.6) Determination of Endothelium Integrity

The activity of the compounds according to the invention is characterized by means of an in vitro permeability assay on "human umbilical venous cells" (HUVEC). Using the EOS apparatus (EC IS: Electric Cell-substrate Impedance Sensing; Applied Biophysics Inc; Troy, N.Y.), it is possible to measure continuously variations in the transendothelial electrical resistance (TEER) across an endothelial cell monolayer plated over gold electrodes. HUVECs are sown on a 96-well sensor electrode plate (96W1 E, Ibidi GmbH, Martinsried, Germany). Hyperpermeability of the confluent cell monolayer formed is induced by stimulation with kininogen, prekallikrein and factor XII (100 nM each). The compounds according to the invention are added prior to the addition of the substances indicated above. The customary concentrations of the compounds are $1 \times 10^{-10}$ to $1 \times 10^{-6}$ M.

a.7) Determination of the In Vitro Permeability of Endothelial Cells

In a further hyperpermeability model, the activity of the substances on the modulation of macromolecular permeability is determined. HUVECs are sown on a fibronectin-coated Transwell filter membrane (24-well plates, 6.5 mm insert with 0.4 µM polycarbonate membrane; Costar #3413). The filter membrane separates the upper from the lower cell culture space, with the confluent endothelial cell layer on the floor of the upper cell culture space. 250 g/ml of 40 kDa FITC dextan (Invitrogen, D1844) are added to the medium of the upper chamber. Hyperpermeability of the monolayer is induced by stimulation with kininogen, prekallikrein and factor XII (100 nM each). Every 30 min, medium samples are removed from the lower chamber and relative fluorescence as a parameter for changes in macromolecular permeability as a function of time is determined using a fluorimeter. The compounds according to the invention are added prior to the addition of the substances indicated above. The customary concentrations of the compounds are $1 \times 10^{-10}$ to $1 \times 10^{-6}$ M.

b) Determination of Antithrombotic Activity (In Vivo)

b.1) Arterial Thrombosis Model (Iron(II) Chloride-Induced Thrombosis) in Combination with ear Bleeding Time in Rabbits The antithrombotic activity of the FXIa inhibitors is tested in an arterial thrombosis model. Thrombus formation is triggered here by causing chemical injury to a region in the carotid artery in rabbits. Simultaneously, the ear bleeding time is determined.

Male rabbits (Crl:KBL (NZW)BR, Charles River) receiving a normal diet and having a body weight of 2.2-2.5 kg are anaesthetized by intramuscular administration of xylazine and ketamine (Rompun, Bayer, 5 mg/kg and Ketavet, Pharmacia & Upjohn GmbH, 40 mg/kg body weight). Anaesthesia is furthermore maintained by intravenous administration of the same preparations (bolus: continuous infusion) via the right auricular vein.

The right carotid artery is exposed and the vessel injury is then caused by wrapping a piece of filter paper (10 mm×10 mm) on a Parafilm® strip (25 mm×12 mm) around the carotid artery without disturbing the blood flow. The filter paper contains 100 µL of a 13% strength solution of iron(II) chloride (Sigma) in water. After 5 min, the filter paper is removed and the vessel is rinsed twice with aqueous 0.9% strength sodium chloride solution. 30 min after the injury the injured region of the carotid artery is extracted surgically and any thrombotic material is removed and weighed.

The test substances are administered either intravenously to the anaesthetized animals via the femoral vein or orally to the awake animals via gavage, in each case 5 min and 2 h, respectively, before the injury.

Ear bleeding time is determined 2 min after injury to the carotid artery. To this end, the left ear is shaved and a defined 3 mm-long incision (blade Art. Number 10-150-10, Martin, Tuttlingen, Germany) is made parallel to the longitudinal axis of the ear. Care is taken here not to damage any visible vessels. Any blood that extravasates is taken up in 15 second intervals using accurately weighed filter paper pieces, without touching the wound directly. Bleeding time is calculated as the time from making the incision to the point in time where no more blood can be detected on the filter paper. The volume of the extravasated blood is calculated after weighing of the filter paper pieces.

c) Determination of the Effect on Extravasation/Oedema Formation and/or Neovascularization in the Eye (In Vivo)

c.1) Test of the Efficacy of Substances in the Laser-Induced Choroidal Neovascularization Model This study serves to investigate the efficacy of a test substance on reduction of extravasation/oedema formation and/or choroidal neovascularization in the rat model of laser-induced choroidal neovascularization.

To this end, pigmented rats of the Brown-Norway strain not showing any signs of ophthalmic disorders are selected and randomized into treatment groups. On day 0, the animals are anaesthetized by intraperitoneal injection (15 mg/kg xylazine and 80 mg/kg ketamine) Following instillation of a drop of a 0.5% strength tropicamide solution to dilate the pupils, choroidal neovascularization is triggered on six defined locations around the optical nerve using a 532 nm argon laser photocoagulator (diameter 50-75 μm, intensity 150 mW, duration 100 ms). The test substance and the appropriate vehicle (e.g. PBS, isotonic saline) are administered either systemically by the oral or intraperitonal route, or topically to the eye by repeated administration as eye drops or intravitreal injection. The body weight of all the animals is determined before the start of the study, and then daily during the study.

On day 21, an angiography is carried out using a fluorescence fundus camera (e.g. Kowe, HRA). Under anaesthesia and after another pupil dilation, a 10% strength sodium fluorescein dye is injected subcutaneously (s.c.). 2-10 min later, pictures of the eye background are taken. The degree of extravasation/the oedema, represented by the leakage of fluorescein, is assessed by two to three blinded observers and classified into degrees of severity from 0 (no extravasation) to 3 (strong colouration exceeding the actual lesion).

The animals are sacrificed on day 23, after which the eyes are removed and fixated in 4% strength paraformaldehyde solution for one hour at room temperature. After one washing, the retina is carefully peeled off and the sclera-choroidea complex is stained using an FITC isolectin B4 antibody and then applied flat to a microscope slide. The preparations obtained in this manner are evaluated using a fluorescence microscope (Apotom, Zeiss) at an excitation wavelength of 488 nm. The area or volume of the choroidal neovascularization (in $\mu m^2$ and $\mu m^3$, respectively) is calculated by morphometric analysis using Axiovision 4.6 software.

c.2) Test of the Efficacy of Substances in the Oxygen-Induced Retinopathy Model

It has been shown that oxygen-induced retinopathy is a useful animal model for the study of pathological retinal angiogenesis. This model is based on the observation that hyperoxia during early postnatal development in the retina causes arrest or delay of the growth of normal retinal blood vessels. When, after a 7-day hyperoxia phase, the animals are returned to normoxic room air, this is equivalent to relative hypoxia since the retina is missing the normal vessels which are required to ensure adequate supply of the neural tissue under normoxic conditions. The ischaemic situation caused in this manner results in an abnormal neovascularization which has some similarities with pathophysiological neovascularization in eye disorders such as wet AMD. In addition, the neovascularization caused is highly reproducible, quantifiable and an important parameter for examining the disease mechanisms and possible treatments for various forms of retinal disorders.

The aim of this study is to examine the efficacy of daily systemically administered doses of the test compound on the growth of retinal vessels in the oxygen-induced retinopathy model. Neonates of C57Bl/6 mice and their mothers are exposed to hyperoxia (70% oxygen) on postnatal day 7 (PD7) for 5 days. From PD12, the mice are kept under normoxic conditions (room air, 21% oxygen) until PD17. From day 12 to day 17, the mice are treated daily with the test substance or the corresponding vehicle. On day 17, all mice are anaesthetized with isoflurane and then sacrificed by cervical fracture. The eyes are removed and fixated in 4% formalin. After washing in phosphate-buffered saline, the retina is excised, a flat preparation thereof is produced and this is stained with isolectin B4 antibody. Quantification of neovascularization is carried out using a Zeiss ApoTome.

C) Working Examples for Pharmaceutical Compositions

The substances according to the invention can be converted to pharmaceutical preparations as follows:

Tablet:

Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm.

Production:

The mixture of the compound of Example 1, lactose and starch is granulated with a 5% strength solution (m/m) of the PVP in water. After drying, the granules are mixed with the magnesium stearate for 5 min. This mixture is compressed using a conventional tableting press (see above for format of the tablet).

Oral Suspension:

Composition:

1000 mg of the compound of Example 1, 1000 mg of ethanol (96%), 400 mg of Rhodigel (xanthan gum) (from FMC, USA) and 99 g of water.

10 ml of oral suspension correspond to a single dose of 100 mg of the compound of the invention.

Production:

The Rhodigel is suspended in ethanol, and the compound of Example 1 is added to the suspension.

The water is added while stirring. The mixture is stirred for about 6 h until swelling of the Rhodigel is complete.

Solution or Suspension for Topical Administration to the Eye (Eye Drops):

A sterile pharmaceutical preparation for topical administration to the eye can be prepared by reconstituting a lyophilisate of the inventive compound in sterile saline. Suitable preservatives for such a solution or suspension are, for example, benzalkonium chloride, thiomersal or phenylmercury nitrate in a concentration range of from 0.001 to 1 per cent by weight.

Solution or Suspension for Topical Administration to the Eye (Eye Drops):

A sterile pharmaceutical preparation for topical administration to the eye can be prepared by reconstituting a lyophilisate of the inventive compound in sterile saline. Suitable preservatives for such a solution or suspension are, for example, benzalkonium chloride, thiomersal or phenylmercury nitrate in a concentration range of from 0.001 to 1 per cent by weight.

The invention claimed is:
1. A compound of the formula

(I)

in which
R¹ is a group of the formula where * is the attachment point to the oxopyridine ring,
R⁶ is chlorine,
R⁷ is fluorine, cyano, difluoromethyl, or difluoromethoxy,
R⁸ is hydrogen,
R² is chlorine, cyano, methoxy, or difluoromethoxy,
R³ is methyl, ethyl, n-propyl, or n-butyl,
where methyl may be substituted by a substituent selected from the group consisting of cyclopropyl, cyclobutyl, cyclohexyl, tetrahydro-2H-pyranyl, oxazolyl, and pyridyl,
in which cyclobutyl and cyclohexyl may be substituted by 1 to 2 substituents selected independently from the group consisting of hydroxyl and methoxy,
and
in which oxazolyl may be substituted by a methyl substituent,
and
where ethyl, n-propyl, and n-butyl may be substituted by a substituent selected from the group consisting of methoxy and trifluoromethoxy,
R⁴ is hydrogen,
R⁵ is a group of the formula where # is the attachment point to the nitrogen atom,
R¹² is hydrogen or fluorine,
R¹³ is hydroxyl or —NHR¹⁴,
in which
R¹⁴ is hydrogen, methyl, or ethyl,
or a salt thereof, a solvate thereof, or a solvate of the salt thereof.

2. The compound according to claim 1, wherein
R¹ is a group of the formula where * is the attachment point to the oxopyridine ring,
R⁶ is chlorine,
R⁷ is cyano,
R⁸ is hydrogen,
R² is chlorine or methoxy,
R³ is methyl or ethyl,
where methyl is substituted by a substituent selected from the group consisting of tetrahydro-2H-pyranyl, oxazolyl, and pyridyl,
in which oxazolyl may be substituted by a methyl substituent,
and
where ethyl may be substituted by a methoxy substituent,
R⁴ is hydrogen,
R⁵ is a group of the formula where # is the attachment point to the nitrogen atom,
R¹² is hydrogen,
R¹³ is hydroxyl or —NHR¹⁴,
in which
R¹⁴ is hydrogen or methyl,
or a salt thereof, a solvate thereof, or a solvate of the salt thereof.

3. A process for preparing a compound of the formula (I) or the salt thereof, solvate thereof, or the solvate of the salt thereof according to claim 1, wherein either
a compound of the formula (II)

R
is reacted in the first stage with a compound of the formula (III)

in the presence of a dehydrating reagent, and
optionally converted in a second stage by acidic or basic ester
hydrolysis to a compound of the formula (I),
or
a compound of the formula

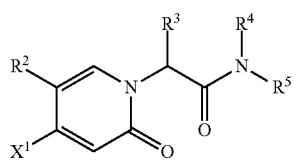

(IV)

in which
X¹ is chlorine, bromine, or iodine
is reacted with a compound of the formula

R¹-Q    (V)

in which
Q is —B(OH)$_2$, a boronic ester, or —BF$_3^-$K$^+$,
under Suzuki coupling conditions to give a compound of the formula (I).

4. A process of using a compound, a salt thereof, a solvate thereof, or a solvate of a salt thereof according to claim 1 for production of a pharmaceutical composition, the process comprising preparing the pharmaceutical composition comprising (i) the compound, the salt thereof, the solvate thereof, or the solvate of the salt thereof and (ii) inert, non-toxic pharmaceutically suitable excipients in a form suitable for oral administration.

5. A method of using a compound according to claim 1 for treatment and/or prophylaxis of a thrombotic or thromboembolic disorder, the method comprising administering a therapeutically effective amount of the compound to a patient in need thereof.

6. A method of using a compound according to claim 1 for treatment and/or prophylaxis of an ophthalmic disorder, the method comprising administering a therapeutically effective amount of the compound to a patient in need thereof.

7. A method of using a compound according to claim 1 for treatment and/or prophylaxis of hereditary angiooedema or an inflammatory disorder of the intestine, the method comprising administering a therapeutically effective amount of the compound to a patient in need thereof.

8. A pharmaceutical composition comprising a compound, a salt thereof, a solvate thereof, or a solvate of a salt thereof according to claim 1 in combination with an inert, nontoxic, pharmaceutically suitable excipient.

9. A method for treatment and/or prophylaxis of a thrombotic or thromboembolic disorder, the method comprising administering a therapeutically effective amount of a pharmaceutical composition according to claim 8 to a patient in need thereof.

10. A method for treatment and/or prophylaxis of an ophthalmic disorder, the method comprising administering a therapeutically effective amount of a pharmaceutical composition according to claim 8 to a patient in need thereof.

11. A method for treatment and/or prophylaxis of hereditary angiooedema, or an inflammatory disorder of the intestine, the method comprising administering a therapeutically effective amount of a pharmaceutical composition according to claim 8 to a patient in need thereof.

12. A method for combating a thrombotic or thromboembolic disorder or an ophthalmic disorder or hereditary angiooedema or an inflammatory disorder of the intestine, in man or animal, by administration of a therapeutically effective amount of at least one compound according to claim 1; or a medicament comprising the compound in combination with an inert, nontoxic, pharmaceutically suitable excipient.

13. The process according to claim 3, wherein Q is boronic acid pinacol ester.

14. The method of claim 7 wherein the inflammatory disorder of the intestine is Crohn's disease or ulcerative colitis.

15. The method of claim 11 wherein the inflammatory disorder of the intestine is Crohn's disease or ulcerative colitis.

16. The method of claim 12 wherein the inflammatory disorder of the intestine is Crohn's disease or ulcerative colitis.

* * * * *